US009090621B2

(12) United States Patent
Goldstein

(10) Patent No.: US 9,090,621 B2
(45) Date of Patent: Jul. 28, 2015

(54) TYROSINE KINASE INHIBITORS

(71) Applicant: Principia Biopharma Inc., South San Francisco, CA (US)

(72) Inventor: David Michael Goldstein, Redwood City, CA (US)

(73) Assignee: Principia Biopharma Inc., South San Francisco, CA (US)

(*) Notice: Subject to any disclaimer, the term of this patent is extended or adjusted under 35 U.S.C. 154(b) by 0 days.

(21) Appl. No.: 14/255,842

(22) Filed: Apr. 17, 2014

(65) Prior Publication Data

US 2014/0309223 A1 Oct. 16, 2014

Related U.S. Application Data

(60) Division of application No. 13/929,179, filed on Jun. 27, 2013, now Pat. No. 8,759,358, which is a continuation of application No. 13/859,569, filed on Apr. 9, 2013, now Pat. No. 8,957,080.

(51) Int. Cl.
| *A01N 43/90* | (2006.01) |
| *A61K 31/519* | (2006.01) |
| *C07D 487/10* | (2006.01) |
| *C07D 487/04* | (2006.01) |
| *A61K 31/5377* | (2006.01) |
| *A61K 45/06* | (2006.01) |
| *A61K 9/00* | (2006.01) |
| *A61K 47/26* | (2006.01) |
| *A61K 47/38* | (2006.01) |
| *A61K 9/20* | (2006.01) |
| *A61K 9/48* | (2006.01) |

(52) U.S. Cl.
CPC ............... *C07D 487/10* (2013.01); *A61K 9/00* (2013.01); *A61K 9/0019* (2013.01); *A61K 9/2013* (2013.01); *A61K 9/2018* (2013.01); *A61K 9/2054* (2013.01); *A61K 9/2059* (2013.01); *A61K 9/4858* (2013.01); *A61K 31/519* (2013.01); *A61K 31/5377* (2013.01); *A61K 45/06* (2013.01); *A61K 47/26* (2013.01); *A61K 47/38* (2013.01); *C07D 487/04* (2013.01)

(58) Field of Classification Search
None
See application file for complete search history.

(56) References Cited

U.S. PATENT DOCUMENTS

| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,514,711 A | 5/1996 | Kitano et al. |
| 5,792,771 A | 8/1998 | App et al. |
| 6,410,486 B2 | 6/2002 | Wetterich et al. |
| 6,660,744 B1 | 12/2003 | Hirst et al. |
| 7,217,682 B2 | 5/2007 | Mori |
| 7,700,648 B2 | 4/2010 | Mori |
| 2003/0153752 A1 | 8/2003 | Hirst et al. |
| 2003/0187001 A1 | 10/2003 | Calderwood et al. |
| 2004/0157847 A1 | 8/2004 | Field et al. |
| 2005/0008640 A1 | 1/2005 | Waegell et al. |
| 2005/0026945 A1 | 2/2005 | Kafka et al. |
| 2005/0065176 A1 | 3/2005 | Field et al. |
| 2006/0025383 A1 | 2/2006 | Wishart et al. |
| 2006/0058297 A1 | 3/2006 | Roifman et al. |
| 2006/0058324 A1 | 3/2006 | Capraro et al. |
| 2007/0149464 A1 | 6/2007 | Billen et al. |
| 2007/0149550 A1 | 6/2007 | Billen et al. |
| 2007/0232668 A1 | 10/2007 | Priebe et al. |
| 2007/0232688 A1 | 10/2007 | Orchansky et al. |
| 2008/0146643 A1 | 6/2008 | Billen et al. |
| 2008/0176865 A1 | 7/2008 | Billen et al. |
| 2009/0306396 A1 | 12/2009 | Toyoshima et al. |
| 2010/0113520 A1 | 5/2010 | Miller |
| 2010/0144705 A1 | 6/2010 | Miller |
| 2011/0021518 A1 | 1/2011 | Magnuson et al. |
| 2012/0028981 A1 | 2/2012 | Miller |
| 2014/0142099 A1 | 5/2014 | Owens |

FOREIGN PATENT DOCUMENTS

| CN | 101880243 A | 11/2010 |
| EP | 0461546 A2 | 12/1991 |
| EP | 0493767 A2 | 7/1992 |
| EP | 0908457 A1 | 4/1999 |
| FR | 2535721 A1 | 5/1984 |

(Continued)

OTHER PUBLICATIONS

Arnold, Lee D. et al., "Pyrrolo[2,3-d]pyrimidines Containing an Extended 5-Substituent as Potent and Selective Inhibitors of Ick I," *Bioorganic & Medicinal Chemistry Letters*, 10:2167-2170 (2000).
Basheer, A., et al., "Enols of Substituted Cyanomalonamides," *J. Org. Chem.* 72:5297-5312 (2007).
Burchat, A.F., et al., "Pyrrolo[2,3-d]pyrimidines Containing an Extended 5-Substituent as Potent and Selective Inhibitors of Ick II," *Bioorganic & Medicinal Chemistry Letters*, 10:2171-2174 (2000).
Calderwood, David J., et al., "Pyrrolo[2,3-d]pyrimidines Containing Diverse N-7 Substituents as Potent Inhibitors of Lck," *Bioorganic & Medicinal Chemistry Letters*, 12:1683-1686 (2002).
CAS RN 26272-41-3, Nov. 16, 1984.

(Continued)

*Primary Examiner* — Jeffrey H Murray
(74) *Attorney, Agent, or Firm* — Finnegan, Henderson, Farabow, Garrett & Dunner, LLP

(57) ABSTRACT

The present disclosure provides compounds and pharmaceutically acceptable salts thereof that are tyrosine kinase inhibitors, in particular BLK, BMX, EGFR, HER2, HER4, ITK, TEC, BTK, and TXK and are therefore useful for the treatment of diseases treatable by inhibition of tyrosine kinases such as cancer and inflammatory diseases such as arthritis, and the like. Also provided are pharmaceutical compositions containing such compounds and pharmaceutically acceptable salts thereof and processes for preparing such compounds and pharmaceutically acceptable salts thereof.

8 Claims, No Drawings

(56) References Cited

FOREIGN PATENT DOCUMENTS

| | | |
|---|---|---|
| GB | 2447933 A | 10/2008 |
| JP | 42008308 B4 | 4/1967 |
| JP | 56-63950 A | 5/1981 |
| JP | 200-1450 | 1/1990 |
| JP | 04-177244 A | 6/1992 |
| JP | 2005-239657 A | 9/2005 |
| WO | WO 95/24190 | 9/1995 |
| WO | WO 95/31432 A1 | 11/1995 |
| WO | WO 98/41499 A1 | 9/1998 |
| WO | WO 99/14216 | 3/1999 |
| WO | WO 01/72751 A1 | 10/2001 |
| WO | WO 03/050080 A1 | 6/2003 |
| WO | WO 03/082807 A2 | 10/2003 |
| WO | WO 2004/016259 A1 | 2/2004 |
| WO | WO 2004/074283 A1 | 9/2004 |
| WO | WO 2005/023773 A1 | 3/2005 |
| WO | WO 2005/030184 A2 | 4/2005 |
| WO | WO 2005/085210 A1 | 9/2005 |
| WO | WO 2006/134468 A1 | 12/2006 |
| WO | WO 2007/043401 A1 | 4/2007 |
| WO | WO 2007/087068 A2 | 8/2007 |
| WO | WO 2008/005954 A2 | 1/2008 |
| WO | WO 2008/039218 A2 | 4/2008 |
| WO | WO 2008/054827 A2 | 5/2008 |
| WO | WO 2008/061740 A1 | 5/2008 |
| WO | WO 2008/072053 A2 | 6/2008 |
| WO | WO 2008/072077 A2 | 6/2008 |
| WO | WO 2008/121742 A2 | 10/2008 |
| WO | WO 2010/009342 A2 | 1/2010 |
| WO | WO 2011/046964 A2 | 4/2011 |
| WO | WO 2011/060440 A2 | 5/2011 |
| WO | WO 2011/152351 A1 | 12/2011 |
| WO | WO 2011/153514 A2 | 12/2011 |
| WO | WO 2012/158764 A1 | 11/2012 |
| WO | WO 2012/158795 A1 | 11/2012 |
| WO | WO 2012/158810 A1 | 11/2012 |
| WO | WO 2012/158843 A2 | 11/2012 |
| WO | WO 2013/003629 A2 | 1/2013 |
| WO | WO 2013/010136 A2 | 1/2013 |
| WO | WO 2013/010380 A1 | 1/2013 |
| WO | WO 2013/010868 A1 | 1/2013 |
| WO | WO 2013/010869 A1 | 1/2013 |
| WO | WO 2013/059738 A2 | 4/2013 |
| WO | WO 2013/102059 A1 | 7/2013 |
| WO | WO 2013/116382 A1 | 8/2013 |
| WO | WO 2013/191965 A1 | 12/2013 |
| WO | WO 2014/022569 A1 | 2/2014 |
| WO | WO 2014/078578 A1 | 5/2014 |

OTHER PUBLICATIONS

Cohen, Michael S., et al., "Structural Bioinformatics-Based Design of Selective, Irreversible Kinase Inhibitors," Science, vol. 308, May 27, 2005.
Donald, Alastair, et al., "Rapid Evolution of 6-Phenylpurine Inhibitors of Protein Kinase B through Structure-Based Design," J. Med. Chem., 50:2289-2292 (2007).
International Preliminary Report on Patentability for International Application No. PCT/US2010/056890, mailed Nov. 16, 2010.
International Search Report, PCT/US2010/056890, mailed Nov. 16, 2010.
Kamath, S. and Buolamwini John K., "Receptor-Guided Alignment-Based Comparative 3D-QSAR Studies of Benzylidene Malonitrile Tyrphostins as EGFR and HER-2 Kinase Inhibitors," J. Med. Chem., 46:4657-4668 (2003).
Knight, Z.A., "A membrane capture assay for lipid kinase activity," Nature Protocols, vol. 2, No. 10 (2007).
Miller, Rand M., "Electrophilic Fragment-Based Design of Reversible Covalent Kinase Inhibitors," J. Am. Chem. Soc. 135(14):5298-5301 (2013).
Office Action issued Apr. 12, 2013 in Chinese Application No. 201080061570.1.
Pan, Zhengying, et al., "Discovery of Selective Irreversible Inhibitors for Bruton's Tyrosine Kinase," ChemMedChem, 2:58-61 (2007).
Proenca, Fernanda and Costa, Marta, "A simple and eco-friendly approach for the synthesis of 2-imino and 2-oxo-2H-chromene-3-carboxamides," Green Chem., 10:995-998 (2008).
Rellos, Peter et al., "Structure and Regulation of the Human Nek2 Centrosomal Kinase," Journal of Biological Chemistry, 282(9):6833-6842, (2007).
Sammes, M.P., et al., "α-Cyano-sulphonyl Chlorides : Their Preparation and Reactions with Amines, Alcohols, and Enamines," J. Chem. Soc. (C) 2151-2155 (1971).
Santilli Arthur A. and Osdene T.S., "8,9,10,11-Tetrahydro-12H-benzo[5,6]quinoxalino[2,3-e][1,4]diazepin-12-ones Examples of a New Heterocyclic Ring System,", J. Org. Chem. 29:2066-2068 (1964).
Serafimova, Iana M., et al., "Reversible targeting of noncatalytic cysteines with chemically tuned electrophiles," Nature Chemical Biology, 8, 471-476 (2012).
Wang, "Cyanoacetamide Multicomponent Reaction (I): Parallel Synthesis of Cyanoacetamides," J. Comb. Chem. 11:920-927 (2009).
Wang, Gary T., et al., "Substituted 4-amino-1H-pyrazolo[3,4-d]pyrimidines as multi-targeted inhibitors of insulin-like growth factor-I receptor (IGFIR) and members of ErbB-family receptor kinases," Bioorganic & Medicinal Chemistry Letters 20:6067-6071.
Wells, Geoffrey et al., "Structural Studies on Bioactive Compounds. 32.[1] Oxidation of Tyrphostin Protein Tyrosine Kinase Inhibitors with Hypervalent Iodine Reagents," J. Med. Chem. 43:1550-1562 (2000).
International Search Report and Written Opinion mailed Jul. 5, 2012 for PCT Application No. PCT/US2012/038092.
International Search Report mailed Feb. 1, 2013 for PCT Application No. PCT/US2012/038214.
File History of U.S. Appl. No. 13/929,179, "Tyrosine Kinase Inhibitors" in the name of David Michael Goldstein, filed Jun. 27, 2013.
File History of U.S. Appl. No. 13/929,004, "Tyrosine Kinase Inhibitors" in the name of David Michael Goldstein, filed Jun. 27, 2013.
Armesto et al., "Efficient photochemical synthesis of 2-vinylcyclopropanecarbaldehydes, precursors of cyclopropane components present in pyrethroids, by using the oxa-di-π-methane rearrangement," Tetrahedron, 66: 8690-8697 (2010).
Bernhart et al., "Synthesis and Antiarrhythmic activity of new [(Dialkylamino)alkyl]phridylacetamides," J. Med. Chem., 26:451-455 (1983).
Burini et al., "Efficient Synthesis of 4-Cyano 2,3-Dihydrooxazoles by Direct Amination of 2-Alkylidene 3-Oxo Nitriles," SYNLETT, 17: 2673-2675 (2005).
Deng et al., "Reversible phospho-Smad$_3$ signalling between tumour suppression and fibrocarcinogenesis in chronic hepatitis B infection," British Society for Immunology, Clinical and Experimental Immunology, 176: 102-111 (2013).
Elinson et al., "Electrochemical transformation of cyanoacetic ester and alkylidenecyanoacetic esters into 3-substituted 1,2-dicyanocyclopropane-1,2-dicarboxylates," Russian Chemical Bulletin, 47(6): 1133-1136 (1998).
Elliott et al., "The Pyrethrins and Related Compounds. Part XVIII. Insecticidal 2,2-Dimethylcyclopropanecarboxylates with New Unsaturated 3-Substituents," Journal of the Chemical Society, Perkin Transactions 1: Organic and Bio-Organic Chemistry (1972-1999) (1974), (21), 2470-4.
Elliott et al., "Insecticidal activity of the pyrethrins and related compounds X.[a] 5-benzyl-3-furylmethyl 2,2-dimethyicyclopropanecarboxylates with ethylenic substituents at position 3 on the cyclopropane ring," Pestic. Sci., 7: 499-502 (1976).
Fioravanti et al., "Parallel Solution-Phase Synthesis of Acrylonitrile Scaffolds Carrying $_L$-α-Amino Acidic or D-Glycosyl Residues," J. Comb. Chem., 8: 808-811 (2006).
Gyoung et al, "Regiospecific synthesis of 2-allylated-5-substituted tetrazoles via palladium-catalyzed reaction of nitriles, trimethylsilyl azide, and allyl acetates," Tetrahedron Letters, 41(21): 4193-4196 (2000).
Jenner, "Steric effects in high pressure Knoevenagel reactions," Tetrahedron Letters, 42(2): 243-245 (2001).
Kamijo et al., "Tetrazole synthesis via the palladium-catalyzed three component coupling reaction," Molecular Diversity, 6: 181-192 (2003).

(56) References Cited

OTHER PUBLICATIONS

Kojima et al., "Stereoselective synthesis of activated cyclopropanes with an α-pyridinium acetamide bearing an 8-phenylmenthyl group as the chiral auxiliary," *Tetrahedron Letters*, 45(18): 3565-3568 (2004).

Komura et al., "Layered silicate PLS-1: A new solid base catalyst for C-C bond forming reactions," *Catalysis Communications*, 8(4): 644-648 (2007).

Kotz et al., "The Action of Chloroform on Methylene and Methenyl Groups," *Journal fuer Praktische Chemie (Leipzig)*, Abstract, 74: 425-48 (1907).

Lou et al., "Bruton's Tyrosine Kinase Inhibitors: Approaches to Potent and Selective Inhibition, Preclinical and Clinical Evaluation for Inflammatory Diseases and B Cell Malignancies," *J. Med. Chem.*, 55(10): 4539-4550 (2012).

Maas et al., "Conjugate Addition of Dialkylaluminum Chlorides to Alkylidenemalonic Acid Derivatives," *Synthesis*, 10: 1792-1798 (1999).

Maurya et al., "Catalyst-free stereoselective cyclopropanation of electron deficient alkenes with ethyl diazoacetate," *RSC Advances*, 3: 15600-15603 (2013).

Neplyuev, "Studies of triacylmethanes VII. 1,1,3,3-Tetraacyl-3-arylazo-1-propenes," *Zhurnal Organicheskoi Khimii*, Abstract, 15(3): 563-6 (1979).

Neplyuev, "Nitration and nitrosation of 1,1,3,3-tetraacyl-1-propenes" *Ukrainskii Khimicheskii Zhurnal (Russian Edition)*, Abstract, 49(2): 192-4 (1983).

Porter et al., "The discovery of potent, orally bioavailable pyrimidine-5-carbonitrile-6-alkyl CXCR2 receptor antagonists," *Bioorganic & Medicinal Chemistry Letters*, 24: 3285-3290 (2014).

Schwarz et al., "Novel Cyclopropyl β-Amino Acid Analogues of Pregabalin and Gabapentin That Target the α2-δ Protein," *J. Med. Chem.*, 48:3026-3035 (2005).

SciFinder® dated May 9, 2011, 8:13 pm.
SciFinder® dated May 9, 2011, 8:23 pm.
SciFinder® dated May 9, 2011, 8:33 pm.
SciFinder® dated May 9, 2011, 9:06 pm.
SciFinder® dated May 10, 2011, 10:04 am.
SciFinder® dated May 10, 2011, 10:20 am.
SciFinder® dated May 10, 2011, 10:46 am.

Stevens et al, "Synthesis of Substituted Cyclopropylphosphonates by Michael Induced Ring Closure (MIRC) Reactions," *Synlett*, 7: 1089-1092 (2002).

Verhé et al., "Preparation of 2,2-Dialkylcyclopropanes Geminally Substituted with Electron-Withdrawing Groups," *Synthesis*, 7: 530-2 (1978).

Verhé et al., "Thermal Lactonization of Brominated Alkylidenemalonates: Synthesis of 2-Buten-4-Olides," *Bulletin des Societes Chimiques Beiges*, 87(3): 215-222 (1978).

Verhé et al, "Synthesis of 1,1-Bis(Hydroxymethyl) Cyclopropanes," *Organic Preparations and Procedures International*, 13(1): 13-18(1981).

Vo et al., "Transformations of Resin-Bound Pyridinium Ylides: I. A Stereoselective Synthesis of 2,2,3-Trisubstituted Cyclopropanecarboxylates," *Tetrahedron Letters*, 38(46): 7951-7954 (1997).

Zhang et al., "Organic base catalyzed carbonyl allylation of methyl trifluoropyruvate with activated alkenes," *Tetrahedron*, 65: 83-86 (2009).

Zimmerman et al., "The Diverted Di-π-Methane Rearrangement; Mechanistic and Exploratory Organic Photochemistry," *Organic Letters*, 4(7): 1155-1158 (2002).

PCT Notification of Transmittal of the International Search Report and the Written Opinion of the International Searching Authority, or the Declaration for International Application No. PCT/US2013/058614, mailed Nov. 5, 2013.

File History of U.S. Appl. No. 13/859,569, "Tyrosine Kinase Inhibitors" in the name of David Michael Goldstein, filed Apr. 9, 2013.

File History of U.S. Appl. No. 14/185,687, "Tyrosine Kinase Inhibitors" in the name of David Michael Goldstein, filed Feb. 20, 2014.

File History of U.S. Appl. No. 14/341,421, "Tyrosine Kinase Inhibitors" in the name of David Michael Goldstein, filed Jul. 25, 2014.

File History of U.S. Appl. No. 14/117,927, "Pyrazolopyrimidine Derivatives As Tyrosine Kinase Inhibitors" in the name of David Michael Goldstein, filed Nov. 15, 2013.

File History of U.S. Appl. No. 14/117,933, "Tyrosine Kinase Inhibitors" in the name of David Michael Goldstein, filed Nov. 15, 2013.

File History of U.S. Appl. No. 14/374,788, "Pyrazolopyrimidine Compounds As Kinase Inhibitors," in the name of Tim Owens, filed Jul. 25, 2014.

File History of U.S. Appl. No. 14/464,602, "Pyrazqlopyrimidine Compounds As Kinase Inhibitors," in the name of Tim Owens, filed Aug. 20, 2014.

File History of U.S. Appl. No. 14/084,519, "Purinone Derivatives As Tyrosine Kinase Inhibitors," in the name of Timothy D. Owens, filed Nov. 19, 2013.

TYROSINE KINASE INHIBITORS

The present disclosure provides compounds that are tyrosine kinase inhibitors, in particular BLK, BMX, EGFR, HER2, HER4, ITK, TEC, BTK, and TXK and are therefore useful for the treatment of diseases treatable by inhibition of tyrosine kinases such as cancer and inflammatory diseases such as arthritis, and the like. Also provided are pharmaceutical compositions containing such compounds and processes for preparing such compounds.

The human genome contains at least 500 genes encoding protein kinases. Many of these kinases have been implicated in human disease and as such represent potentially attractive therapeutic targets. For example EGFR is overexpressed in breast, head and neck cancers and the overexpression is correlated with poor survival (see Do N. Y., et al., Expression of c-ErbB receptors, MMPs and VEGF in squamous cell carcinoma of the head and neck. *Oncol Rep.* August 12:229-37. 2004 and Foley J., et al., EGFR signaling in breast cancer: bad to the bone. *Semin Cell Dev Biol.* 21:951-60. 2010). HER2, another EGFR family member, also is amplified or overexpressed in up to 30% of breast cancers, also correlating with poor survival (see Murphy C. G, Modi S. HER2 breast cancer therapies: a review. *Biologics* 3:289-301. 2009). HER4, also in the EGFR family, is overexpressed in head and neck squamous cell carcinomas (see Rosen F. S., et al. The primary immunodeficiencies. *New Engl. J. Med.* 333:431-40. 1995). Other studies show decreased expression of HER4 in certain cancers and suggest tumor suppressor activity (see Thomasson M, et al., ErbB4 is downregulated in renal cell carcinoma—a quantitative RT-PCR and immunohistochemical analysis of the epidermal growth factor receptor family. *Acta Oncol.* 43:453-9. 2004). Overall the data support a role for members of the EGFR family in cancer. ITK, a member of the TEC kinase family, is involved in activation of T cells and mast cells (see Iyer A. S. et al. Absence of Tec Family Kinases Interleukin-2 Inducible T cell Kinase (Itk) and Bruton's Tyrosine Kinase (Btk) Severely Impairs Fc{epsilon}RI-dependent Mast Cell Responses. *J. Biol. Chem.;* 286:9503-13. 2011) and is a potential target in inflammatory immune diseases such as asthma. Mice deficient in ITK are resistant to development of allergic asthma (see Sahu N, et al., Differential sensitivity to Itk kinase signals for T helper 2 cytokine production and chemokine-mediated migration. *J. Immunol.* 180:3833-8. 2008). Another family member, BMX, is involved in supporting tumor angiogenesis through it's role in the tumor vascular endothelium (see Tu T, et al., Bone marrow X kinase-mediated signal transduction in irradiated vascular endothelium. *Cancer Res.* 68:2861-9. 2008) and is also progressively up-regulated during bladder cancer progression (see Guo S., et al., Tyrosine Kinase ETK/BMX Is Up-Regulated in Bladder Cancer and Predicts Poor Prognosis in Patients with Cystectomy. *PLoS One.* 6:e17778. 2011) suggesting a potential therapeutic target in this type cancer. The B lymphoid kinase (BLK) is linked through genetic association with a variety of rheumatic diseases including systemic lupus erythematosus and systemic sclerosis (see Ito I, et al., Association of the FAM167A-BLK region with systemic sclerosis. *Arthritis Rheum.* 62:890-5. 2010).

Bruton's tyrosine kinase (abbreviated as BTK), a member of the Tec family non-receptor tyrosine kinases that is essential for B cell signaling downstream from the B-cell receptor. It is expressed in B cells and other hematopoietic cells such as monocytes, macrophages and mast cells. It functions in various aspects of B cell function that maintain the B cell repertoire (see Gauld S. B. et al., B cell antigen receptor signaling: roles in cell development and disease. Science, 296:1641-2. 2002)). Clinical validation of the role of B cells in RA has been provided by the efficacy of Rituxan (an anti-CD20 antibody), which depletes B cells as a mechanism of action (see Perosa F., et al., CD20-depleting therapy in autoimmune diseases: from basic research to the clinic. *J Intern Med.* 267: 260-77. 2010 and Dörner T, et al. Targeting B cells in immune-mediated inflammatory disease: a comprehensive review of mechanisms of action and identification of biomarkers. *Pharmacol Ther.* 125:464-75. 2010). Btk is known to be required for B cell development because patients with the disease X-linked agammaglobulinemia (see Rosen F. S., et al., The primary immunodeficiencies. *N Engl J Med.* 333: 431-40. 1995). Notably, small-molecule BTK inhibitors in pre-clinical development have been shown to be efficacious in collagen-induced arthritis (see Pan Z., et al., Discovery of selective irreversible inhibitors for Bruton's tyrosine kinase. *J. Med. Chem.* 2:58-61. 2007). However, the potential advantage of a BTK inhibitor (beyond the inherent advantage of a small-molecule over a biologic) is that modulation of BTK can inhibit B cell function without permanent removal of the B cell itself. Therefore, the long periods of low B cell levels experienced with Rituxan should be avoidable by targeting BTK.

In addition, the disease modifying activities of BTK are expected to extend beyond those of Rituxan because of effects on addition cellular targets that are involved in propagation of disease. For instance, antigen induced mast cell degranulation is impaired in mast cells derived from the bone marrow of BTK deficient mice, demonstrating that BTK is downstream of the FcεR1 receptor (see Setoguchi R., et al., Defective degranulation and calcium mobilization of bone-marrow derived mast cells from Xid and BTK-deficient mice. *Immunol Lett.* 64:109-18. 1998). A similar signaling module exists in monocytes and macrophages for the FcγR1 receptor indicating BTK inhibition is highly likely to modulate TNF production in response to IgG. Both mast cells and macrophages are thought to contribute to propagation of the inflammatory cytokine environment of the diseased synovium.

In addition to the peripheral and synovial effects of BTK inhibition described above, there is evidence that BTK inhibition will have bone protective effects in the inflamed joint (see Gravallese E. M., et al., Synovial tissue in rheumatoid arthritis is a source of osteoclast differentiation factor. *Arthritis Rheum.* 43:250-8. 2000). Studies with mice that are either deficient in BTK or have impaired BTK function have demonstrated that Rank ligand-induced osteoclast differentiation is impaired in the absence of BTK function (see Lee S. H., et. al., The tec family tyrosine kinase BTK Regulates RANKL-induced osteoclast maturation. *J. Biol. Chem.* 283:11526-34. 2008). Taken together these studies suggest a BTK inhibitor could inhibit or reverse the bone destruction that occurs in RA patients. Given the importance of B cells in autoimmune disease, BTK inhibitors could also have utility in other autoimmune diseases such as systemic lupus erythematosus (see Shlomchik M. J., et. al., The role of B cells in lpr/lpr-induced autoimmunity *J. Exp Med.* 180:1295-1306. 1994). Notably, an irreversible BTK inhibitor has been shown to display efficacy in the mouse MRL/lpr lupus model, reducing autoantibody production and renal damage (see Honigberg L. A., The Bruton tyrosine kinase inhibitor PCI-32765 blocks B-cell activation and is efficacious in models of autoimmune disease and B-cell malignancy. *Proc. Natl. Acad. Sci.* 107: 13075-80. 2010).

There is also potential for BTK inhibitors for treating allergic diseases (see Honigberg, L., et. al., The selective BTK inhibitor PCI-32765 blocks B cell and mast cell activation and prevents mouse collagen induced arthritis. *Clin. Immu-*

*nol.* 127 S1:S111. 2008). In addition, the irreversible inhibitor suppresses passive cutaneous anaphylaxis (PCA) induced by IgE antigen complex in mice (see Honigberg, L., et. al., The selective BTK inhibitor PCI-32765 blocks B cell and mast cell activation and prevents mouse collagen induced arthritis. *Clin. Immunol.* 127 S1:S111. 2008). These findings are in agreement with those noted with BTK-mutant mast cells and knockout mice and suggest that BTK inhibitors may be useful for the treatment of asthma, an IgE-dependent allergic disease of the airway.

In addition, platelet aggregation in response to collagen or collagen-related peptide is impaired in XLA patients who lack BTK function (see Quek L. S, et al., A role for Bruton's tyrosine kinase (BTK) in platelet activation by collagen. *Curr. Biol.* 8:1137-40.1998). This is manifested by changes downstream from GPIV, such as phosphorylation of PLCgamma2 and calcium flux, which suggests potential utility in treating thromboembolic diseases.

Preclinical studies with a selective inhibitor of BTK have shown effects on spontaneous canine B cell lymphomas suggesting a potential utility in human lymphomas or other hematologic malignancies including chronic lymphocytic leukemia.

Accordingly, there is a need for compounds that inhibit tyrosine kinases thereby providing treatment for diseases such as autoimmune diseases, thromboembolic diseases and cancer. The present disclosure can fulfill this need and related needs.

In one aspect, this disclosure is directed to a compound of Formula (IA) or a pharmaceutically acceptable salt thereof:

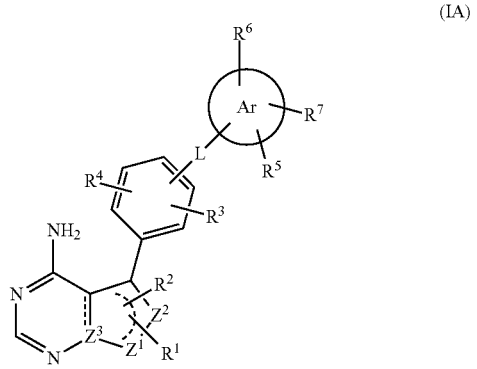

(IA)

wherein:
dashed lines are an optional bond;
$Z^1$, $Z^2$, and $Z^3$ are —N— or —CH—, provide that at least one and not more than two of $Z^1$, $Z^2$, and $Z^3$ are simultaneously —N—;
L is O, CO, CH$_2$, S, SO, SO$_2$, NR, NRCO, CONR, NR'SO$_2$, SO$_2$NR', or NRCONR, where (each R and R' is independently hydrogen or alkyl);
Ar is aryl, heteroaryl, cycloalkyl or heterocyclyl;
one of $R^1$ and $R^5$ is hydrogen, alkyl, hydroxy, alkoxy, halo, haloalkyl, or haloalkoxy and the other is —Z-(EWG)-C(CN)=CHR$^c$ where Z is bond, NR$^a$ (where R$^a$ is hydrogen or alkyl), O, S, SO, SO$_2$, alkylene, cycloalkylene, heteroalkylene, —(Z$^a$)$_{n1}$-aryl-, or —(Z$^a$)$_{n1}$-heteroaryl (wherein n1 is 0 or 1, Z$^a$ is NR$^a$ (where R$^a$ is hydrogen or alkyl), O, S, SO, SO$_2$, alkylene, or heteroalkylene and aryl or heteroaryl is optionally substituted with one or two substituents independently selected from halo, alkyl, alkoxy, alkylthio, haloalkyl, or haloalkoxy), EWG is a bond or an electron withdrawing group, and R$^c$ is alkyl, haloalkoxy, substituted alkyl, cycloalkyl, cycloalkyleneNR$^d$R$^e$ or cycloalkylene(alkylene) NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro;

$R^2$ is hydrogen, alkyl, hydroxy, alkoxy, cyano, halo or haloalkyl;

$R^3$ is hydrogen, alkyl, cyclopropyl, hydroxy, alkoxy, cyano, halo, haloalkyl or haloalkoxy;

$R^4$ is hydrogen, alkyl, alkynyl, cyclopropyl, alkylamino, dialkylamino, alkylthio, alkylsulfonyl, carboxy, alkoxycarbonyl, alkylaminosulfonyl, dialkylaminosulfonyl, —CONH$_2$, alkylaminocarbonyl, dialkylaminocarbonyl, 3, 4 or 5 membered heterocylyl, hydroxy, alkoxy, cyano, halo, haloalkyl or haloalkoxy; and $R^6$ and $R^7$ are independently hydrogen, alkyl, hydroxy, alkoxy, halo, haloalkyl, haloalkoxy, carboxy, alkoxycarbonyl, cyano, —CONH$_2$, amino, or monosubstituted or disubstituted amino; provided that: (a) when

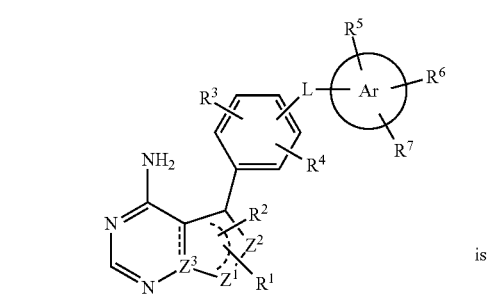

is

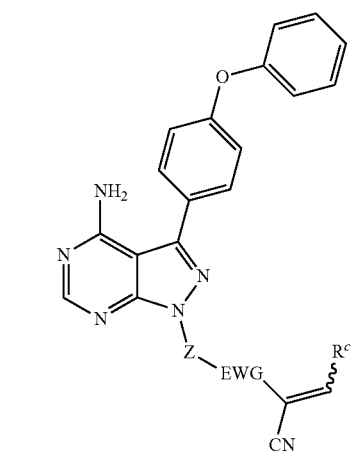

where (i) when R$^c$ is cyclopropyl, tert-butyl, —C(CH$_3$)$_2$CH$_2$OH, —C(CH$_3$)$_2$N(CH$_3$)$_2$, cyclopentyl, isopropyl, —C(CH$_3$)$_2$OCH$_2$CH$_3$, or azetidin-3-yl, then —Z-EWG- is not

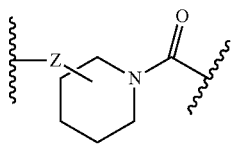

where Z is a bond or methylene; (ii) when $R^c$ is cyclopropyl then —Z-EWG- is not

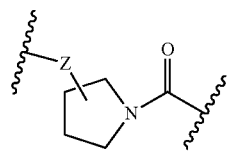

where Z is bond or methylene, and (iii) when $R^c$ is cyclopropyl and Z is cyclohexyl, then EWG is not —NHCO— where NH is bonded to cyclohexyl or (b) the compound of Formula (IA) is not 2-(3-(4-amino-5-(4-phenoxyphenyl)-7H-pyrrolo[2,3-d]pyrimidin-7-yl)piperidine-1-carbonyl)-3-cyclopropylacrylonitrile; or a pharmaceutically acceptable salt thereof.

In one aspect, the compound of Formula (IA) or a pharmaceutically acceptable salt thereof is a compound of Formula (I'):

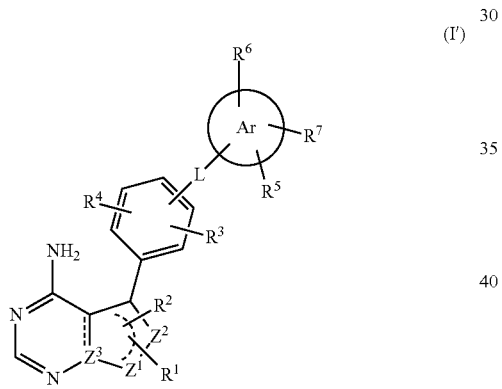

wherein:
dashed lines are an optional bond;
$Z^1$, $Z^2$, and $Z^3$ are —N— or —CH—, provide that at least one and not more than two of $Z^1$, $Z^2$, and $Z^3$ are simultaneously —N—;
L is O, CO, CH$_2$, S, SO, SO$_2$, NR, NRCO, CONR, NR'SO$_2$, SO$_2$NR', or NRCONR, where (each R and R' is independently hydrogen or alkyl);
Ar is aryl, heteroaryl, cycloalkyl or heterocyclyl;
one of $R^1$ and $R^5$ is hydrogen, alkyl, hydroxy, alkoxy, halo, haloalkyl, or haloalkoxy and the other is —Z-(EWG)-C(CN)=CHR$^c$ where Z is bond, NR$^a$ (where R$^a$ is hydrogen or alkyl), O, S, SO, SO$_2$, alkylene, cycloalkylene, heteroalkylene, —(Z$^a$)$_{n1}$-aryl-, or —(Z$^a$)$_{n1}$-heteroaryl (wherein n1 is 0 or 1, Z$^a$ is NR$^a$ (where R$^a$ is hydrogen or alkyl), O, S, SO, SO$_2$, alkylene, or heteroalkylene and aryl or heteroaryl is optionally substituted with one or two substituents independently selected from halo, alkyl, alkoxy, alkylthio, haloalkyl, or haloalkoxy), EWG is a bond or an electron withdrawing group, and R$^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl;

$R^2$ is hydrogen, alkyl, hydroxy, alkoxy, cyano, halo or haloalkyl;

$R^3$ is hydrogen, alkyl, cyclopropyl, hydroxy, alkoxy, cyano, halo, haloalkyl or haloalkoxy;

$R^4$ is hydrogen, alkyl, alkynyl, cyclopropyl, alkylamino, dialkylamino, alkylthio, alkylsulfonyl, carboxy, alkoxycarbonyl, alkylaminosulfonyl, dialkylaminosulfonyl, —CONH$_2$, alkylaminocarbonyl, dialkylaminocarbonyl, 3, 4 or 5 membered heterocylyl, hydroxy, alkoxy, cyano, halo, haloalkyl or haloalkoxy; and $R^6$ and $R^7$ are independently hydrogen, alkyl, hydroxy, alkoxy, halo, haloalkyl, haloalkoxy, carboxy, alkoxycarbonyl, cyano, —CONH$_2$, amino, or monosubstituted or disubstituted amino; provided that: (a) when

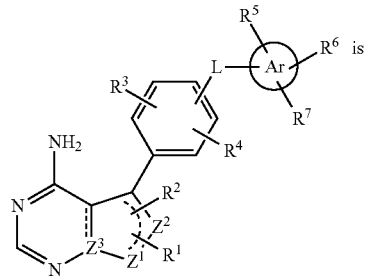

is

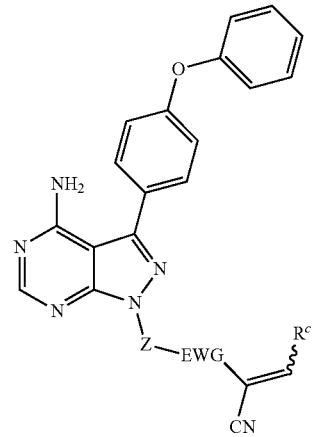

where (i) when $R^c$ is cyclopropyl, tert-butyl, —C(CH$_3$)$_2$CH$_2$OH, —C(CH$_3$)$_2$N(CH$_3$)$_2$, cyclopentyl, isopropyl, —C(CH$_3$)$_2$OCH$_2$CH$_3$, or azetidin-3-yl, then —Z-EWG- is not

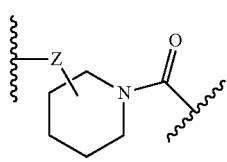

where Z is a bond or methylene; (ii) when $R^c$ is cyclopropyl then —Z-EWG- is not

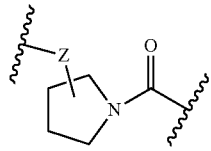

where Z is bond or methylene, and (iii) when $R^c$ is cyclopropyl and Z is cyclohexyl, then EWG is not —NHCO— where NH is bonded to cyclohexyl or (b) the compound of Formula (I') is not 2-(3-(4-amino-5-(4-phenoxy-phenyl)-7H-pyrrolo[2,3-d]pyrimidin-7-yl)piperidine-1-carbonyl)-3-cyclopropylacrylonitrile; or a pharmaceutically acceptable salt thereof.

In another aspect, the compound of Formula (I') or a pharmaceutically acceptable salt thereof is a compound of Formula (I):

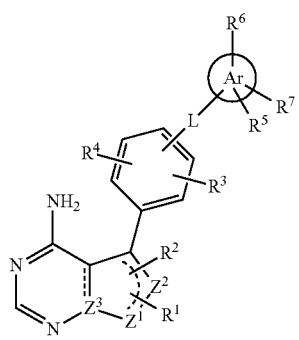

(I)

wherein:
dashed lines are an optional bond;
$Z^1$, $Z^2$, and $Z^3$ are —N— or —CH—, provide that at least one and not more than two of $Z^1$, $Z^2$, and $Z^3$ are simultaneously —N—;
L is O, CO, CH$_2$, S, SO, SO$_2$, NR, NRCO, CONR, NR'SO$_2$, SO$_2$NR', or NRCONR, where (each R and R' is independently hydrogen or alkyl);
Ar is aryl, heteroaryl, cycloalkyl or heterocyclyl;
one of $R^1$ and $R^5$ is hydrogen, alkyl, hydroxy, alkoxy, halo, haloalkyl, or haloalkoxy and the other is —Z-(EWG)-C(CN)=CHR$^c$ where Z is bond, NR$^a$ (where R$^a$ is hydrogen or alkyl), O, S, SO, SO$_2$, alkylene, cycloalkylene, heteroalkylene, —(Z$^a$)$_{n1}$-aryl-, or —(Z$^a$)$_{n1}$-heteroaryl (wherein n1 is 0 or 1, Z$^a$ is NR$^a$ (where R$^a$ is hydrogen or alkyl), O, S, SO, SO$_2$, alkylene, or heteroalkylene and aryl or heteroaryl is optionally substituted with one or two substituents independently selected from halo, alkyl, alkoxy, alkylthio, haloalkyl, or haloalkoxy), EWG is a bond or an electron withdrawing group, and $R^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl;
$R^2$ is hydrogen, alkyl, hydroxy, alkoxy, cyano, halo or haloalkyl;
$R^3$ and $R^4$ are independently hydrogen, alkyl, hydroxy, alkoxy, cyano, halo, haloalkyl or haloalkoxy; and
$R^6$ and $R^7$ are independently hydrogen, alkyl, hydroxy, alkoxy, halo, haloalkyl, haloalkoxy, carboxy, alkoxycarbonyl, cyano, —CONH$_2$, amino, or monosubstituted or disubstituted amino;

provided that: (a) when

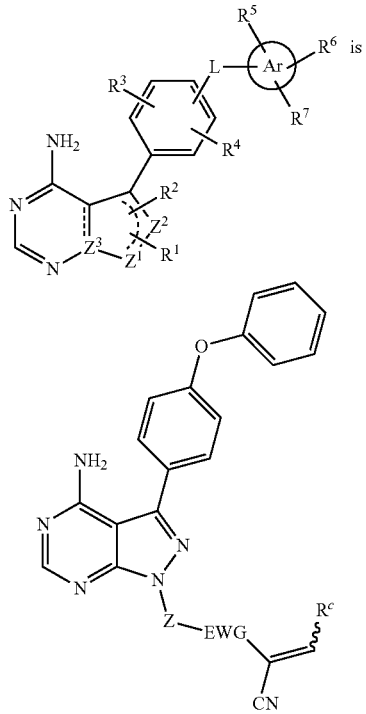

where (i) when $R^c$ is cyclopropyl, tert-butyl, —C(CH$_3$)$_2$CH$_2$OH, —C(CH$_3$)$_2$N(CH$_3$)$_2$, cyclopentyl, isopropyl, —C(CH$_3$)$_2$OCH$_2$CH$_3$, or azetidin-3-yl, then —Z-EWG- is not

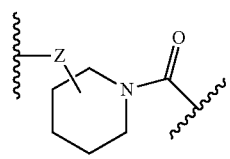

where Z is a bond or methylene; (ii) when $R^c$ is cyclopropyl then —Z-EWG- is not

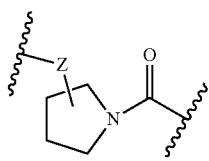

where Z is bond or methylene, and (iii) when $R^c$ is cyclopropyl and Z is cyclohexyl, then EWG is not —NHCO— where NH is bonded to cyclohexyl or (b) the compound of Formula (I) is not 2-(3-(4-amino-5-(4-phenoxyphenyl)-7H-pyrrolo[2,3-d]pyrimidin-7-yl)piperidine-1-carbonyl)-3-cyclopropylacrylonitrile; or a pharmaceutically acceptable salt thereof.

In a second aspect, this disclosure is directed to a pharmaceutical composition comprising a compound of Formula (IA), (I') or (I) (or any of the embodiments thereof described herein), or a pharmaceutically acceptable salt thereof; and a pharmaceutical acceptable excipient.

In a third aspect, this disclosure is directed to a method of treating a disease treatable by inhibition of a tyrosine kinase such as BLK, BMX, EGFR, HER2, HER4, ITK, TEC, BTK, and TXK, preferably BTK, in a patient which method comprises administering to the patient in need thereof, a pharmaceutical composition comprising a compound of Formula (IA), (I') or (I) (or any of the embodiments thereof described herein) or a pharmaceutically acceptable salt thereof, and a pharmaceutically acceptable excipient. In one embodiment the disease is inflammatory disease such as arthritis, kidney disease, or cancer such as B-cell non-Hodgkin lymphoma.

In one embodiment of this aspect, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. Preferably, the disease is rheumatoid arthritis. Preferably, the autoimmune disease is lupus. In another embodiment of this aspect, the patient in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In another embodiment of this aspect, the patient in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. In another embodiment of this aspect, the patient is suffering from inflammatory skin disease which includes, by way of example, dermatitis, contact dermatitis, eczema, urticaria, rosacea, and scarring psoriatic lesions in the skin, joints, or other tissues or organs.

In yet another embodiment of this aspect, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, the compound of Formula (IA), (I') or (I) (or any of the embodiments thereof described herein), is administered in combination with another an anti-cancer agent e.g., the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, Nexavar®, Tarceva®, Sutent®, Tykerb®, Sprycel®, Crizotinib, Xalkori®, or LY294002.

In yet another embodiment, the patient in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed to use of compound of Formula (IA), (I') or (I) (and any embodiments thereof described herein) as a medicament. In one embodiment, the use of compound of Formula (IA), (I') or (I) is for treating a disease mediated by a kinase, preferably BTK, more preferably the disease is an inflammatory disease or a proliferative disease such as cancer.

In a fifth aspect is the use of a compound of Formula (IA), (I') or (I) (or any of the embodiments thereof described herein), in the manufacture of a medicament for treating an inflammatory disease in a patient in which the activity of a tyrosine kinase such as BLK, BMX, EGFR, HER2, HER4, ITK, TEC, BTK, and TXK, preferably, BTK contributes to the pathology and/or symptoms of the disease. In one embodiment of this aspect, the tyrosine kinase protein is BTK. In another embodiment of this aspect, the inflammatory disease is respiratory, cardiovascular, or proliferative diseases.

In any of the aforementioned aspects involving the treatment of proliferative disorders, including cancer, are further embodiments comprising administering the compound of Formula (IA), (I') or (I) (or any of the embodiments thereof described herein), in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, paclitaxel, Taxol™, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol. When combination therapy is used, the agents can be administered simultaneously or sequentially.

In a sixth aspect, this disclosure is directed to an intermediate of Formula (II):

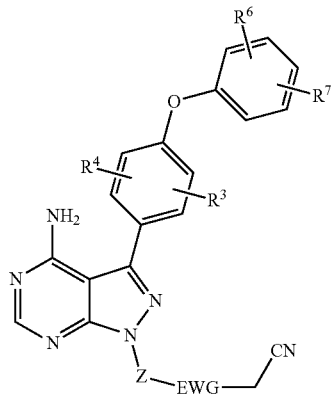

(II)

wherein:

$R^3$ and $R^4$ are independently hydrogen, alkyl, haloalkyl, fluoro or chloro; preferably $R^4$ is hydrogen and $R^3$ is fluoro, preferably fluoro is at the 2-position of the phenyl ring, the carbon atom of the phenyl ring attached to pyrazolopyrimidine ring being the 1-position;

$R^6$ and $R^7$ are independently hydrogen or fluoro; preferably $R^6$ and $R^7$ are hydrogen; preferably $R^6$ and $R^7$ are fluoro, more preferably, $R^6$ and $R^7$ are attached at the 2- and 3-position of the phenyl ring, the carbon atom attached to the phenyl ring substituted with $R^3$ and $R^4$ being position 1;

—Z-EWG- is:

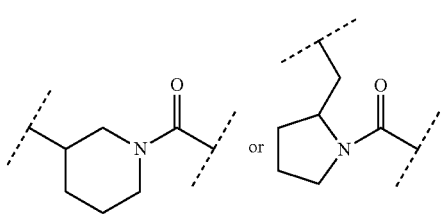

where each ring is optionally substituted with one or two substituents selected from alkyl, fluoro, or hydroxy; preferably —Z-EWG- is:

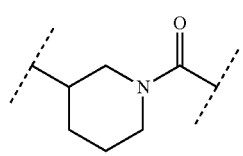

optionally substituted with one or two substituents selected from alkyl, fluoro, or hydroxy. More preferably, —Z-EWG- is

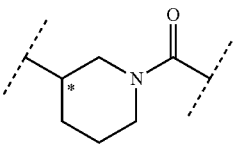

where the stereochemistry at *C is (R). Preferably —Z-EWG- is:

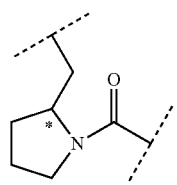

where the stereochemistry at *C is (RS), (R) or (S); preferably (R). Preferably the stereochemistry at *C is (S).

provided that at least one of $R^3$, $R^4$, $R^6$ and $R^7$ is not hydrogen, preferably one of $R^3$ and $R^4$ is not hydrogen.

In a seventh aspect, this disclosure is directed to an intermediate of Formula (III):

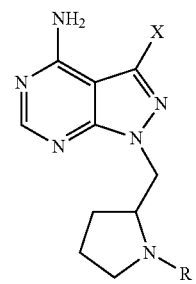

(III)

where:

X is halo, preferably iodo;

R is an amino protecting group, —COCH$_2$CN or —CO—C(CN)=CHR$^c$ where R$^c$ is alkyl, substituted alkyl, cycloalkyl, cycloalkyleneNR$^d$R$^e$ or cycloalkylene(alkylene)NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro; or a salt thereof.

Preferably,

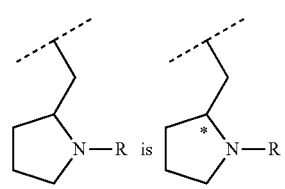

where the stereochemistry at *C is (R) or (S).

Preferably, the stereochemistry at *C is (S) when R$^c$ is alkyl, cycloalkyl, alkyl [substituted with hydroxy, alkoxy, —NRR' (where R is alkyl, cycloalkyl, hydroxyalkyl, or alkoxyalkyl and R' is alkyl) or heterocycloamino which is optionally substituted with one or two groups independently selected from alkyl or hydroxyl], or 3 to 6 membered saturated monocyclic heterocyclyl containing one or two heteroatoms selected from N, O, or S and optionally substituted with one or two substituents selected from hydroxy, alkyl or fluoro.

Preferably, the stereochemistry at *C is (S) when where $R^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl.

Preferably, the stereochemistry at *C is (R) when $R^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom and which is optionally substituted with one or two groups independently selected from alkyl or hydroxyl. Preferably, the stereochemistry at *C is (R) when $R^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

In an eighth aspect, this disclosure is directed to an intermediate of Formula (IV):

(IV)

where:
X' is hydroxy or a leaving group, preferably halo;
R is —COCH$_2$CN or —CO—C(CN)=CHR$^c$ where R$^c$ is alkyl, substituted alkyl, cycloalkyl, cycloalkyleneNR$^d$R$^e$ or cycloalkylene(alkylene)NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro;
or a salt thereof.
Preferably,

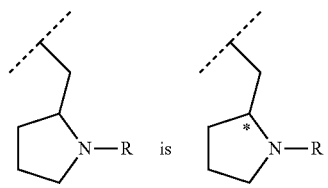

where the stereochemistry at *C is (R) or (S). Preferably, the stereochemistry at *C is (S) when R$^c$ is alkyl, cycloalkyl, alkyl [substituted with hydroxy, alkoxy, —NRR' (where each R is alkyl, cycloalkyl, hydroxyalkyl, or alkoxyalkyl and R' is alkyl) or heterocycloamino which is optionally substituted with one or two groups independently selected from alkyl or hydroxyl], or 3 to 6 membered saturated monocyclic heterocyclyl containing one or two heteroatoms selected from N, O, or S and optionally substituted with one or two substituents selected from hydroxy, alkyl or fluoro. Preferably, where R$^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl.

Preferably, the stereochemistry at *C is (R) when R$^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom and which is optionally substituted with one or two groups independently selected from alkyl or hydroxyl. Preferably, R$^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

In a ninth aspect, provided is a process of preparing a compound of Formula (Id):

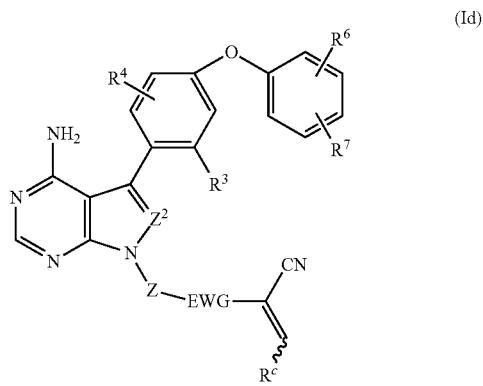

(Id)

where:
Z$^2$ is —N—;
R$^3$ is fluoro;
R$^4$ is hydrogen;
R$^6$ and R$^7$ are independently hydrogen or fluoro;
—Z-EWG- is

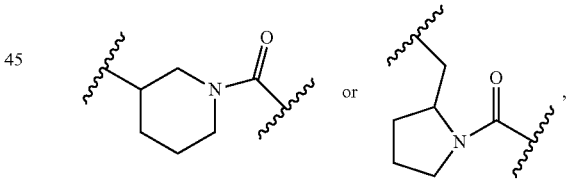

each ring optionally substituted with one or two substituents independently selected from alkyl, hydroxy, or halo, and the carbonyl and sulfonyl group in

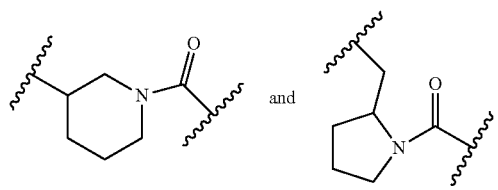 [SMILES: *C(=O)N1CCCC(*)C1 ; *CC1CCCN1C(*)=O]

is attached to —C(CN)=CHR$^c$; and
R$^c$ is alkyl, haloalkoxy, substituted alkyl, cycloalkyl, cycloalkyleneNR$^d$R$^e$ or cycloalkylene(alkylene)NR$^d$R$^e$ (where $R^d$ and $R^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro; or a pharmaceutical salt thereof;
comprising:
(a) reacting a compound of Formula (A):

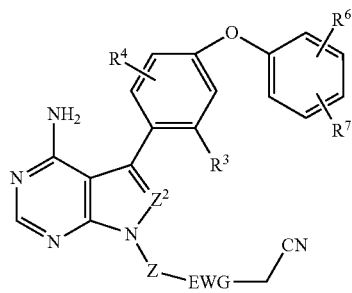

(A)

wherein:
$Z^2$ is —N—;
$R^3$ is fluoro;
$R^4$ is hydrogen;
$R^6$ and $R^7$ are independently hydrogen or fluoro;
—Z-EWG- is:

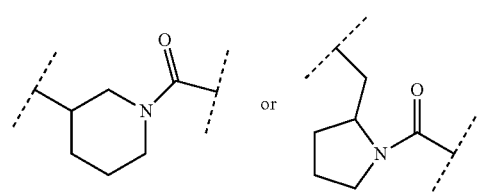

where each ring is optionally substituted with one or two substituents selected from alkyl, fluoro, or hydroxy;

with an aldehyde of formula $R^cCHO$ where $R^c$ is alkyl, substituted alkyl, cycloalkyl, cycloalkyleneNR$^d$R$^e$ or cycloalkylene(alkylene)NR$^d$R$^e$ (where $R^d$ and $R^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro; or (b) reacting a compound of formula (B):

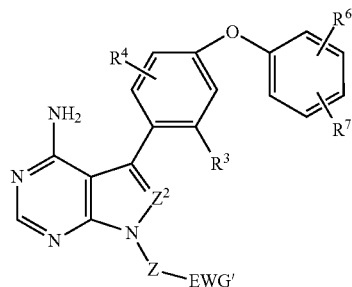

(B)

where $Z^2$, $R^3$, $R^4$, $R^5$, and $R^6$ are as defined above; and

—Z-EWG' is

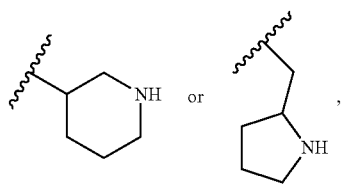 [SMILES: *C1CCCNC1 ; *CC1CCCN1]

each ring optionally substituted with one or two substituents independently selected from alkyl, hydroxy, or halo;

with a compound of formula $R^cCOX$ where X is a leaving group and $R^c$ is as defined above;

(c) optionally making an acid addition salt of a compound obtained from Steps (a) or (b) above;

(d) optionally making a free base of a compound obtained from Steps (a) or (b) above.

In one embodiment, in the process above,

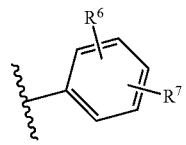

is a ring of formula: phenyl or

In another embodiment, in the process above,

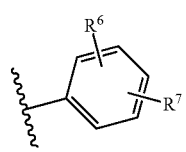

is a ring of formula: phenyl or

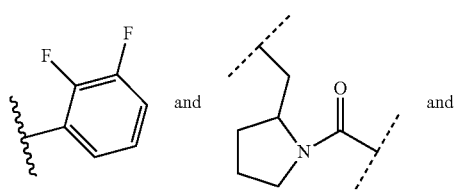

-continued

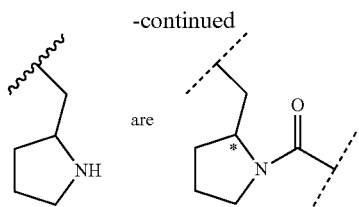

and

respectively, where the stereochemistry at *C is (R) or (S). Preferably, the stereochemistry at *C is (S) when $R^c$ is alkyl, cycloalkyl, alkyl substituted with hydroxy, alkoxy, —NRR' (where each R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro. Preferably, where $R^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl.

Preferably, the stereochemistry at *C is (R) when $R^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom and which is optionally substituted with one or two groups independently selected from alkyl or hydroxyl. Preferably, $R^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

In yet another embodiment, in the process above,

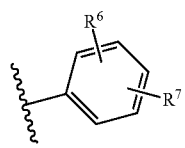

is a ring of formula: phenyl or

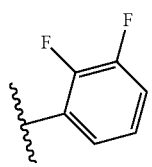 [SMILES: *c1cccc(F)c1F]

and —Z-EWG- is

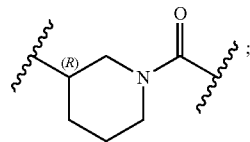

$R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where each R is alkyl, cycloalkyl, hydroxyalkyl, or alkoxyalkyl and R' is hydrogen or alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro. Preferably, $R^c$ is isopropyl, tert-butyl, —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methyl-piperidin-3-yl, or 4-tetrahydropyranyl. Preferably, $R^c$ is isopropyl or —C(CH$_3$)$_2$morpholine-4-yl.

Preferably, the compound of Formula (Id) is:
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;
(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;
(R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile; or
(R)-2-(3-(4-amino-3-(2,3-difluoro-4-phenoxyphenyl)-1H-pyrazolo[3,4-d]pyrimidin-1-yl)piperidine-1-carbonyl)-4-methyl-4-morpholinopent-2-enenitrile;
or a mixture of R and S isomers;
or an individual (E) or (Z) isomer thereof;

Definitions:

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkynyl" means a linear saturated monovalent hydrocarbon radical of two to six carbon atoms or a branched saturated monovalent hydrocarbon radical of three to six carbon atoms that contains a triple bond, e.g., ethynyl, propynyl, 2-propynyl, butynyl (including all isomeric forms), pentynyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —$SO_2R$ radical where R is alkyl as defined above, e.g., methylsulfonyl, ethylsulfonyl, and the like.

"Amino" means a —$NH_2$.

"Alkylamino" means a —NHR radical where R is alkyl as defined above, e.g., methylamino, ethylamino, propylamino, or 2-propylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Aminocarbonyl" means a —CONRR' radical where R is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., —$CONH_2$, methylaminocarbonyl, 2-dimethylaminocarbonyl, and the like. When R is hydrogen and R' is alkyl in —CONRR', the group is also referred to herein as alkylaminocarbonyl and when R and R' are both alkyl in —CONRR', the group is also referred to herein as dialkylaminocarbonyl.

"Aminosulfonyl" means a —$SO_2NRR'$ radical where R is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., —$SO_2NH_2$, methylaminosulfonyl, dimethylaminosulfonyl, and the like. When R is hydrogen and R' is alkyl in —$SO_2NRR'$, the group is also referred to herein as alkylaminosulfonyl and when R and R' are both alkyl in —$SO_2NRR'$, the group is also referred to herein as dialkylaminosulfonyl.

"Acyl" means a —COR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., acetyl, propionyl, benzoyl, pyridinylcarbonyl, and the like. When R is alkyl, the radical is also referred to herein as alkylcarbonyl.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Cycloalkylene" means a cyclic saturated divalent hydrocarbon radical of three to ten carbon atoms wherein one or two carbon atoms may be replaced by an oxo group, e.g., cyclopropylene, cyclobutylene, cyclopentylene, or cyclohexylene, and the like.

"Carboxy" means —COOH.

"Disubstituted amino" means a —NRR' radical where R and R' are independently alkyl, cycloalkyl, cycloalkylalkyl, acyl, aryl, aralkyl, heteroaryl, heteroaralkyl, heterocyclyl, heterocyclylalkyl, or substituted alkyl, each as defined herein, and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., dimethylamino, phenylmethylamino, and the like. When the R and R' groups are alkyl, the disubstituted amino group may be referred to herein as dialkylamino.

The term "electron withdrawing group" refers to a chemical substituent that modifies the electrostatic forces acting on a nearby chemical reaction center by withdrawing negative charge from that chemical reaction center. Thus, electron withdrawing groups draw electrons away from a reaction center. As a result, the reaction center is fractionally more positive than it would be in the absence of the electron-withdrawing group. In some embodiments, the chemical reaction center is one of the two carbons forming the carbon-carbon double bond (olefin). In some embodiments, the chemical reaction center is the olefin carbon attached to EWG. The electron withdrawing group functions to draw charge or electrons away from this olefin carbon thereby making the olefin carbon electron deficient (relative to the absence of the electron withdrawing group). The electron deficient olefin carbon is thereby rendered more reactive toward electron rich chemical groups, such as the sulfhydryl of a kinase active site cysteine.

Some non-limiting examples of EWG include, but are not limited to, —NR'—, —CH(haloalkyl)-, —S(O$_2$), —S(O), —CO—, —NR'CO—, —NR'SO$_2$—, —PO(OR')—,

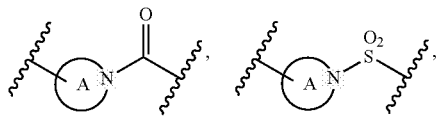

heteroaryl, or aryl; wherein each R' is independently hydrogen, alkyl, substituted alkyl, or cycloalkyl; ring A is heterocycloamino where the carbonyl and sulfonyl groups are attached to —C(CN)=CHR$^c$ in the definition of R$^1$ and R$^5$ in compound of Formula (IA), (I') or (I); and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl, preferably from hydrogen, alkyl, alkoxy, hydroxyl, cyano, nitro, halo, haloalkyl, haloalkoxy, alkylthio, or alkylsulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, or pyridinyl N-oxide optionally substituted as defined in previous paragraph. In —NR'CO— and —NR'SO$_2$ groups, the CO and the SO$_2$ groups are attached to —C(CN)=CHR$^c$.

Preferably, EWG is —NR'CO—, —NR'SO$_2$—,

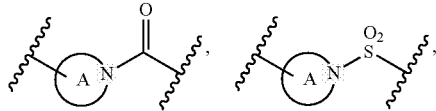

heteroaryl, or aryl; wherein each R' is independently hydrogen, alkyl, substituted alkyl, cycloalkyl; ring A is heterocycloamino where the carbonyl and sulfonyl groups are attached to —C(CN)=CHR$^c$ in the definition of R$^1$ and R$^5$ in compound of Formula (IA), (I') or (I); and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl, preferably from hydrogen, alkyl, alkoxy, hydroxyl, cyano, nitro, halo, haloalkyl, haloalkoxy, alkylthio, alkylsulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, or pyridinyl N-oxide optionally substituted as defined in previous paragraph.

In the compounds of Formula (IA), (I') or (I), when R$^1$ or R$^5$ is —Z-(EWG)—C(CN)=CHR$^c$ and the ring to which R$^1$ or R$^5$ is attached is an electron deficient π system, both Z and EWG can be a bond and the carbon atom substituted with the cyano group in —C(CN)=CHR$^c$ can directly attach to such electron deficient ring. A ring has electron deficient π system when it is substituted with an electron withdrawing group or the ring itself is electron deficient e.g., heteroaryl rings containing electronegative ring atoms such as nitrogen, oxygen or sulfur.

In some embodiments, a composition of the present disclosure comprises a compound corresponding to Formula (IA), (I') or (I) (or a pharmaceutically acceptable salt thereof) in which R$^1$ or R$^5$ is —Z-(EWG)-C(CN)=CHR$^c$ and the ring to which R$^1$ or R$^5$ is attached is an electron deficient π system. In such embodiments, Z and EWG may each be bonds and the carbon atom substituted with the cyano group in —C(CN)=CHR$^c$ can directly attach to such electron deficient ring. In general, a ring has electron deficient π system when it is substituted with an electron withdrawing group or the ring itself is electron deficient, e.g., heteroaryl rings containing electronegative ring atoms such as nitrogen, oxygen or sulfur.

For example, the ring

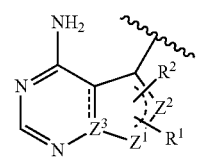

is an electron deficient π system when it is unsubstituted or substituted with halo, cyano or haloalkyl and Ar can be an electron deficient π system when Ar is heteroaryl e.g.,

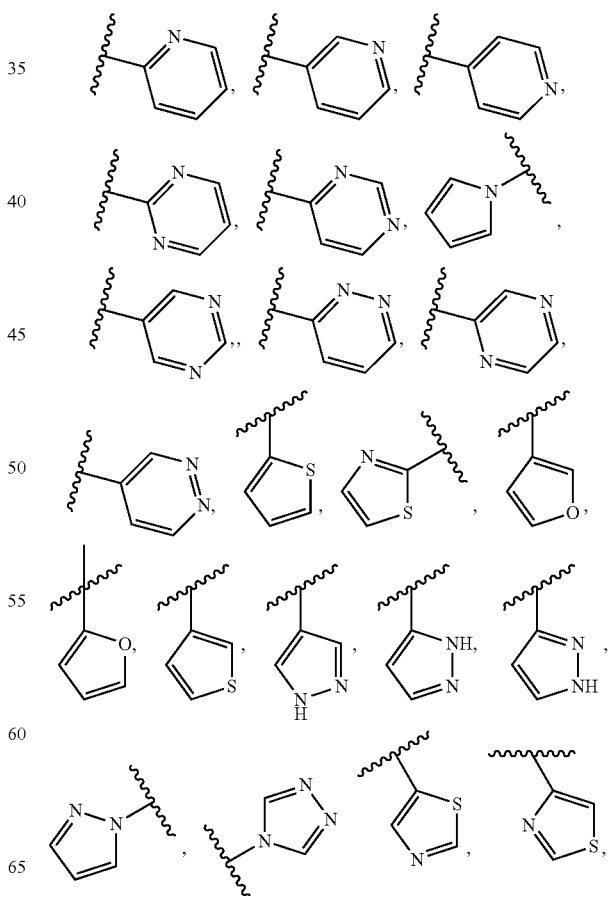

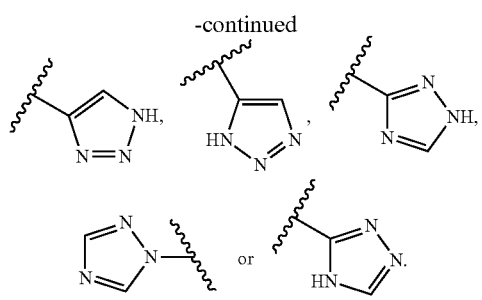

substituted with $R^5$ or $R^6$ or phenyl substituted with $R^5$ or $R^6$ where at least one of $R^5$ or $R^6$ is an electron withdrawing group i.e., halo, haloalkyl, carboxy, alkoxycarbonyl, cyano, or —$CONH_2$.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the alkyl is substituted with only fluoro, it is referred to in this Application as fluoroalkyl.

"Haloalkoxy" means a —OR radical where R is haloalkyl as defined above e.g., —$OCF_3$, —$OCHF_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocyclylalkyl" means a -(alkylene)-R radical where R is heterocyclyl ring as defined above e.g., tetraydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C provided that at least one of the ring atoms is N. Additionally, one or two ring carbon atoms in the heterocycloamino ring can optionally be replaced by a —CO— group. When the heterocycloamino ring is unsaturated it can contain one or two ring double bonds provided that the ring is not aromatic. The heterocyloamino ring can optionally be substituted with one, two, or three substituents independently selected from alkyl, hydroxyl, alkoxy, cyano, nitro, halo, haloalkyl, haloalkoxy, alkylthio, alkylsulfonyl, carboxy, alkoxycarbonyl, aminocarbonyl or aminosulfonyl, amino, alkylamino, or dialkylamino unless otherwise stated herein.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroaralkyl" means a -(alkylene)-R radical where R is heteroaryl as defined above.

"Heteroalkylene" means an -(alkylene)-radical where one, two or three carbons in the alkylene chain is replaced by —O—, N(H, alkyl, or substituted alkyl), S, SO, $SO_2$, or CO.

"Monosubstituted amino" means a —NHR radical where R is alkyl, cycloalkyl, cycloalkylalkyl, acyl, aryl, aralkyl, heteroaryl, heteroaralkyl, heterocyclyl, heterocyclylalkyl, or substituted alkyl, each as defined herein, and wherein the aryl, heteroaryl, or heterocyclyl ring either alone or part of another group e.g., aralkyl, is optionally substituted with one, two, or three substituents independently selected from alkyl, alkoxy, halo, haloalkoxy, hydroxyl, carboxy, or alkoxycarbonyl, e.g., methylamino, phenylamino, hydroxyethylamino, and the like. When R is alkyl, the monosubstituted amino group may be referred to herein as alkylamino.

The present disclosure also includes the prodrugs of compounds of Formula (IA), (I') or (I) (or any of the embodiments thereof described herein). The term prodrug is intended to represent covalently bonded carriers, which are capable of releasing the active ingredient of Formula (IA), (I') or (I) (or any of the embodiments thereof described herein), when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (IA), (I') or (I) (or any of the embodiments thereof described herein), include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (IA), (I') or (I)), amides (e.g., trifluoroacetylamino, acetylamino, and the like), and the like. Prodrugs of compounds of Formula (IA), (I') or (I) (or any of the embodiments thereof described herein), are also within the scope of this disclosure.

The present disclosure also includes protected derivatives of compounds of Formula (IA), (I') or (I) (or any of the embodiments thereof described herein). For example, when compounds of Formula (IA), (I') or (I) (or any of the embodiments thereof described herein), contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (IA), (I') or (I) (or any of the embodiments thereof described herein), can be prepared by methods well known in the art.

The present disclosure also includes polymorphic forms (amorphous as well as crystalline) and deuterated forms of compounds of Formula (IA), (I') or (I) (or any of the embodiments thereof described herein).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry or isomeric form is specifically indicated.

Certain compounds of Formula (IA), (I') or (I) (or any of the embodiments thereof described herein), can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (IA), (I') or (I) (or any of the embodiments thereof described herein), are within the scope of this disclosure.

"Oxo" or "carbonyl" means C=(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Substituted alkyl" means alkyl group as defined herein which is substituted with one, two, or three substituents independently selected from hydroxyl, alkoxy, carboxy, cyano, carboxy, alkoxycarbonyl, alkylthio, alkylsulfonyl, halo, —CONRR' or —NRR' (where each R is hydrogen, alkyl, cycloalkyl, hydroxyalkyl, or alkoxyalkyl, and each R' is hydrogen, alkyl, or cycloalkyl) or heterocyclyl (preferably heterocycloamino) which is optionally substituted with one or two groups independently selected from alkyl, hydroxyl, alkoxy, alkylthio, alkylsulfonyl, halo, or —CONRR' where R and R' are as defined above.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (IA), (I') or (I) (or any of the embodiments thereof described herein), that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of the Disclosure are shown in Tables 1 and 2 below:

TABLE 1

| Cpd # | Stereo-chem | $Z^3$ | $R^2$ | R⁴/R³ phenyl group | R⁶/R⁷ phenyl group | —Z—EWG— | $R^C$ | Mass Spec $M^+ + 1$ |
|---|---|---|---|---|---|---|---|---|
| 1 | | N | — | phenyl | phenyl | 3-piperidinyl-N-C(O)- | cyclopropyl | 506 |
| 2 | | N | — | phenyl | phenyl | 2-(pyrrolidinyl-N-acetyl)methyl | cyclopropyl | 506 |
| 3 | | N | — | phenyl | phenyl | 4-piperidinyl-N-C(O)- | cyclopropyl | 506 |
| 4 | | N | — | 3-methoxyphenyl | 3,4-diClphenyl | 3-piperidinyl-N-C(O)- | cyclopropyl | 604 |

TABLE 1-continued

| Cpd # | Stereo-chem | $Z^3$ | $R^2$ | R4/R3 aryl | R6/R7 aryl | —Z—EWG— | $R^C$ | Mass Spec $M^+ + 1$ |
|---|---|---|---|---|---|---|---|---|
| 5 | | N | — | 3-methoxyphenyl | 3,4-diClphenyl | 2-(CH2-)pyrrolidine-N-C(O)- | cyclopropyl | 604 |
| 6 | | N | — | 3-methoxyphenyl | 3,4-diClphenyl | 4-piperidinyl-N-C(O)- | cyclopropyl | 604 |
| 7 | | N | — | phenyl | phenyl | 3-piperidinyl-N-C(O)- | tert-butyl | 522 |
| 8 | | N | — | phenyl | phenyl | 4-piperidinyl-N-C(O)- | tert-butyl | 522 |
| 9 | | N | — | 3-methoxyphenyl | 3,4-diClphenyl | 4-piperidinyl-N-C(O)- | tert-butyl | 620 |

TABLE 1-continued
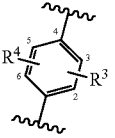
| Cpd # | Stereo-chem | $Z^3$ | $R^2$ | 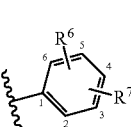 | 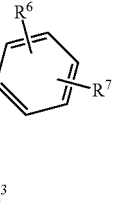 | —Z—EWG— | $R^C$ | Mass Spec $M^+ + 1$ |
|---|---|---|---|---|---|---|---|---|
| 10 | | N | — | phenyl | phenyl | 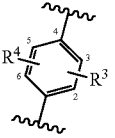 | tert-butyl | 522 |
| 11 | 1s,4s | N | — | phenyl | phenyl | 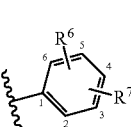 | cyclopropyl | 520 |
| 12 | | N | — | 3-methoxyphenyl | 3,4-diClphenyl | 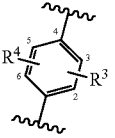 | tert-butyl | 620 |
| 13 | 1r,4r | N | — | 3-methoxyphenyl | 3,4-diClphenyl | 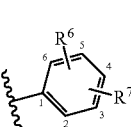 | cyclopropyl | 618 |
| 14 | 1s,4s | N | — | phenyl | phenyl | 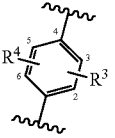 | tert-butyl | 536 |

TABLE 1-continued
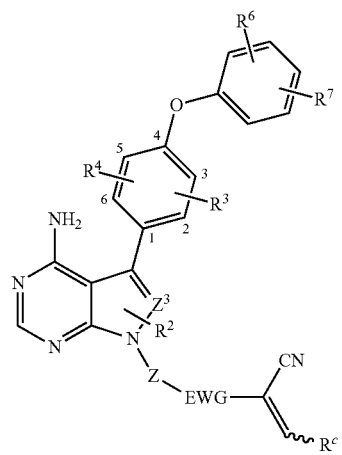
| Cpd # | Stereo-chem | $Z^3$ | $R^2$ | <br>R⁴⟨⟩R³ | <br>R⁶⟨⟩R⁷ | —Z—EWG— | $R^C$ | Mass Spec $M^+ + 1$ |
|---|---|---|---|---|---|---|---|---|
| 15A | R | N | — | phenyl | 3-Fphenyl | piperidine-C(O)— | cyclopropyl | 524 |
| 15B | S | | | | | | | — |
| 16 | 1r,4r | N | — | 3-methoxyphenyl | 3,4-diClphenyl | cyclohexyl-NHC(O)— | tert-butyl | 634 |
| 17A | R | N | — | phenyl | 3,5-diFphenyl | piperidine-C(O)— | cyclopropyl | 542 |
| 17B | S | | | | | | | — |
| 18A | R | N | — | 2-Fphenyl | phenyl | piperidine-C(O)— | cyclopropyl | 524 |
| 18B | S | | | | | | | — |
| 19 | | N | — | 3-methoxyphenyl | 3,4-diClphenyl | piperidine-C(O)— | tert-butyl | 622 |

TABLE 1-continued
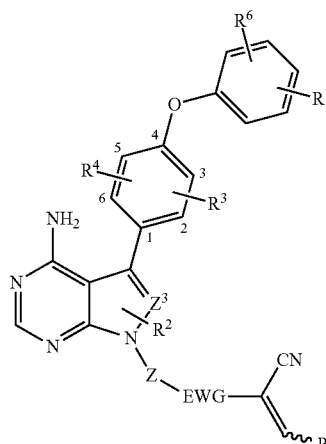
| Cpd # | Stereo-chem | $Z^3$ | $R^2$ | 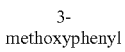 |  | —Z—EWG— | $R^C$ | Mass Spec $M^+ + 1$ |
|---|---|---|---|---|---|---|---|---|
| 20 | 1s,4s | N | — | 3-methoxyphenyl | 3,4-diClphenyl |  | cyclopropyl | 618 |
| 21 | 1s,4s | N | — | 3-methoxyphenyl | 3,4-diClphenyl | 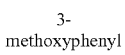 | tert-butyl | 635 |
| 22A | R | N | — | phenyl | phenyl |  | cyclopropyl | 506 |
| 22B | S | | | | | | | 506 |
| 23A | R | N | — | phenyl | phenyl |  | tert-butyl | 522 |
| 23B | S | | | | | | | — |
| 24A | R | N | — | phenyl | 3-Fphenyl |  | cyclopropyl | 524.2 |
| 24B | S | | | | | | | — |

TABLE 1-continued
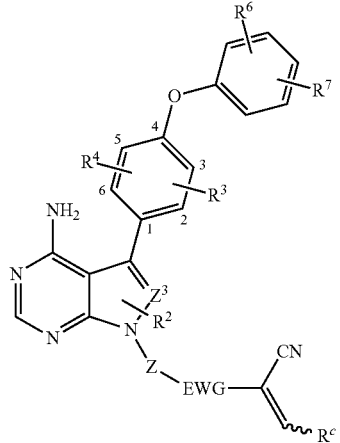
| Cpd # | Stereo-chem | $Z^3$ | $R^2$ | 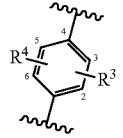 | 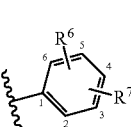 | —Z—EWG— | $R^C$ | Mass Spec $M^+ + 1$ |
|---|---|---|---|---|---|---|---|---|
| 25A | R | N | — | phenyl | 3,4-diFphenyl | 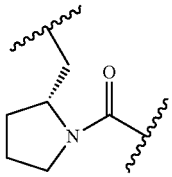 [SMILES: *C[C@H]1CCCN1C(*)=O] | cyclopropyl | 542.2 |
| 25B | S | | | | | | | — |
| 27A | R | N | — | 2-Fphenyl | phenyl | 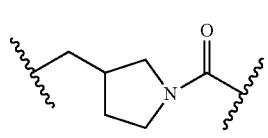 [SMILES: *CC1CCN(C(*)=O)C1] | cyclopropyl | 524.2 |
| 27B | S | | | | | | | 524 |
| 28 | | N | — | phenyl | phenyl | 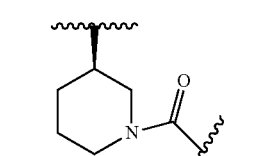 | tert-butyl | 522 |
| 29A | R | N | — | phenyl | phenyl | 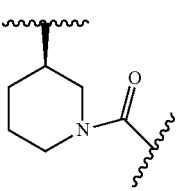 [SMILES: *C(=O)N1CCC[C@@H](*)C1] | tert-butyl | 522 |
| 29B | S | | | | | | | — |
| 30A | R | N | — | phenyl | phenyl | 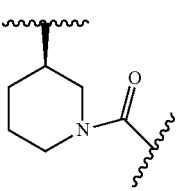 [SMILES: *C(=O)N1CCC[C@@H](*)C1] | cyclopropyl | 506 |
| 30B | S | | | | | | | — |

TABLE 1-continued
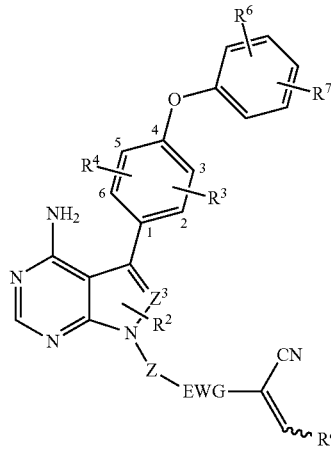
| Cpd # | Stereo-chem | $Z^3$ | $R^2$ | 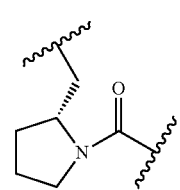 [SMILES: *C[C@H]1CCCN1C(*)=O] | 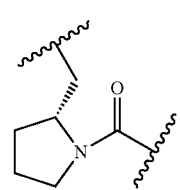 [SMILES: *C[C@H]1CCCN1C(*)=O] | —Z—EWG— | $R^C$ | Mass Spec $M^+ + 1$ |
|---|---|---|---|---|---|---|---|---|
| 31A | R | N | — | phenyl | 2,3-diFphenyl | 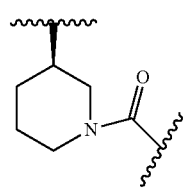 [SMILES: *C(=O)N1CCC[C@@H](*)C1] | cyclopropyl | 542.40 |
| 31B | S | | | | | | | 542.15 |
| 32A | R | N | — | phenyl | 2,6-diFphenyl | 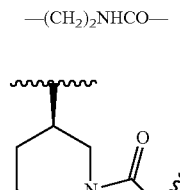 | cyclopropyl | 542 |
| 32B | S | | | | | | | 542.30 |
| 33A | R | N | — | phenyl | 2-Fphenyl | 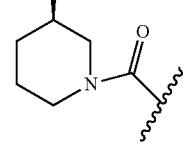 | cyclopropyl | 524.2 |
| 33B | S | | | | | | | — |
| 34 | | N | — | phenyl | phenyl | —(CH$_2$)$_2$NHCO— | cyclopropyl | 466 |
| 35A | R | N | — | phenyl | 2,3-diFphenyl | 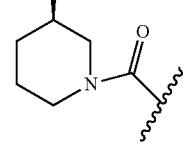 | cyclopropyl | 542 |
| 35B | S | | | | | | | — |

TABLE 1-continued

| Cpd # | Stereo-chem | $Z^3$ | $R^2$ | [R3/R4 aryl] | [R6/R7 aryl] | —Z—EWG— | $R^C$ | Mass Spec $M^+ + 1$ |
|---|---|---|---|---|---|---|---|---|
| 36A | R | N | — | phenyl | 2,6-diFphenyl | 3-piperidinyl-N-C(O)- | cyclopropyl | 542 |
| 36B | S | | | | | | | — |
| 37A | R | N | — | phenyl | 2,5-diFphenyl | 3-piperidinyl-N-C(O)- | cyclopropyl | 542 |
| 37B | S | | | | | | | — |
| 38A | R | N | — | phenyl | 2-Fphenyl | 2-pyrrolidinylmethyl-N-C(O)- | cyclopropyl | 524 |
| 38B | S | | | | | | | — |
| 39A | R | N | — | phenyl | 2,5-diFphenyl | 2-pyrrolidinylmethyl-N-C(O)- | cyclopropyl | 542 |
| 39B | S | | | | | | | 542.30 |
| 40A | R | N | — | 2-Fphenyl | 3-Fphenyl | 2-pyrrolidinylmethyl-N-C(O)- | cyclopropyl | 542.30 |
| 40B | S | | | | | | | 542 |

TABLE 1-continued

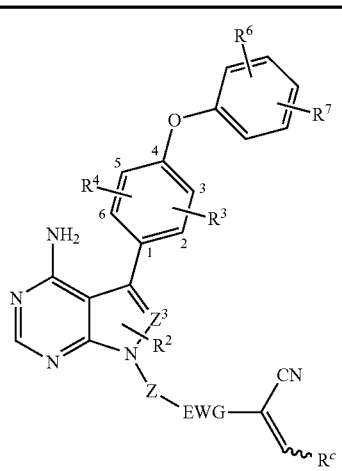

| Cpd # | Stereo-chem | $Z^3$ | $R^2$ | 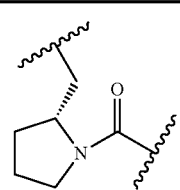 | 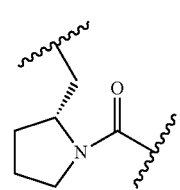 | —Z—EWG— | $R^C$ | Mass Spec $M^+ + 1$ |
|---|---|---|---|---|---|---|---|---|
| 41A | R | N | — | 2-Fphenyl | 3,5-diFphenyl | 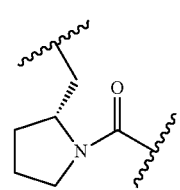 [SMILES: *C[C@H]1CCCN1C(*)=O] | cyclopropyl | 560 |
| 41B | S | | | | | | | — |
| 42A | R | N | — | 3-Fphenyl | phenyl | | cyclopropyl | 524.45 |
| 42B | S | | | | | | | — |
| 43A | R | N | — | 2-Fphenyl | 2,3-diFphenyl | | cyclopropyl | 560.40 |
| 43B | S | | | | | | | 560 |
| 44A | R | N | — | 2-Fphenyl | 2,6-diFphenyl | | cyclopropyl | 560.40 |
| 44B | S | | | | | | | 560.30 |
| 45 | | N | — | 2-Fphenyl | phenyl | —$(CH_2)_2$NHCO— | cyclopropyl | |
| 46 | | N | — | 2-Fphenyl | phenyl | —$C(CH_3)_2CH_2$NHCO— | cyclopropyl | |
| 47 | | N | — | 2-Fphenyl | phenyl | —$CH_2C(CH_3)_2$NHCO— | cyclopropyl | |
| 48 | | N | — | 2-Fphenyl | phenyl | —$(CH_2)_2NHSO_2$— | cyclopropyl | |
| 49 | | N | — | 2-Fphenyl | phenyl | —$(CH_2)_2N(CH_3)SO_2$— | cyclopropyl | |

TABLE 1-continued

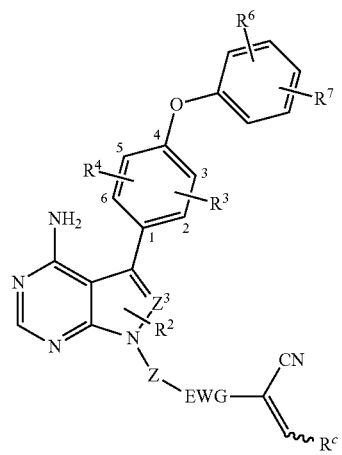

| Cpd # | Stereo-chem | $Z^3$ | $R^2$ | R⁴⁵⁶R³ (2-position) | R⁶⁵R⁷ phenyl | —Z—EWG— | $R^C$ | Mass Spec $M^+ + 1$ |
|---|---|---|---|---|---|---|---|---|
| 50 | | N | — | 2-Fphenyl | phenyl | —(CH₂)₂OCO— | cyclopropyl | |
| 51 | | N | — | 2-Fphenyl | phenyl | —CH₂C(CH₃)₂OCO— | cyclopropyl | |
| 52 | | N | — | 2-Fphenyl | phenyl | —CH₂CH₂SO₂— | cyclopropyl | |
| 53 | | N | — | 2-Fphenyl | phenyl | 5-CH₂oxazol-2-yl | cyclopropyl | |
| 54A | R | CH | — | phenyl | phenyl | (3-piperidinyl-N-acyl) | cyclopropyl | 505 |
| 54B | S | | | | | | | — |
| 55A | R | CH | — | phenyl | 3,5-diFphenyl | (3-piperidinyl-N-acyl) | cyclopropyl | 541 |
| 55B | S | | | | | | | — |
| 56A | R | CH | — | 2-Fphenyl | phenyl | (3-piperidinyl-N-acyl) | cyclopropyl | 523 |
| 56B | S | | | | | | | — |
| 57A | R | CH | — | phenyl | phenyl | (2-pyrrolidinylmethyl-N-acyl) | cyclopropyl | — |
| 57B | S | | | | | | | 505 |

TABLE 1-continued
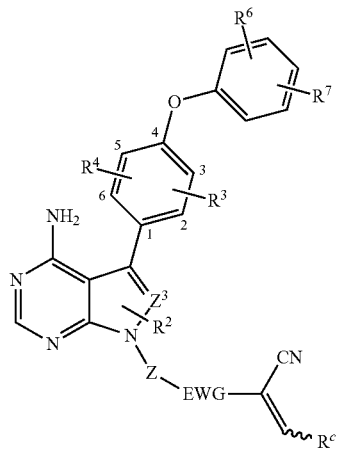
| Cpd # | Stereo-chem | $Z^3$ | $R^2$ | [Ar1] | [Ar2] | —Z—EWG— | $R^C$ | Mass Spec $M^+ + 1$ |
|---|---|---|---|---|---|---|---|---|
| 58A | R | CH | — | phenyl | 3,5-diFphenyl | pyrrolidine-CH2-C(O)- | cyclopropyl | — |
| 58B | S | | | | | | | 541 |
| 59A | R | CH | — | 2-Fphenyl | phenyl | pyrrolidine-CH2-C(O)- | cyclopropyl | — |
| 59B | S | | | | | | | 523 |
| 60A | R | C | $CH_3$ | phenyl | phenyl | piperidine-C(O)- | cyclopropyl | |
| 60B | S | | | | | | | |
| 61A | R | C | $CH_3$ | phenyl | 3,5-diFphenyl | piperidine-C(O)- | cyclopropyl | |
| 61B | S | | | | | | | |
| 62A | R | C | $CH_3$ | 2-Fphenyl | phenyl | piperidine-C(O)- | cyclopropyl | |
| 62B | S | | | | | | | |

TABLE 1-continued

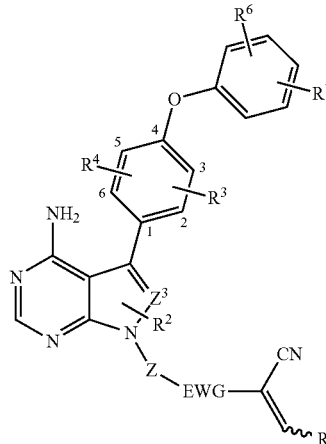

| Cpd # | Stereo-chem | $Z^3$ | $R^2$ | 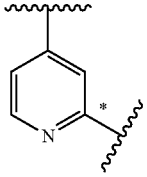 | | —Z—EWG— | $R^C$ | Mass Spec $M^+ + 1$ |
|---|---|---|---|---|---|---|---|---|
| 63A | R | C | $CH_3$ | phenyl | phenyl | (pyrrolidine-CO) | cyclopropyl | — |
| 63B | S | | | | | | | 519 |
| 64A | R | C | $CH_3$ | phenyl | 3,5-diFphenyl | (pyrrolidine-CO) | cyclopropyl | — |
| 64B | S | | | | | | | 555 |
| 65A | R or S | C | $CH_3$ | 2-Fphenyl | phenyl | (pyrrolidine-CO) | cyclopropyl | — |
| 65B | | | | | | | | 536 |
| 66 | RS | N | — | phenyl | phenyl | (3-pyrrolidine-CO) | cyclopropyl | 506 |
| 67 | — | N | — | phenyl | phenyl | —$CH_2C(CH_3)_2$—$CH_2NHCO$— | cyclopropyl | 508 |
| 68 | | N | — | phenyl | phenyl | (pyridyl) | cyclopropyl | 472 |

* attached to —C(CN)=$R^c$

TABLE 1-continued
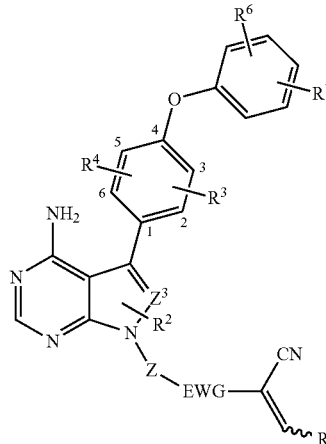
| Cpd # | Stereo-chem | $Z^3$ | $R^2$ | 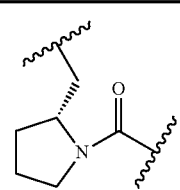 | 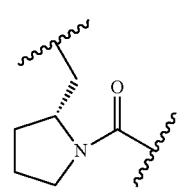 [SMILES: *C[C@H]1CCCN1C(*)=O] | —Z—EWG— | $R^C$ | Mass Spec $M^+ + 1$ |
|---|---|---|---|---|---|---|---|---|
| 69A | R | N | — | 2-methylphenyl | phenyl | 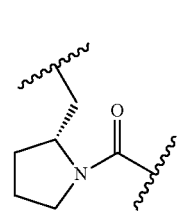 [SMILES: *C[C@H]1CCCN1C(*)=O] | cyclopropyl | 520 |
| 69B | S | | | | | | | |
| 70A | R | N | — | 2-chlorophenyl | phenyl | 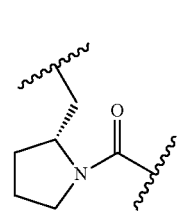 [SMILES: *C[C@H]1CCCN1C(*)=O] | cyclopropyl | 541 |
| 70B | S | | | | | | | — |
| 71A | R | N | — | phenyl | 2,5-diFphenyl | 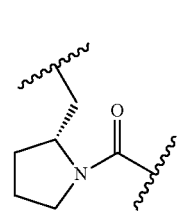 [SMILES: *C[C@H]1CCCN1C(*)=O] | —CH(CH$_3$)$_2$ | — |
| 71B | S | | | | | | | 544.20 |
| 72A | R | N | — | 2-Fphenyl | 3-Fphenyl | 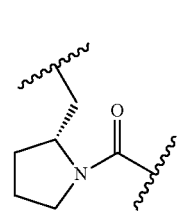 [SMILES: *C[C@H]1CCCN1C(*)=O] | —C(CH$_3$)$_2$NH$_2$ | 559 |
| 72B | S | | | | | | | 558.90 |
| 73A | R | N | — | 2-Fphenyl | 3-Fphenyl | 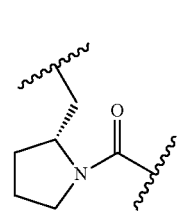 [SMILES: *C[C@H]1CCCN1C(*)=O] | —CH(CH$_3$)$_2$ | — |
| 73B | S | | | | | | | 544 |

TABLE 1-continued

| Cpd # | Stereo-chem | Z³ | R² | [Ar1] | [Ar2] | —Z—EWG— | R^C | Mass Spec M⁺ + 1 |
|---|---|---|---|---|---|---|---|---|
| 74A | R | N | — | 2-Fphenyl | phenyl | pyrrolidine-carbonyl | tert-butyl | 540 |
| 74B | S | | | | | | | — |
| 75A | R | N | — | phenyl | 2,6-diFphenyl | pyrrolidine-carbonyl | —CH(CH₃)₂ | — |
| 75B | S | | | | | | | 544.45 |
| 76A | R | N | — | phenyl | 2,3-diFphenyl | pyrrolidine-carbonyl | —CH(CH₃)₂ | — |
| 76B | S | | | | | | | 544.05 |
| 77A | R | C | CH₃ | phenyl | phenyl | pyrrolidine-carbonyl | —C(CH₃)₂N(CH₃)₂ | — |
| 77B | S | | | | | | | 564 |
| 78A | R | N | — | 2-Fphenyl | 2,6-diFphenyl | pyrrolidine-carbonyl | —CH(CH₃)₂ | — |
| 78B | S | | | | | | | 562.25 |

TABLE 1-continued
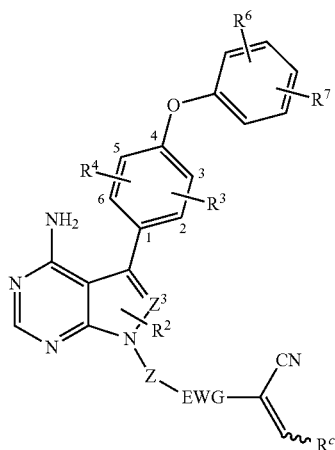
| Cpd # | Stereo-chem | $Z^3$ | $R^2$ | R4,R3 aryl | R6,R7 aryl | —Z—EWG— | $R^C$ | Mass Spec $M^+ + 1$ |
|---|---|---|---|---|---|---|---|---|
| 79A | R | N | — | 2-Fphenyl | phenyl | (4,4-difluoropyrrolidine) | cyclopropyl | — |
| 79B | S | | | | | | | 560.10 |
| 80A | R | N | — | 2-Fphenyl | phenyl | (4,4-difluoropyrrolidine) | —CH(CH$_3$)$_2$ | — |
| 80B | S | | | | | | | 562.1 |
| 81A | R | N | — | 2-Fphenyl | phenyl | (pyrrolidine) | —CH(CH$_3$)$_2$ | 526.35 |
| 81B | S | | | | | | | 526.35 |
| 82A | R | N | — | 2-Fphenyl | phenyl | (pyrrolidine) | —C(CH$_3$)$_2$NH$_2$ | 541 |
| 82B | S | | | | | | | 541 |
| 83A | R | N | — | 2-Fphenyl | phenyl | (pyrrolidine) | —C(CH$_3$)$_2$NHCH$_3$ | 555 |
| 83B | S | | | | | | | 555.05 |

TABLE 1-continued

| Cpd # | Stereo-chem | $Z^3$ | $R^2$ | R⁴⁻⁶⁻R³ (2,3) | R⁶⁻⁵⁻R⁷ (1,2,3) | —Z—EWG— | $R^C$ | Mass Spec M⁺ + 1 |
|---|---|---|---|---|---|---|---|---|
| 84A | R | N | — | 2-Fphenyl | phenyl | pyrrolidinyl-C(O)- | —C(CH₃)₂N(CH₃)₂ | 569 |
| 84B | S | | | | | | | 569 |
| 85A | R | N | — | 2-Fphenyl | phenyl | pyrrolidinyl-C(O)- | —C(CH₃)₂—NHCH₂CH₃ | 569 |
| 85B | S | | | | | | | 569 |
| 86A | R | N | — | 2-Fphenyl | phenyl | pyrrolidinyl-C(O)- | —C(CH₃)₂NH—CH(CH₃)₂ | — |
| 86B | S | | | | | | | 583 |
| 87A | R | N | — | 2-Fphenyl | phenyl | pyrrolidinyl-C(O)- | —C(CH₃)₂NH-cyclopropyl | — |
| 87B | S | | | | | | | 581 |
| 88A | R | N | — | 2-Fphenyl | phenyl | pyrrolidinyl-C(O)- | —C(CH₃)₂—NH(CH₂)₂OCH₃ | — |
| 88B | S | | | | | | | 599 |

TABLE 1-continued
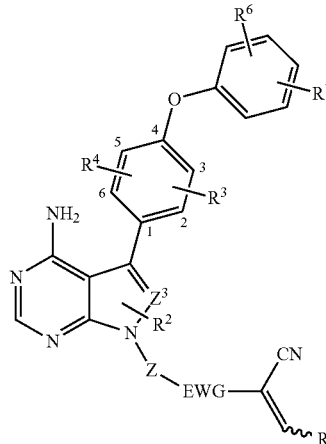
| Cpd # | Stereo-chem | $Z^3$ | $R^2$ | 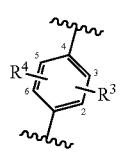 | 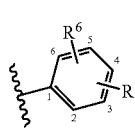 | —Z—EWG— | $R^C$ | Mass Spec $M^+ + 1$ |
|---|---|---|---|---|---|---|---|---|
| 89A | R | N | — | 2-Fphenyl | phenyl | 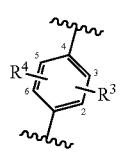 | —C(CH$_3$)$_2$—OCH$_2$CH$_3$ | 570 |
| 89B | S | | | | | | | 570 |
| 90A | R | N | — | 2-Fphenyl | phenyl | 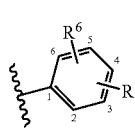 | 1-amino-cycloprop-1-yl | 539 |
| 90B | S | | | | | | | |
| 91A | R | N | — | 2-Fphenyl | phenyl | 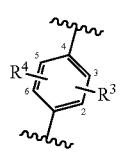 | 1-methylamino-cycloprop-1-yl | |
| 91B | S | | | | | | | |
| 92A | R | N | — | 2-Fphenyl | phenyl | 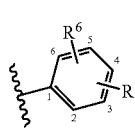 | 1-ethylamino-cycloprop-1-yl | |
| 92B | S | | | | | | | |
| 93A | R | N | — | 2-Fphenyl | phenyl | 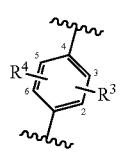 | 1-isopropyl-aminocycloprop-1-yl | |
| 93B | S | | | | | | | |

TABLE 1-continued
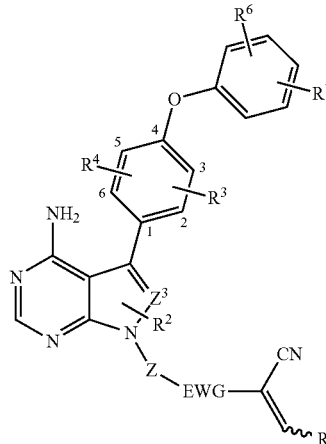
| Cpd # | Stereo-chem | $Z^3$ | $R^2$ | 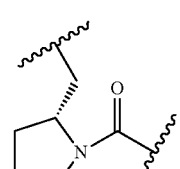 |  | —Z—EWG— | $R^C$ | Mass Spec $M^+ + 1$ |
|---|---|---|---|---|---|---|---|---|
| 94A | R | N | — | 2-Fphenyl | phenyl | 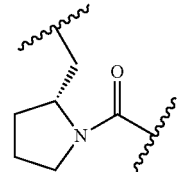 [SMILES: *C[C@H]1CCCN1C(*)=O] | pyrrolidin-2-yl | |
| 94B | S | | | | | | | |
| 95A | R | N | — | 2-Fphenyl | phenyl | 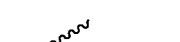 | —C(CH$_3$)$_2$-morpholin-4-yl | 611 |
| 95B | S | | | | | | | 611 |
| 96A | R | N | — | 2-Fphenyl | phenyl | 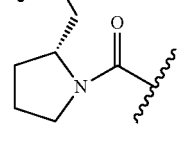 | 1-diethylamino-methylcyclopent-1-yl | |
| 96B | S | | | | | | | |
| 97A | R | N | — | 2-Fphenyl | phenyl | 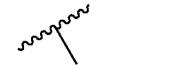 | 1-dimethylamino-methylcyclopent-1-yl | |
| 97B | S | | | | | | | |
| 98A | R | N | — | 2-Fphenyl | phenyl | 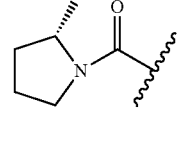 | 1-methyl-piperidin-4-yl | |
| 98B | S | | | | | | | |

TABLE 1-continued
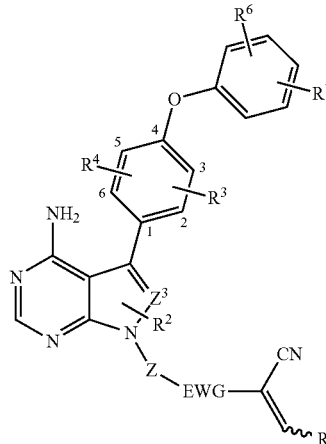
| Cpd # | Stereo-chem | $Z^3$ | $R^2$ | 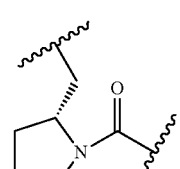 | 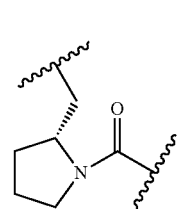 [SMILES: *C[C@H]1CCCN1C(*)=O] | —Z—EWG— | $R^C$ | Mass Spec $M^+ + 1$ |
|---|---|---|---|---|---|---|---|---|
| 99A | R | N | — | 2-Fphenyl | phenyl | 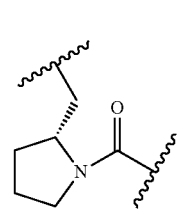 [SMILES: *C[C@H]1CCCN1C(*)=O] | tetrahydro-pyran-4-yl | |
| 99B | S | | | | | | | |
| 100A | R | N | — | 2-Fphenyl | phenyl | 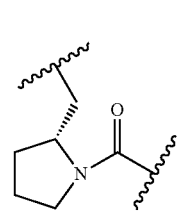 [SMILES: *C[C@H]1CCCN1C(*)=O] | piperidin-4-yl | |
| 100B | S | | | | | | | |
| 101A | R | N | — | 2-Fphenyl | phenyl | 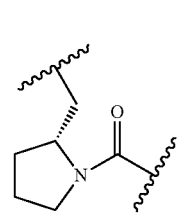 [SMILES: *C[C@H]1CCCN1C(*)=O] | piperidin-3-yl | |
| 101B | S | | | | | | | |
| 102A | R | N | — | 2-Fphenyl | 2,3-diFphenyl |  | —CH(CH$_3$)$_2$ | 562 |
| 102B | S | | | | | | | 562 |
| 103A | R | N | — | 2-Fphenyl | 2,3-diFphenyl | 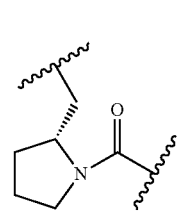 [SMILES: *C[C@H]1CCCN1C(*)=O] | —C(CH$_3$)$_3$ | — |
| 103B | S | | | | | | | 576 |

TABLE 1-continued

| Cpd # | Stereo-chem | Z³ | R² | R⁴⟨⟩R³ | R⁶⟨⟩R⁷ | —Z—EWG— | R^C | Mass Spec M⁺ + 1 |
|---|---|---|---|---|---|---|---|---|
| 104A | R | N | — | 2-Fphenyl | 2,3-diFphenyl | pyrrolidine-C(=O)- | —C(CH₃)₂NH₂ | 577 |
| 104B | S | | | | | | | 577 |
| 105A | R | N | — | 2-Fphenyl | 2,3-diFphenyl | pyrrolidine-C(=O)- | —C(CH₃)₂NHCH₃ | 591 |
| 105B | S | | | | | | | 591 |
| 106A | R | N | — | 2-Fphenyl | 2,3-diFphenyl | pyrrolidine-C(=O)- | —C(CH₃)₂N(CH₃)₂ | 605 |
| 106B | S | | | | | | | 605 |
| 107A | R | N | — | 2-Fphenyl | 2,3-diFphenyl | pyrrolidine-C(=O)- | —C(CH₃)₂—NHCH₂CH₃ | 605 |
| 107B | S | | | | | | | — |
| 108A | R | N | — | 2-Fphenyl | 2,3-diFphenyl | pyrrolidine-C(=O)- | —C(CH₃)₂NH—CH(CH₃)₂ | — |
| 108B | S | | | | | | | 583 |

TABLE 1-continued
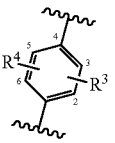
| Cpd # | Stereo-chem | $Z^3$ | $R^2$ |  | 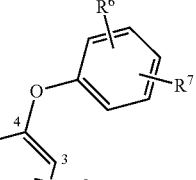 | —Z—EWG— | $R^C$ | Mass Spec $M^+ + 1$ |
|---|---|---|---|---|---|---|---|---|
| 109A | R | N | — | 2-Fphenyl | 2,3-diFphenyl | 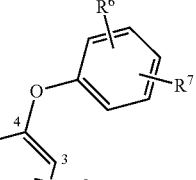 | —C(CH$_3$)$_1$NH-cyclopropyl | |
| 109B | S | | | | | | | |
| 110A | R | N | — | 2-Fphenyl | 2,3-diFphenyl | 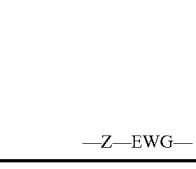 | —C(CH$_3$)$_2$—NH(CH$_2$)$_2$OCH$_3$ | |
| 110B | S | | | | | | | |
| 111A | R | N | — | 2-Fphenyl | 2,3-diFphenyl | 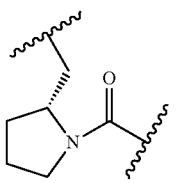 [SMILES: *C[C@H]1CCCN1C(*)=O] | —C(CH$_3$)$_2$—OCH$_2$CH$_3$ | 606 |
| 111B | S | | | | | | | 606 |
| 112A | R | N | — | 2-Fphenyl | 2,3-diFphenyl | 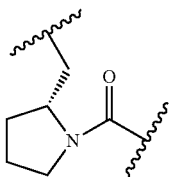 [SMILES: *C[C@H]1CCCN1C(*)=O] | 1-amino-cycloprop-1-yl | |
| 112B | S | | | | | | | |
| 113A | R | N | — | 2-Fphenyl | 2,3-diFphenyl | 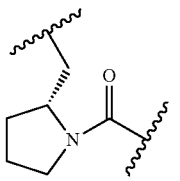 [SMILES: *C[C@H]1CCCN1C(*)=O] | 1-methylamino-cycloprop-1-yl | |
| 113B | S | | | | | | | |

TABLE 1-continued
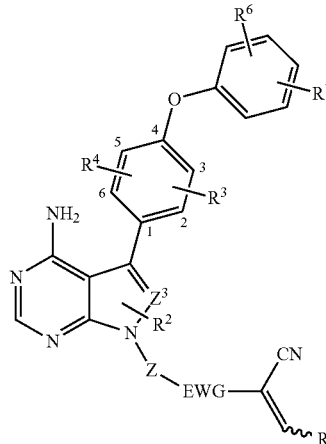
| Cpd # | Stereo-chem | $Z^3$ | $R^2$ | 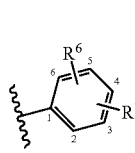 | 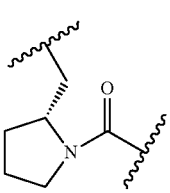 [SMILES: *C[C@H]1CCCN1C(*)=O] | —Z—EWG— | $R^C$ | Mass Spec $M^+ + 1$ |
|---|---|---|---|---|---|---|---|---|
| 114A | R | N | — | 2-Fphenyl | 2,3-diFphenyl | 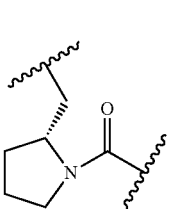 [SMILES: *C[C@H]1CCCN1C(*)=O] | 1-ethylamino-cycloprop-1-yl | |
| 114B | S | | | | | | | |
| 115A | R | N | — | 2-Fphenyl | 2,3-diFphenyl | 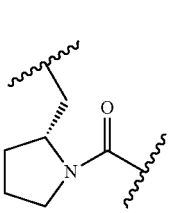 [SMILES: *C[C@H]1CCCN1C(*)=O] | 1-isopropylamino-cycloprop-1-yl | |
| 115B | S | | | | | | | |
| 116A | R | N | — | 2-Fphenyl | 2,3-diFphenyl | 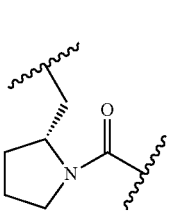 [SMILES: *C[C@H]1CCCN1C(*)=O] | pyrrolidin-2-yl | |
| 115B | S | | | | | | | |
| 117A | R | N | — | 2-Fphenyl | 2,3-diFphenyl | 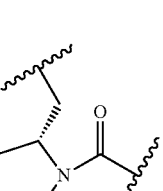 | —C(CH$_3$)$_2$-morpholin-4-yl | |
| 117B | S | | | | | | | |
| 118A | R | N | — | 2-Fphenyl | 2,3-diFphenyl |  | 1-diethylamino-methylcyclopent-1-yl | |
| 118B | S | | | | | | | |

TABLE 1-continued
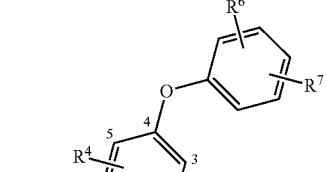
| Cpd # | Stereo-chem | $Z^3$ | $R^2$ | 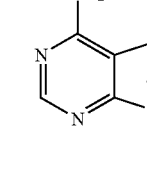 | 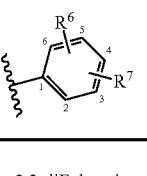 | —Z—EWG— | $R^C$ | Mass Spec $M^+ + 1$ |
|---|---|---|---|---|---|---|---|---|
| 119A<br>119B | R<br>S | N | — | 2-Fphenyl | 2,3-diFphenyl | 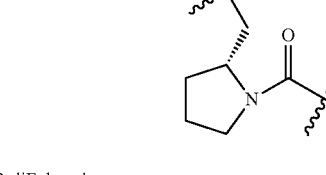 | 1-dimethylamino-methylcyclopent-1-yl | |
| 120A<br>120B | R<br>S | N | — | 2-Fphenyl | 2,3-diFphenyl | 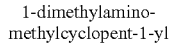 | 1-methylpiperidin-4-yl | |
| 121A<br>121B | R<br>S | N | — | 2-Fphenyl | 2,3-diFphenyl | 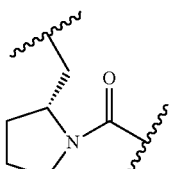 | tetrahydropyran-4-yl | |
| 122A<br>122B | R<br>S | N | — | 2-Fphenyl | 2,3-diFphenyl | 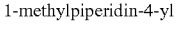 | piperidin-4-yl | |
| 123A<br>123B | R<br>S | N | — | 2-Fphenyl | 2,3-diFphenyl | 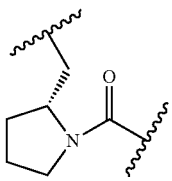 [SMILES: *C[C@H]1CCCN1C(*)=O] | piperidin-3-yl | |

TABLE 1-continued
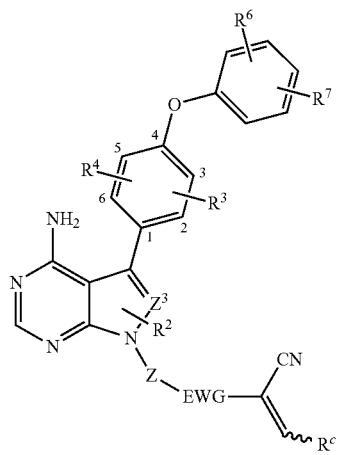
| Cpd # | Stereo-chem | Z³ | R² | 2-Fphenyl | phenyl | —Z—EWG— | Rᶜ | Mass Spec M⁺ + 1 |
|---|---|---|---|---|---|---|---|---|
| 124A | R | N | — | 2-Fphenyl | phenyl | (3-piperidinyl carbonyl) | —CH(CH$_3$)$_2$ | 526 |
| 124B | S | | | | | | | — |
| 125A | R | N | — | 2-Fphenyl | phenyl | (3-piperidinyl carbonyl) | —C(CH$_3$)$_3$ | 540 |
| 125B | S | | | | | | | — |
| 126A | R | N | — | 2-Fphenyl | phenyl | (3-piperidinyl carbonyl) | —C(CH$_3$)$_2$NH$_2$ | 542 |
| 126B | S | | | | | | | — |
| 127A | R | N | — | 2-Fphenyl | phenyl | (3-piperidinyl carbonyl) | —C(CH$_3$)$_2$NHCH$_3$ | |
| 127B | S | | | | | | | — |
| 128A | R | N | — | 2-Fphenyl | phenyl | (3-piperidinyl carbonyl) | —C(CH$_3$)$_2$N(CH$_3$)$_2$ | 569 |
| 128B | S | | | | | | | — |

TABLE 1-continued

| Cpd # | Stereo-chem | $Z^3$ | $R^2$ | R³/R⁴ aryl | R⁶/R⁷ aryl | —Z—EWG— | $R^C$ | Mass Spec $M^+ + 1$ |
|---|---|---|---|---|---|---|---|---|
| 129A | R | N | — | 2-Fphenyl | phenyl | 3-piperidinyl-N-C(O)- | —C(CH$_3$)$_2$—NHCH$_2$CH$_3$ | |
| 129B | S | | | | | | | |
| 130A | R | N | — | 2-Fphenyl | phenyl | 3-piperidinyl-N-C(O)- | —C(CH$_3$)$_2$NH—CH(CH$_3$)$_2$ | |
| 130B | S | | | | | | | |
| 131A | R | N | — | 2-Fphenyl | phenyl | 3-piperidinyl-N-C(O)- | —C(CH$_3$)$_2$NH-cyclopropyl | |
| 131B | S | | | | | | | |
| 132A | R | N | — | 2-Fphenyl | phenyl | 3-piperidinyl-N-C(O)- | —C(CH$_3$)$_2$—NH(CH$_2$)$_2$OCH$_3$ | |
| 132B | S | | | | | | | |
| 133A | R | N | — | 2-Fphenyl | phenyl | 3-piperidinyl-N-C(O)- | —C(CH$_3$)$_2$—OCH$_2$CH$_3$ | 570 |
| 133B | S | | | | | | | — |

TABLE 1-continued
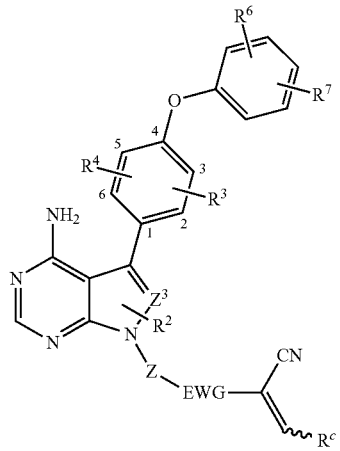
| Cpd # | Stereo-chem | $Z^3$ | $R^2$ | 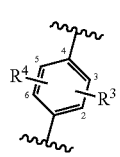 | 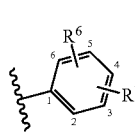 | —Z—EWG— | $R^C$ | Mass Spec $M^+ + 1$ |
|---|---|---|---|---|---|---|---|---|
| 134A | R | N | — | 2-Fphenyl | phenyl | 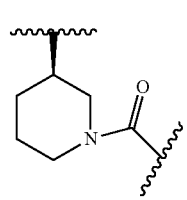 [SMILES: *C(=O)N1CCC[C@@H](*)C1] | 1-amino-cycloprop-1-yl | |
| 134B | S | | | | | | | |
| 135A | R | N | — | 2-Fphenyl | phenyl | 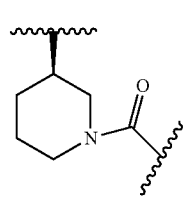 [SMILES: *C(=O)N1CCC[C@@H](*)C1] | 1-methylamino-cycloprop-1-yl | |
| 135B | S | | | | | | | |
| 136A | R | N | — | 2-Fphenyl | phenyl | 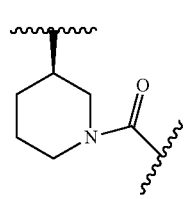 [SMILES: *C(=O)N1CCC[C@@H](*)C1] | 1-ethylamino-cycloprop-1-yl | |
| 136B | S | | | | | | | |
| 137A | R | N | — | 2-Fphenyl | phenyl | 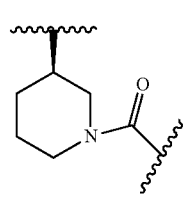 [SMILES: *C(=O)N1CCC[C@@H](*)C1] | 1-isopropylamino-cycloprop-1-yl | |
| 137B | S | | | | | | | |
| 138A | R | N | — | 2-Fphenyl | phenyl | 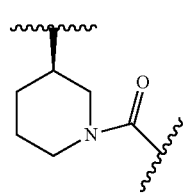 [SMILES: *C(=O)N1CCC[C@@H](*)C1] | pyrrolidin-2-yl | |
| 138B | S | | | | | | | |

TABLE 1-continued

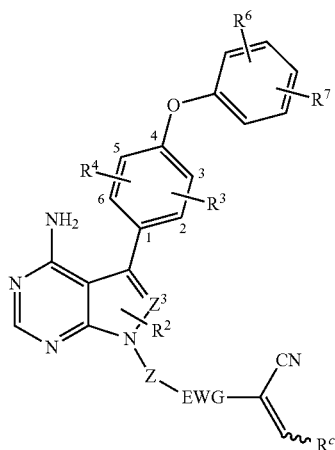

| Cpd # | Stereo-chem | $Z^3$ | $R^2$ | [2-F-phenyl ring] | [phenyl ring] | —Z—EWG— | $R^C$ | Mass Spec $M^+ + 1$ |
|---|---|---|---|---|---|---|---|---|
| 139A | R | N | — | 2-Fphenyl | phenyl | [3-piperidinyl-N-acyl] | —C(CH$_3$)$_2$-morpholin-4-yl | 611 |
| 139B | S | | | | | | | — |
| 140A | R | N | — | 2-Fphenyl | phenyl | [3-piperidinyl-N-acyl] | 1-diethylamino-methylcyclopent-1-yl | |
| 140B | S | | | | | | | |
| 141A | R | N | — | 2-Fphenyl | phenyl | [3-piperidinyl-N-acyl] | 1-dimethylamino-methylcyclopent-1-yl | |
| 141B | S | | | | | | | |
| 142A | R | N | — | 2-Fphenyl | phenyl | [3-piperidinyl-N-acyl] | 1-methylpiperidin-4-yl | |
| 142B | S | | | | | | | |
| 143A | R | N | — | 2-Fphenyl | phenyl | [3-piperidinyl-N-acyl] | tetrahydropyran-4-yl | |
| 143B | S | | | | | | | |

TABLE 1-continued
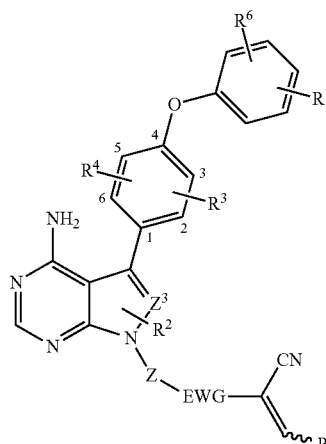
| Cpd # | Stereo-chem | $Z^3$ | $R^2$ | 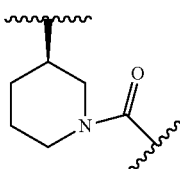 | 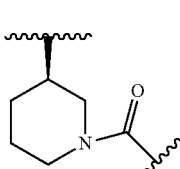 | —Z—EWG— | $R^C$ | Mass Spec $M^+ + 1$ |
|---|---|---|---|---|---|---|---|---|
| 144A | R | N | — | 2-Fphenyl | phenyl | 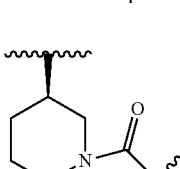 | piperidin-4-yl | |
| 144B | S | | | | | | | |
| 145A | R | N | — | 2-Fphenyl | phenyl | 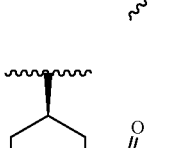 | piperidin-3-yl | |
| 145B | S | | | | | | | |
| 146A | R | N | — | 2-Fphenyl | 2,3-diFphenyl | 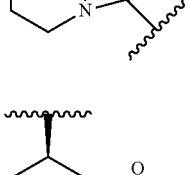 | cyclopropyl | 560 |
| 146B | S | | | | | | | — |
| 147A | R | N | — | 2-Fphenyl | 2,3-diFphenyl | 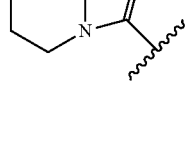 | —CH(CH$_3$)$_2$ | 562 |
| 147B | S | | | | | | | — |
| 148A | R | N | — | 2-Fphenyl | 2,3-diFphenyl | 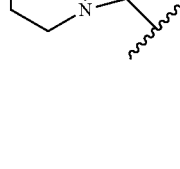 | —C(CH$_3$)$_3$ | 576 |
| 148B | S | | | | | | | — |

TABLE 1-continued
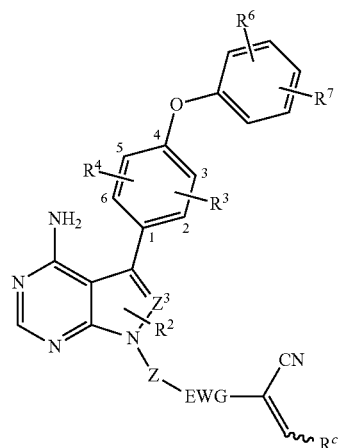
| Cpd # | Stereo-chem | $Z^3$ | $R^2$ | 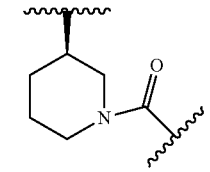 [SMILES: *C(=O)N1CCC[C@@H](*)C1] | 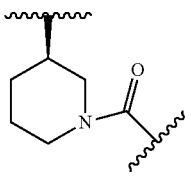 [SMILES: *C(=O)N1CCC[C@@H](*)C1] | —Z—EWG— | $R^C$ | Mass Spec $M^+ + 1$ |
|---|---|---|---|---|---|---|---|---|
| 149A | R | N | — | 2-Fphenyl | 2,3-diFphenyl | 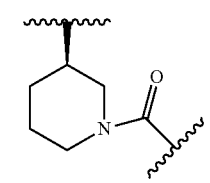 [SMILES: *C(=O)N1CCC[C@@H](*)C1] | —C(CH$_3$)$_2$NH$_2$ | 577 |
| 149B | S | | | | | | | — |
| 150A | R | N | — | 2-Fphenyl | 2,3-diFphenyl | 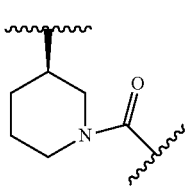 [SMILES: *C(=O)N1CCC[C@@H](*)C1] | —C(CH$_3$)$_2$NHCH$_3$ | |
| 150B | S | | | | | | | |
| 151A | R | N | — | 2-Fphenyl | 2,3-diFphenyl | 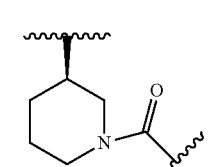 | —C(CH$_3$)$_2$N(CH$_3$)$_2$ | 605 |
| 151B | S | | | | | | | — |
| 152A | R | N | — | 2-Fphenyl | 2,3-diFphenyl | 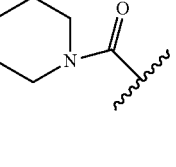 | —C(CH$_3$)$_2$—NHCH$_2$CH$_3$ | |
| 152B | S | | | | | | | |
| 153A | R | N | — | 2-Fphenyl | 2,3-diFphenyl |  | —C(CH$_3$)$_2$NH—CH(CH$_3$)$_2$ | |
| 153B | S | | | | | | | |

TABLE 1-continued

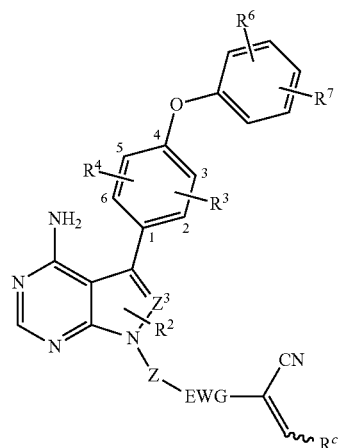

| Cpd # | Stereo-chem | $Z^3$ | $R^2$ | R⁴/R³ aryl | R⁶/R⁷ aryl | —Z—EWG— | $R^C$ | Mass Spec $M^+ + 1$ |
|---|---|---|---|---|---|---|---|---|
| 154A | R | N | — | 2-Fphenyl | 2,3-diFphenyl | piperidine-CO | —C(CH₃)₂NH-cyclopropyl | |
| 154B | S | | | | | | | |
| 155A | R | N | — | 2-Fphenyl | 2,3-diFphenyl | piperidine-CO | —C(CH₃)₂—NH(CH₂)₂OCH₃ | |
| 155B | S | | | | | | | |
| 156A | R | N | — | 2-Fphenyl | 2,3-diFphenyl | piperidine-CO | —C(CH₃)₂—OCH₂CH₃ | 606 |
| 156B | S | | | | | | | — |
| 157A | R | N | — | 2-Fphenyl | 2,3-diFphenyl | piperidine-CO | 1-amino-cycloprop-1-yl | |
| 157B | S | | | | | | | |
| 158A | R | N | — | 2-Fphenyl | 2,3-diFphenyl | piperidine-CO | 1-methylamino-cycloprop-1-yl | |
| 158B | S | | | | | | | |

TABLE 1-continued

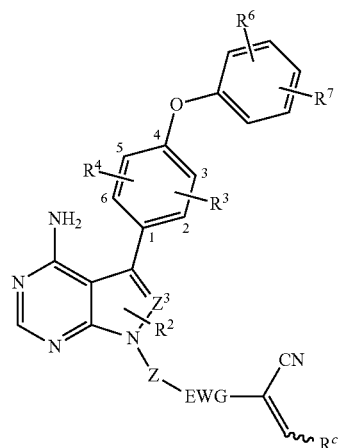

| Cpd # | Stereo-chem | $Z^3$ | $R^2$ | $R^4$/$R^3$ aryl | $R^6$/$R^7$ aryl | —Z—EWG— | $R^C$ | Mass Spec $M^+ + 1$ |
|---|---|---|---|---|---|---|---|---|
| 159A | R | N | — | 2-Fphenyl | 2,3-diFphenyl | piperidine-C(O)- | 1-ethylamino-cycloprop-1-yl | |
| 159B | S | | | | | | | |
| 160A | R | N | — | 2-Fphenyl | 2,3-diFphenyl | piperidine-C(O)- | 1-isopropylamino-cycloprop-1-yl | |
| 160B | S | | | | | | | |
| 161A | R | N | — | 2-Fphenyl | 2,3-diFphenyl | piperidine-C(O)- | pyrrolidin-2-yl | |
| 161B | S | | | | | | | |
| 162A | R | N | — | 2-Fphenyl | 2,3-diFphenyl | piperidine-C(O)- | —C(CH$_3$)$_2$-morpholin-4-yl | 647.3 |
| 162B | S | | | | | | | — |
| 163A | R | N | — | 2-Fphenyl | 2,3-diFphenyl | piperidine-C(O)- | 1-diethylamino-methylcyclopent-1-yl | |
| 163B | S | | | | | | | |

TABLE 1-continued
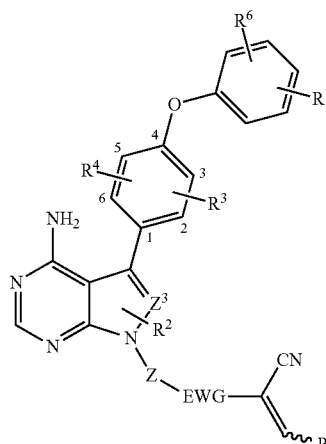
| Cpd # | Stereo-chem | $Z^3$ | $R^2$ | 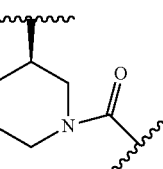 | 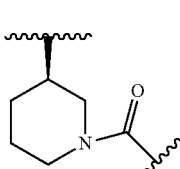 | —Z—EWG— | $R^C$ | Mass Spec $M^+ + 1$ |
|---|---|---|---|---|---|---|---|---|
| 164A | R | N | — | 2-Fphenyl | 2,3-diFphenyl | 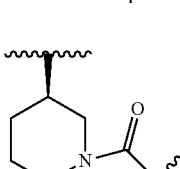 | 1-dimethylamino-methylcyclopent-1-yl | |
| 164B | S | | | | | | | |
| 165A | R | N | — | 2-Fphenyl | 2,3-diFphenyl | 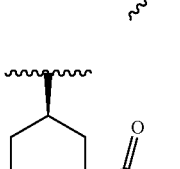 | 1-methylpiperidin-4-yl | |
| 165B | S | | | | | | | |
| 166A | R | N | — | 2-Fphenyl | 2,3-diFphenyl | | tetrahydropyran-4-yl | |
| 166B | S | | | | | | | |
| 167A | R | N | — | 2-Fphenyl | 2,3-diFphenyl | | piperidin-4-yl | |
| 167B | S | | | | | | | |
| 168A | R | N | — | 2-Fphenyl | 2,3-diFphenyl | 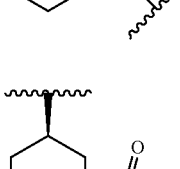 | piperidin-3-yl | |
| 168B | S | | | | | | | |

TABLE 1-continued
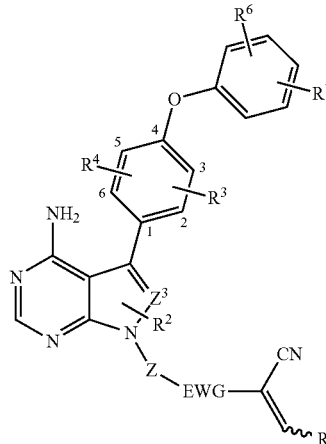
| Cpd # | Stereo-chem | $Z^3$ | $R^2$ | 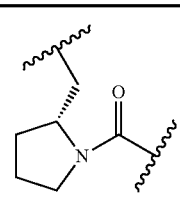 | 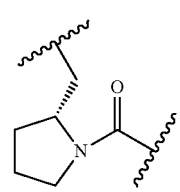 [SMILES: *C[C@H]1CCCN1C(*)=O] | —Z—EWG— | $R^C$ | Mass Spec $M^+ + 1$ |
|---|---|---|---|---|---|---|---|---|
| 169A | R | N | — | 2-Fphenyl | phenyl | 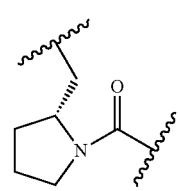 [SMILES: *C[C@H]1CCCN1C(*)=O] | —C(CH$_3$)$_2$-piperidin-1-yl | 609 |
| 169B | S | | | | | | | 609 |
| 170A | R | CH | — | 2-Fphenyl | phenyl | 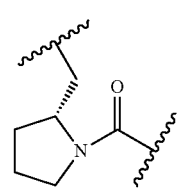 [SMILES: *C[C@H]1CCCN1C(*)=O] | —C(CH$_3$)$_2$N(CH$_3$)$_2$ | — |
| 170B | S | | | | | | | 468 |
| 171A | R | CH | — | phenyl | 2,3-diFphenyl | | cyclopropyl | — |
| 171B | S | | | | | | | 541 |
| 172A | R | CH | — | phenyl | 2,3-diFphenyl | | —CH(CH$_3$)$_2$ | — |
| 172B | S | | | | | | | 543 |
| 173A | R | CH | — | phenyl | 2,3-diFphenyl | 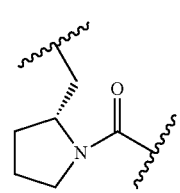 [SMILES: *C[C@H]1CCCN1C(*)=O] | —C(CH$_3$)$_3$ | — |
| 173B | S | | | | | | | 557 |

TABLE 1-continued
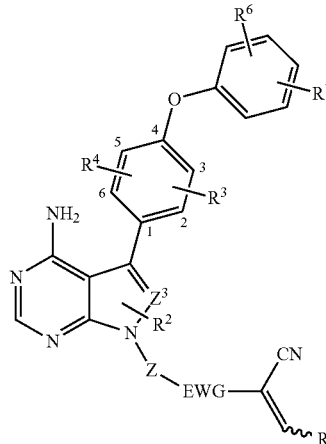
| Cpd # | Stereo-chem | $Z^3$ | $R^2$ | 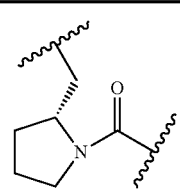 | 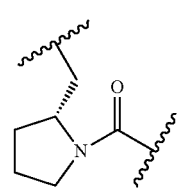 [SMILES: *C[C@H]1CCCN1C(*)=O] | —Z—EWG— | $R^C$ | Mass Spec $M^+ + 1$ |
|---|---|---|---|---|---|---|---|---|
| 174A | R | CH | — | phenyl | 2,3-diFphenyl | 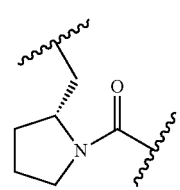 [SMILES: *C[C@H]1CCCN1C(*)=O] | —C(CH$_3$)$_2$N(CH$_3$)$_2$ | — |
| 174B | S | | | | | | | 586 |
| 175A | R | CH | — | phenyl | phenyl | 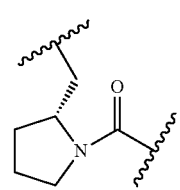 [SMILES: *C[C@H]1CCCN1C(*)=O] | —C(CH$_3$)$_2$N(CH$_3$)$_2$ | 550 |
| 175B | S | | | | | | | 550 |
| 176A | R | CH | — | phenyl | phenyl | 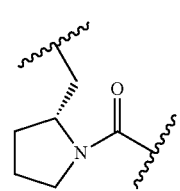 [SMILES: *C[C@H]1CCCN1C(*)=O] | —CH(CH$_3$)$_2$ | 507 |
| 176B | S | | | | | | | 507 |
| 177A | R | CH | — | 2-Fphenyl | phenyl | | —C(CH$_3$)$_2$NH$_2$ | 540 |
| 177B | S | | | | | | | 540 |
| 178A | R | CH | — | 2-Fphenyl | phenyl | | —C(CH$_3$)$_2$N(CH$_3$)$_2$ | 550 |
| 178B | S | | | | | | | — |

TABLE 1-continued

| Cpd # | Stereo-chem | Z³ | R² | R³/R⁴ ring | R⁶/R⁷ ring | —Z—EWG— | Rᶜ | Mass Spec M⁺ + 1 |
|---|---|---|---|---|---|---|---|---|
| 179A | R | CH | — | phenyl | phenyl | (2-pyrrolidinyl-CH₂)C(O)— | —C(CH₃)₂-morpholin-4-yl | 592 |
| 179B | S | | | | | | | 592 |
| 180A | R | CH | — | phenyl | phenyl | (2-pyrrolidinyl-CH₂)C(O)— | —C(CH₃)₂N(CH₂CH₃)₂ | 578 |
| 180B | S | | | | | | | 578 |
| 181A | R | CH | — | phenyl | phenyl | (2-pyrrolidinyl-CH₂)C(O)— | —C(CH₃)₂OCH₂CH₃ | 551 |
| 181B | S | | | | | | | 551 |
| 182A | R | N | — | 2-Fphenyl | phenyl | —(CH₂)CH(CH₃)NHCO— | tert-butyl | 514— |
| 182B | S | | | | | | | — |
| 183A | R | N | — | 2-Fphenyl | phenyl | —(CH₂)CH(CH₃)NHCO— | isopropyl | 500— |
| 184B | S | | | | | | | — |
| 184A | R | N | — | 2-Fphenyl | phenyl | —(CH₂)*CH(CH₃)NHCO— | —C(CH₃)₂OCH₂CH₃ | 544— |
| 184B | S | | | | | | | — |
| 185A | R | N | — | 2-Fphenyl | phenyl | —(CH₂)*CH(CH₃)NHCO— | —C(CH₃)₂N(CH₃)₂ | 543— |
| 185B | S | | | | | | | — |
| 186 | | N | — | 2-Fphenyl | phenyl | (2R-pyrrolidinyl-CH₂)C(O)— | 2(S)pyrrolidin-2-yl | 553 |

TABLE 1-continued

| Cpd # | Stereo-chem | $Z^3$ | $R^2$ | R³/R⁴ aryl | R⁶/R⁷ aryl | —Z—EWG— | $R^C$ | Mass Spec M⁺ + 1 |
|---|---|---|---|---|---|---|---|---|
| 187 | | N | — | 2-Fphenyl | phenyl | (2R)-pyrrolidinyl-CO— | 2(R)pyrrolidin-2-yl | 553 |
| 188 | R | N | — | 2-Fphenyl | phenyl | —(CH₂)*CH(CH₃)NHCO— | —C(CH₃)₂NH₂ | 515 |
| 189 | | N | — | phenyl | phenyl | —(CH₂)₂N(CH₃)CO— | cyclopropyl | 480 |
| 190A | R | N | — | 2-Fphenyl | phenyl | (2R)-pyrrolidinyl-CO— | —C(CH₃)₂piperidin-1-yl | 609 |
| 190B | S | | | | | | | |
| 191 | S | N | — | 2-Fphenyl | phenyl | —(CH₂)*CH(CH₃)NHCO— | tert-butyl | 514 |
| 192 | S | N | — | 2-Fphenyl | phenyl | —(CH₂)*CH(CH₃)NHCO— | iso-propyl | 500 |
| 193 | S | N | — | 2-Fphenyl | phenyl | —(CH₂)*CH(CH₃)NHCO— | —C(CH₃)₂N(CH₃)₂ | 543 |
| 194 | S | N | — | 2-Fphenyl | phenyl | —(CH₂)*CH(CH₃)NHCO— | —C(CH₃)₂OCH₂CH₃ | 544 |
| 195 | S | N | — | 2-Fphenyl | phenyl | —(CH₂)*CH(CH₃)NHCO— | —C(CH₃)₂NH₂ | 515 |
| 196 | S | N | — | 2-Fphenyl | phenyl | —(CH₂)*CH(CH₃)NHCO— | cyclopropyl | 498 |
| 197A | R | N | — | 2-Fphenyl | phenyl | (2R)-pyrrolidinyl-CO— | 3-methyloxetan-3-yl | — |
| 197B | S | | | | | | | 554.3 | or an RS mixture of enantiomers; or an E or Z isomer, or a pharmaceutically acceptable salt thereof.

Note: In the table above, the letter A refers to the R isomer and B refers to its corresponding S isomer e.g., 168A =R isomer and 168B is the corresponding S isomer of the same compound.

and are named as follows:
2-(3-(4-amino-3-(4-phenoxyphenyl)-1H-pyrazolo[3,4-d]pyrimidin-1-yl)piperidine-1-carbonyl)-3-cyclopropylacrylonitrile*;
2-(2-((4-amino-3-(4-phenoxyphenyl)-1H-pyrazolo[3,4-d]pyrimidin-1-yl)methyl)pyrrolidine-1-carbonyl)-3cyclopropylacrylonitrile*;
2-(4-(4-amino-3-(4-phenoxyphenyl)-1H-pyrazolo[3,4-d]pyrimidin-1-yl)piperidine-1-carbonyl)-3-cyclopropylacrylonitrile*;
2-(3-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile*;
2-(2-((4-amino-3-(4-(3,4-dichlorophenoxy(3-methoxyphenyl)-1H-pyrazolo[3,4-d]pyrimidin-1-yl)methyl)pyrrolidine-1-carbonyl)-3-cyclopropylacrylonitrile*;
2-(4-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile*;
2-(3-(4-amino-3-(4-phenoxyphenyl)-1H-pyrazolo[3,4-d]pyrimidin-1-yl)piperidine-1-carbonyl)4,4-dimethylpent-2-enenitrile*;
2-(4-(4-amino-3-(4-phenoxyphenyl)-1H-pyrazolo[3,4-d]pyrimidin-1-yl)piperidine-1-carbonyl)-4,4-dimethylpent-2-enenitrile*;
2-(4-(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile*;
2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile*;
N-((1s,4s)-4-(4-amino-3-(4-phenoxyphenyl)-1H-pyrazolo[3,4-d]pyrimidin-1-yl)cyclohexyl)-2-cyano-3-cyclopropylacrylamide*;
2-(2-((4-amino-3-(4-(3,4-dichlorophenoxy)-3-methoxyphenyl)-1H-pyrazolo[3,4-d]pyrimidin-1-yl)methyl)pyrrolidine-1-carbonyl)-4,4-dimethylpent-2-enenitrile*;
N-((1r,4r)-4-(4-amino-3-(4-(3,4-dichlorophenoxy)-3-methoxyphenyl)-1H-pyrazolo[3,4-d]pyrimidin-1-yl)cyclohexyl)-2-cyano-3-cyclopropylacrylamide*;
N-((1s,4s)-4-(4-amino-3-(4-phenoxyphenyl)-1H-pyrazolo[3,4-d]pyrimidin-1-yl)cyclohexyl)-2-cyano-4,4-dimethylpent-2-enamide*;
(R)-2-(3-(4-amino-3-(4-(3-fluorophenoxy)phenyl)-1H-pyrazolo[3,4-d]pyrimidin-1-yl)piperidine-1-carbonyl)-3-cyclopropylacrylamide;
(S)-2-(3-(4-amino-3-(4-(3-fluorophenoxy)phenyl)-1H-pyrazolo[3,4-d]pyrimidin-1-yl)piperidine-1-carbonyl)-3-cyclopropylacrylamide;
N-((1r,4r)-4-(4-amino-3-(4-(3,4-dichlorophenoxy)-3-methoxyphenyl)-1H-pyrazolo[3,4-d]pyrimidin-1-yl)cyclohexyl)-2-cyano-4,4-dimethylpent-2-enamide*;
(R)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylamide;
(S)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylamide;
(R)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylamide;
(S)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylamide;
2-(3 -(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile*;
N-((1s,4s)-4-(4-amino-3-(4-(3,4-dichlorophenoxy)-3-methoxyphenyl)-1H-pyrazolo[3,4-d]pyrimidin-1-yl)cyclohexyl)-2-cyano-3-cyclopropylacrylamide*;
N-((1s,4s)-4-(4-amino-3-(4-(3,4-dichlorophenoxy)-3-methoxyphenyl)-1H-pyrazolo[3,4-d]pyrimidin-1-yl)cyclohexyl)-2-cyano-4,4-dimethylpent-2-enamide*;
(R)-2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile*;
(R)-2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile;
(S)-2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile;23
(R)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;
2-(3-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile*;
(R)-2-(3 -(4-amino-3-(4-phenoxyphenyl)-1H-pyrazolo[3,4-d]pyrimidin-1-yl)piperidine-1-carbonyl)-4,4-dimethylpent-2-enenitrile*;
(S)-2-(3-(4-amino-3-(4-phenoxyphenyl)-1H-pyrazolo[3,4-d]pyrimidin-1-yl)piperidine-1-carbonyl)-4,4-dimethylpent-2-enenitrile*;
(R)-2-(3-(4-amino-3-(4-phenoxyphenyl)-1H-pyrazolo[3,4-d]pyrimidin-1-yl)piperidine-1-carbonyl)-3cyclopropylacrylamide*; 30
(R)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile;
(R)-2-(3-(4-amino-3-(4-(2-fluorophenoxy)phenyl)-1H-pyrazolo[3,4-d]pyrimidin-1-yl)piperidine-1-carbonyl)-3-cyclopropylacrylamide;

(S)-2-(3-(4-amino-3-(4-(2-fluorophenoxy)phenyl)-1H-pyrazolo[3,4-d]pyrimidin-1-yl)piperidine-1-carbonyl)-3-cyclopropylacrylamide;
N-(2-(4-amino-3-(4-phenoxyphenyl)-1H-pyrazolo[3,4-d]pyrimidin-1-yl)ethyl)-2-cyano-3-cyclopropylacrylamide;
(R)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylamide;
(S)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylamide;
(R)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylamide;
(S)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylamide;
(R)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylamide;
(S)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylamide;
(R)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(4-(2,5-difluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(2-fluoro-4-(3,5-difluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(3-fluoro-4-(phenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(2-fluoro-4-(2,3-difluorophenoxy)phenyl)-1H-pyrazolo[3,4d]primidin-1-yl)methyl)pyrrolidine-1-carbonyl)-3-cyclopropylacrylonitrile;
(S)-2-(2-((4-amino-3-(2-fluoro-4-(2,3-difluorophenoxy)phenyl)-1H-pyrazolo[3,4-d]pyrimidin-1-yl)methyl)pyrrolidine-1-carbonyl)-3-cyclopropylacrylonitrile;
(R)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile;
(S)-2-(2-((4-amino-3-(2-fluoro-4-(2,6-difluorophenoxy)phenyl)-1H-pyrazolo[3,4-d]pyrimidin-1-yl)methyl)pyrrolidine-1-carbonyl)-3-cyclopropylacrylonitrile;
N-(2-(4-amino-3-(2-fluoro-4-phenoxyphenyl)-1H-pyrazolo[3,4-d]pyrimidin-1-yl)ethyl)-2-cyano-3-cyclopropylacrylamide;
N-(2-(4-amino-3-(2-fluoro-4-phenoxyphenyl)-1H-pyrazolo[3,4-d]pyrimidin-1-yl)-2-methylpropyl)-2-cyano-3-cyclopropylacrylamide;
N-(1-(4-amino-3-(2-fluoro-4-phenoxyphenyl)-1H-pyrazolo[3,4d]pyrimidin-1-yl)-2-methylpropan-2-yl)-2-cyano-3-cyclopropylacrylamide;
N-(2-(4-amino-3-(2-fluoro-4-phenoxyphenyl)-1H-pyrazolo[3,4-d]pyrimidin-1-yl)ethyl)-1-cyano-2-cyclopropylethenesulfonamide;
N-(2-(4-amino-3-(2-fluoro-4-phenoxyphenyl)-1H-pyrazolo[3,4-d]pyrimidin-1-yl)ethyl)-1-cyano-2-cyclopropyl-N-methylethenesulfonamide;
2-(4-amino-3-(2-fluoro-4-phenoxyphenyl)-1H-pyrazolo[3,4-d]pyrimidin-1-yl)ethyl2-cyano-3-cyclopropylacrylate;
1-(4-amino-3-(2-fluoro-4-phenoxyphenyl)-1H-pyrazolo[3,4-d]pyrimidin-1-yl)-2-methylpropan-2-yl 2-cyano-3-cyclopropylacrylate;
2-((2-(4-amino-3-(2-fluoro-4-phenoxyphenyl)-1H-pyrazolo[3,4-d]pyrimidin-1-yl)ethyl)sulfonyl)-3-cyclopropylacrylonitrile;
2-(5-((4-amino-3-(2-fluoro-4-phenoxyphenyl)-1H-pyrazolo[3,4-d]pyrimidin-1-yl)methyl)oxazol-2-yl)-3-cyclopropylacrylonitrile; 53
(R)-2-(3-(4-amino-5-(4-phenoxyphenyl)-7H-pyrrolo[2,3-d]pyrimidin-7-yl)piperidine-1-carbonyl)-3-cyclopropylacrylonitrile*;
(S)-2-(3-(4-amino-5-(4-phenoxyphenyl)-7H-pyrrolo[2,3-d]pyrimidin-7-yl)piperidine-1-carbonyl)-3-cyclopropylacrylonitrile*;
(R)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile;
(S)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile;
(R)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile;
(S)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile;
(R)-2-(2-((4-amino-5-(4-phenoxyphenyl)-7H-pyrrolo[2,3-d]pyrimidin-7-yl)methyl)pyrrolidine-1-carbonyl)-3-cyclopropylacrylonitrile;
(S)-2-(2-((4-amino-5-(4-phenoxyphenyl)-7H-pyrrolo[2,3-d]pyrimidin-7-yl)methyl)pyrrolidine-1-carbonyl)-3-cyclopropylacrylonitrile;
(R)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile;
(S)-2-(2-((4-amino-5-(4-(3,5-difluorophenoxy)phenyl)-7H-pyrrolo[2,3-d]pyrimidin-7-yl)methyl)pyrrolidine-1-carbonyl)-3-cyclopropylacrylonitrile; 58
R)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile;
(S)-2-(2-((4-amino-5-(2-fluoro-4-phenoxyphenyl)-7H-pyrrolo[2,3-d]pyrimidin-7-yl)methyl)pyrrolidine-1-carbonyl)-3-cyclopropylacrylonitrile;
(R)-2-(3-(4-amino-6-methyl-5-(4-phenoxyphenyl)-7H-pyrrolo[2,3-d]pyrimidin-7-yl)piperidine-1-carbonyl)-3-cyclopropylacrylonitrile;

(S)-2-(3-(4-amino-6-methyl-5-(4-phenoxyphenyl)-7H-pyrrolo[2,3-d]pyrimidin-7-yl)piperidine-1-carbonyl)-3-cyclopropylacrylonitrile;

(R)-2-(3-(4-amino-5-(4-(3,5-difluorophenoxy)phenyl)-6-methyl-7H-pyrrolo[2,3-d]pyrimidin-7-yl)piperidine-1-carbonyl)-3-cyclopropylacrylonitrile;

(S)-2-(3-(4-amino-5-(4-(3,5-difluorophenoxy)phenyl)-6-methyl-7H-pyrrolo[2,3- ]pyrimidin-7-yl)piperidine-1-carbonyl)-3-cyclopropylacrylonitrile;

2-((3R)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile;

2-((3S)-3-(4-amino-5-(2-fluoro-4-phenoxyphenyl)-6-methyl-7H-pyrrolo[2,3-d]pyrimidin-7-yl)piperidine-1-carbonyl)-3-cyclopropylacrylonitrile;

(R)-(2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile;

(S)-(2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile;

(R)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile;

(S)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile;

(R)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile; or (S)-2-(2-((4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile; 65

2-(3-((4-amino-3-(4-phenoxyphenyl)-1H-pyrazolo[3,4-d]pyrimidin-1-yl)methyl)pyrrolidine-1-carbonyl)-3cyclopropylacrylonitrile*;

N-(3-(4-amino-3-(4-phenoxyphenyl)-1H-pyrazolo[3,4-d]pyrimidin-1-yl)-2,2-dimethylpropyl)-2-cyano-3-cyclopropylacrylamide;

2-(4-(4-amino-3-(4-phenoxyphenyl)-1H-pyrazolo[3,4-d]pyrimidin-1-yl)pyridin-2-yl)-3-cyclopropylacrylonitrile*;

(R)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-methyl-4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile;

(S)-2-(2-((4-amino-3-(2-chloro-4-phenoxyphenyl)-1H-pyrazolo[3,4-d]pyrimidin-1-yl)methyl)pyrrolidine-1-carbonyl)-3-cyclopropylacrylonitrile;

(R)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,5-difluorophenoxy)phenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4,4-dimethylpent-2-enenitrile;

(R)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,6-difluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,3-difluorophenoxy)phenyl)-1H-pyrazolo[3,4-d]pyrimidin-1-yl)methyl)pyrrolidine-1-carbonyl)-4-methylpent-2-enenitrile;

(R)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(S)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile; 77

(R)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile;

(S)-2-(2-((4-amino-3-(4-(2,6-difluorophenoxy)-2-fluorophenyl)-1H-pyrazolo[3,4-d]pyrimidin-1-yl)methyl)pyrrolidine-1-carbonyl)-4-methylpent-2-enenitrile;

(R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile;

(S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-3-cyclopropylacrylonitrile;

(R)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)-4,4-difluoropyrrolidine-1-carbonyl)-4-methylpent-2-enenitrile; 80

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(methylamino)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(dimethylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(isopropylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-((2-methoxyethyl)amino)-4-methylpent-2-enenitrile
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-ethoxy-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(methylamino)cyclopropyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(ethylamino)cyclopropyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-(isopropylamino)cyclopropyl)acrylonitrile;
2-((S)-2-((4-amino-3-(2-fluoro-4-phenoxyphenyl)-1H-pyrazolo[3,4-d]pyrimidin-1-yl)methyl)pyrrolidine-1-carbonyl)-3-(pyrrolidin-2-yl)acrylonitrile;
2-((R)-2-((4-amino-3-(2-fluoro-4-phenoxyphenyl)-1H-pyrazolo[3,4d]pyrimidin-1-yl)methyl)pyrrolidine-1-carbonyl)-3-(pyrrolidin-2-yl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-((dimethylamino)methyl)cyclopentyl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-methylpiperidin-4-yl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(tetrahydro-2H-pyran-4-yl)acrylonitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-3-(piperidin-4-yl)acrylonitrile;
2-((S)-2-((4-amino-3-(2-fluoro-4-phenoxyphenyl)-1H-pyrazolo[3,4-d]pyrimidin-1-yl)methyl)pyrrolidine-1-carbonyl)-3-(piperidin-3-yl)acrylonitrile;
2-((R)-2-((4-amino-3-(2-fluoro-4-phenoxyphenyl)-1H-pyrazolo[3,4-]pyrimidin-1-yl)methyl)pyrrolidine-1-carbonyl)-3-(piperidin-3-yl)acrylonitrile;
(S)-2-(2-((4-amino-3-(4-(2,3-difluorophenoxy)-2-fluorophenyl)-1H-pyrazolo[3,4-]pyrimidin-1-yl)methyl)pyrrolidine-1-carbonyl)-4-methylpent-2-enenitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4,4-dimethylpent-2-enenitrile;
(S)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;
(R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;
(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile;
(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-(methylamino)pent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(dimethylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(ethylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(isopropylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-(cyclopropylamino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-((2-methoxyethyl)amino)-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-aminocyclopropyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(methylamino)cyclopropyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(ethylamino)cyclopropyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-(isopropylamino)cyclopropyl)acrylonitrile;

2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile;

2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(pyrrolidin-2-yl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methyl-4-morpholinopent-2-enenitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((diethylamino)methyl)cyclopentyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)methyl)cyclopentyl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-((dimethylamino)methyl)cyclopentyl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(1-methylpiperidin-4-yl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(tetrahydro-2H-pyran-4-yl)acrylonitrile;

(S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile;

(R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-4-yl)acrylonitrile;

2-((S)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile;

2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-(piperidin-3-yl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(R)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(S)-4-amino-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-methyl-4-(methylamino)pent-2-enenitrile;
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;
(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(ethylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(isopropylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-(cyclopropylamino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-((2-methoxyethyl)amino)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;
(S)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-aminocyclopropyl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-(methylamino)cyclopropyl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-(ethylamino)cyclopropyl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-(isopropylamino)cyclopropyl)acrylonitrile;
2-((R)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile;
2-((S)-3-(4-amino-3-(2-fluoro-4-phenoxyphenyl)-1H-pyrazolo[3,4-d]pyrimidin-1-yl)piperidine-1-carbonyl)-3-(pyrrolidin-2-yl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-((diethylamino)methyl)-cyclopentyl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-((dimethylamino)methyl)cyclopentyl)-acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(1-methylpiperidin-4-yl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(tetrahydro-2H-pyran-4-yl)acrylonitrile;
(R)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile;
(S)-2-(3-(4-amino-3-(2-fluoro-4-phenoxyphenyl)-1H-pyrazolo[3,4-d]pyrimidin-1-yl)piperidine-1-carbonyl)-3-(piperidin-4-yl)acrylonitrile;
2-((R)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile;
2-((S)-3-(4-amino-3-(2-fluoro-4-phenoxyphenyl)-1H-pyrazolo[3,4-d]pyrimidin-1-yl)piperidine-1-carbonyl)-3-(piperidin-3-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-cyclopropylacrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4,4-dimethylpent-2-enenitrile;

(R)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(S)-4-amino-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-(methylamino)pent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(dimethylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(ethylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(isopropylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-(cyclopropylamino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-((2-methoxyethyl)amino)-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-aminocyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(methylamino)cyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(ethylamino)cyclopropyl)-acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-(isopropylamino)-cyclopropyl)acrylonitrile;

2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile;

2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(pyrrolidin-2-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-4-methyl-4-morpholinopent-2-enenitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((diethylamino)methyl)-cyclopentyl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((dimethylamino)methyl)-cyclopentyl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-((dimethylamino)-methyl)cyclopentyl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(1-methylpiperidin-4-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(tetrahydro-2H-pyran-4-yl)acrylonitrile;

(R)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile;

(S)-2-(3-(4-amino-3-(4-(2,3-difluorophenoxy)-2-fluorophenyl)-1H-pyrazolo[3,4-d]pyrimidin-1-yl)piperidine-1-carbonyl)-3-(piperidin-4-yl)acrylonitrile;

2-((R)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile;

2-((S)-3-(4-amino-3-(4-(2,3-difluorophenoxy)-2-fluorophenyl)-1H-pyrazolo[3,4-d]pyrimidin-1-yl)piperidine-1-carbonyl)-3-(piperidin-3-yl)acrylonitrile;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(R)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(S)-2-(2-((4-amino-5-(2-fluoro-4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(R)-2-(2-((4-amino-5-(4-(2,3-difluorophenoxy)phenyl)-7H-pyrrolo[2,3-d]pyrimidin7-yl)methyl)pyrrolidine-1-carbonyl)-3-cyclopropylacrylonitrile;

(S)-2-(2-((4-amino-5-(4-(2,3-difluorophenoxy)phenyl)-7H-pyrrolo[2,3-d]pyrimidin-7-yl)methyl)pyrrolidine-1-carbonyl)-3-cyclopropylacrylonitrile;

(R)-2-(2-((4-amino-5-(4-(2,3-difluorophenoxy)phenyl)-7H-pyrrolo[2,3-d]pyrimidin7-yl)methyl)pyrrolidine-1-carbonyl)-4-methylpent-2-enenitrile;

(S)-2-(2-((4-amino-5-(4-(2,3-difluorophenoxy)phenyl)-7H-pyrrolo[2,3-d]pyrimidin-7-yl)methyl)pyrrolidine-1-carbonyl)-4-methylpent-2-enenitrile;

(R)-2-(2-((4-amino-5-(4-(2,3-difluorophenoxy)phenyl)-7H-pyrrolo[2,3-d]pyrimidin7-yl)methyl)pyrrolidine-1-carbonyl)-4,4-dimethylpent-2-enenitrile;

(S)-2-(2-((4-amino-5-(4-(2,3-difluorophenoxy)phenyl)-7H-pyrrolo [2,3-d]pyrimidin-7-yl)methyl)pyrrolidine-1-carbonyl)-4,4-dimethylpent-2-enenitrile;

(R)-2-(2-((4-amino-5-(4-(2,3-difluorophenoxy)phenyl)-7H-pyrrolo[2,3 -d]pyrimidin7-yl)methyl)pyrrolidine-1-carbonyl)-4-(dimethylamino)-4-methylpent-2-enenitrile;

(S)-2-(2-((4-amino-5-(4-(2,3-difluorophenoxy)phenyl)-7H-pyrrolo [2,3-d]pyrimidin-7-yl)methyl)pyrrolidine-1-carbonyl)-4-(dimethylamino)-4-methylpent-2-enenitrile;

(R)-2-(2-((4-amino-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(S)-2-(2-((4-amino-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(R)-2-(2-((4-amino-5-(4-phenoxyphenyl)-7H-pyrrolo[2,3-d]pyrimidin-7-yl)methyl)pyrrolidine-1-carbonyl)-4-methylpent-2-enenitrile;

(S)-2-(2-((4-amino-5-(4-phenoxyphenyl)-7H-pyrrolo[2,3-d]pyrimidin-7-yl)methyl)pyrrolidine-1-carbonyl)-4-methylpent-2-enenitrile;

(R)-4-amino-2-(2-((4-amino-5-(2-fluoro-4-phenoxyphenyl)-7H-pyrrolo[2,3-d]pyrimidin-7-yl)methyl)pyrrolidine-1-carbonyl)-4-methylpent-2-enenitrile;

(S)-4-amino-2-(2-((4-amino-5-(2-fluoro-4-phenoxyphenyl)-7H-pyrrolo[2,3-d]pyrimidin-7-yl)methyl)pyrrolidine-1-carbonyl)-4-methylpent-2-enenitrile;

(R)-2-(2-((4-amino-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(S)-2-(2-((4-amino-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile;

(R)-2-(2-((4-amino-5-(4-phenoxyphenyl)-7H-pyrrolo[2,3-d]pyrimidin-7-yl)methyl)pyrrolidine-1-carbonyl)-4-methyl-4-morpholinopent-2-enenitrile (S)-2-(2-((4-amino-5-(4-phenoxyphenyl)-7H-pyrrolo[2,3-d]pyrimidin-7-yl)methyl)pyrrolidine-1-carbonyl)-4-methyl-4-morpholinopent-2-enenitrile;

(R)-2-(2-((4-amino-5-(4-phenoxyphenyl)-7H-pyrrolo[2,3-d]pyrimidin-7-yl)methyl)pyrrolidine-1-carbonyl)-4-(diethylamino)-4-methylpent-2-enenitrile;

(S)-2-(2-((4-amino-5-(4-phenoxyphenyl)-7H-pyrrolo[2,3-d]pyrimidin-7-yl)methyl)pyrrolidine-1-carbonyl)-4-(diethylamino)-4-methylpent-2-enenitrile;

(R)-2-(2-((4-amino-5-(4-phenoxyphenyl)-7H-pyrrolo[2,3-d]pyrimidin-7-yl)methyl)pyrrolidine-1-carbonyl)-4-ethoxy-4-methylpent-2-enenitrile;

(S)-2-(2-((4-amino-5-(4-phenoxyphenyl)-7H-pyrrolo[2,3-d]pyrimidin-7-yl)methyl)pyrrolidine-1-carbonyl)-4-ethoxy-4-methylpent-2-enenitrile;

(R)-N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide (R)-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(R)-N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;

(R)-N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-((S)-pyrrolidin-2-yl)acrylonitrile;

2-((R)-2-((4-amino-3-(2-fluoro-4-phenoxyphenyl)-1H-pyrazolo[3,4-d]pyrimidin-1-yl)methyl)pyrrolidine-1-carbonyl)-3-((R)-pyrrolidin-2-yl)acrylonitrile;

(R)-4-amino-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(S)-4-amino-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

N-(2-(4-amino-3-(4-phenoxyphenyl)-1H-pyrazolo[3,4-d]pyrimidin-1-yl)ethyl)-2-cyano-3-cyclopropyl-N-methylacrylamide;

(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-(piperidin-1-yl)pent-2-enenitrile;

(S)-N-(1-(4-amino-3-(2-fluoro-4-phenoxyphenyl)-1H-pyrazolo[3,4-d]pyrimidin-1-yl)propan-2-yl)-2-cyano-4,4-dimethylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4-(dimethylamino)-4-methylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-4-ethoxy-4-methylpent-2-enamide;

(S)-4-amino-N-(1-(4-amino-3-(2-fluoro-4-phenoxyphenyl)-1H-pyrazolo[3,4-d]pyrimidin-1-yl)propan-2-yl)-2-cyano-4-methylpent-2-enamide;

(S)-N-(1-(4-amino-3-(2-fluoro-4-phenoxyphenyl)-1H-pyrazolo[3,4-d]pyrimidin-1-yl)propan-2-yl)-2-cyano-3-cyclopropylacrylamide;

or a mixture of R and S isomers or an individual (E) or (Z) isomer thereof;

or a pharmaceutically acceptable salt thereof.

*=cpds not in claims.

TABLE 2

| Cpd # | Stereochem | $Z^3$ | $R^2$ | | —Z—EWG— | $R^c$ |
|---|---|---|---|---|---|---|
| 1 | RS | N | — | phenyl | 4-CF$_3$phenyl | cyclopropyl |
| | | | | | (3-piperidinyl carbonyl) | |
| 2 | RS | N | — | phenyl | 4-CF$_3$phenyl | cyclopropyl |
| | | | | | (4-piperidinyl carbonyl) | |
| 3 | RS | N | — | phenyl | 4-CF$_3$phenyl | tert-butyl |
| | | | | | (3-piperidinyl carbonyl) | |

TABLE 2-continued
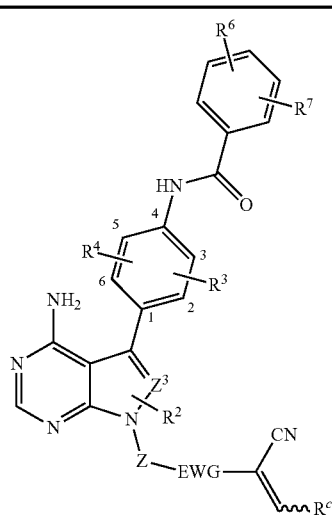
| Cpd # | Stereochem | Z³ | R² | | | —Z—EWG— | Rᶜ |
|---|---|---|---|---|---|---|---|
| 4 | RS | N | — | phenyl | 4-CF₃phenyl | 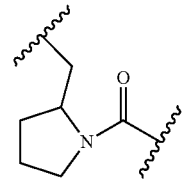 | cyclopropyl |
| 5 | RS | N | — | phenyl | 4-CF₃phenyl | 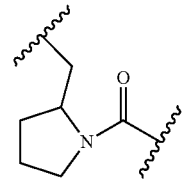 | tert-butyl |
| 6 | RS | N | — | phenyl | 4-CF₃phenyl | 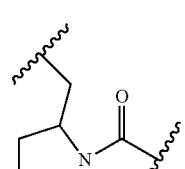 | tert-butyl |
| 7 | 1r,4r | N | — | phenyl | 3-CF₃phenyl | 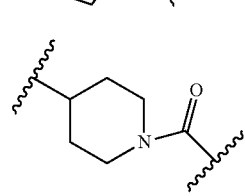 | cyclopropyl |
| 8 | 1r,4r | N | — | phenyl | 4-CF₃phenyl | 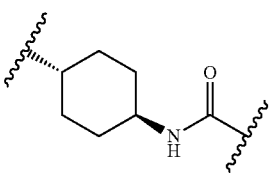 [SMILES: *C(=O)N[C@H]1CC[C@H](*)CC1] | tert-butyl |

TABLE 2-continued

| Cpd # | Stereochem | $Z^3$ | $R^2$ | [3,4-diyl aryl] | [benzamide aryl] | —Z—EWG— | $R^c$ |
|---|---|---|---|---|---|---|---|
| 9 | 1s,4s | N | — | phenyl | 4-CF$_3$phenyl | cyclohexyl-NHC(O)- | cyclopropyl |
| 10 | 1s,4s | N | — | phenyl | 4-CF$_3$phenyl | cyclohexyl-NHC(O)- | tert-butyl | and are named as follows:

N-(4-(4-amino-1-(1-(2-cyano-3-cyclopropylacryloyl)piperidin-3-yl)-1H-pyrazolo[3,4-d]pyrimidin-3-yl)phenyl)-4-(trifluoromethyl)benzamide;

N-(4-(4-amino-1-(1-(2-cyano-3-cyclopropylacryloyl)piperidin-4-yl)-1H-pyrazolo[3,4-d]pyrimidin-3-yl)phenyl)-4-(trifluoromethyl)benzamide;

N-(4-(4-amino-1-(1-(2-cyano-4,4-dimethylpent-2-enoyl)piperidin-3-yl)-1H-pyrazolo[3,4-d]pyrimidin-3-yl)phenyl)-4-(trifluoromethyl)benzamide;

N-(4-(4-amino-1-((1-(2-cyano-3-cyclopropylacryloyl)pyrrolidin-2-yl)methyl)-1H-pyrazolo[3,4-d]pyrimidin-3-yl)phenyl)-4-(trifluoromethyl)benzamide;

N-(4-(4-amino-1-((1-(2-cyano-4,4-dimethylpent-2-enoyl)pyrrolidin-2-yl)methyl)-1H-pyrazolo[3,4-d]pyrimidin-3-yl)phenyl)-4-(trifluoromethyl)benzamide;

N-(4-(4-amino-1-(1-(2-cyano-4,4-dimethylpent-2-enoyl)piperidin-4-yl)-1H-pyrazolo[3,4-d]pyrimidin-3-yl)phenyl)-4-(trifluoromethyl)benzamide;

N-(4-(4-amino-1-((1r,4r)-4-(2-cyano-3-cyclopropylacrylamido)cyclohexyl)-1H-pyrazolo[3,4-d]pyrimidin-3-yl)phenyl)-4-(trifluoromethyl)benzamide;

N-(4-(4-amino-1-((1r,4r)-4-(2-cyano-4,4-dimethylpent-2-enamido)cyclohexyl)-1H-pyrazolo[3,4-d]pyrimidin-3-yl)phenyl)-4-(trifluoromethyl)benzamide;

N-(4-(4-amino-1-((1s,4s)-4-(2-cyano-3-cyclopropylacrylamido)cyclohexyl)-1H-pyrazolo[3,4-d]pyrimidin-3-yl)phenyl)-4-(trifluoromethyl)benzamide;

N-(4-(4-amino-1-((1s,4s)-4-(2-cyano-4,4-dimethylpent-2-enamido)cyclohexyl)-1H-pyrazolo[3,4-d]pyrimidin-3-yl)phenyl)-4-(trifluoromethyl)benzamide;

or and E or Z isomer thereof or a pharmaceutically acceptable salt thereof.

Embodiments

Embodiment A

In one embodiment, a compound of Formula (I) is as defined above (or a pharmaceutically acceptable salt thereof) in which the fused bicyclic moiety thereof has the structure:

is:

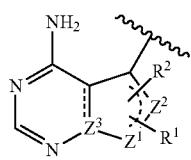

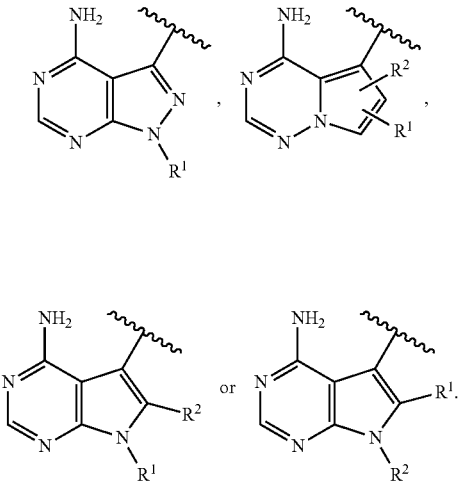

Preferably,

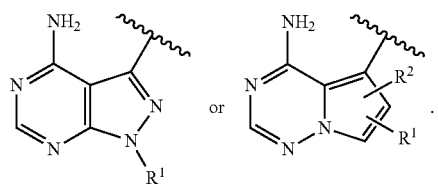

Preferably,

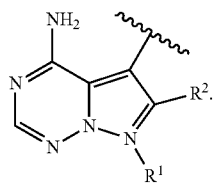

Preferably,

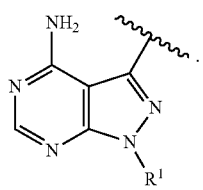

Preferably,

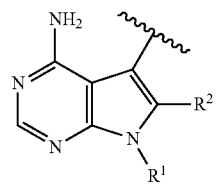

Embodiment B

In another embodiment, a compound of Formula (I) is as defined above (or a pharmaceutically acceptable salt thereof) or as more specifically defined in embodiment (A) and groups contained therein, wherein in one group of compounds L is O, S, SO, $SO_2$, NR or NHCONH; preferably O, S, NH, or N(methyl), or NHCONH; more preferably L is O or NHCONH. Within this embodiment, in one group of compounds L is O. Within this embodiment, in one group of compounds L is NHCONH, NHCO, or CONH, preferably NHCONH. Within this embodiment and groups contained therein, in one group of compounds $R^2$ is hydrogen, methyl, fluoro, or trifluoromethyl, preferably hydrogen or methyl, more preferably hydrogen.

Embodiment C

In another embodiment, a compound of Formula (I) is as defined above (or a pharmaceutically acceptable salt thereof) or as more specifically defined in embodiments (A) and/or (B) and groups contained therein, in one group of compounds $R^3$ and $R^4$ are independently hydrogen, alkyl, alkoxy, cyano, halo, haloalkyl or haloalkoxy; preferably $R^3$ and $R^4$ are independently hydrogen, methyl, fluoro, methoxy, chloro, trifluoromethyl, or trifluoromethoxy. Preferably, $R^3$ and $R^4$ are independently hydrogen or fluoro. Preferably, in one group of compounds

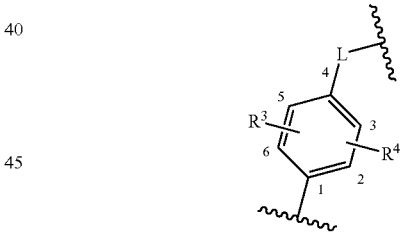

is a ring of formula:

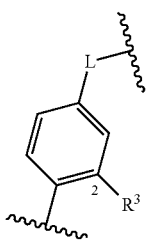

where $R^3$ is methyl, ethyl, chloro, fluoro or trifluoromethyl, preferably methyl, ethyl, chloro or fluoro, more preferably methyl, ethyl, or chloro, even more preferably chloro or fluoro, particularly preferably fluoro. Preferably, in another group of compounds is a ring of formula

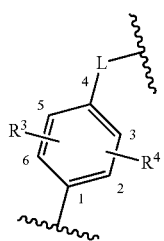

is a ring of formula

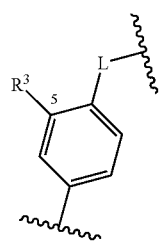

where R³ is alkyl or halo, preferably methyl, chloro or fluoro. Preferably, in yet another group of compounds

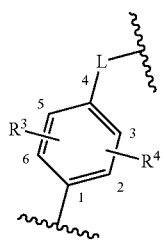

is a ring of formula

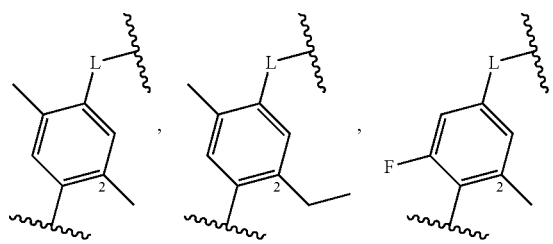

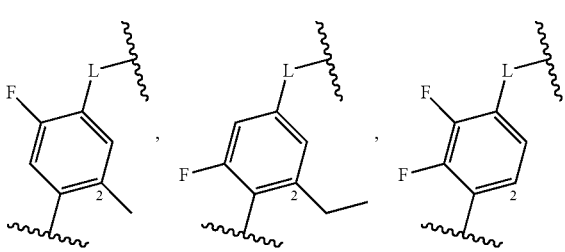

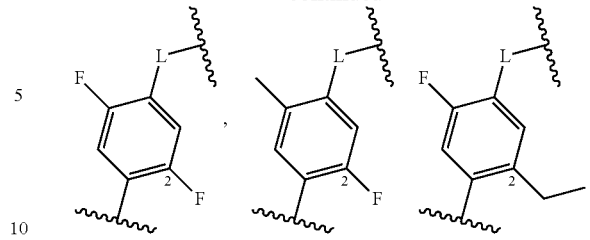

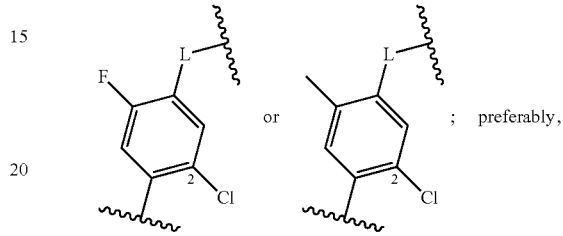

, 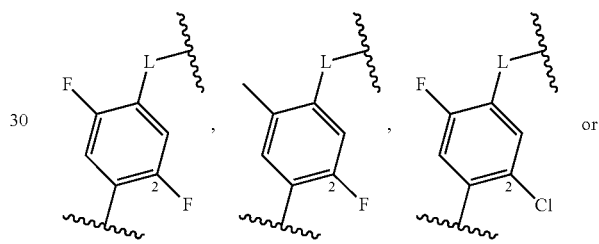 or

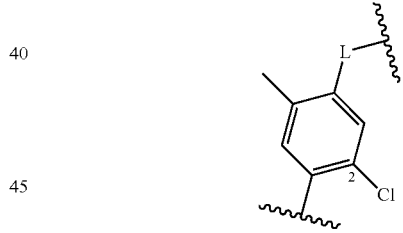

Embodiment D—

In another embodiment, a compound of Formula (I) is as defined above (or a pharmaceutically acceptable salt thereof) or as more specifically defined in embodiments (A), (B) and/or (C) and groups contained therein, wherein in one group of compounds R⁶ and R⁷ are independently hydrogen, alkyl, alkoxy, halo, haloalkyl, haloalkoxy, or cyano. Preferably, R⁶ and R⁷ are independently hydrogen, methyl, methoxy, fluoro, chloro, trifluoromethyl, trifluoromethoxy, or cyano. Preferably, in another group of compounds:

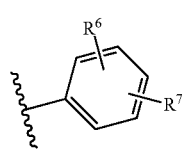

is a ring of formula:

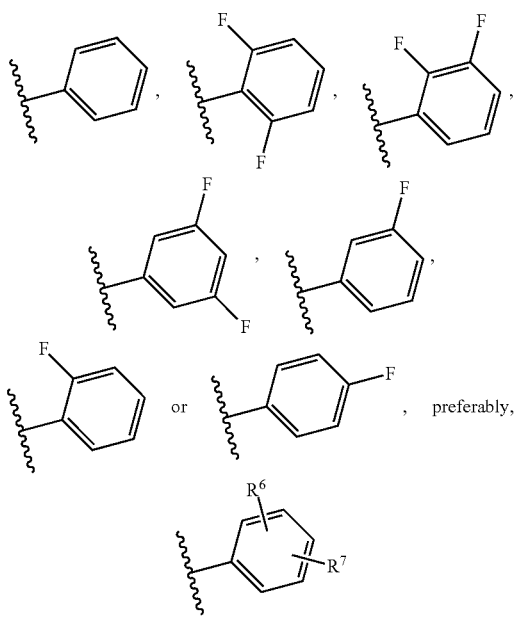, preferably, is a ring of formula:

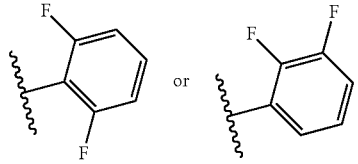 [SMILES: *c1c(F)cccc1F ; *c1cccc(F)c1F]

Embodiment E

In another embodiment, a compound of Formula (I) is as defined above (or a pharmaceutically acceptable salt thereof) or as more specifically defined in embodiments (A), (B), (C) and/or (D) and groups contained therein, wherein in one group of compounds:

(a) $R^5$ is hydrogen, alkyl, alkoxy, halo, haloalkyl, haloalkoxy, or cyano. Preferably, $R^5$ is hydrogen, methyl, methoxy, fluoro, chloro, trifluoromethyl, trifluoromethoxy, or cyano;

$R^1$ is —Z-(EWG)-C(CN)=CHR$^c$ where Z is bond, NR$^a$ (where R$^a$ is hydrogen or alkyl), —O—, —S—, —S(O)—, —S(O$_2$)—, alkylene, cycloalkylene, heteroalkylene, aryl or heteroaryl, EWG is an electron withdrawing group, and R$^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl;

and L is O.

(b) In another group of compounds $R^1$ is hydrogen, alkyl, alkoxy, halo, haloalkyl, haloalkoxy, or cyano. Preferably, $R^1$ is hydrogen, methyl, methoxy, fluoro, chloro, trifluoromethyl, trifluoromethoxy, or cyano;

$R^5$ is —Z-(EWG)-C(CN)=CHR$^c$ where Z is bond, NR$^a$ (where R$^a$ is hydrogen or alkyl), —O—, —S—, —S(O)—, —S(O$_2$)—, alkylene, cycloalkylene, aryl, heteroaryl, or heteroalkylene, EWG is an electron withdrawing group, and R$^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl;

and L is NHCONH, NHCO or CONH.

(c) Within the groups in embodiment (E), e.g., subparts (a) and (b), in one group of compounds Z is bond, NR$^a$, O, or methylene and EWG is —CH(haloalkyl)-, —NR'—, —S(O$_2$)—, —S(O)—, —C(O)—, —NR'C(O)—, —NR'S(O$_2$)—, —PO(OR')—,

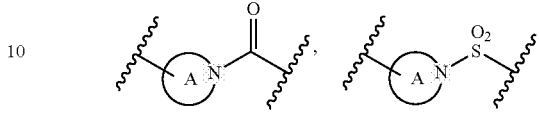

heteroaryl, or aryl; wherein each R' is independently hydrogen, alkyl, substituted alkyl, or cycloalkyl; ring A is heterocycloamino where the carbonyl and sulfonyl groups are attached to —C(CN)=CHR$^c$ in the definition of R$^1$ and R$^5$ in compound of Formula (I); and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl, preferably hydrogen, alkoxy, alkyl, cyano, nitro, halo, alkylsulfonyl, haloalkyl, or haloalkoxy Within the groups in (c), in one group of compounds EWG is aryl or heteroaryl, preferably, EWG is selected from:

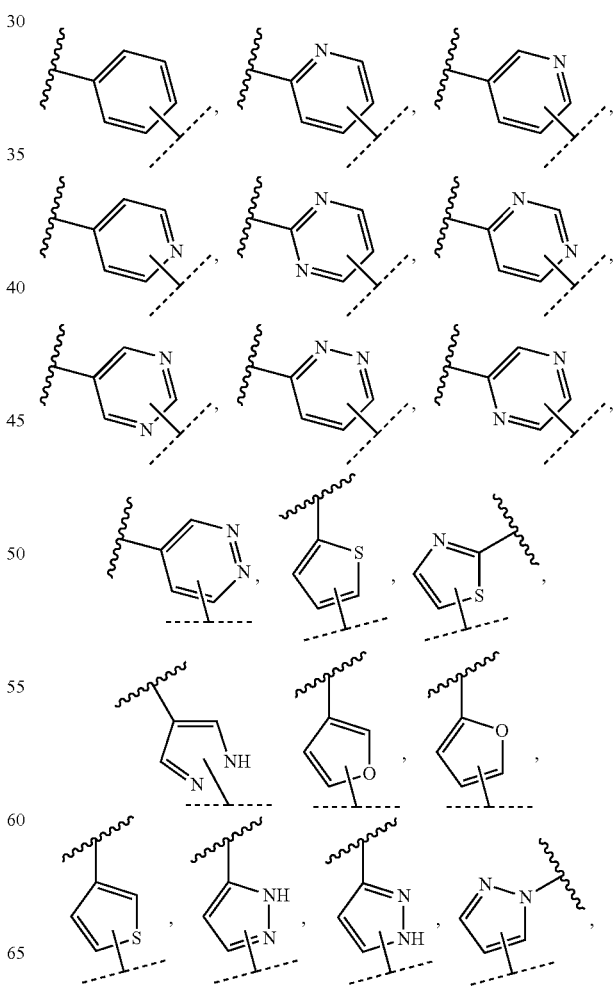

-continued

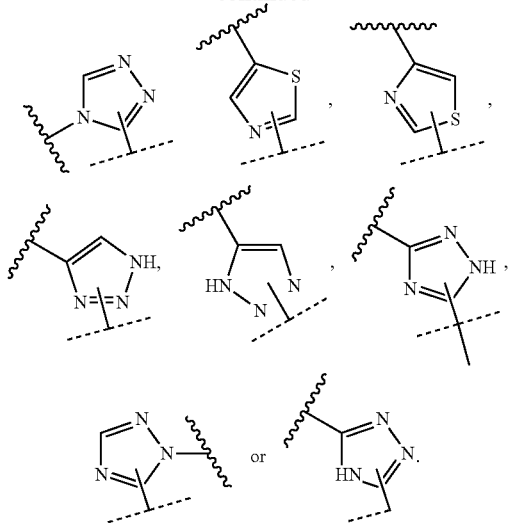

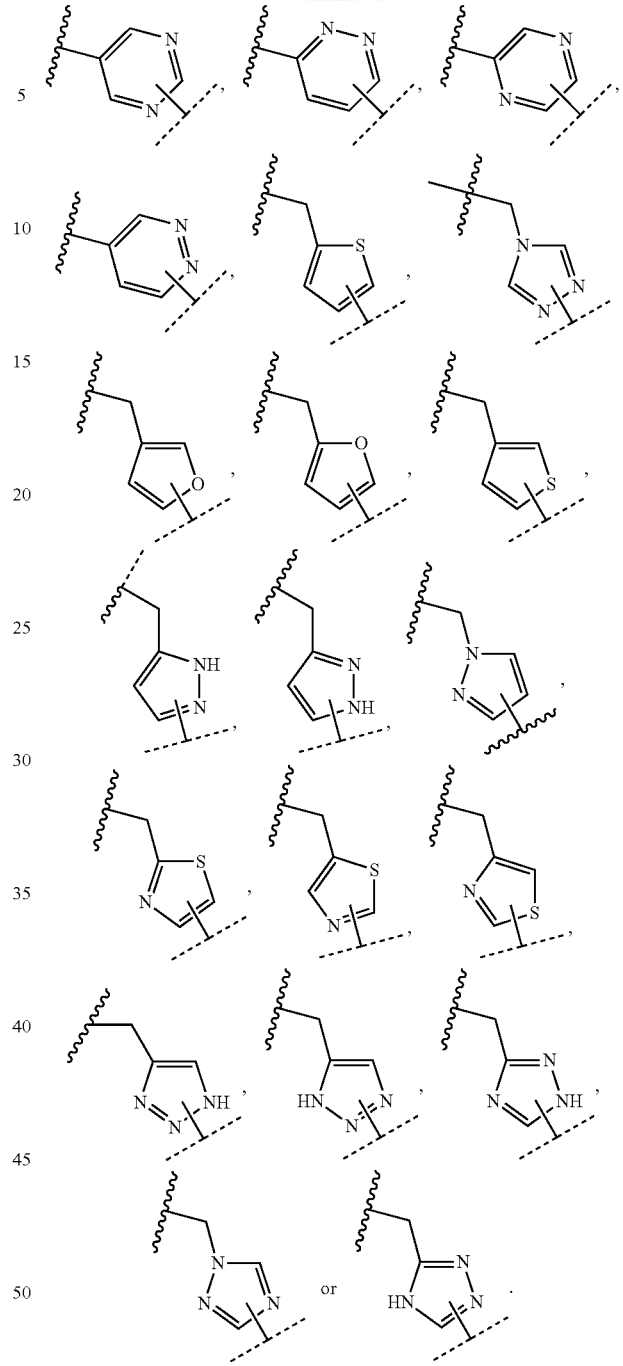

wherein
each such ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably when EWG is heteroaryl wherein heteroaryl ring is six membered ring shown above, then Z is a bond, O, or $NR^a$, preferably a bond;

symbol denotes point of attachment of the ring to —Z— when Z is other than bond and directly to the rest of the molecule when Z is a bond; and

is bond attaching the ring to —C(CN)=$CHR^c$.
Preferably, in another group of compounds EWG is oxazol-5-yl that is connected at the 2-position to —C(CN)=$CHR^c$
(d) Within the groups in embodiment (E) e.g., subparts (a) and (b), in one group of compounds —Z-EWG- is selected from:

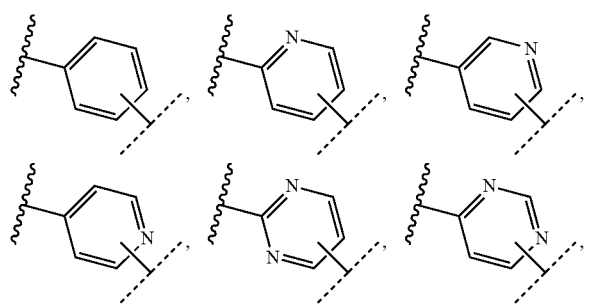

each substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.
Preferably, —Z-EWG- is selected from: phenyl, 2-, 3-, or 4-pyridyl substituted as defined above.
(i) Within the groups in embodiment (E), e.g., subparts (a), (b), (c), and/or (d) and groups contained therein, in one group of compounds when EWG is a six membered ring, then the —C(CN)=$CH(R^c)$ group is attached to the carbon atom in the six membered ring that is preferably meta to the carbon atom that attaches the six membered ring to —Z—.

(ii) Within the groups in embodiment (E), e.g., (a), (b), (c), and/or (d) and groups contained therein, in one group of compounds when EWG is a five membered ring, then the —C(CN)=CH(R$^c$) group is attached to the atom in the five membered ring that is preferably ortho to the atom that attaches the five membered ring to —Z—.

(e) Within groups in (c), in one group of compounds Z is bond, NR$^a$, O, or methylene and EWG is

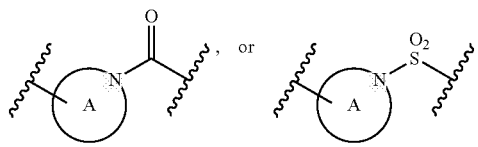

where ring A is heterocycloamino where the carbonyl and sulfonyl groups are attached to —C(CN)=CHR$^c$ in the definition of R$^1$ and R$^5$ in compound of Formula (I); and heterocycloamino is substituted with one or two substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, ring A is pyrrolidinyl, piperidinyl, or piperazinyl optionally substituted with methyl, or fluoro.

Within embodiment (e) and groups contained therein Z is a bond, methylene, or O. Preferably, —Z-EWG- is:

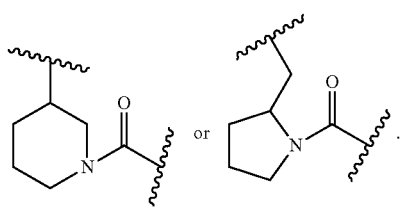 [SMILES: *C(=O)N1CCCC(*)C1 ; *CC1CCCN1C(*)=O]

Preferably, —Z-EWG- is:

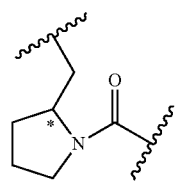 [SMILES: *CC1CCCN1C(*)=O]

where the stereochemistry at *C is (R).

(f) In another group of compounds R$^1$ is hydrogen, alkyl, alkoxy, halo, haloalkyl, haloalkoxy, or cyano. Preferably, R$^1$ is hydrogen, methyl, methoxy, fluoro, chloro, trifluoromethyl, trifluoromethoxy, or cyano;

R$^5$ is —Z-(EWG)-C(CN)=CHR$^c$ where Z is bond and EWG bond, and R$^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl;

and L is NHCONH, NHCO or CONH when Ar is an electron deficient π system.

(g) Within groups in embodiment (E) i.e., (a) and (b), in one group of compounds Z is bond, or alkylene and EWG —OCO—, —SO$_2$—, —NR'CO— or —NR'SO$_2$—. Preferably, EWG is —NR'CO— or —NR'SO$_2$—, more preferably —NHCO—. Within groups in (g) and groups contained therein, in one group of compounds Z is alkylene, preferably ethylene, —C(CH$_3$)$_2$—CH$_2$—, or —CH$_2$—C(CH$_3$)$_2$—, preferably methylene or —CH$_2$—C(CH$_3$)$_2$—.

Embodiment F

Within compounds of Formula (I) as defined above, wherein in embodiments (A), (B), (C), (D), and/or (E) and groups contained therein, and wherein in subparts (a)-(g) of Embodiment E and groups contained therein, one group of compounds R$^c$ is methyl, ethyl, tert-butyl, isopropyl, cyclopropyl, trifluoromethyl, 2,2,2-trifluoroethyl, 2-methyl-2-methylaminoethyl, 2-methyl-2-dimethylaminoethyl, or 1-methylaminocycloprop-1-ylene, or 1-dimethylaminocycloprop-1-ylene; preferably R$^c$ is cyclopropyl or tert-butyl, more preferably R$^c$ is cyclopropyl.

Embodiment G

In another embodiment, within the compound of Formula (I) as defined above wherein in embodiments (A), (B), (C), (D), (E), and/or (F), and groups contained therein, in one group of compounds the

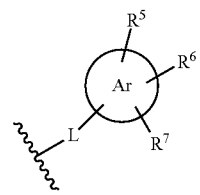

group is attached at the 4-position of the phenyl ring, the carbon atom of the phenyl ring attached to

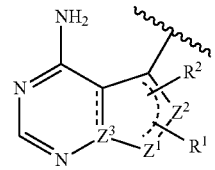

being carbon 1.

(i) Within the groups in embodiment G, in one group of compounds,

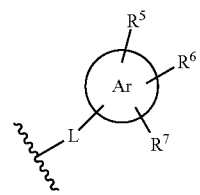

is phenyl.

(ii) Within groups in embodiment G, in another group of compounds when R$^1$ is hydrogen, alkyl, alkoxy, halo, haloalkyl, haloalkoxy, or cyano, then, Ar is phenyl substituted at meta or para, preferably meta position with R$^5$, and R$^6$ is ortho or para to R$^5$.

(iii) Within groups in embodiment G, in another group of compounds when R$^1$ is hydrogen, alkyl, alkoxy, halo, haloalkyl, haloalkoxy, or cyano, then, Ar is heteroaryl, preferably pyridyl substituted with R$^5$ at carbon adjacent to ring nitrogen in the pyridyl ring, and R$^6$ is ortho or para to R$^5$.

(iv) Within groups in embodiment G, in another group of compounds when R$^5$ is hydrogen, alkyl, alkoxy, halo, haloalkyl, haloalkoxy, or cyano, then, Ar is phenyl substituted at meta and/or para with $R^5$ or $R^6$ the carbon atom of Ar attached to phenyl being position 1. Preferably, $R^5$ or $R^6$ is chloro or trifluoromethyl.

(v) Within groups in embodiment G, in another group of compounds when $R^5$ is hydrogen, alkyl, alkoxy, halo, haloalkyl, haloalkoxy, or cyano, Ar is heteroaryl, preferably pyridyl or pyrimidinyl optionally substituted with $R^5$-$R^7$.

(vi) Within groups in embodiment G, in another group of compounds when $R^1$ is hydrogen, alkyl, alkoxy, halo, haloalkyl, haloalkoxy, or cyano, then, Ar is heterocyclyl, preferably, piperidinyl, pyrrolidinyl, 2,3-dihydroindolyl.

(vii) Within groups in embodiment G, in another group of compounds when $R^5$ is hydrogen, alkyl, alkoxy, halo, haloalkyl, haloalkoxy, or cyano, then, Ar is a ring of formula:

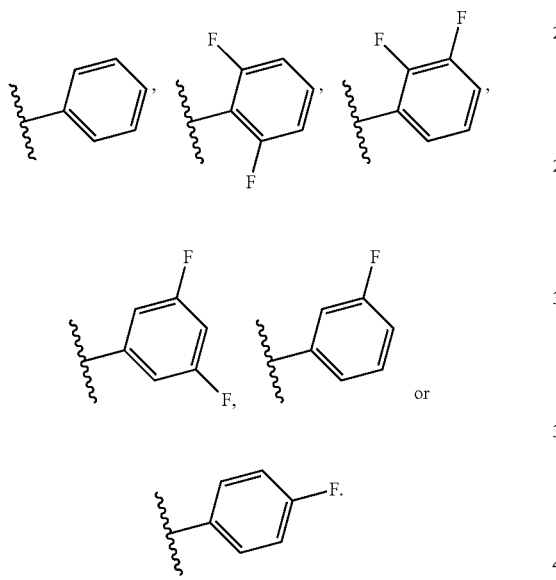

Preferably,

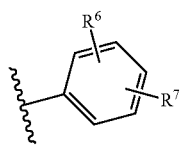

is a ring of formula:

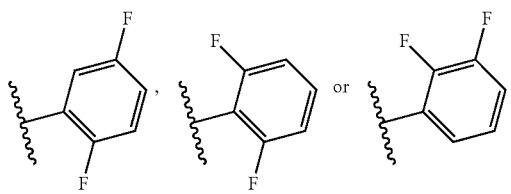

Embodiment H

In yet another embodiment, the compound of Formula (I) as defined above has the structure (Ia) or (Ib) shown below:

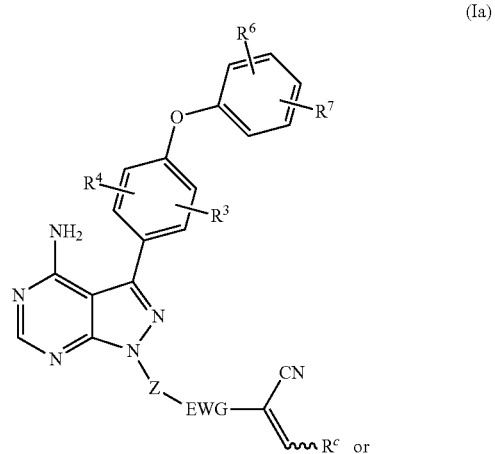

(Ia)

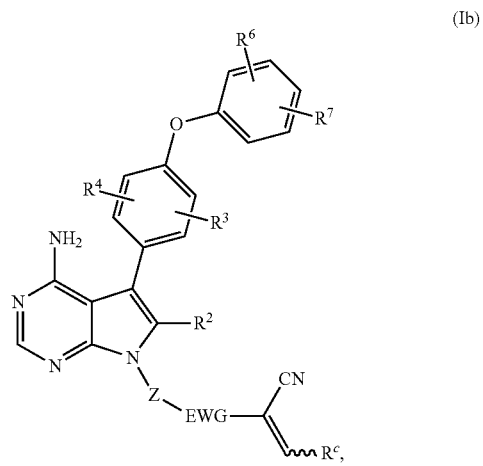

(Ib)

wherein:

$R^2$ is hydrogen or alkyl;

$R^3$ and $R^4$ are independently hydrogen, alkyl, haloalkyl, fluoro or chloro;

$R^6$ and $R^7$ are independently hydrogen or fluoro;

Z is a bond, alkylene, or alkylene-O— wherein —O— is connected to EWG;

EWG is —CO—, —NR'CO—, —NR'SO$_2$—,

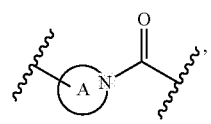

—SO$_2$— or a five membered heteroaryl ring where R' is hydrogen or alkyl and ring A is 2-pyrrolidinyl or 3-piperidinyl, each ring optionally substituted with one or two alkyl provided that (i) when Z is a bond then EWG is 3-piperidinylcarbonyl optionally substituted with one or two alkyl; (ii) when Z is alkylene-O— then EWG is —CO— and (iii) when Z is alkylene, then ring A is not 3-piperidinylcarbonyl optionally substituted with one or two alkyl; and $R^c$ is cycloalkyl, alkyl, or substituted alkyl; provided that: when Z is

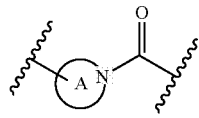

then at least one of $R^2$, $R^3$, $R^4$ and $R^5$ is hydrogen. (note: for the groups in the definition of EWG, left side of the group is attached to Z and right side is attached to —C(CN)=$R^c$ e.g., in —NR'CO—, NR' is attached to Z and CO is attached to) —C(CN)=$R^c$.

(i) Within embodiment H, in one group of compound the compound of Formula (I) has structure (Ia).

(ii) Within embodiment H, in another group of compounds the compound of Formula (I) has structure (Ib).

(a) Within the embodiment (H) and groups contained therein, in one group of compounds:

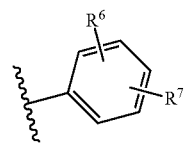

is a ring of formula:

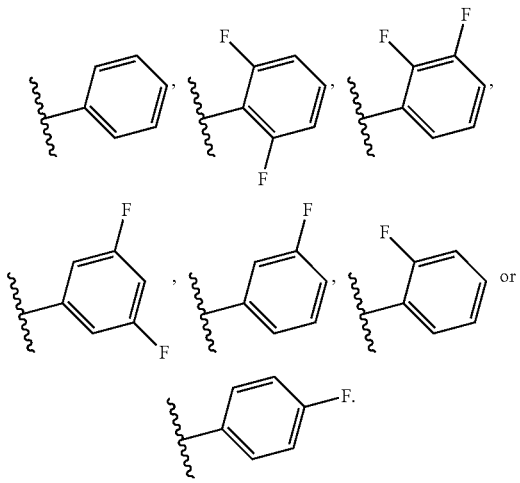

Preferably,

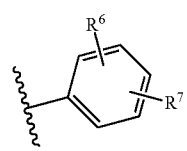

is a ring of formula:

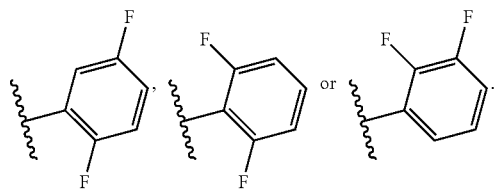

(b) Within embodiment (H) and groups contained therein, and subpart (a) of Embodiment (H) and groups contained therein, in one group of compounds:

$R^2$ is hydrogen or alkyl, preferably hydrogen or methyl, more preferably hydrogen;

$R^3$ and $R^4$ are independently hydrogen, methyl, ethyl, trifluoromethyl, fluoro or chloro. Preferably, within groups in (b), in one group of compounds

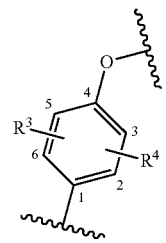

is a ring of formula:

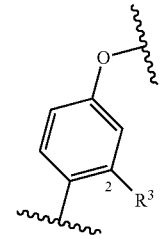

where $R^3$ is methyl, ethyl, chloro, fluoro or trifluoromethyl, preferably methyl, ethyl, chloro or fluoro, more preferably, methyl, ethyl, or chloro, even more preferably chloro or fluoro, particularly preferably fluoro. Preferably, within groups in (b), in another group of compounds

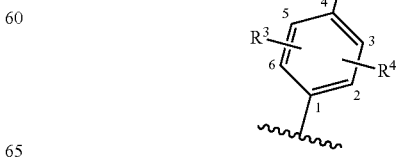

is a ring of formula

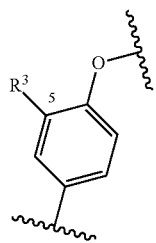

where R³ is alkyl or halo, preferably methyl, chloro or fluoro. Preferably, within groups in (b), in yet another group of compounds

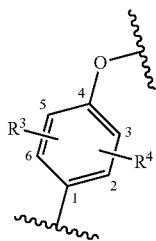

is a ring of formula

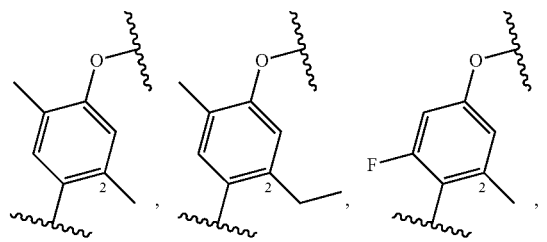

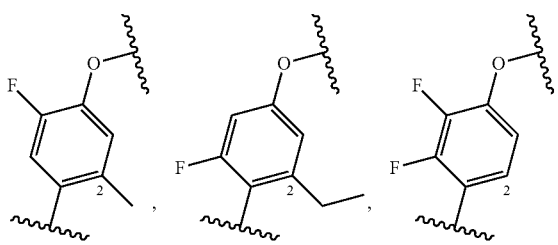

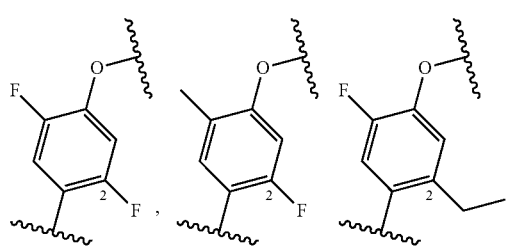

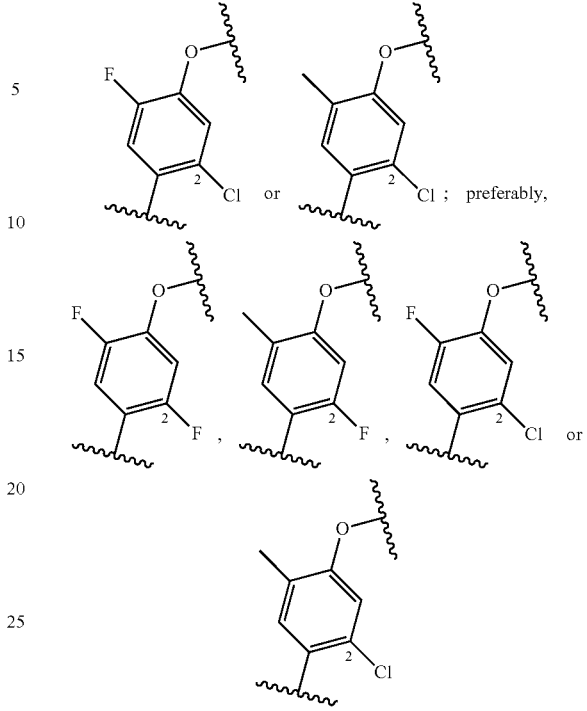

(c) Within embodiment (H) and groups contained therein, and subpart (a) and/or (b) of Embodiment (H) and groups contained therein, in one group of compounds:

Z is a alkylene, or alkylene-O— wherein —O— is connected to EWG;

EWG is —CO—, —NR'CO—, —NR'SO₂—, or —SO₂— where R' is hydrogen or alkyl, preferably hydrogen or methyl. Preferably, within groups in (c), in one group of compounds is —Z-EWG- is -(alkylene)-NR'CO—, -(alkylene)-NR'SO₂—, -(alkylene)-OCO—, or -(alkylene)-SO₂— wherein Z is ethylene, —C(CH₃)₂—CH₂—, or —CH₂—C(CH₃)₂— and EWG is —NHCO—, —N(CH₃)CO—, —NHSO₂—, —N(CH₃)SO₂—, —SO₂—, or —OCO—, more preferably Z is ethylene, —C(CH₃)₂—CH₂—, or —CH₂—C(CH₃)₂— and EWG is —NHCO—, —N(CH₃)CO—, —NHSO₂—, or —N(CH₃)SO₂—, even more preferably, EWG is —NHCO—.

(d) Within embodiment (H) and groups contained therein, and subpart (a) and/or (b) of Embodiment (H) and groups contained therein, in another group of compounds:

Z is a bond or alkylene; and
EWG is

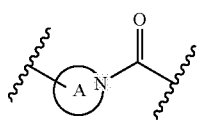

ring A is pyrrolidinyl or piperidinyl, each ring optionally substituted with one or two alkyl, preferably methyl. Within the groups in subpart (d), in one group of compounds —Z-EWG- is 3(R)-piperidin-1-carbonyl. Within the groups in subpart (d), in another group of compounds —Z-EWG- is 2-CH₂-pyrrolidin-1-ylcarbonyl, 2-CH(CH₃)-pyrrolidin-1-ylcarbonyl; 2-CH₂-3,3-dimethylpyrrolidin-1-ylcarbonyl or 2-CH₂-4,4-dimethylpyrrolidin-1-ylcarbonyl the carbon atom of the pyrrolidinyl ring attached to —CH₂— having (R) stereochemistry.

(e) Within embodiment (H) and groups contained therein, and subpart (a) and/or (b) of Embodiment (H) and groups contained therein, in another group of compounds:

Z is alkylene; and

EWG is a five membered heteroaryl ring, preferably Z is methylene, ethylene, —C(CH₃)₂CH₂—, —CH₂—C(CH₃)₂— and Z is oxazolyl, more preferably —Z-EWG- is 2-C(CN)=CR$^c$-oxazol-5-yl.

(f) Within embodiment (H) and groups contained therein, and subpart (a) and/or (b) and/or (c) and/or (d) and/or (e) and groups contained therein, in one group of compounds R$^c$ is cycloalkyl, alkyl, or substituted alkyl, preferably, isopropyl, tert-butyl or 1-dimethylamino-1-methylethyl, more preferably cyclopropyl.

Embodiment I:

In yet another embodiment, the compound of Formula (IA) as defined above has the structure (Ic) below:

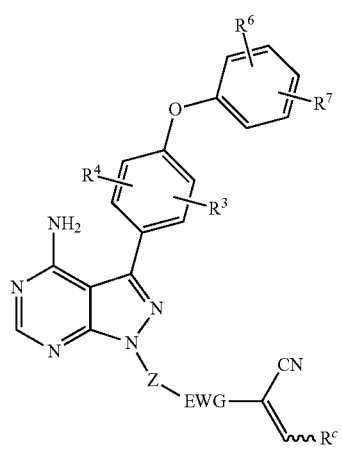

(Ic)

wherein:

R³ and R⁴ are independently hydrogen, alkyl, haloalkyl, fluoro or chloro;

R⁶ and R⁷ are independently hydrogen or fluoro;

Z-EWG is:

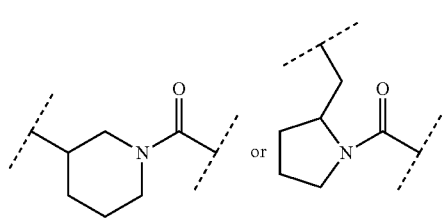

each ring optionally substituted with one or two substituents selected from alkyl, fluoro, or hydroxy; and R$^c$ is cycloalkyl, alkyl, substituted alkyl, cycloalkyleneNR$^d$R$^e$ or cycloalkylene(alkylene)NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro;

provided that at least one of R³, R⁴, R⁵ and R⁶ is not hydrogen, preferably one of R³ and R⁴ is not hydrogen.

(a) Within the embodiment (I) and groups contained therein, in one group of compounds:

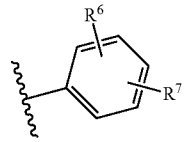

is a ring of formula:

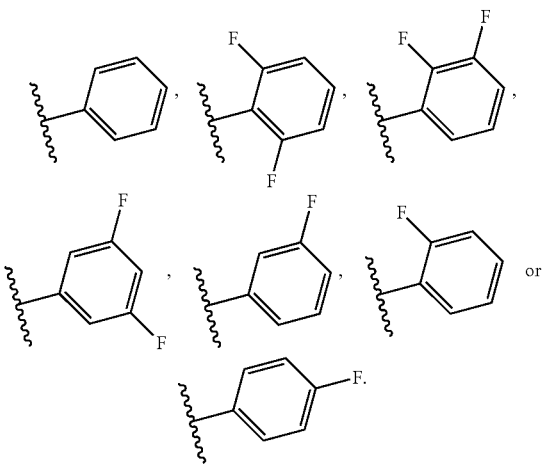

Preferably,

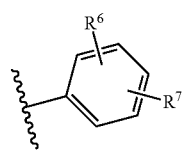

is a ring of formula: phenyl,

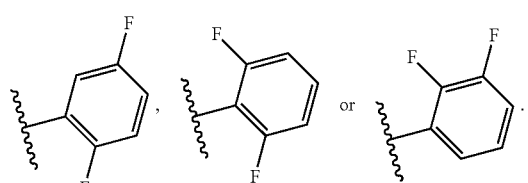

Within (a), in one group of compounds

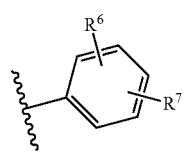

is phenyl. Within (a), in another group of compounds

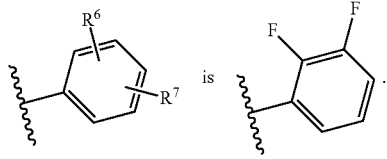 is 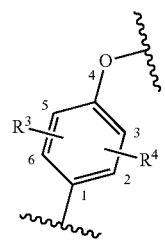.

Within (a), in yet another group of compounds

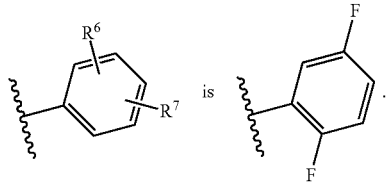 is 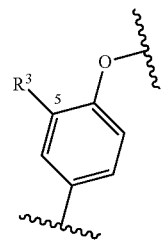.

(b) Within embodiment (I) and groups contained therein, and subpart (a) of Embodiment (I) and groups contained therein, in one group of compounds:

$R^3$ and $R^4$ are independently hydrogen, methyl, ethyl, trifluoromethyl, fluoro or chloro. Preferably, within groups in (b), in one group of compounds

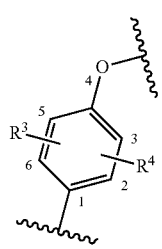

is a ring of formula:

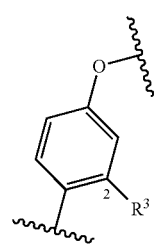

where $R^3$ is methyl, ethyl, chloro, fluoro or trifluoromethyl, preferably methyl, ethyl, chloro or fluoro, more preferably, methyl, ethyl, or chloro, even more preferably chloro or fluoro, particularly preferably fluoro. Preferably, within groups in (b), in another group of compounds

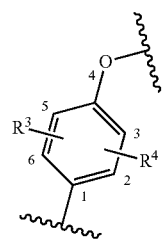

is a ring of formula

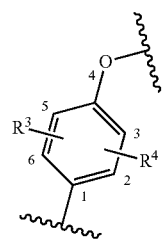

where $R^3$ is alkyl or halo, preferably methyl, chloro or fluoro. Preferably, within groups in (b), in yet another group of compounds

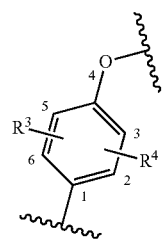

is a ring of formula

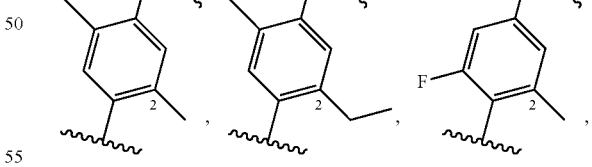
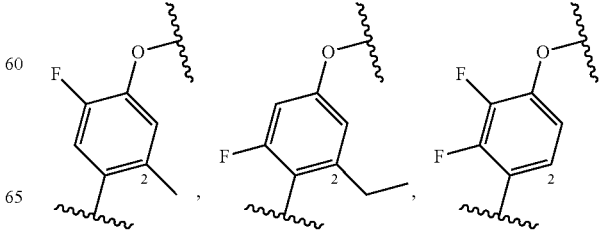

-continued

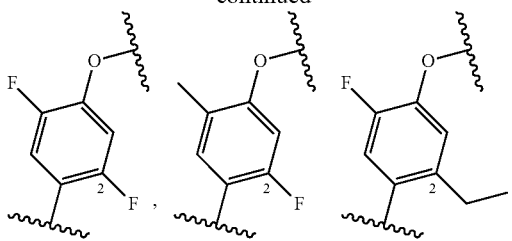

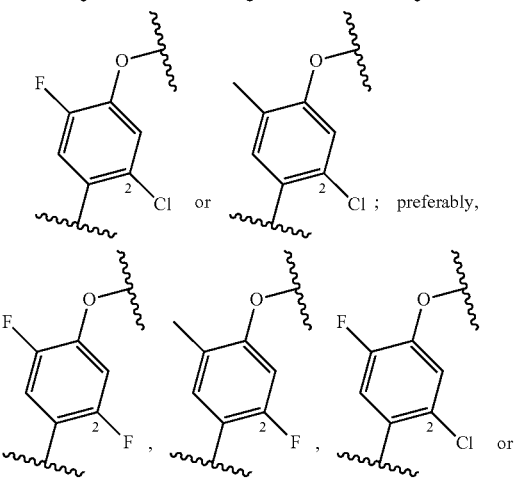

(c) Within embodiment (I) and groups contained therein, and subpart (a) and/or (b) of Embodiment (I) and groups contained therein, in one group of compounds:

Z-EWG is:

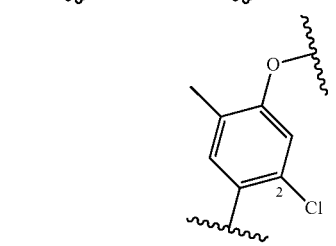

optionally substituted with one or two substituents selected from alkyl, fluoro, or hydroxy. Within the groups in subpart (c), in one group of compounds —Z-EWG- is

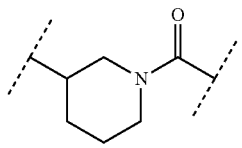

where the stereochemistry at *C is (R).

(d) Within embodiment (I) and groups contained therein, and subpart (a) and/or (b) of Embodiment (I) and groups contained therein, in one group of compounds:

Z-EWG is:

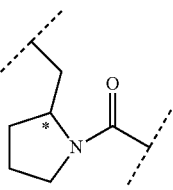

Within the groups in subpart (d), in one group of compounds

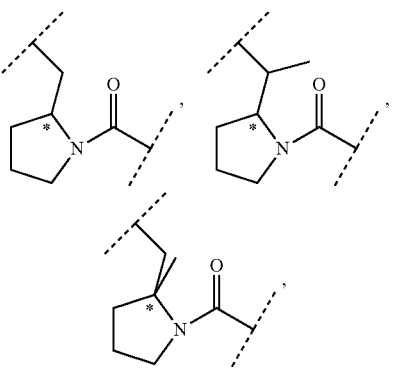

—Z-EWG- is

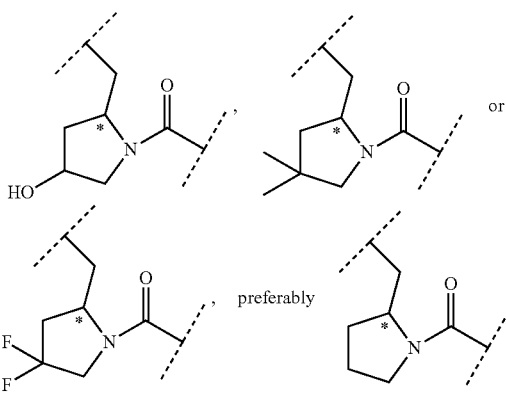

where the stereochemistry at *C is (RS), (R) or (S); preferably (R). More preferably (S).

(e) Within embodiment (I) and groups contained therein, and subpart (a) and/or (b) and/or (c) and/or (d) and groups contained therein, in one group of compounds $R^c$ is cycloalkyl, preferably cyclopropyl.

(f) Within embodiment (I) and groups contained therein, and subpart (a) and/or (b) and/or (c) and/or (d) and groups contained therein, in one group of compounds $R^c$ is alkyl, preferably isopropyl or tert-butyl, more preferably isopropyl.

(g) Within embodiment (I) and groups contained therein, and subpart (a) and/or (b) and/or (c) and/or (d) and groups contained therein, in one group of compounds $R^c$ is substituted alkyl, preferably, alkyl substituted with alkoxy or NRR' (where R is hydrogen, alkyl, alkoxyalkyl or cycloalkyl and R' is hydrogen or alkyl), or heterocyclyl which is optionally substituted with one or two groups independently selected from alkyl, preferably $R^c$ is —C(CH$_3$)$_2$NH$_2$, —C(CH$_3$)$_2$ NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$morpholine-4-yl. Within groups in (g), in one group of compounds R$^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$ or —C(CH$_3$)$_2$NH(CH$_2$)$_2$OCH$_3$. Within groups in (g), in another group of compounds R$^c$ is —C(CH$_3$)$_2$NHcyclopropyl. Within groups in (g), in yet another group of compounds R$^c$ is —C(CH$_3$)$_2$OCH$_2$CH$_3$. Within groups in (g), in yet another group of compounds R$^c$ is —C(CH$_3$)$_2$morpholine-4-yl. Within groups in (g), in yet another group of compounds R$^c$ is —C(CH$_3$)$_2$NH$_2$.

(h) Within embodiment (I) and groups contained therein, and subpart (a) and/or (b) and/or (c) and/or (d) and groups contained therein, in one group of compounds R$^c$ is cycloalkylene(alkylene)NR$^d$R$^e$ (where R$^d$ and R$^e$ are independently hydrogen, alkyl, or cycloalkyl), preferably

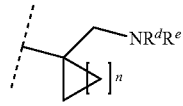

where n is 1-3, R$^d$ is hydrogen, methyl or ethyl, and R$^e$ is hydrogen, methyl, ethyl, or isopropyl.

(i) Within embodiment (I) and groups contained therein, and subpart (a) and/or (b) and/or (c) and/or (d) and groups contained therein, in one group of compounds R$^c$ is cycloalkyleneNR$^d$R$^e$ (where R$^d$ and R$^e$ are independently hydrogen, or alkyl), preferably

where R$^e$ is hydrogen, methyl, ethyl or isopropyl.

(j) Within embodiment (I) and groups contained therein, and subpart (a) and/or (b) and/or (c) and/or (d) and groups contained therein, in one group of compounds R$^c$ is 3 to 6 membered saturated monocyclic heterocyclyl containing one or two heteroatoms selected from N, O, or S and optionally substituted with one or two substituents selected from hydroxy, alkyl or fluoro; preferably pyrrolidinyl, piperidinyl, tetrahydrofuranyl, or tetrahydropyranyl, more preferably 2-pyrrolidinyl, 3- or 4-piperidinyl, 1-methylpiperidin-4-yl, 1-methylpiperidin-3-yl, or 4-tetrahydropyranyl.

Embodiment (J):

In further embodiments 1-100 below, the present disclosure includes:

1. A compound of Formula (I) or a pharmaceutically acceptable salt thereof:

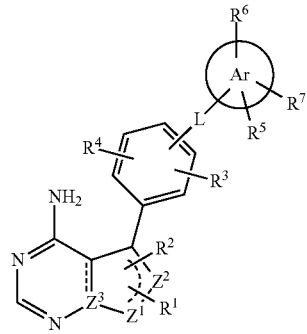

wherein:

dashed line is an optional double bond;

Z$^1$, Z$^2$, and Z$^3$ are —N— or CH, provide that at least one and not more than two of Z$^1$, Z$^2$, and Z$^3$ are simultaneously N;

L is O, CO, CH$_2$, S, SO, SO$_2$, NR, NRCO, CONR, NR'SO$_2$, SO$_2$NR', or NRCONR, where (each R and R' is independently hydrogen or alkyl);

Ar is aryl, heteroaryl, cycloalkyl or heterocyclyl;

one of R$^1$ and R$^5$ is hydrogen, alkyl, hydroxy, alkoxy, halo, haloalkyl, or haloalkoxy and the other is —Z-(EWG)-C(CN)=CHR$^c$ where Z is bond, NR$^a$ (where R$^a$ is hydrogen or alkyl), —O—, S, SO, SO$_2$, alkylene, cycloalkylene, heteroalkylene, —(Z$^a$)$_{n1}$-aryl, or —(Z$^a$)$_{n1}$-heteroaryl (wherein n1 is 0 or 1, Z$^a$ is NR$^a$ (where R$^a$ is hydrogen or alkyl), —O—, S, SO, SO$_2$, alkylene, or heteroalkylene and aryl or heteroaryl is optionally substituted with one or two substituents independently selected from halo, alkyl, alkoxy, alkylthio, haloalkyl, or haloalkoxy), EWG is a bond or an electron withdrawing group, and R$^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl;

R$^2$ is hydrogen, alkyl, hydroxy, alkoxy, cyano, halo or haloalkyl;

R$^3$ and R$^4$ are independently hydrogen, alkyl, hydroxy, alkoxy, cyano, halo, haloalkyl or haloalkoxy; and R$^6$ and R$^7$ are independently hydrogen, alkyl, hydroxy, alkoxy, halo, haloalkyl, haloalkoxy, carboxy, alkoxycarbonyl, cyano, —CONH$_2$, amino, monosubstituted and disubstituted amino;

provided that:

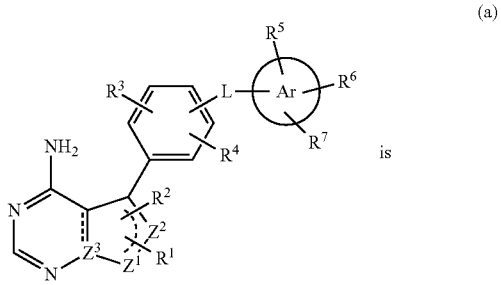

is

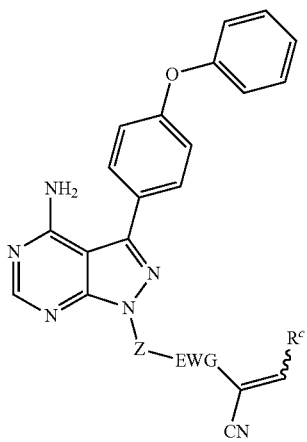

where (i) when $R^c$ is cyclopropyl, tert-butyl, —C(CH$_3$)$_2$CH$_2$OH, —C(CH$_3$)$_2$N(CH$_3$)$_2$, cyclopentyl, isopropyl, —C(CH$_3$)$_2$OCH$_2$CH$_3$, or azetidin-3-yl, then —Z-EWG- is not

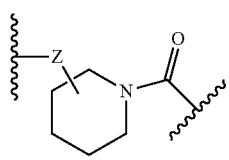

where Z is a bond or methylene; (ii) when $R^c$ is cyclopropyl then —Z-EWG- is not

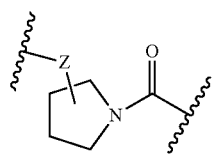

where Z is bond or methylene, and (iii) when $R^c$ is cyclopropyl and Z is cyclohexyl, then EWG is not —NHCO— where NH is bonded to cyclohexyl, and (b) the compound of Formula (IA) is not 2-(3-(4-amino-5-(4-phenoxyphenyl)-7H-pyrrolo[2,3-d]pyrimidin-7-yl)piperidine-1-carbonyl)-3-cyclopropylacrylonitrile; or a pharmaceutically acceptable salt thereof.

2. The compound or salt of previous embodiment 1 wherein:

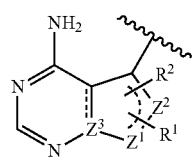

is:

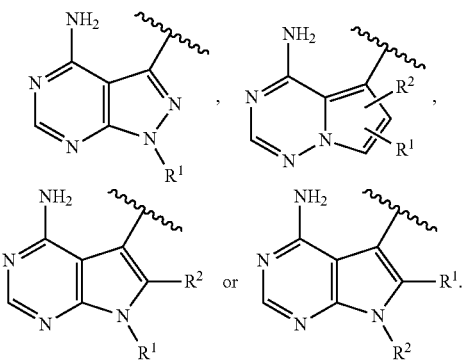

Preferably,

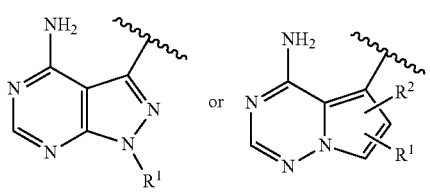

Preferably,

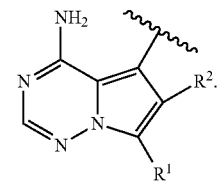

Preferably,

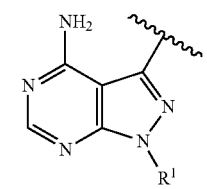

Preferably,

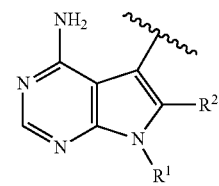

3. The compound or salt of previous embodiment 1 or 2 wherein L is O, S, SO, SO$_2$, NR or NHCONH; preferably O, S, NH, or N(methyl), or NHCONH;

4. The compound or salt of previous embodiment 1 or 2 wherein L is O or NHCONH.

5. The compound or salt of previous embodiment 1 or 2 wherein L is O.
6. The compound or salt of previous embodiment 1 or 2 wherein L is NHCONH, NHCO, or CONH, preferably NHCONH.
7. The compound or salt of any of the previous embodiments 1-6 wherein $R^2$ is hydrogen, methyl, fluoro, or trifluoromethyl, preferably hydrogen.
8. The compound or salt of any of the previous embodiments 1-7 wherein $R^3$ and $R^4$ are independently hydrogen, alkyl, alkoxy, cyano, halo, haloalkyl or haloalkoxy; preferably $R^3$ and $R^4$ are independently hydrogen, methyl, fluoro, methoxy, chloro, trifluoromethyl, or trifluoromethoxy. Preferably, $R^3$ and $R^4$ are independently hydrogen or fluoro.
9. The compound or salt of any of the previous embodiments 1-8 wherein $R^6$ and $R^7$ are independently hydrogen, alkyl, alkoxy, halo, haloalkyl, haloalkoxy, or cyano. Preferably, $R^6$ and $R^7$ are independently hydrogen, methyl, methoxy, fluoro, chloro, trifluoromethyl, trifluoromethoxy, or cyano.
10. The compound or salt of any of the previous embodiments 1-9 wherein:
   $R^5$ is hydrogen, alkyl, alkoxy, halo, haloalkyl, haloalkoxy, or cyano. Preferably, $R^5$ is hydrogen, methyl, methoxy, fluoro, chloro, trifluoromethyl, trifluoromethoxy, or cyano;
   $R^1$ is —Z-(EWG)-C(CN)=$CHR^c$ where Z is bond, $NR^a$ (where $R^a$ is hydrogen or alkyl), —O—, S, SO, $SO_2$, alkylene, cycloalkylene, heteroalkylene, aryl or heteroaryl,
   EWG is an electron withdrawing group, and $R^c$ is alkyl, haloalkoxy, substituted alkyl, cycloalkyl, cycloalkylene$NR^d$ $R^e$ where $R^d$ and $R^e$ are independently hydrogen, alkyl, or cycloalkyl;
   and L is O.
11. The compound or salt of any of the previous embodiments 1-9 wherein:
   $R^1$ is hydrogen, alkyl, alkoxy, halo, haloalkyl, haloalkoxy, or cyano. Preferably, $R^1$ is hydrogen, methyl, methoxy, fluoro, chloro, trifluoromethyl, trifluoromethoxy, or cyano;
   $R^5$ is —Z-(EWG)-C(CN)=$CHR^c$ where Z is bond, $NR^a$ (where $R^a$ is hydrogen or alkyl), —O—, S, SO, $SO_2$, alkylene, cycloalkylene, aryl, heteroaryl, or heteroalkylene,
   EWG is an electron withdrawing group, and $R^c$ is alkyl, haloalkoxy, substituted alkyl, cycloalkyl, cycloalkylene$NR^d$ $R^e$ where $R^d$ and $R^e$ are independently hydrogen, alkyl, or cycloalkyl;
   and L is NHCONH, NHCO or CONN.
12. The compound or salt of any of the previous embodiments 1-11 wherein Z is bond, $NR^a$, O, or methylene and EWG is —CH(haloalkyl)-, —NR'—, —S($O_2$), —S(O), —CO—, —NR'CO—, —NR'$SO_2$—, —PO(OR')—,

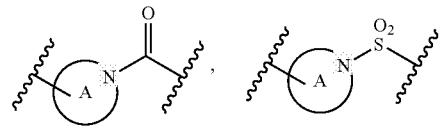

heteroaryl, or aryl; wherein each R' is independently hydrogen, alkyl, substituted alkyl, or cycloalkyl; ring A is heterocycloamino where the carbonyl and sulfonyl groups are attached to —C(CN)=$CHR^c$ in the definition of $R^1$ and $R^5$ in compound of Formula (I); and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl, preferably hydrogen, alkoxy, alkyl, cyano, nitro, halo, alkylsulfonyl, haloalkyl, or haloalkoxy 13. The compound or salt of any of the previous embodiments 1-12 wherein EWG is aryl or heteroaryl, preferably, EWG is selected from:

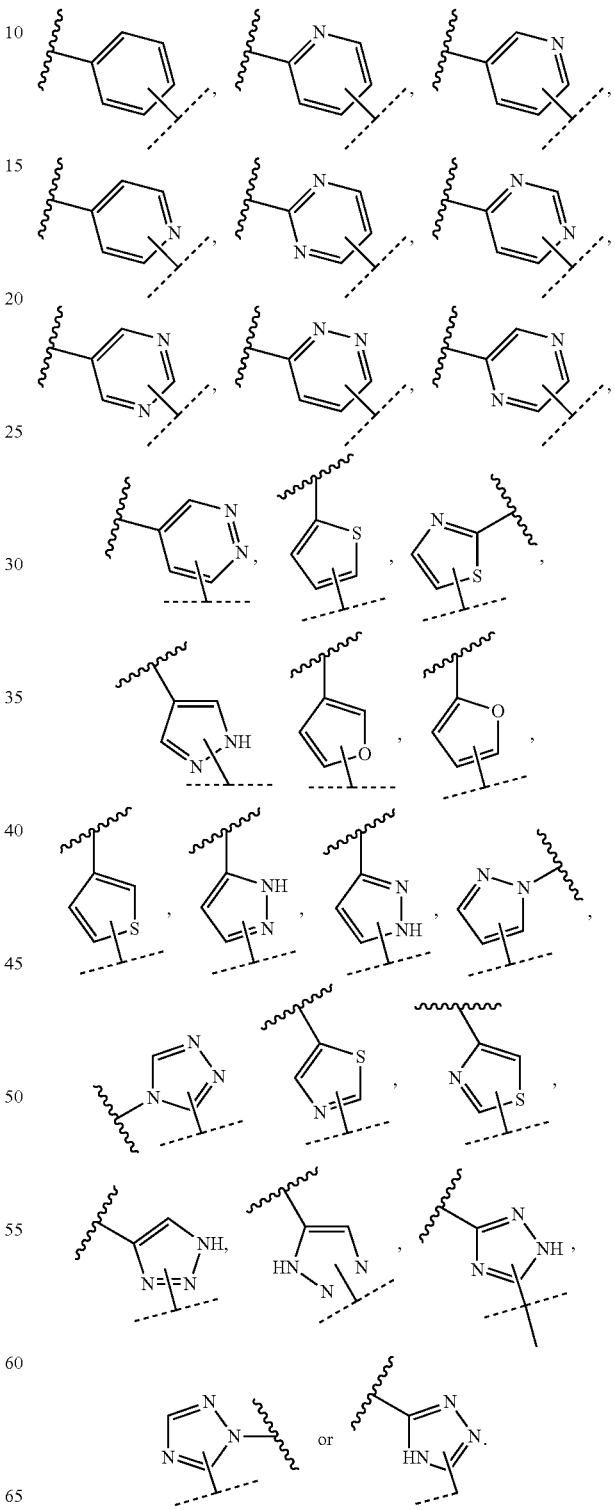

each substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably when EWG is heteroaryl wherein heteroaryl ring is six membered ring shown above, then Z is a bond, O, or NR$^a$, preferably a bond.

symbol denotes point of attachment of the ring to —Z— when Z is other than bond and directly to the rest of the molecule when Z is a bond and

is bond attaching the ring to —CH=C(R$^b$)(EWG).

14. The compound or salt of any of the previous embodiments 1-12 wherein —Z-EWG- is selected from:

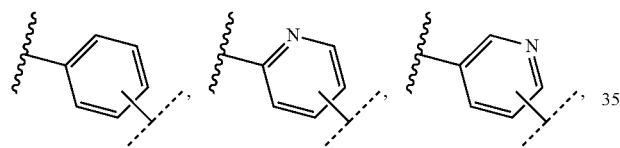

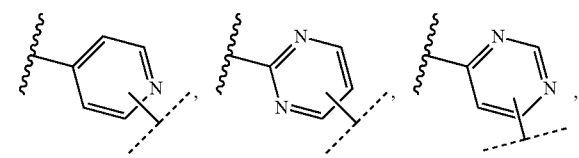

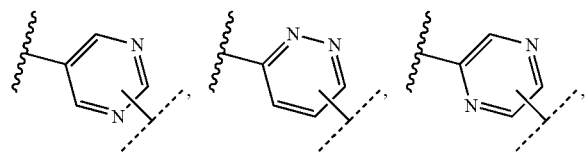

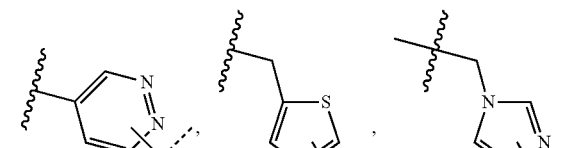

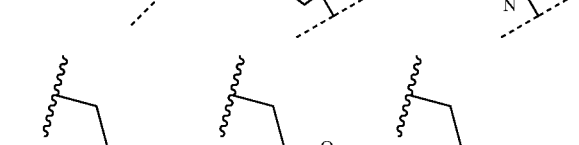

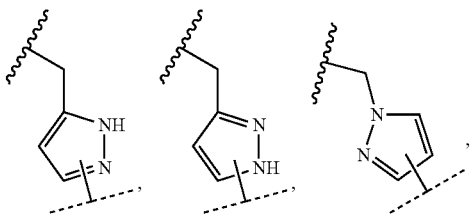

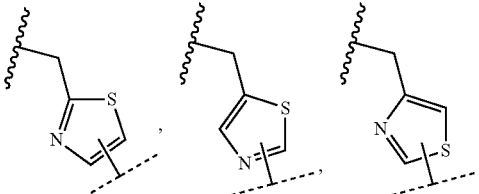

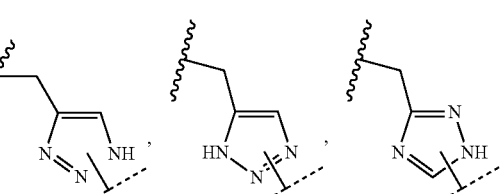

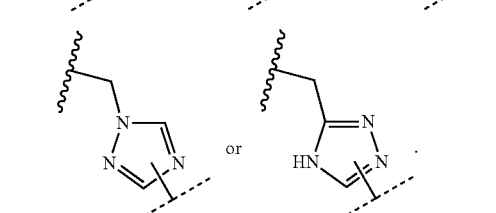

each substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Preferably, —Z-EWG- is selected from: phenyl, 2-, 3-, or 4-pyridyl substituted as above.

15. The compound or salt of any of the previous embodiments 1-12 wherein Z is bond, NR$^a$, O, or methylene and EWG is

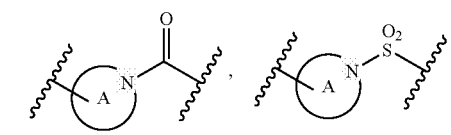

where ring A is heterocycloamino where the carbonyl and sulfonyl groups are attached to —C(CN)=CHR$^c$ in the definition of R$^1$ and R$^5$ in compound of Formula (I); and heterocycloamino is substituted with one or two substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, ring A is pyrrolidinyl, piperidinyl, or piperazinyl optionally substituted with methyl, or fluoro. Preferably, Z is a bond, methylene, or O.

Preferably, —Z-EWG- is:

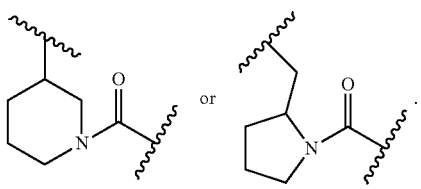 [SMILES: *C(=O)N1CCCC(*)C1 ; *CC1CCCN1C(*)=O]

16. The compound or salt of any of the previous embodiments 1-8 and 11 wherein $R^1$ is hydrogen, alkyl, alkoxy, halo, haloalkyl, haloalkoxy, or cyano. Preferably, $R^1$ is hydrogen, methyl, methoxy, fluoro, chloro, trifluoromethyl, trifluoromethoxy, or cyano;

$R^5$ is —Z-(EWG)-C(CN)=CHR$^c$ where Z is bond and EWG bond, and $R^c$ is alkyl, haloalkoxy, substituted alkyl, cycloalkyl, cycloalkyleneNR$^d$R$^e$ where $R^d$ and $R^e$ are independently hydrogen, alkyl, or cycloalkyl;

and L is NHCONH, NHCO or CONH; and when Ar is an electron deficient π system.

17. The compound or salt of any of the previous embodiments 1-12 wherein Z is bond, or alkylene and EWG —NR'CO—, —NR'SO$_2$—. Preferably, EWG is —NHCO—.

18. The compound or salt of any of the previous embodiments 1-17 wherein $R^c$ is tert-butyl, isopropyl, cyclopropyl, trifluoromethyl, 2,2,2-trifluoroethyl, 2-methyl-2-methylaminoethyl, 2-methyl-2-dimethylaminoethyl, or 1-methylaminocycloprop-1-ylene, or 1-dimethylaminocycloprop-1-ylene.

19. The compound or salt of any of the previous embodiments 1-18 wherein the

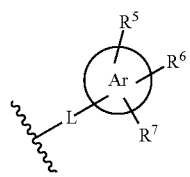

group is attached at the 4-position of the phenyl ring, the carbon atom of the phenyl ring attached to

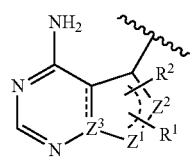

being carbon 1.

20. The compound or salt of any of the previous embodiments 1-19 wherein

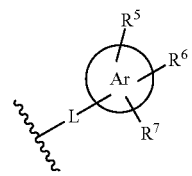

is phenyl.

21. The compound or salt of the previous embodiment 20 wherein when $R^1$ is hydrogen, alkyl, alkoxy, halo, haloalkyl, haloalkoxy, or cyano, then the phenyl ring is substituted at meta or para, preferably meta position with $R^5$, and $R^6$ is ortho or para to $R^5$.

22. The compound or salt of any of the previous embodiments 1-19 wherein $R^1$ is hydrogen, alkyl, alkoxy, halo, haloalkyl, haloalkoxy, or cyano, Ar is heteroaryl, preferably pyridyl substituted with $R^5$ at carbon adjacent to ring nitrogen in the pyridyl ring.

23. The compound or salt of any of the previous embodiments 1-19 wherein $R^5$ is hydrogen, alkyl, alkoxy, halo, haloalkyl, haloalkoxy, or cyano, preferably, Ar is phenyl substituted at meta and/or para with $R^5$ or $R^6$ which are preferably chloro or trifluoromethyl, the carbon atom of Ar attached to phenyl being position 1.

24. The compound or salt of any of the previous embodiments 1-19 wherein $R^5$ is hydrogen, alkyl, alkoxy, halo, haloalkyl, haloalkoxy, or cyano, Ar is heteroaryl, preferably pyridyl or pyrimidinyl optionally substituted with $R^5$-$R^7$.

25. The compound or salt of the previous embodiment 1 wherein the compound of Formula (I) has the structure:

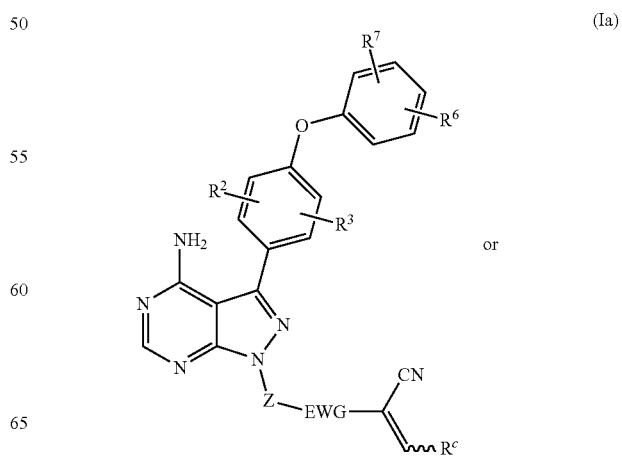

(Ia)

or

-continued

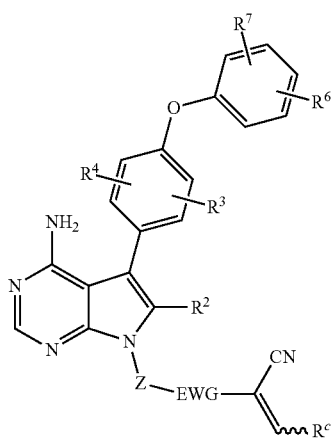

(Ib)

wherein:

R² is hydrogen or alkyl;

R³ and R⁴ are independently hydrogen, alkyl, haloalkyl, fluoro or chloro;

R⁶ and R⁷ are independently hydrogen or fluoro;

Z is a bond, alkylene, or alkylene-O— wherein —O— is connected to EWG;

EWG is —CO—, —NR'CO—, —NR'SO₂—,

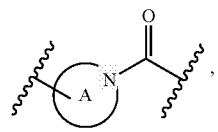

—SO₂— or a five membered heteroaryl ring where R' is hydrogen or alkyl and ring A is 2-pyrrolidinyl or 3-piperidinyl, each ring optionally substituted with one or two alkyl provided that that (i) when Z is a bond then EWG is 3-piperidinylcarbonyl optionally substituted with one or two alkyl; (ii) when Z is alkylene-O— then EWG is —CO— and (iii) when Z is alkylene, then ring A is not 3-piperidinylcarbonyl optionally substituted with one or two alkyl; and R$^c$ is cycloalkyl, alkyl, or substituted alkyl; provided that: when Z is

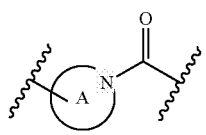

then at least one of R², R³, R⁴ and R⁵ is hydrogen.

26. The compound or salt of the previous embodiment 25 wherein the compound of Formula (I) has structure (Ia).

27. The compound of the previous embodiment 25 wherein the compound of Formula (I) has structure (Ib).

28. The compound or salt of any of the previous embodiments 25-27 wherein:

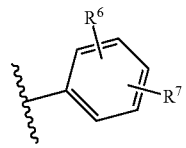

is a ring of formula:

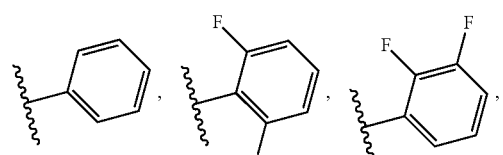

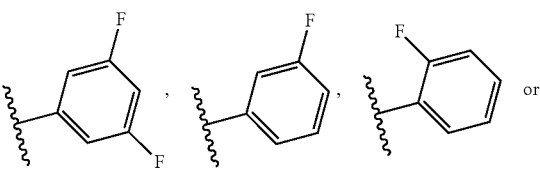

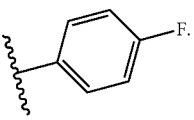

29. The compound or salt of any of the previous embodiments 25-27 wherein:

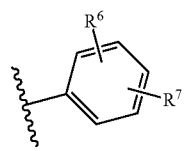

is a ring of formula:

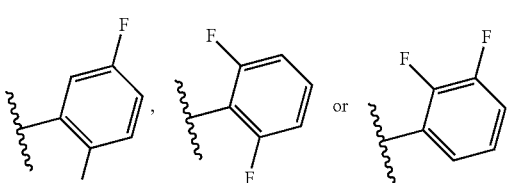

30. The compound or salt of any of the previous embodiments 25, 27, 28 and 29 wherein R² is hydrogen or alkyl, preferably hydrogen or methyl, more preferably hydrogen; and R³ and R⁴ are independently hydrogen, methyl, ethyl, trifluoromethyl, fluoro or chloro.

31. The compound or salt of any of the previous embodiments 25, 27, 28 and 29 wherein R² is hydrogen or alkyl, preferably hydrogen or methyl, more preferably hydrogen; and

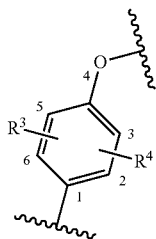

is a ring of formula:

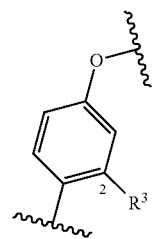

where R³ is methyl, ethyl, chloro, fluoro or trifluoromethyl, preferably methyl, ethyl, chloro or fluoro, more preferably, methyl, ethyl, or chloro, even more preferably chloro or fluoro, particularly preferably fluoro.

32. The compound or salt of any of the previous embodiments 25, 27, 28 and 29 wherein R² is hydrogen or alkyl, preferably hydrogen or methyl, more preferably hydrogen; and

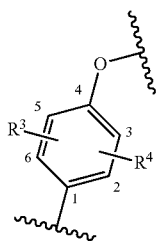

is a ring of formula

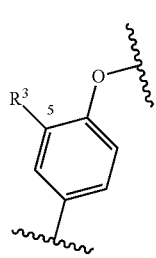

where R³ is alkyl or halo, preferably methyl, chloro or fluoro.

32. The compound or salt of any of the previous embodiments 25, 27, 28 and 29 wherein R² is hydrogen or alkyl, preferably hydrogen or methyl, more preferably hydrogen; and

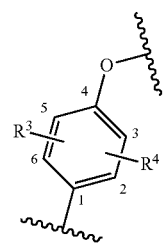

is a ring of formula

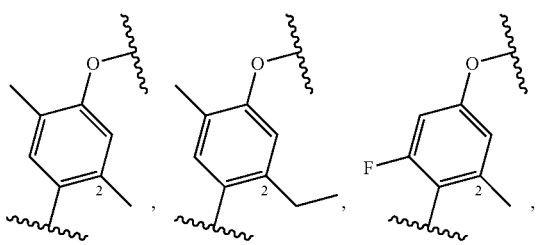

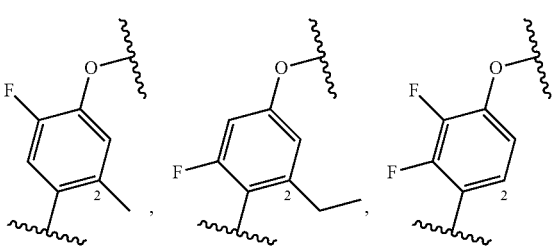

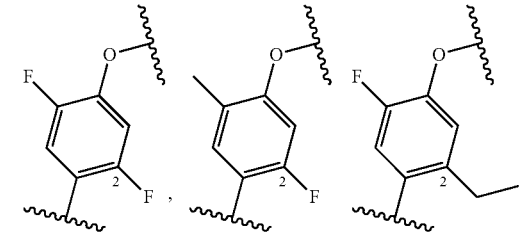

; preferably,

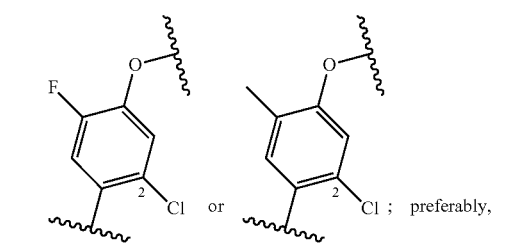

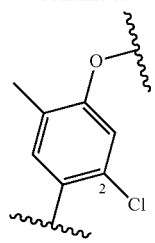

33. The compound or salt of any of the previous embodiments 25-32 wherein:

Z is a alkylene, or alkylene-O— wherein —O— is connected to EWG;

EWG is —CO—, —NR'CO—, —NR'SO$_2$—, or —SO$_2$— where R' is hydrogen or alkyl, preferably hydrogen or methyl.

34. The compound or salt of any of the previous embodiments 25-32 wherein —Z-EWG- is -(alkylene)-NR'CO—, -(alkylene)-NR'SO$_2$—, -(alkylene)-OCO—, or -(alkylene)-SO$_2$ wherein Z is ethylene, —C(CH$_3$)$_2$—CH$_2$—, or —CH$_2$—C(CH$_3$)$_2$— and EWG is —NHCO—, —N(CH$_3$)CO—, —NHSO$_2$—, —N(CH$_3$)SO$_2$—, —SO$_2$—, or —OCO—.

34. The compound or salt of any of the previous embodiments 25-32 wherein Z is ethylene, —C(CH$_3$)$_2$—CH$_2$—, or —CH$_2$—C(CH$_3$)$_2$— and EWG is —NHCO—, —N(CH$_3$)CO—, —NHSO$_2$—, or —N(CH$_3$)SO$_2$—, even more preferably, EWG is —NHCO—.

35. The compound or salt of any of the previous embodiments 25-32 wherein Z is a bond or alkylene; and EWG is

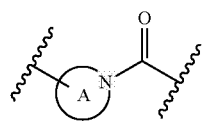

where ring A is pyrrolidinyl or piperidinyl optionally substituted with one or two alkyl, preferably methyl.

36. The compound or salt of the previous embodiment 35 wherein —Z-EWG- is 2(R)-piperidin-1-carbonyl.

37. The compound or salt of the previous embodiment 35 wherein —Z-EWG- is 2-CH$_2$-pyrrolidin-1-ylcarbonyl, 2-CH(CH$_3$)-pyrrolidin-1-ylcarbonyl; 2-CH$_2$-3,3-dimethylpyrrolidin-1-ylcarbonyl or 2-CH$_2$-4,4-dimethylpyrrolidin-1-ylcarbonyl, preferably 2-CH$_2$-pyrrolidin-1-ylcarbonyl, the C-2 carbon of the pyrrolidin-1-yl ring substituted with CH$_2$ having R stereochemistry.

38. The compound or salt of any of the previous embodiments 25-32 wherein Z is alkylene; and EWG is a five membered heteroaryl ring, preferably Z is methylene, ethylene, —C(CH$_3$)$_2$ CH$_2$—, or —CH$_2$—C(CH$_3$)$_2$— and Z is oxazolyl, more preferably —Z-EWG- is 2-C(CN)=CR$^c$-oxazol-5-yl.

39. The compound or salt of any of the previous embodiments 25-38 wherein R$^c$ is cycloalkyl, alkyl, or substituted alkyl, preferably, R$^c$ is isopropyl, tert-butyl or 1-dimethylamino-1-methylethyl, more preferably R$^c$ is cyclopropyl.

40. A compound of Formula (Ic) or a pharmaceutically acceptable salt thereof:

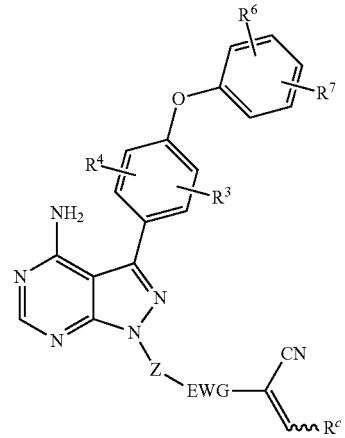

(Ic)

wherein:

R$^3$ and R$^4$ are independently hydrogen, alkyl, haloalkyl, fluoro or chloro;

R$^6$ and R$^7$ are independently hydrogen or fluoro;

Z-EWG is:

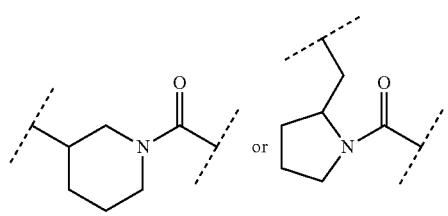

each ring optionally substituted with one or two substituents selected from alkyl, fluoro, or hydroxy; and R$^c$ is cycloalkyl, alkyl, substituted alkyl, cycloalkyleneNR$^d$R$^e$ or cycloalkylene(alkylene)NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro;

provided that at least one of R$^3$, R$^4$, R$^5$ and R$^6$ is not hydrogen, preferably one of R$^3$ and R$^4$ is not hydrogen.

41. The compound or salt of the previous embodiment 40 wherein:

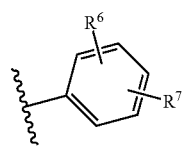

is a ring of formula:

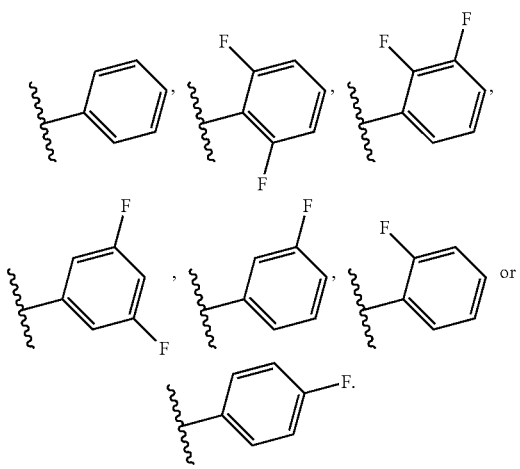

42. The compound or salt of the previous embodiment 40 wherein:

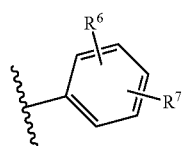

is a ring of formula: phenyl,

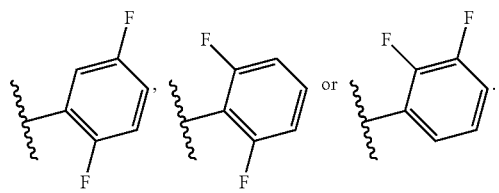

43. The compound or salt of the previous embodiment 40 wherein:

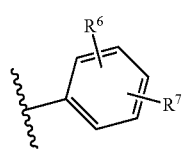

is phenyl.

44. The compound or salt of the previous embodiment 40 wherein:

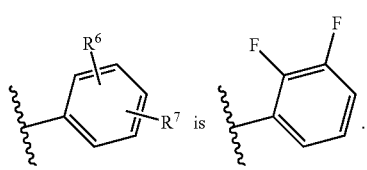 is

45. The compound of any of the embodiments 40-44 wherein:
$R^3$ and $R^4$ are independently hydrogen, methyl, ethyl, trifluoromethyl, fluoro or chloro.

46. The compound or salt of any of the previous embodiments 40-44 wherein:

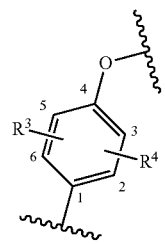

is a ring of formula:

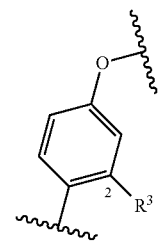

where $R^3$ is fluoro.

47. The compound or salt of any of the previous embodiments 40-46 wherein:
Z-EWG is:

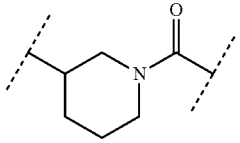

optionally substituted with one or two substituents selected from alkyl, fluoro, or hydroxy. Preferably, —Z-EWG- is

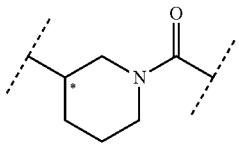

where the stereochemistry at *C is (R). Preferably, —Z-EWG- is

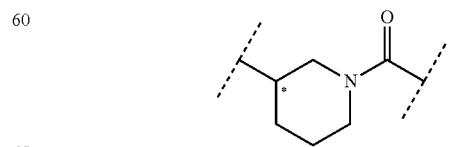

where the stereochemistry at *C is (S).

48. The compound or salt of any of the previous embodiments 40-46 wherein:

Z-EWG is:

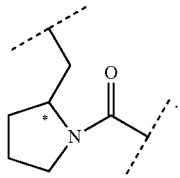

Preferably, —Z-EWG- is

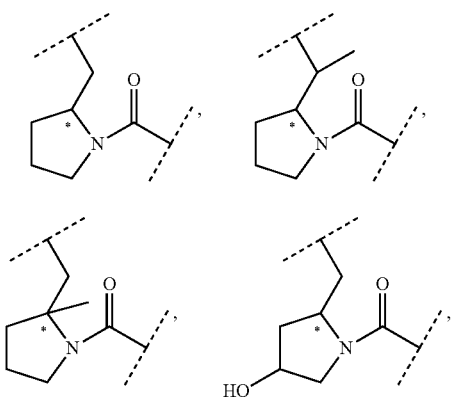

lp;1p

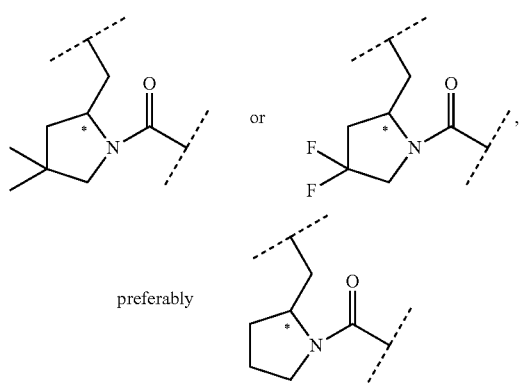

preferably where the stereochemistry at *C is (RS), (R) or (S), more preferably (R).

49. The compound or salt of any of the previous embodiments 40-46 wherein:

Z-EWG is:

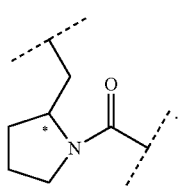

Preferably, —Z-EWG- is

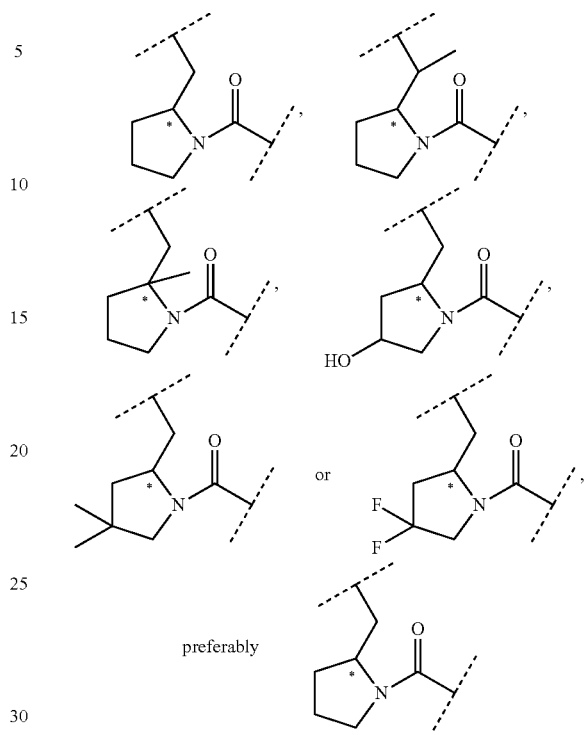

preferably

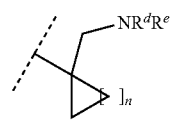

where the stereochemistry at *C is (S).

50. The compound or salt of any of the previous embodiments 40-49 wherein $R^c$ is cycloalkyl, preferably cyclopropyl.

51. The compound or salt of any of the previous embodiments 40-49 wherein $R^c$ is alkyl, preferably isopropyl or tert-butyl, more preferably isopropyl.

52. The compound or salt of any of the previous embodiments 40-49 wherein $R^c$ is substituted alkyl, preferably, alkyl substituted with alkoxy or NRR' (where R is hydrogen, alkyl, alkoxyalkyl or cycloalkyl and R' is hydrogen or alkyl), or heterocycicyl which is optionally substituted with one or two groups independently selected from alkyl), more preferably $R^c$ is —C(CH$_3$)$_2$NH$_2$, —C(CH$_3$)$_2$NHCH$_3$, —C(CH$_3$)$_2$N(CH$_3$)$_2$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$morpholine-4-yl, even more preferably —C(CH$_3$)$_2$NH$_2$.

53. The compound or salt of any of the previous embodiments 40-49 wherein $R^c$ is cycloalkylene(alkylene)-NR$^d$R$^e$ (where R$^d$ and R$^e$ are independently hydrogen, alkyl, or cycloalkyl), preferably

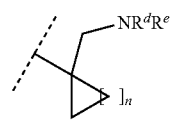

where n is 1-3, $R^d$ is hydrogen, methyl or ethyl, and $R^e$ is hydrogen, methyl, ethyl, or isopropyl.

54. The compound or salt of any of the previous embodiments 40-49 wherein $R^c$ is cycloalkyleneNR$^d$R$^e$ (where R$^d$ and R$^e$ are independently hydrogen, or alkyl), preferably

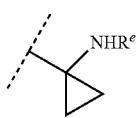

where $R^e$ is hydrogen, methyl, ethyl or isopropyl.

55. The compound or salt of any of the previous embodiments 40-49 wherein $R^c$ is 3 to 6 membered saturated monocyclic heterocyclyl containing one or two heteroatoms selected from N, O, or S and optionally substituted with one or two substituents selected from hydroxy, alkyl or fluoro; preferably pyrrolidinyl, piperidinyl, tetrahydrofuranyl, or tetrahydropyranyl, more preferably 2-pyrrolidinyl, 3- or 4-piperidinyl, 1-methylpiperidin-4-yl, 1-methylpiperidin-3-yl, or 4-tetrahydropyranyl.

56. A compound of Formula (Id) or a pharmaceutically acceptable salt thereof:

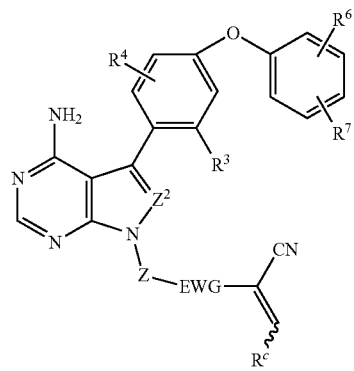

(Id)

wherein:

$Z^2$ is —N— or $CR^2$ where $R^2$ is hydrogen or alkyl;

$R^3$ and $R^4$ are independently hydrogen, methyl, chloro, fluoro, cyclopropyl, hydroxy, methoxy, cyano, trifluoromethyl or trifluoromethoxy;

$R^6$ and $R^7$ are independently hydrogen, methyl, methoxy, fluoro, chloro, trifluoromethyl, trifluoromethoxy, or cyano;

—Z-EWG- is -(alkylene)-NR'CO—, -(alkylene)-NR'SO$_2$—,

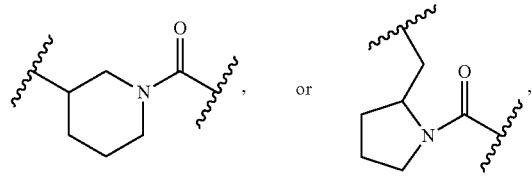 [SMILES: *C(=O)N1CCCC(*)C1 ; *CC1CCCN1C(*)=O]

each ring optionally substituted with one or two substituents independently selected from alkyl, hydroxy, or halo, (preferably alkyl or halo), and the carbonyl and sulfonyl group in -(alkylene)-NR'CO—, -(alkylene)-NR' SO$_2$—,

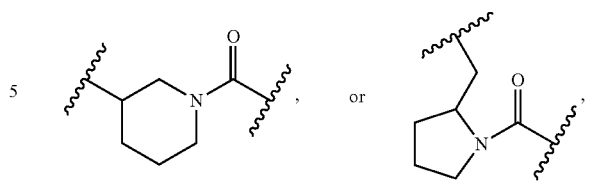

is attached to —C(CN)=CHR$^c$; and each R' is independently hydrogen or alkyl; and $R^c$ is alkyl, haloalkoxy, substituted alkyl, cycloalkyl, cycloalkyleneNR$^d$R$^e$ or cycloalkylene(alkylene)NR$^d$R$^e$ (where R$^d$ and R$^e$ are independently hydrogen, alkyl, or cycloalkyl), or 3 to 6 membered saturated monocyclic heterocyclyl containing one or two heteroatoms selected from N, O, or S and optionally substituted with one or two substituents selected from hydroxy, alkyl or fluoro; provided that: (a) when

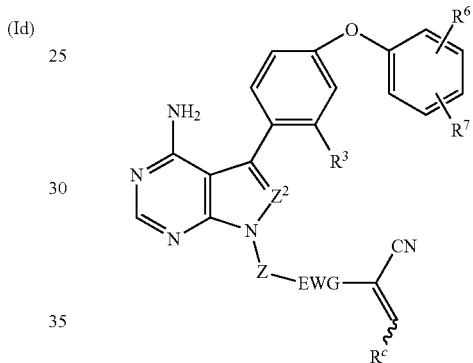

is:

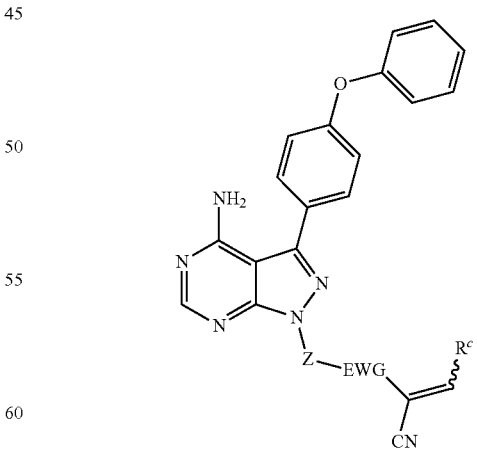

then (i) when R$^c$ is cyclopropyl, tert-butyl, —C(CH$_3$)$_2$CH$_2$OH, —C(CH$_3$)$_2$N(CH$_3$)$_2$, cyclopentyl, isopropyl, —C(CH$_3$)$_2$OCH$_2$CH$_3$, or azetidin-3-yl, then —Z-EWG- is not

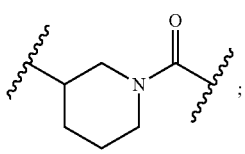 [SMILES: *C(=O)N1CCCC(*)C1]

and (ii) when $R^c$ is cyclopropyl then —Z-EWG- is not

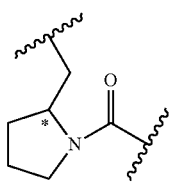 [SMILES: *CC1CCCN1C(*)=O]

where the stereochemistry at *C is (R); (b) when

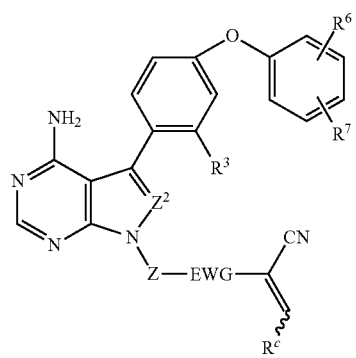

is:

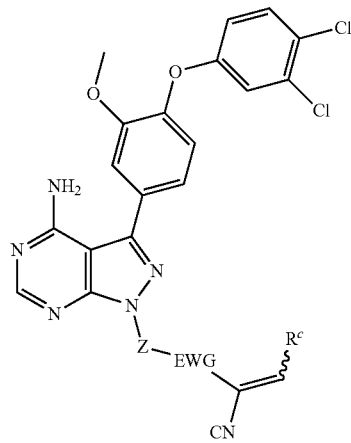

where $R^c$ is cyclopropyl or tert-butyl, then —Z-EWG- is not

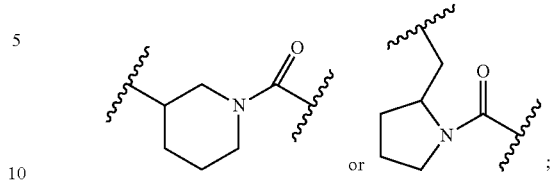

or (c) the compound of Formula (I) is not 2-(3-(4-amino-5-(4-phenoxyphenyl)-7H-pyrrolo[2,3-d]pyrimidin-7-yl)piperidine-1-carbonyl)-3-cyclopropylacrylonitrile; or a pharmaceutically acceptable salt thereof.

57. The compound or salt of the previous embodiment 56 wherein:
$R^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl or 3 to 6 membered saturated monocyclic heterocyclyl containing one or two heteroatoms selected from N, O, or S and optionally substituted with one or two substituents selected from hydroxy, alkyl or fluoro; and

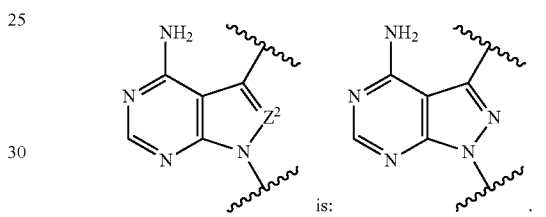

is:

58. The compound or salt of the previous embodiment 56 wherein $R^c$ is alkyl, haloalkoxy, substituted alkyl, cycloalkyl, cycloalkyleneNR$^d$R$^e$ where R$^d$ and R$^e$ are independently hydrogen, alkyl, or cycloalkyl or 3 to 6 membered saturated monocyclic heterocyclyl containing one or two heteroatoms selected from N, O, or S and optionally substituted with one or two substituents selected from hydroxy, alkyl or fluoro; and

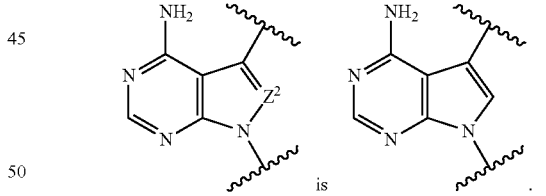

is

59. The compound or salt of any of the previous embodiments 56-58 wherein:

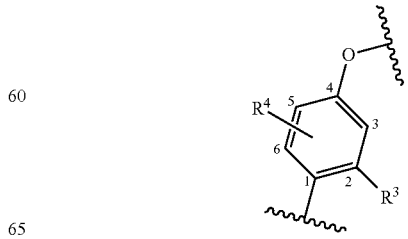

is a ring of formula:

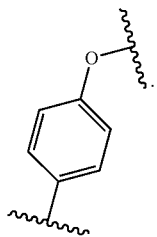 [SMILES: *Oc1ccc(*)cc1]

60. The compound or salt of any of the previous embodiments 56-58 wherein:

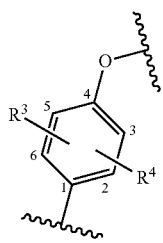

is a ring of formula

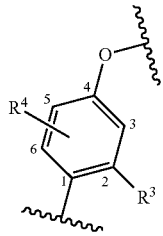

where $R^3$ is methyl, ethyl, chloro, fluoro, cyclopropyl, hydroxy, methoxy, trifluoromethyl or trifluoromethoxy.

61. The compound or salt of any of the previous embodiments 56-58 wherein:

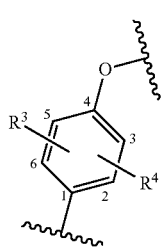

is a ring of formula

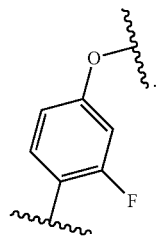 [SMILES: *Oc1ccc(*)c(F)c1]

62. The compound or salt of any of the previous embodiments 56-58 wherein:

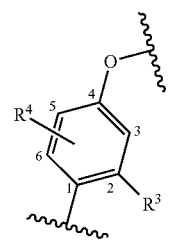

is a ring of formula:

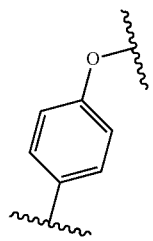 and 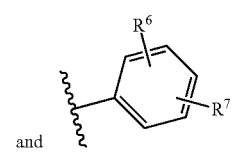

is a ring of formula:

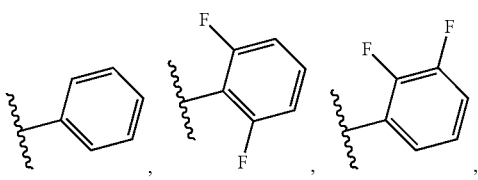

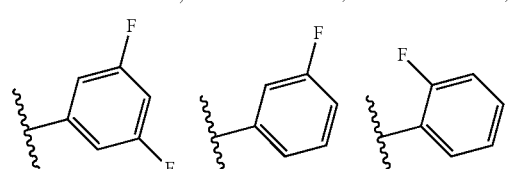

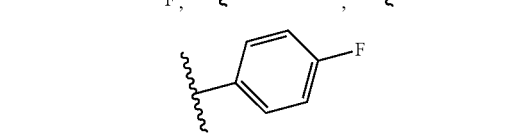

63. The compound or salt of any of the previous embodiments 56-58 wherein:

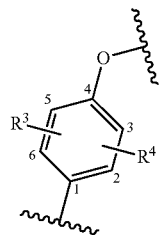

is a ring of formula

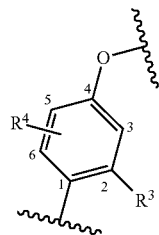

where R³ is methyl, ethyl, chloro, fluoro, cyclopropyl, hydroxy, methoxy, trifluoromethyl or trifluoromethoxy; and

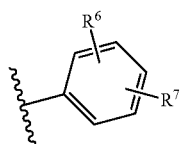

is a ring of formula:

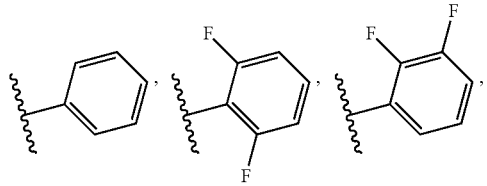

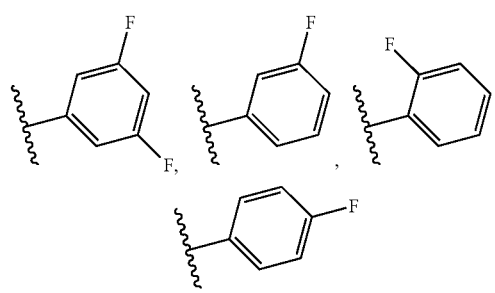

or

64. The compound or salt of any of the previous embodiments 56-58 wherein:

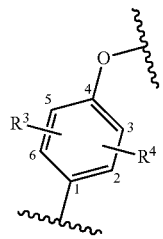

is a ring of formula

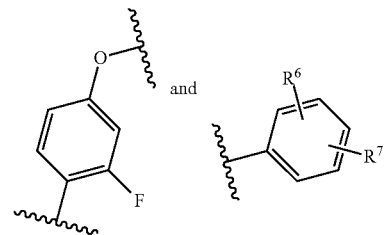

is a ring of formula:

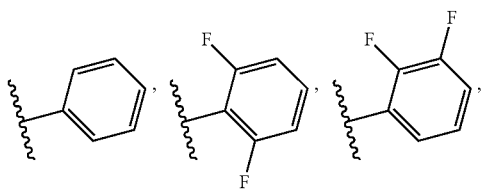

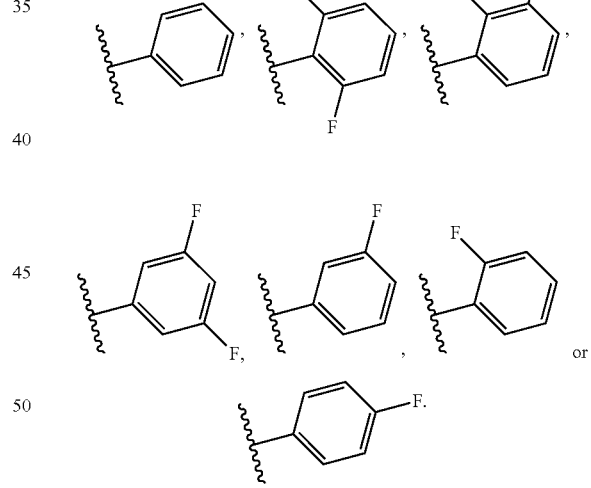

or

65. The compound or salt of the previous embodiment 62 wherein:

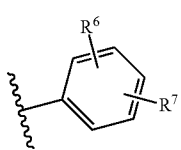

is a ring of formula:

66. The compound or salt of the previous embodiment 63 wherein:

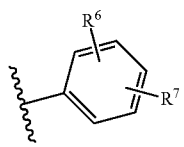

is a ring of formula: phenyl or

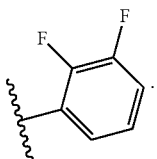

67. The compound or salt of the previous embodiment 64 wherein:

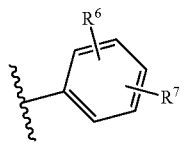

is a ring of formula: phenyl or

68. The compound or salt of any of the previous embodiments 56-60 and 62 wherein:
—Z-EWG- is

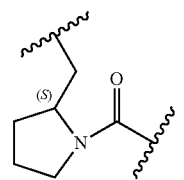

optionally substituted with one or two substituents independently selected from alkyl, hydroxy, or halo (preferably alkyl or halo, more preferably is unsubstituted); and $R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro. Preferably, $R^c$ is alkyl substituted with heterocycloamino which is optionally substituted with one or two groups independently selected from alkyl or hydroxyl.

69. The compound or salt of the previous embodiment 68 wherein $R^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. Preferably, $R^c$ is —C(CH$_3$)$_2$morpholine-4-yl, 2-pyrrolidinyl, 3- or 4-piperidinyl, 1-methylpiperidin-4-yl, 1-methylpiperidin-3-yl, or 4-tetrahydropyranyl.

70. The compound or salt of any of the previous embodiments 63, 65 and 66 wherein:
—Z-EWG- is

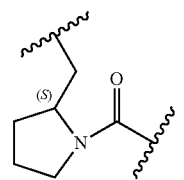

optionally substituted with one or two substituents independently selected from alkyl, hydroxy, or halo (preferably alkyl or halo, more preferably is unsubstituted); and $R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

71. The compound or salt of the previous embodiment 70 wherein $R^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. Preferably, $R^c$ is —C(CH$_3$)$_2$morpholine-4-yl, 2-pyrrolidinyl, 3- or 4-piperidinyl, 1-methylpiperidin-4-yl, 1-methylpiperidin-3-yl, or 4-tetrahydropyranyl.

72. The compound or salt of the previous embodiment 69 and 71 where $R^c$ is isopropyl, tert-butyl, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. Preferably, $R^c$ is —C(CH$_3$)$_2$morpholine-4-yl, 2-pyrrolidinyl, 3- or 4-piperidinyl, 1-methylpiperidin-4-yl, 1-methylpiperidin-3-yl, or 4-tetrahydropyranyl.

73. The compound or salt of any of the previous embodiments 61, 64 and 67 wherein:
—Z-EWG- is

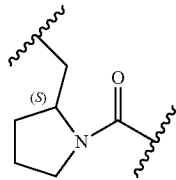

optionally substituted with one or two substituents independently selected from alkyl, hydroxy, or halo (preferably alkyl or halo, more preferably is unsubstituted); and $R^c$ is alkyl, cycloalkyl, cycloalkyleneNR$^d$R$^e$ (where $R^d$ and $R^e$ are independently hydrogen or alkyl), alkyl substituted with hydroxy, alkoxy, —NRR' (where each R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

74. The compound or salt of thye previous embodiment 73 wherein $R^c$ is isopropyl, tert-butyl, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. Preferably, $R^c$ is —C(CH$_3$)$_2$morpholine-4-yl, 2-pyrrolidinyl, 3- or 4-piperidinyl, 1-methylpiperidin-4-yl, 1-methylpiperidin-3-yl, or 4-tetrahydropyranyl.

75. The compound or salt of any of the previous embodiments 60 and 62 wherein:
—Z-EWG- is

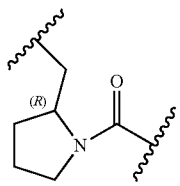

optionally substituted with one or two substituents independently selected from alkyl, hydroxy, or halo (preferably alkyl or halo, more preferably is unsubstituted); and $R^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom and which is optionally substituted with one or two groups independently selected from alkyl or hydroxyl.

76. The compound or salt of the previous embodiment 75 wherein $R^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

77. The compound or salt of any of the previous embodiments 63, 65 and 66 wherein:
—Z-EWG- is

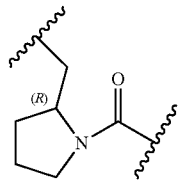

optionally substituted with one or two substituents independently selected from alkyl, hydroxy, or halo (preferably alkyl or halo, more preferably is unsubstituted); and $R^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom which is optionally substituted with one or two groups independently selected from alkyl or hydroxyl.

78. The compound or salt of the previous embodiment 77 wherein $R^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

79. The compound or salt of any of the previous embodiments 61, 64 and 67 wherein:
—Z-EWG- is

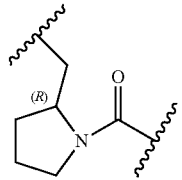

optionally substituted with one or two substituents independently selected from alkyl, hydroxy, or halo (preferably alkyl or halo, more preferably is unsubstituted); and $R^c$ is alkyl substituted with —NRR' (where each R is hydrogen, alkyl, cycloalkyl, hydroxyalkyl, or alkoxyalkyl and R' is hydrogen) or heterocycloamino which is attached to alkyl via nitrogen ring atom and is optionally substituted with one or two groups independently selected from alkyl or hydroxyl; and the stereochemistry at *C is (R).

80. The compound or salt of the previous embodiment 79 wherein $R^c$ is —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

81. The compound or salt of any of the previous embodiment 76, 78, or 80 wherein $R^c$ is —C(CH$_3$)$_2$NH$_2$ or —C(CH$_3$)$_2$morpholine-4-yl.

82. The compound or salt of any of the previous embodiments 56-60 and 62 wherein:
—Z-EWG- is

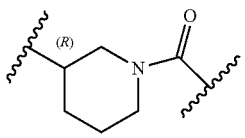

which is optionally substituted with one or two substituents independently selected from alkyl, hydroxy, or halo (preferably alkyl or halo, more preferably is unsubstituted);

$R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where each R is alkyl, cycloalkyl, hydroxyalkyl, or alkoxyalkyl and R' is hydrogen or alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

83. The compound of any of the previous embodiments 63, 65 and 70 wherein:
—Z-EWG- is —Z-EWG- is

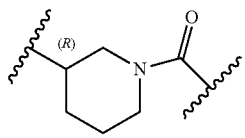

which is optionally substituted with one or two substituents independently selected from alkyl, hydroxy, or halo (preferably alkyl or halo, more preferably is unsubstituted);

$R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where each R is alkyl, cycloalkyl, hydroxyalkyl, or alkoxyalkyl and R' is hydrogen or alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

84. The compound or salt of any of the previous embodiments 61, 64 and 67 wherein:
—Z-EWG- is —Z-EWG- is

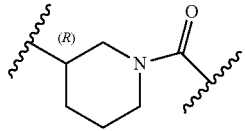

which is optionally substituted with one or two substituents independently selected from hydrogen, alkyl, hydroxy, or halo (preferably alkyl or halo, more preferably is unsubstituted);

$R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where each R is alkyl, cycloalkyl, hydroxyalkyl, or alkoxyalkyl and R' is hydrogen or alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

85. The compound or salt of the previous embodiment 83 wherein $R^c$ is isopropyl, tert-butyl, —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. Preferably, $R^c$ is isopropyl or —C(CH$_3$)$_2$morpholine-4-yl.

86. The compound or salt of the previous embodiment 84 wherein $R^c$ is isopropyl, tert-butyl, —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, —C(CH$_3$)$_2$OCH$_2$CH$_3$, —C(CH$_3$)$_2$N(CH$_3$)$_2$, —C(CH$_3$)$_2$morpholine-4-yl, cyclopropyl, 2-pyrrolidinyl, 3- or 4-piperidinyl, 1-methylpiperidin-4-yl, 1-methylpiperidin-3-yl, or 4-tetrahydropyranyl. Preferably, $R^c$ is isopropyl or —C(CH$_3$)$_2$morpholine-4-yl.

87. The compound or salt of any of the previous embodiments 56-60 and 62 wherein:
—Z-EWG- is —CH$_2$*CH(CH$_3$)NHCO— where the stereochemistry at *C is (S), RS or (R); and $R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

88. The compound or salt of any of the previous embodiments 63, 65 and 66 wherein:
—Z-EWG- is —CH$_2$*CH(CH$_3$)NHCO— where the stereochemistry at *C is (S), RS or (R); and $R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

89. The compound or salt of any of the previous embodiments 61, 64 and 67 wherein:
—Z-EWG- is —CH$_2$*CH(CH$_3$)NHCO— where the stereochemistry at *C is (S), RS or (R); and $R^c$ is alkyl, cycloalkyl, cycloalkyleneNR$^d$R$^e$ (where R$^d$ and R$^e$ are independently hydrogen or alkyl), alkyl substituted with hydroxy, alkoxy, —NRR' (where each R is alkyl, cycloalkyl, hydroxyalkyl, or alkoxyalkyl and R' is alkyl) or heterocycloamino which is optionally substituted with one or two groups independently selected from alkyl or hydroxyl, or 3 to 6 membered saturated monocyclic heterocyclyl containing one or two heteroatoms selected from N, O, or S and optionally substituted with one or two substituents selected from hydroxy, alkyl or fluoro.

90. The compound or salt of any of the previous embodiments 87-89 wherein $R^c$ is isopropyl, tert-butyl, —C(CH$_3$)$_2$OCH$_2$CH$_3$, —C(CH$_3$)$_2$N(CH$_3$)$_2$, cyclopropyl, 2-pyrrolidinyl, 3- or 4-piperidinyl, 1-methylpiperidin-4-yl, 1-methylpiperidin-3-yl, or 4-tetrahydropyranyl, —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

91. The compound or salt of the previous embodiment 90 wherein:

R$^c$ is isopropyl, tert-butyl, cyclopropyl, —C(CH$_3$)$_2$NH$_2$, —C(CH$_3$)$_2$NHCH$_3$, —C(CH$_3$)$_2$NHCH$_2$CH$_3$, —C(CH$_3$)$_2$NHCH(CH$_3$)$_2$, —C(CH$_3$)$_2$NHcyclopropyl, —C(CH$_3$)$_2$NH(CH$_2$)$_2$OCH$_3$, or —C(CH$_3$)$_2$morpholine-4-yl.

92. A compound selected from the group:
(S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile;
(R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile;
(R)-4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile;
(S)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(R)-2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile;
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile;
(R)-2-(3-(4-amino-3-(4-(2,3-difluorophenoxy)-2-fluorophenyl)-1H-pyrazolo[3,4-d]pyrimidin-1-yl)piperidine-1-carbonyl)-4-ethoxy-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-ethoxy-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4,4-dimethylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile;
(R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile; or
(R)-2-(3-(4-amino-3-(2,3-difluoro-4-phenoxyphenyl)-1H-pyrazolo[3,4-d]pyrimidin-1-yl)piperidine-1-carbonyl)-4-methyl-4-morpholinopent-2-enenitrile;
or a mixture of R and S isomers;
or an individual (E) or (Z) isomer thereof;
or a pharmaceutically acceptable salt thereof.

93. A pharmaceutical composition comprising a compound or salt of any of the embodiments 1-92, and a pharmaceutically acceptable excipient 94. A method of treating a disease treatable by inhibition of a kinase in a patient which method comprises administering to the patient in need thereof, a pharmaceutical composition comprising a compound or salt of any of the embodiments 1-93 and a pharmaceutically acceptable excipient.

95. The method of embodiment 94 wherein the kinase is BTK.

96. The method of any of the embodiment 94 or 95 wherein the disease is an inflammatory disease or cancer and the compound or salt of embodiment 1-92 is administered optionally in combination with one or more anticancer or anti-inflammatory agent.

97. Compound or salt of any of the embodiments 1-92 for use as a medicament;

98. Compound or salt of embodiment 97 wherein the use is for treating a disease treatable by inhibition of a kinase in a patient.

99. Compound or salt of embodiment 97 or 98 wherein the use is treating a disease treatable by inhibition of BTK.

100. Compound of embodiment 98 or 99 wherein the use is treating an inflammatory disease or cancer and the compound of is administered optionally in combination with one or more anticancer or anti-inflammatory agent.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (IA), (I') or (I) where $Z^1$ is nitrogen, $Z^2$ is carbon or nitrogen and $Z^3$ is carbon Ar, $R^1$, $R^3$, $R^4$, $R^6$, $R^7$, and L, Ar are as defined above and $R^5$ is hydrogen, alkyl, hydroxy, alkoxy, halo, haloalkyl, or haloalkoxy can be prepared as illustrated and described in Scheme A below.

Scheme A

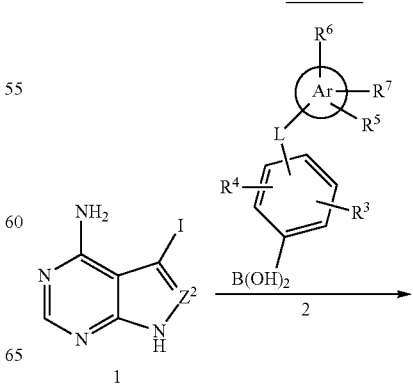

179

-continued

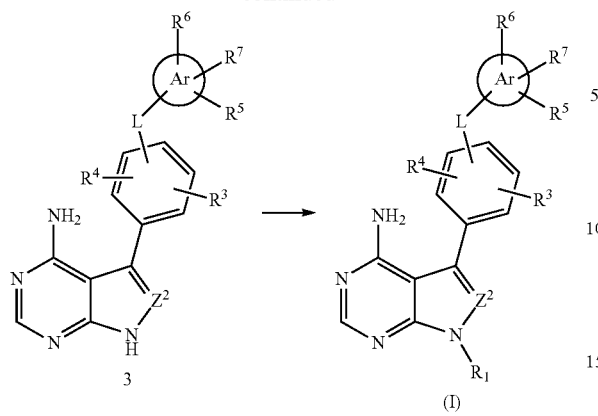

(I)

Coupling of an iodo compound of formula 1 where with a boronic acid compound of formula 2 or boronate esters thereof. Ar, $R^1$, $R^3$, $R^4$, $R^5$, $R^6$, $R^7$, L, and Ar are as defined above under Suzuki coupling reaction conditions provides a compound of formula 3. The Suzuki coupling reaction can be carried out in organic solvents (such as toluene, benzene, N,N-dimethylformamide (DMF), tetrahydrofuran, methanol, ethanol, acetonitrile, dimethoxyethane, acetone and the like) or water in the presence of base (such as sodium ethylate, sodium hydroxide, potassium hydroxide, sodium bicarbonate, potassium bicarbonate, potassium carbonate, sodium carbonate, triethylamine, and the like) and a palladium catalyst (such as tetrakis(triphenylphosphine)palladium, dichlorobis(triphenylphosphine)palladium, palladium acetate, and the like). The reaction is carried out at room temperature to 120° C. Compounds of formula 1 are either commercially available or can be readily prepared by methods well known in the art.

Treatment of a compound of formula 3 with a compound of formula $R^1$-LG where LG is a suitable leaving group such as halo, tosylate, mesylate, triflate, and the like provides a compound of Formula (IA), (I') or (I). The alkylation or arylation reaction is typically carried out in the presence of a base such as sodium hydride or potassium tert-butoxide, potassium carbonate, and the like, and a catalyst such as 18-crown-6 in a suitable solvent such as N-methylpyrolidone, dimethylformamide, tetrahydrofuran, toluene, and the like.

It will be recognized by a person skilled in the art that precursors to $R^1$ group can be substituted at any step in the synthetic procedure illustrated in Scheme A above and converted to $R^1$ group as defined above at alternate stages in the synthetic process based on feasibility of the transformations. Some such examples are described below:

Substitution of precursors to $R^1$ in the synthesis of compounds of Formula (IA), (I') or (I) when $R^1$ is —Z-(EWG)-C(CN)=CHR$^c$ where Z is a bond or alkylene and EWG is N-carbonylheterocycloamino is illustrated and described in Method (a) below.

180

Method (a):

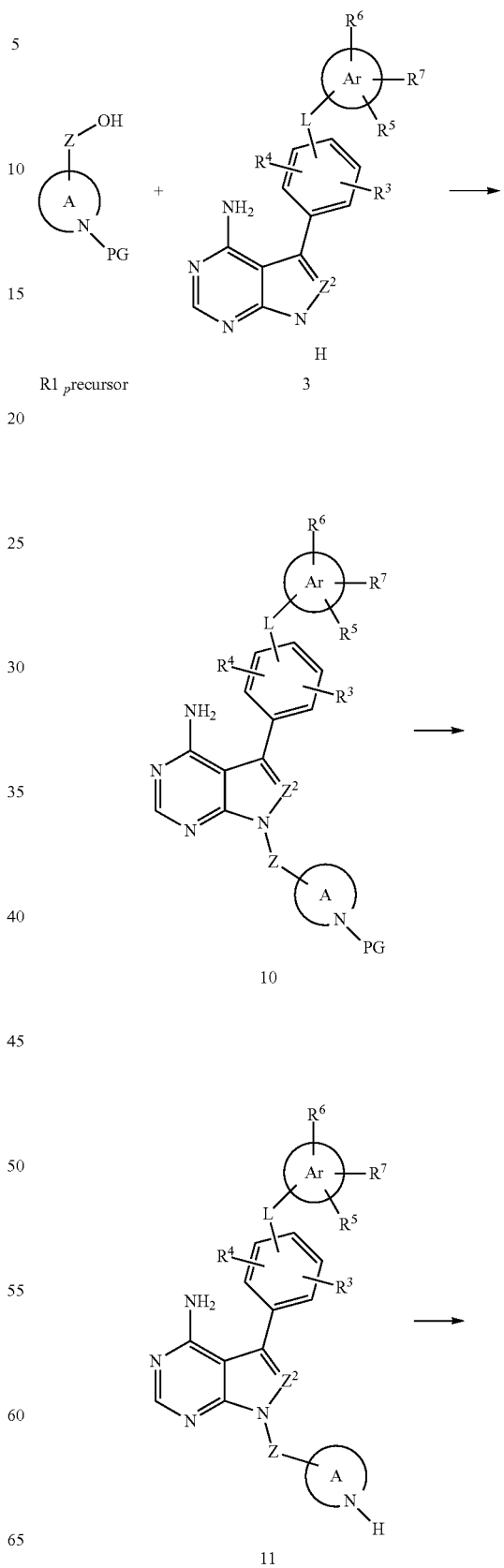

-continued

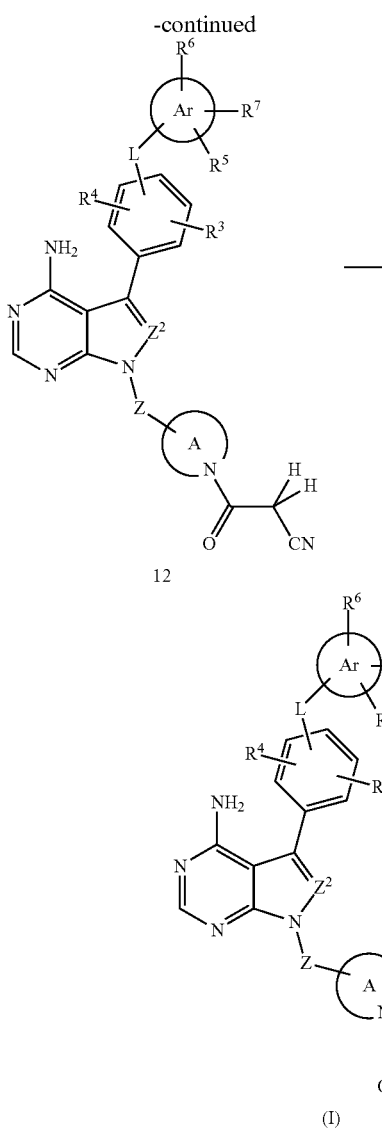

Treatment of a N-protected heterocycloamino $R^1$ precursor compound (Suitable nitrogen protecting groups (PG) include t-butyloxycarbonyl (BOC), carbobenzyloxy (Cbz), or 2-trimethylsilyl-ethoxymethyl (SEM)) bearing an alcohol with a compound of formula 3 under Mitsunobu reaction conditions provides a compound of formula 10 where Ar, $R^3$, $R^4$, $R^5$, $R^6$, $R^7$, L, Ar, and $Z^2$ are as defined above. Removal of the amino protecting group can be effected using strong acid (TFA or HCL in the case of a Boc group, hydrogenolysis in the case of Cbz, or fluoride anion to remove the SEM), to provide the amine of formula 11. Coupling of compound of formula 11 with a compound of formula $CNCH_2CO_2H$ such as 2-cyanoacetic acid or 2-trifluoromethylacetic acid, under standard amide coupling conditions such as carbon diimidazole (CDI) and the like or an acid derivative thereof provides a compound of formula 12. Subsequent condensation of a compound of formula 12 with aldehydes of formula $R^cCHO$ where $R^c$ is as defined above under standard condensation reaction conditions such as using a base such as piperidine and the like, in the presence or absence of acetic acid and the like in solvents such as ethanol and the like at temperatures ranging from room temperature to reflux then provides a compound of Formula (IA), (I') or (I). Aldehydes of formula $R^cCHO$ are either commercially available or they can be prepared by methods know in the art. For example tert-butylaldehyde, isopropylaldehyde and cyclopropylaldehyde are commerically available. Compounds of Formula (IA), (I') or (I) where $R^c$ —$C(CH_3)_2NH_2$, and —$C(CH_3)_2NHCH_3$ can be prepared by reacting a compound of formula 12 with an aldehyde of formula $BocNHC(CH_3)_2CHO$ and $BocN(CH_3)C(CH_3)_2$ CHO respectively, followed by removal of the Boc group. Aldehydes of formula $BocNHC(CH_3)_2CHO$ can be prepared as shown below:

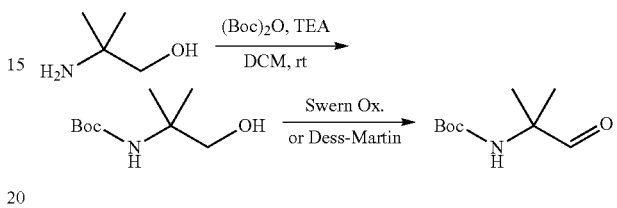

Treatment of 2-amino-2-methylpropan-1-ol with $(Boc)_2O$ in the presence of organic amine provides the corresponding 2-BocNH-2-methylpropan-1-ol which upon reaction with a suitable oxidizing agent provide the desired aldehyde of formula 2-BocNH-2-methylpropanaldehyde.

Aldehydes of formula $BocN(CH_3)C(CH_3)_2CHO$ can be prepared as shown below:

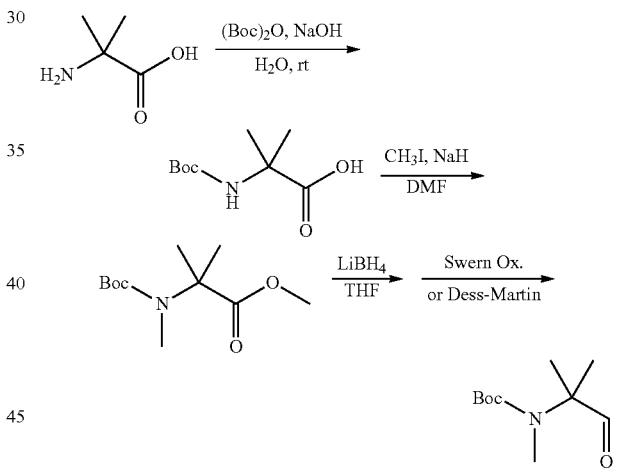

Treatment of 2-amino-2-methylpropanoic with $(Boc)_2O$ in the presence of organic amine provides the corresponding 2-BocNH-2-methylpropanoic which upon reaction with an alkylating agent such as methyl iodide in the presence of sodium hydride provide 2-BocN($CH_3$)-2-methylpropanoic ester. Reduction of the ester group in BocN($CH_3$)-2-methylpropanoic ester with a suitable reducing agent provides the corresponding alcohol which is then covered to the desired aldehyde as described previously.

It will recognized by a person of ordinary skill in the art that the EWG moiety can be assembled at multiple points throughout the synthetic scheme and standard protecting group (PG) strategies can be employed as required.

Compounds of Formula (IA), (I') or (I) where $Z^1$ and $Z^3$ are nitrogen and $Z^2$ is carbon, Ar, $R^1$, $R^3$, $R^4$, $R^6$, $R^7$, and L, Ar are as defined above and $R^5$ is hydrogen, alkyl, hydroxy, alkoxy, halo, haloalkyl, or haloalkoxy can be prepared as illustrated and described in Scheme B below.

Scheme B

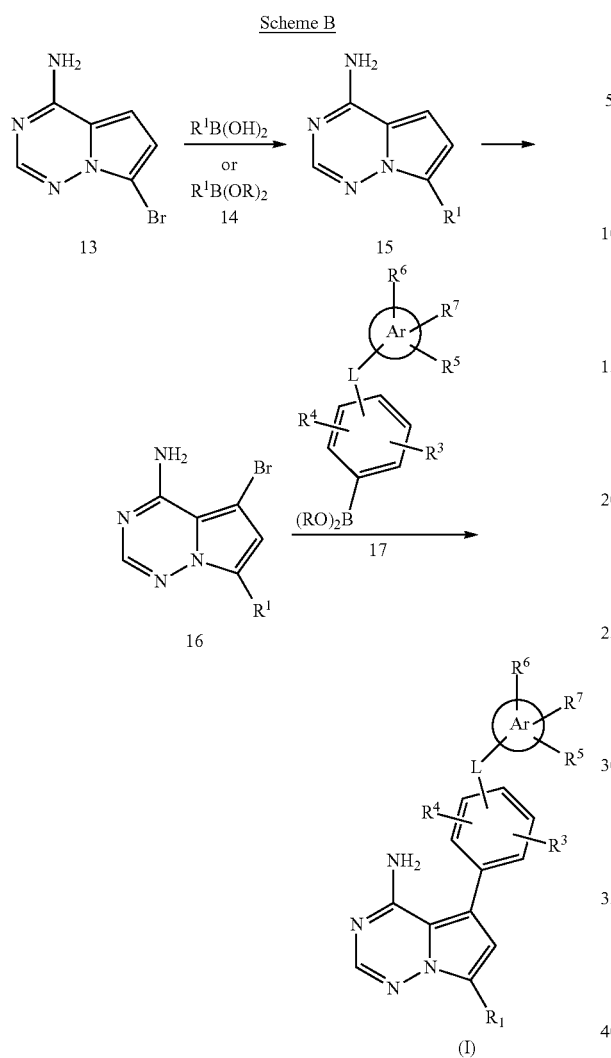

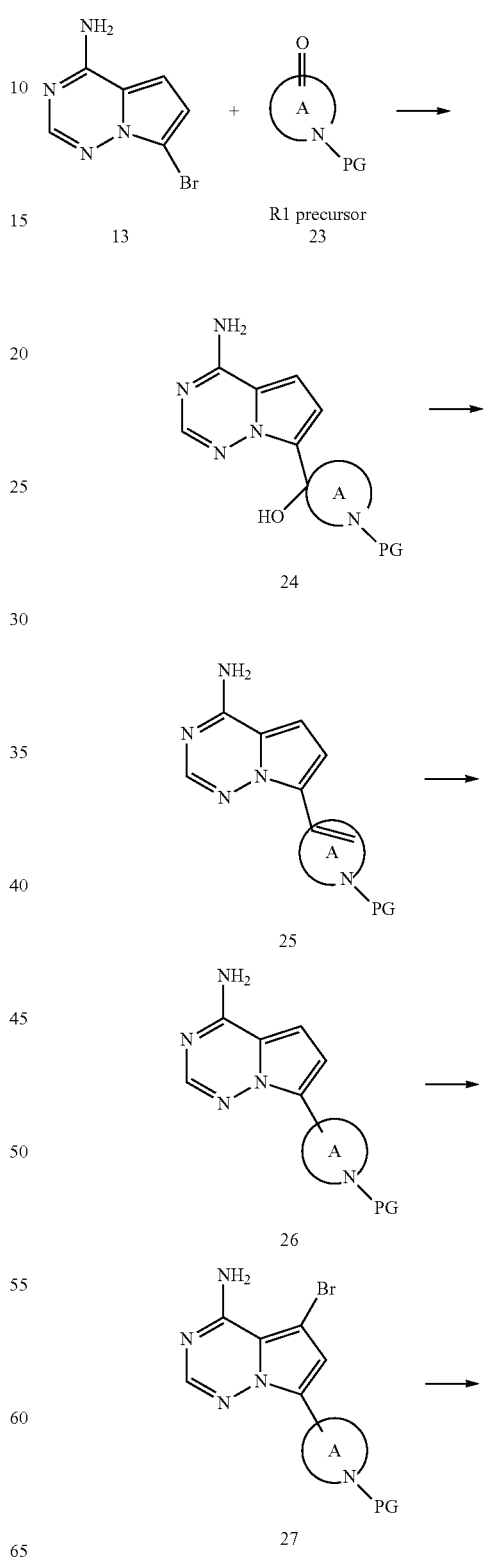

Cross coupling (Suzuki) of a compound of formula 13 (available commercially) with an appropriately substituted boronic acid or boronate esters of formula 13 (as described in Scheme A) provides a compound of formula 15 where $R^1$ is as defined above. Halogenation of compound 15 with a suitable halogenating agent such as N-bromosuccinamide, bromine, and the like, in an organic solvent (such as DMF, dichloromethane, tetrahydrofuran, toluene, acetic acid, water and the like) at temperatures ranging from −78° C. to reflux temperature provides a compound of formula 16. Compound 16 is then coupled with a compound of formula 17 under Suzuki coupling reaction conditions to provide a compound of Formula (IA), (I') or (I) where Ar, $R^1$, $R^3$, $R^4$, $R^5$, $R^6$, $R^7$, L, and Ar are as defined above.

It will be recognized by a person skilled in the art that precursors to $R^1$ can be substituted at any step in Scheme 2 above where $R^1$ exists and converted to $R^1$ at alternate stages in the synthetic process based on feasibility of the transformations. Some such transformations are described below:

Substitution of precursors to $R^1$ in the synthesis of compounds of Formula (IA), (I') or (I) when $R^1$ is —Z-(EWG)-C(CN)=CHR$^c$ where Z is a bond and EWG is N-heterocycloaminocarbonyl is illustrated and described in method (b) below. The EWG moiety can be assembled at multiple points in the synthetic scheme. Standard protecting group (PG) strategies employed by those skilled in the art can be employed as required.

Method (b):

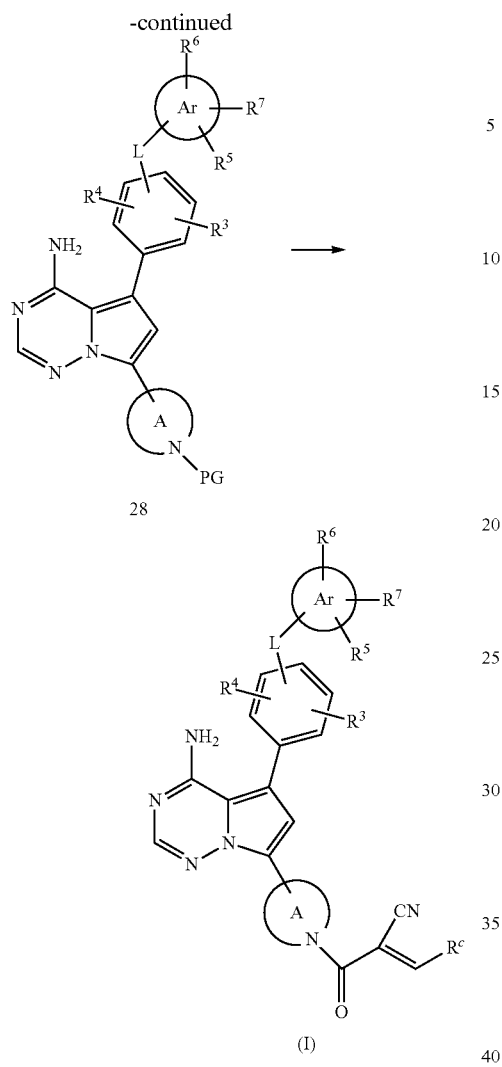

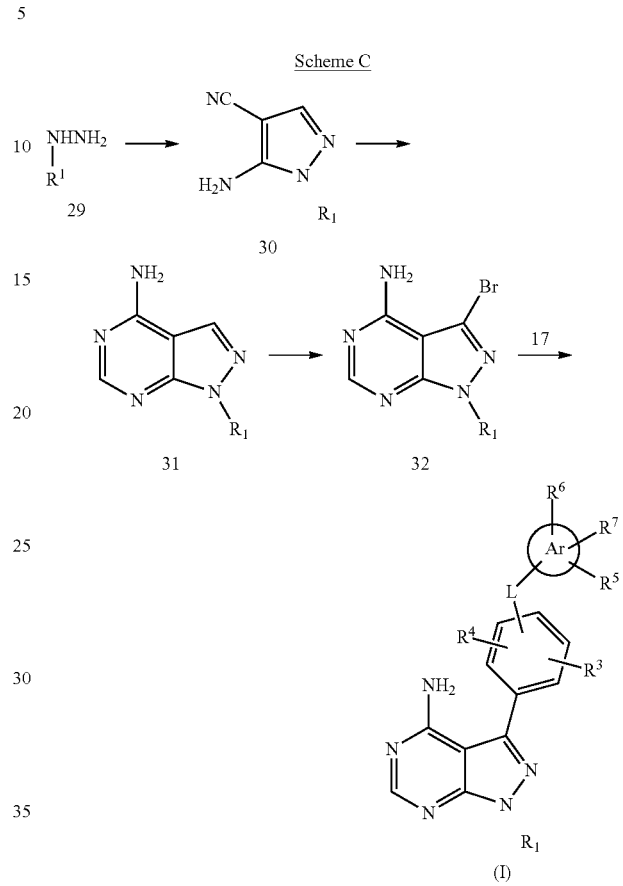

Treatment of compound 13 with trimethylsilyl chloride in solvents such as tetrahydrofuran (THF) at temperatures ranging from 0° C. to room temperature prior to treatment by a Grignard reaction (for example by treatment with isopropyl magnesium chloride in THF at temperatures ranging from 0° C. to room temperature) and subsequent addition of $R^1$ precursor compound of formula 23 bearing a ketone moiety where PG is a suitable protecting group such as tert-butoxycarbonyl (Boc), benzyl (Bn) or 2-trimethylsilyl-ethoxymethyl (SEM)), provides a compound of formula 24 which is converted to a compound of formula 25 under dehydration reaction conditions e.g., treatment of compound 24 with acids such as trifluoroacetic anhydride or trifluoroacetic acid, and the like, in solvents such as pyridine, toluene, methanol, and the like and temperatures ranging from −20° C. to reflux. Reduction of the double bond in the compound of formula 25 with a suitable hydrogenation reaction conditions e.g., with platinum oxide or palladium hydroxide or palladium on carbon in alcoholic solvents such as methanol or ethanol, and the like in the presence or absence of acetic acid and under a hydrogen atmosphere provides a compound of formula 26.

Halogenation of a compound of formula 26 with a suitable halogenating agent as described in scheme B above provides a compound of formula 27 which can then be converted to a compound of Formula (IA), (I') or (I) as described in method a above.

Compounds of Formula (IA), (I') or (I) where $Z^1$ and $Z^2$ are nitrogen and $Z^3$ is carbon and $R^1$, $R^3$, $R^4$, $R^5$, $R^6$, $R^7$, L, and Ar are as defined above can be prepared as illustrated and described in Scheme C below.

Reaction of a hydrazine compound of formula 1 where $R^1$ is as defined above with ethoxymethylene malonitrile in a suitable organic solvent such as ethanol and the like and at temperatures from 0° C. to reflux provide a compound of formula 30. Compound of formula 1 that are either commercially available or readily synthesized by methods that are well known in the art.

Treatment of compound 30 with formamide or formamidine in the absence of solvent or in solvents such as ethanol and the like at temperatures from room temperature to 200° C. provides a compound of formula 31. Halogenation of 31 under halogenating conditions described above provides the compound of formula 32 which can then be converted to a compound of Formula (IA), (I') or (I) as described in Scheme A above.

It will be recognized by a person skilled in the art that precursors to group $R^1$ can be substituted at any step in Scheme C above where $R^1$ exists and then converted to $R^1$ at alternate stages in the synthetic process based on feasibility of the transformations. Some such transformations are described below:

Substitution of precursors to $R^1$ in the synthesis of compounds of Formula (IA), (I') or (I) when $R^1$ is —Z-(EWG)-C(CN)=CHR$^c$ where Z is a bond and EWG is N-carbonylheterocycloamino is illustrated and described in method (c) below. The EWG moiety can be assembled at multiple points in the synthetic scheme. Standard protecting group (PG) strategies employed by those skilled in the art can be employed as required.

Method (c):

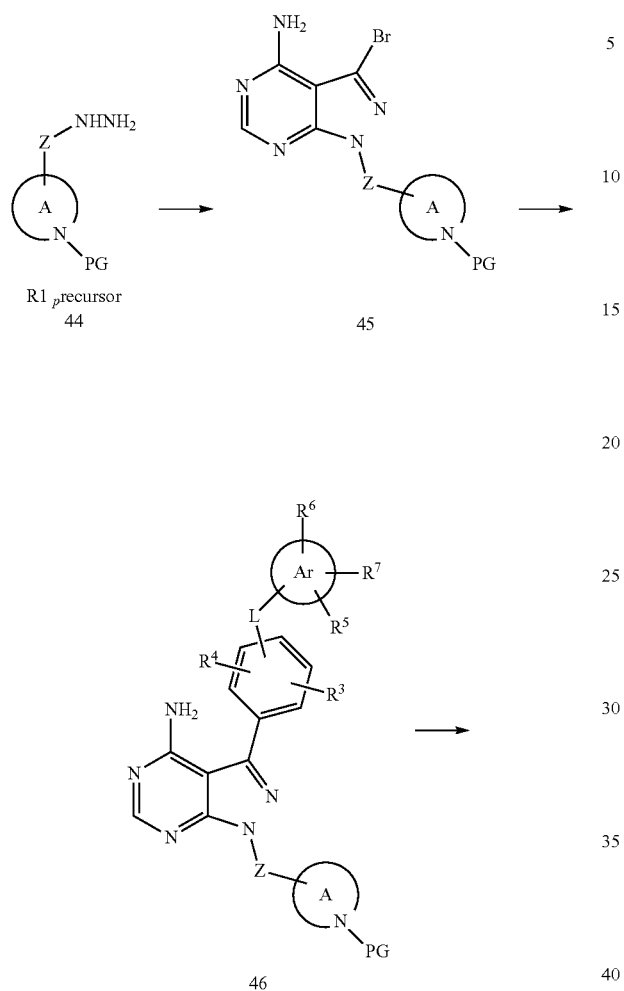

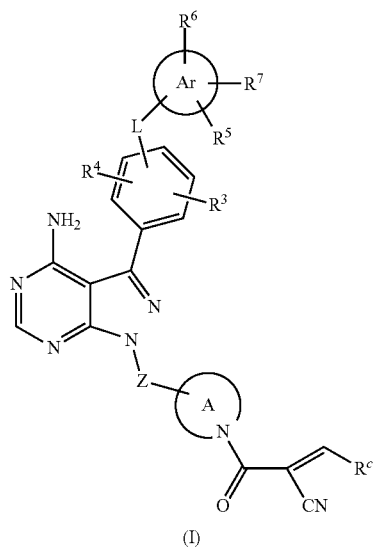

(I)

Substituting compound of formula 33 where Z is a bond or alkylene and where PG is a suitable nitrogen protecting group such as tert-butoxycarbonyl (Boc), benzyl (Bn) or 2-trimethylsilyl-ethoxymethyl (SEM)) with a compound of formula 44 followed by steps 2-5 in Method (g) above provides a compound of formula 46. Removal of the amine protecting group under standard conditions such as HCl in ethyl acetate or trifluoroacetic acid in dichloromethane at 0° C. to reflux for BOC and catalytic hydrogenation in ethyl alcohol for CBZ, provides a compound 46a that can then be converted to a compound of Formula (IA), (I') or (I) by methods previously described in Method a.

Compounds of Formula (IA), (I') or (I) where $Z^1$ is nitrogen and $Z^2$ and $Z^3$ are carbon and $R^1$, $R^3$, $R^4$, $R^5$, $R^6$, $R^7$, L, and Ar are as defined above can be prepared as illustrated and described in Scheme D below.

Scheme D

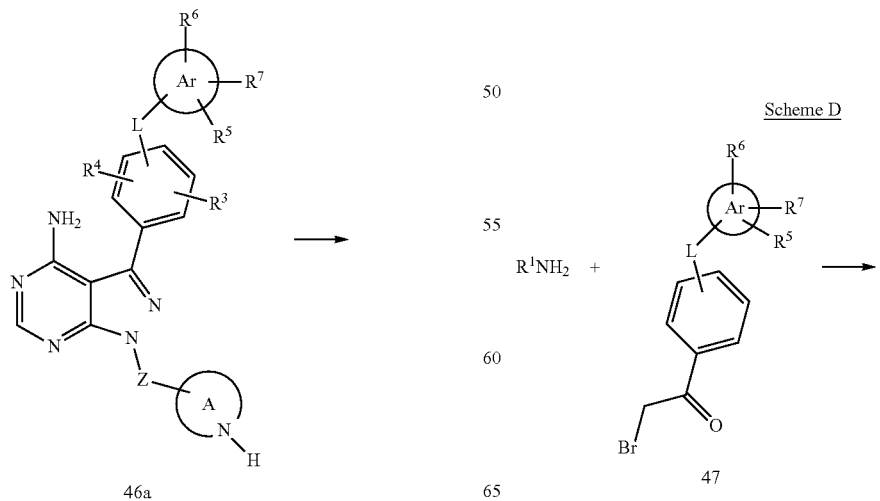

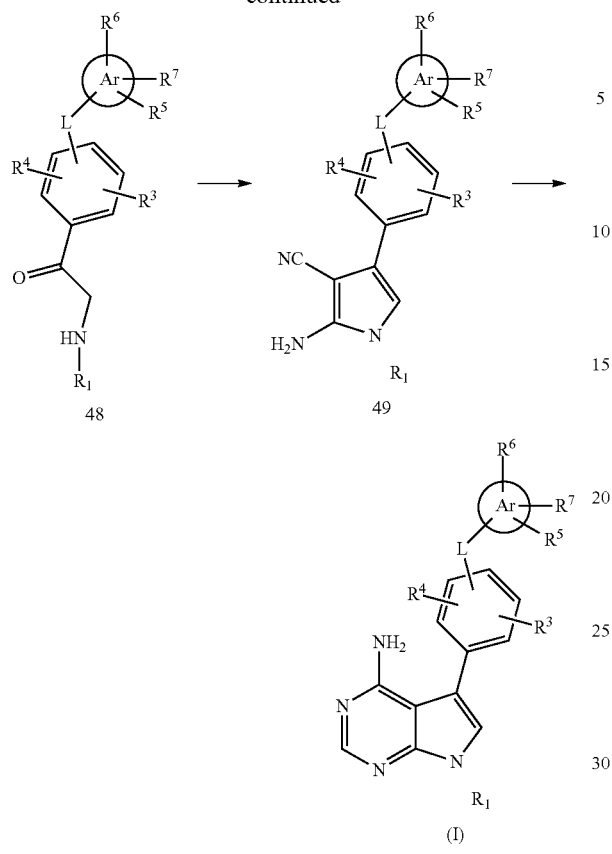

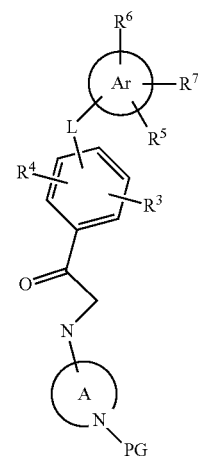

Alkylation of a compound of the formula $R^1NH_2$ where $R^1$ is as defined above with a compound of formula 47 under standard alkylation reaction conditions (e.g., reacting in the presence of a base such as sodium hydride or potassium tert-butoxide, potassium carbonate, and the like, and a catalyst such as 18-crown-6 in a suitable solvent such as N-methylpyrolidone, dimethylformamide, tetrahydrofuran, toluene and the like) provides a compound of formula 48. Reaction of compound 48 with malononitrile and a base such as potassium hydroxide, sodium hydroxide, and the like in a suitable solvent such as methanol or ethanol and the like at temperatures from 0° C. to reflux provides a compound of formula 49 which is then converted to a compound of Formula (IA), (I') or (I) as described in Scheme C above.

As discussed previously, it will be recognized by a person skilled in the art that precursors to group $R^1$ can be substituted at any step in Scheme D above where $R^1$ exists and then converted to $R^1$ at alternate stages in the synthetic process based on feasibility of the transformations. For example, an amine of formula can be used instead of $R^1NH_2$ in Scheme D above to give a compound of respectively, which is then converted to a compound of Formula (IA), (I') or (I) where $R^1$ is -(heterocycloamino)-C(CN)=CHR$^c$ following the procedures described above.

Substitution of precursors to $R^1$ in the synthesis of compounds of Formula (IA), (I') or (I) when $R^1$ is —Z-(EWG)-C(CN)=CHR$^c$ where Z is heteroalkylene or aryl and EWG is —NR'CO— is illustrated and described in Scheme E below.

Scheme E

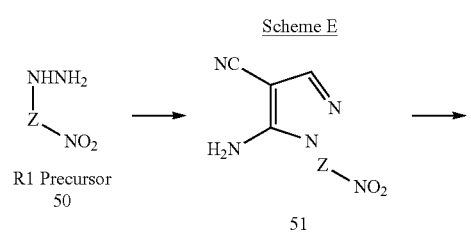

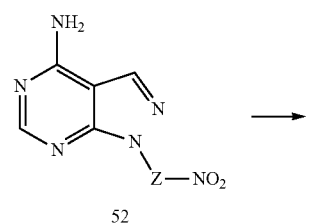

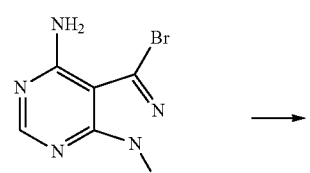

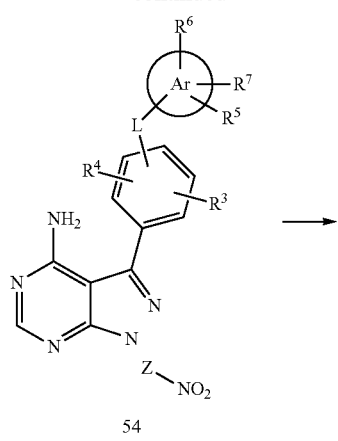

54

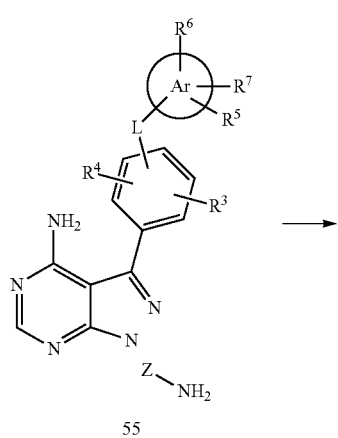

55

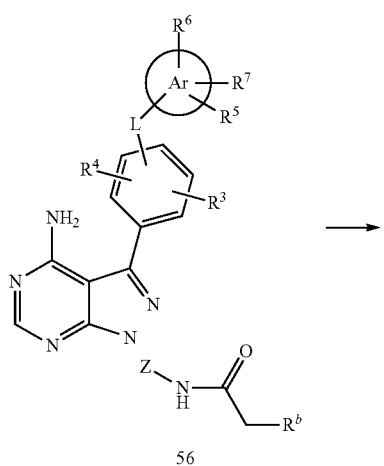

56

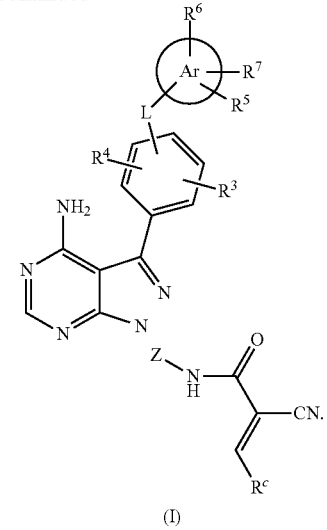

(I)

Treatment of a R¹ precursor containing hydrazines of formula 50 where Z is heteroalkylene or aryl and EWG is —NR'CO— and $R^3$-$R^7$, L and Ar defined above with ethoxymethylene malonitrile as described in Scheme C provides a compound of formula 51 which is converted to a compound of formula 53 as described in Scheme C. Coupling of a bromo compound of formula 53 with a boronic acid compound or boronate esters thereof of formula 17 under Suzuki coupling reaction conditions as described in Scheme A provides a compound of formula 54. Reduction of nitro substituent of compound 54 may be accomplished by treatment with a reducing agent such as zinc powder and the like in a suitable solvent such as acetic acid and the like, or by catalytic hydrogenation to provide a compound of formula 55. Coupling of compounds of formula 55 with a compound of formula $CNCH_2CO_2H$ such as 2-cyanoacetic acid or 2-trifluoromethylacetic acid, under standard amide coupling conditions such as carbon diimidazole (CDI) and the like or an acid derivative thereof provides a compound of formula 56. Subsequent condensation of a compound of formula 56 with aldehydes of formula $R^cCHO$ where $R^c$ is as defined above e.g., t-butyl or cyclopropyl aldehyde, under standard condensation reaction conditions such as using a base such as piperidine and the like, in the presence or absence of acetic acid and the like in solvents such as ethanol and the like at temperatures ranging from room temperature to reflux then provides a compound of Formula (IA), (I') or (I). It will recognized by a person of ordinary skill in the art that the EWG' moiety can be assembled at multiple points throughout the synthetic scheme and standard protecting group (PG) strategies can be employed as required.

Utility

The compounds of Formula (IA), (I') or (I) are tyrosine kinase inhibitors, in particular BTK and hence are useful in the treatment of autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

The compounds of Formula (IA), (I') or (I) are also useful in the treatment of In another embodiment of this aspect, the patient in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In another embodiment of this aspect, the patient in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In another embodiment of this aspect, the patient is suffering from inflammatory skin disease which includes, by way of example, dermatitis, contact dermatitis, eczema, urticaria, rosacea, and scarring psoriatic lesions in the skin, joints, or other tissues or organs.

In yet another embodiment of this aspect, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, the compound of Formula (IA), (I') or (I) is administered in combination with another an anti-cancer agent e.g., the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In yet another embodiment, the patient in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed to use of compound of Formula (IA), (I') or (I) (and any embodiments thereof described herein) for use as a medicament. In one embodiment, the use of compound of Formula (IA), (I') or (I) is for treating inflammatory disease or proliferative diseases.

In a fifth aspect is the use of a compound of Formula (IA), (I') or (I) in the manufacture of a medicament for treating an inflammatory disease in a patient in which the activity of BTK or other tyrosine kinases contributes to the pathology and/or symptoms of the disease. In one embodiment of this aspect, the tyrosine kinase protein is BTK. In another embodiment of this aspect, the inflammatory disease is respiratory, cardiovascular, or proliferative diseases.

In any of the aforementioned aspects involving the treatment of proliferative disorders, including cancer, are further embodiments comprising administering the compound of Formula (IA), (I') or (I) in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, paclitaxel, Taxol™, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol. When combination therapy is used, the agents can be administered simultaneously or sequentially.

Testing

The kinase inhibitory activity of the compounds of the present disclosure can be tested using the in vitro and in vivo assays described in Biological Examples 1-6 below. The ability of the compound of the disclosure to form reversible covalent bond with a cysteine residue of a kinase, preferably Cys481 of BTK (UniprotKB Sequence ID Q06187), can be determined by the assays described in Examples 8-11 below.

Administration and Pharmaceutical Composition

In general, the compounds of this disclosure will be administered in a therapeutically effective amount by any of the accepted modes of administration for agents that serve similar utilities. Therapeutically effective amounts of compounds of Formula (IA), (I') or (I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (IA), (I') or (I) in combination with at least one pharmaceutically acceptable excipient. Acceptable excipients are non-toxic, aid administration, and do not adversely affect the therapeutic benefit of the compound of formula (IA), (I') or (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of formula (IA), (I') or (I) based on the total formulation, with the balance being one or more suitable pharmaceutical excipients. Preferably, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore, contemporaneously or sequentially with a compound of the present disclosure. When a compound of the present disclosure is used contemporaneously with one or more other drugs, a pharmaceutical composition containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the subject is suffering from or at risk of suffering from an autoimmune disease, an inflammatory disease, or an allergy disease, a compound of Formula (IA), (I') or (I) can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subject can be treated with a compound of Formula (IA), (I') or (I) in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'- deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of Formula (IA), (I') or (I) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula (IA), (I') or (I) include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (IA), (I') or (I) include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (IA), (I') or (I) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula (IA), (I') or (I) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula (IA), (I') or (I) include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula (IA), (I') or (I) include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an BTK inhibitor compound of the disclosure include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin Al (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a compound of Formula (IA), (I') or (I) in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

EXAMPLES

The following preparations of compounds of Formula (IA), (I') or (I) and intermediates (References) are given to enable those skilled in the art to more clearly understand and to practice the present disclosure. They should not be considered as limiting the scope of the disclosure, but merely as being illustrative and representative thereof. The ᴗᴗ line at the alkene carbon, in the compounds below denotes that the compounds are isolated as an undefined mixture of (E) and (Z) isomers.

Example 1

Synthesis of (R)-2-(3-(4-amino-3-(4-phenoxyphenyl)-1H-pyrazolo[3,4-d]pyrimidin-1-yl)piperidine-1-carbonyl)-3-cyclopropylacrylonitrile

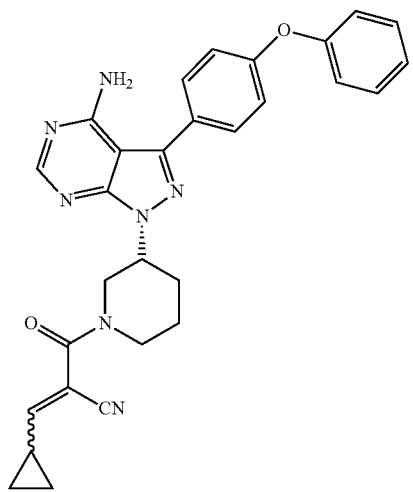

Step 1

A solution of 5-amino-1H-pyrazole-4-carbonitrile (10 g, 92.51 mmol, 1.00 equiv) in formamide (80 mL) was stirred under nitrogen at 165° C. for 5 h. The reaction mixture was cooled to room temperature and the solid was collected by filtration. The filter cake was washed first with 20 mL of water then 20 mL of methanol and dried to yield 9.5 g (76%) of 1H-pyrazolo[3,4-d]pyrimidin-4-amine as a white solid.

Step 2

A mixture of 1H-pyrazolo[3,4-d]pyrimidin-4-amine (150 g, 1.11 mol, 1.00 equiv) and N-iodo-succinimide (375 g, 1.67 mol, 1.58 equiv) in N,N-dimethylformamide (2.5 L) was stirred at 80° C. for 5 h. The reaction mixture was cooled to room temperature and then diluted with 10 L of water. The solid was collected by filtration, washed with 2×1 L of saturated aqueous sodium sulfite and dried under vacuum to give 150 g (52%) of 3-iodo-1H-pyrazolo[3,4-d]pyrimidin-4-amine as a yellow solid.

Step 3

To a stirred mixture of 3-iodo-1H-pyrazolo[3,4-d]pyrimidin-4-amine (5.9 g, 22.6 mmol, 1.00 equiv), (S)-tert-butyl 3-hydroxypiperidine-1-carboxylate (10 g, 50 mmol, 2.2 equiv) and triphenylphosphine (11.8 g, 45 mmol, 2.0 equiv) in tetrahydrofuran (300 mL) at 10° C. was added a solution of diisopropyl azodicarboxylate in tetrahydrofuran (30 mL) dropwise in 30 min. The resulting mixture was stirred at room temperature for 12 h and then concentrated under vacuum. The residue was purified on a silica gel column eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as a yellow solid.

Step 4

A mixture of tert-butyl 3-[4-amino-3-iodo-1H-pyrazolo[3,4-d]pyrimidin-1-yl]piperidine-1-carboxylate (1 g, 2.25 mmol, 1.00 equiv), (4-phenoxyphenyl)boronic acid (530 mg, 2.48 mmol, 1.10 equiv), sodium carbonate (480 mg, 4.53 mmol, 2.01 equiv) and tetrakis(triphenylphosphine)palladium (78 mg, 0.07 mmol, 0.03 equiv) in 1,4-dioxane (60 mL) and water (15 mL) was stirred under nitrogen at 90° C. for 24 h. The reaction mixture was cooled to room temperature and then concentrated under vacuum. The residue was dissolved in 500 mL of dichloromethane. The resulting solution was washed with 200 mL of water, dried over anhydrous sodium sulfate and concentrated under vacuum. The residue was purified on a silica gel column eluted with dichloromethane/methanol (100/1) to give 700 mg (64%) of tert-butyl 3-[4-amino-3-(4-phenoxyphenyl)-1H-pyrazolo[3,4-d]pyrimidin-1-yl]piperidine-1-carboxylate as a yellow solid.

Step 5

A mixture of tert-butyl 3-[4-amino-3-(4-phenoxyphenyl)-1H-pyrazolo[3,4-d]pyrimidin-1-yl]piperidine-1-carboxylate (700 mg, 1.44 mmol, 1.00 equiv) in dichloromethane (100 mL) and trifluoroacetic acid (20 mL) was stirred at room temperature for 12 h. The reaction mixture was concentrated under vacuum to yield 580 mg of crude 3-(4-phenoxyphenyl)-1-(piperidin-3-yl)-1H-pyrazolo[3,4-d]pyrimidin-4-amine as a yellow oil.

Step 6

A mixture of 3-(4-phenoxyphenyl)-1-(piperidin-3-yl)-1H-pyrazolo[3,4-d]pyrimidin-4-amine (580 mg, 1.50 mmol, 1.00 equiv), carbonyldiimidazole (365 mg, 2.25 mmol, 1.50 equiv) and 2-cyanoacetic acid (190 mg, 2.24 mmol, 1.49 equiv) in dichloromethane (100 mL) was stirred at room temperature for 24 h. The reaction mixture was diluted with 100 mL of dichloromethane and washed with 3×100 mL of saturated aqueous ammonium chloride solution. The organic layer was dried over anhydrous sodium sulfate and concentrated under vacuum. The residue was purified on a silica gel column eluted with dichloromethane/methanol (100/1) to give 380 mg (56%) of 3-[3-[4-amino-3-(4-phenoxyphenyl)-1H-pyrazolo[3,4-d]pyrimidin-1-yl]piperidin-1-yl]-3-oxopropanenitrile as a white solid.

Step 7

A mixture of 3-[3-[4-amino-3-(4-phenoxyphenyl)-1H-pyrazolo[3,4-d]pyrimidin-1-yl]piperidin-1-yl]-3-oxopropanenitrile (120 mg, 0.26 mmol, 1.00 equiv), piperidine (27 mg, 0.28 mmol, 1.07 equiv) and cyclopropanecarbaldehyde (28 mg, 0.40 mmol, 1.51 equiv) in methanol (8 mL) was stirred in sealed tube at room temperature for 24 h. The resulting mixture was concentrated under vacuum and the residue was purified on a silica gel column eluted with dichloromethane/methanol (100/1) to give 85.4 mg (64%) of the title compound as a white solid. MS (ESI, pos. ion) m/z: 506 (M+1). $^1$HNMR(300MHz,CDCl$_3$, ppm) 8.392 (1H, s), 7.676~7.581 (2H, t), 7.445~7.393 (2H, t), 7.202~7.097 (5H, m), 6.601~6.566 (1H,d, J=10.5), 5.737(2H,s), 5.010~4.912 (1H,m), 4.691~3.185 (4H,m), 2.464~2.035 (5H,m), 1.275~0.876 (4H,m).

Example 2

Synthesis of 2-((R)-3-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile

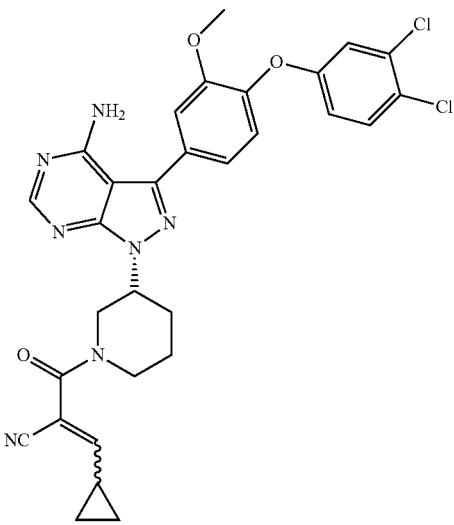

Step 1

A mixture of 3,4-dichlorophenol (38 g, 233.13 mmol, 1.00 equiv), 1-fluoro-2-methoxy-4-nitrobenzene (40 g, 233.75 mmol, 1.00 equiv) and potassium carbonate (64 g, 463.77 mmol, 1.99 equiv) in N,N-dimethylformamide (250 mL) was stirred overnight at 60° C. The resulting solution was diluted with 1000 mL of water, extracted with 3×200 mL of ethyl acetate and the organic layers combined. The resulting mixture was washed with 3×500 mL of brine. The mixture was dried over anhydrous sodium sulfate and concentrated under vacuum to yield 60 g (82%) of 1,2-dichloro-4-(2-methoxy-4-nitrophenoxy)benzene as a brown solid.

Step 2

A mixture of 1,2-dichloro-4-(2-methoxy-4-nitrophenoxy)benzene (60 g, 190.40 mmol, 1.00 equiv), Fe (53 g, 946.43 mmol, 4.97 equiv) and ammonium chloride (10 g, 188.68 mmol, 0.99 equiv) in tetrahydrofuran/water (1/2) (600 mL) was stirred overnight at 60° C. under an inert atmosphere of nitrogen. The mixture was filtered through Celite and the filtrate was concentrated under vacuum. The resulting solution was extracted with 3×500 mL of dichloromethane and the organic layers combined. The resulting mixture was washed with 3×500 mL of brine. The mixture was dried over anhydrous magnesium sulfate and concentrated under vacuum to give 40 g (74%) of 4-(3,4-dichlorophenoxy)-3-methoxyaniline as a light gray solid.

Step 3

A solution of sodium nitrite (14.4 g, 208.70 mmol, 1.98 equiv) in water (500 mL) was added dropwise into a solution of 4-(3,4-dichlorophenoxy)-3-methoxyaniline (30 g, 105.58 mmol, 1.00 equiv) in sulfuric acid (1000 mL) with stirring at 0° C. and the mixture was stirred for 30 min at 0° C. The above mixture was added dropwise to a solution of potassium iodide (1000 mL, 5%) in water with stirring at 50° C. The reaction was completed immediately. The reaction mixture was cooled to room temperature, extracted with 3×500 mL of ethyl acetate and the organic layers combined. The resulting mixture was washed with 3×500 mL of saturated aqueous sodium bicarbonate and 3×500 mL of brine. The mixture was dried over anhydrous sodium sulfate and concentrated under vacuum to give 24 g (crude) of 1,2-dichloro-4-(4-iodo-2-methoxyphenoxy)benzene as red oil.

Step 4

A mixture of 1,2-dichloro-4-(4-iodo-2-methoxyphenoxy) benzene (93 g, 235.43 mmol, 1.00 equiv) in 1,4-dioxane (500 mL), potassium acetate (46 g, 469.39 mmol, 1.99 equiv), 4,4,5,5-tetramethyl-2-(4,4,5,5-tetramethyl-1,3,2-dioxaborolan-2-yl)-1,3,2-dioxaborolane (89 g, 350.39 mmol, 1.49 equiv) and Pd(dppf)Cl$_2$ (4.65 g) was stirred overnight at 90° C. under an inert atmosphere of nitrogen. The reaction mixture was cooled to room temperature and concentrated under vacuum. The residue was dissolved in 500 mL of ethyl acetate and washed with mL of water and brine. The mixture was dried over anhydrous sodium sulfate and concentrated under vacuum. The residue was applied onto a silica gel column with ethyl acetate/petroleum ether (1/100) to yield 10 g (11%) of 2-[4-(3,4-dichlorophenoxy)-3-methoxyphenyl]-4,4,5,5-tetramethyl-1,3,2-dioxaborolane as light yellow oil.

2-[4-(3,4-Dichlorophenoxy)-3-methoxyphenyl]-4,4,5,5-tetramethyl-1,3,2-dioxaborolane was then covered to the title compound following the procedures described in Example 1, steps 4-7 above.

Example 3

Synthesis of (R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile

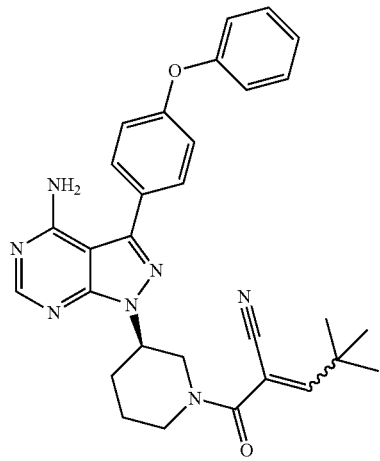 [SMILES: CC(C)(C)C=C(C#N)C(=O)N1CCC[C@@H](n2nc(-c3ccc(Oc4ccccc4)cc3)c3c(N)ncnc32)C1]

A mixture of 3-[3-[4-amino-3-(4-phenoxyphenyl)-1H-pyrazolo[3,4-d]pyrimidin-1-yl]piperidin-1-yl]-3-oxopropanenitrile (150 mg, 0.33 mmol, 1.00 equiv), methanol (15 mL), dichloromethane (5 mL), piperidine (56 mg, 0.66 mmol, 2 equiv) and pivalaldehyde (142 mg, 1.66 mmol, 5 equiv) was stirred for 48 h at 30° C. in a 25-mL sealed tube. The resulting mixture was concentrated under vacuum. The residue was applied onto a silica gel column with dichloromethane/methanol (100/1) to give 45 mg (26%) of (R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile as a white solid. MS (ESI, pos. ion) m/z: 522 (M+1) $^1$HNMR (300MHz,CDCl$_3$, ppm) 8.396 (1H, s), 7.684~7.656 (2H, d,J=8.4), 7.440~7.388 (2H, t), 7.222~7.092 (5H, m), 6.956 (1H,s), 5.613(2H,s), 5.006~4.909 (1H,m), 4.626~3.290 (4H, m), 2.419~1.732 (4H,m), 1.275 (9H,s).

Example 4

Synthesis of 2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile

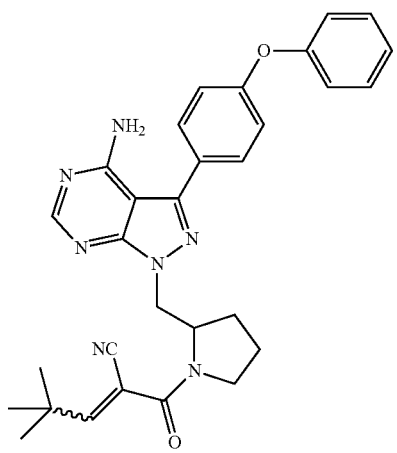 [SMILES: CC(C)(C)C=C(C#N)C(=O)N1CCCC1Cn1nc(-c2ccc(Oc3ccccc3)cc2)c2c(N)ncnc21]

Synthesized as Examples 1 and 3 above but using tert-butyl 2-(hydroxymethyl)-pyrrolidine-1-carboxylate instead of (S)-tert-butyl-3-hydroxypiperidine-1-carboxylate. MS (ESI, pos. ion) m/z: 522 (M+1).

Example 5

Synthesis of (N-((1r,4r)-4-(4-amino-3-(4-phenoxyphenyl)-1H-pyrazolo[3,4-d]pyrimidin-1-yl)cyclohexyl)-2-cyano-3-cyclopropylacrylamide

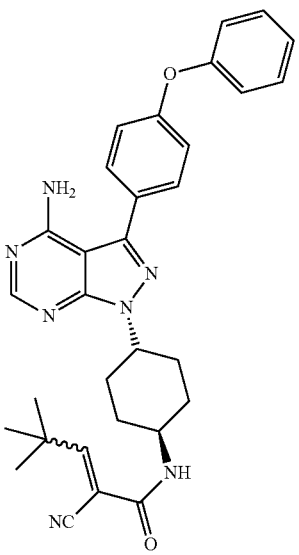

Synthesized as described in Examples 1 and 3 above except using tert-butyl(1r,4r)-4-hydroxycyclohexylcarbamate instead of (S)-tert-butyl3-hydroxypiperidine-1-carboxylate. MS (ESI, pos. ion) m/z: 536 (M+1).

Example 6

Synthesis of 2-(4-(4-amino-3-(4-phenoxyphenyl)-1H-pyrazolo[3,4-d]pyrimidin-1-yl)piperidine-1-carbonyl)-4,4-dimethylpent-2-enenitrile

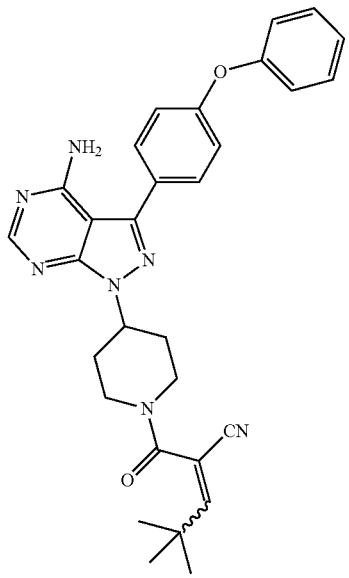 [SMILES: CC(C)(C)C=C(C#N)C(=O)N1CCC(n2nc(-c3ccc(Oc4ccccc4)cc3)c3c(N)ncnc32)CC1]

Synthesized as described in Examples 1 and 3 above except using, tert-butyl-4-hydroxypiperidine-1-carboxylate instead of (S)-tert-butyl3-hydroxypiperidine-1-carboxylate. MS (ESI, pos. ion) m/z: 522 (M+1).

Example 8

Synthesis of (R)-2-(3-(4-amino-3-(4-(3,4-dichlorophenoxy)-3-methoxyphenyl)-1H-pyrazolo-[3,4-d]pyrimidin-1-yl)piperidine-1-carbonyl)-4,4-dimethylpent-2-enenitrile

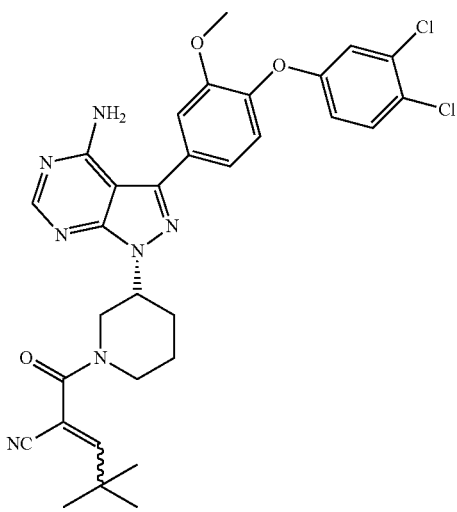

Synthesized as described in Examples 7 and 3 above using pivaldehyde instead of cyclopropanecarbaldehyde. MS (ESI, pos. ion) m/z: 620 (M+1).

Example 9

Synthesis of (R)-N-(4-(4-amino-1-(1-(2-cyano-3-cyclopropylacryloyl)piperidin-3-yl)-1H-pyrazolo[3,4-d]pyrimidin-3-yl)phenyl)-4-(trifluoromethyl)benzamide

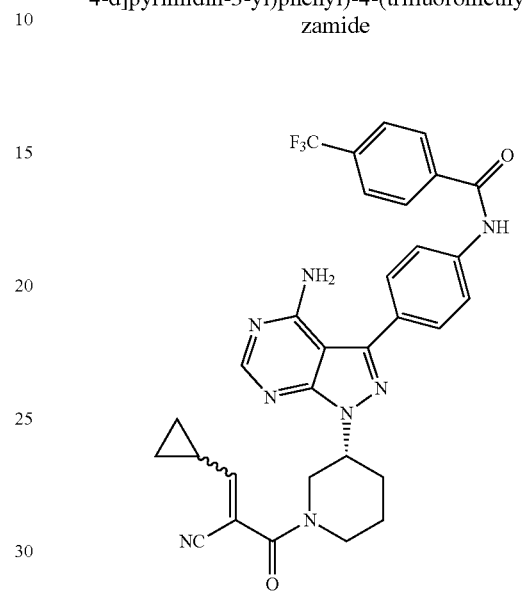

Step 1

A mixture of 3-iodo-1H-pyrazolo[3,4-d]pyrimidin-4-amine (5.9 g, 22.6 mmol, 1.00 equiv), (S)-tert-butyl3-hydroxypiperidine-1-carboxylate (10 g, 50 mmol, 2.2 equiv), triphenylphosphine (11.8 g, 45 mmol, 2 equiv) in tetrahydrofuran (300 mL) was stirred at 10° C. Diisopropyl azodicarboxylate in tetrahydrofuran (30 mL) was dropped in the mixture slowly in 30 min. The resulting mixture was stirred for 12 h at room temperature was and then concentrated under vacuum. The residue was loaded onto a silica gel column and eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as yellow solid. MS (ESI, pos. ion) m/z: 445 (M+1).

Step 2

Into a 250-mL 3-necked round-bottom flask purged and maintained with an inert atmosphere of nitrogen, was placed (R)-tert-butyl 3-[4-amino-3-iodo-1H-pyrazolo[3,4-d]pyrimidin-1-yl]piperidine-1-carboxylate (2 g, 4.50 mmol, 1.00 equiv), 4-borono-benzenaminium chloride (0.934 g), Pd(PPh$_3$)$_4$ (0.312 g), ethylene glycol dimethyl ether (100 mL), sodium carbonate (1.194 g), and water (20 mL). The resulting solution was stirred for 12 h at 80° C. in an oil bath. The resulting mixture was concentrated under vacuum and residue was loaded onto a silica gel column and eluted with dichloromethane/methanol (50:1) to give 1.5 g (81%) of (R)-tert-butyl 3-(4-amino-3-(4-aminophenyl)-1H-pyrazolo[3,4-d]pyrimidin-1-yl)piperidine-1-carboxylate as a brown solid. MS (ESI, pos. ion) m/z: 410 (M+1)

Step 3

Into a 250-mL round-bottom flask, was placed (R)-tert-butyl3-[4-amino-3-(4-aminophenyl)-1H-pyrazolo[3,4-d]pyrimidin-1-yl]piperidine-1-carboxylate (1.0 g, 2.44 mmol, 1.00 equiv), HATU (0.746 g), 4-(trifluoromethyl)benzoic acid (374 mg, 1.97 mmol, 0.81 equiv), triethylamine (500 mg, 4.94 mmol, 2.02 equiv), and N,N-dimethylformamide (50 mL). The resulting solution was stirred for 5 h at 25° C. The resulting mixture was quenched with water. The resulting solution was extracted with ethyl acetate and washed with sodium chloride (sat). The organic layers dried over anhydrous magnesium sulfate and concentrated under vacuum and residue was loaded onto a silica gel column and eluted with dichloromethane/methanol (50:1 to give 1.15 g (81%) of tert-butyl 3-[4-amino-3-(4-[[4-(trifluoromethyl)benzene] amido]phenyl)-1H-pyrazolo[3,4-d]pyrimidin-1-yl]piperidine-1-carboxylate as a brown solid. MS (ESI, pos. ion) m/z: 582 (M+1)

Step 4

Into a 250-mL round-bottom flask, was placed (R)-tert-butyl 3-[4-amino-3-(4-[[4-(trifluoromethyl)benzene]amido] phenyl)-1H-pyrazolo[3,4-d]pyrimidin-1-yl]piperidine-1-carboxylate (1.1 g, 1.89 mmol, 1.00 equiv), and dichloromethane (100 mL). This was followed by the addition of $CF_3COOH$ (20 mL) dropwise with stirring at 25° C. over 10 min. The resulting solution was stirred for 3 h at 25° C. The resulting mixture was concentrated under vacuum to give 0.829 g (91%) of (R)-N-[4-[4-amino-1-(piperidin-3-yl)-1H-pyrazolo[3,4-d]pyrimidin-3-yl]phenyl]-4-(trifluoromethyl)benzamide as brown oil. MS (ESI, pos. ion) m/z: 382 (M+1)

Step 5

Into a 250-mL round-bottom flask, was placed (R)-N-[4-[4-amino-1-(piperidin-4-yl)-1H-pyrazolo[3,4-d]pyrimidin-3-yl]phenyl]-4-(trifluoromethyl)benzamide (828 mg, 1.72 mmol, 1.00 equiv), 2-cyanoacetic acid (220 mg, 2.59 mmol, 1.50 equiv), CDI (420 mg, 2.59 mmol, 1.51 equiv), in dichloromethane (80 mL). The resulting solution was stirred for 12 h at 25° C. The resulting mixture was washed with $NH_4Cl$ and concentrated under vacuum. The residue was loaded onto a silica gel column and eluted with dichloromethane/methanol (50:1) to give 300 mg (32%) of N-(4-[4-amino-1-[1-(2-cyanoacetyl)piperidin-4-yl]-1H-pyrazolo[3,4-d]pyrimidin-3-yl]phenyl)-4-(trifluoromethyl)benzamide as a yellow solid. MS (ESI, pos. ion) m/z: 549 (M+1)

Step 6

Into a 10-mL round-bottom flask, was placed (R)-N-(4-[4-amino-1-[1-(2-cyanoacetyl)piperidin-3-yl]-1H-pyrazolo[3,4-d]pyrimidin-3-yl]phenyl)-4-(trifluoromethyl)-benzamide (65 mg, 0.12 mmol, 1.00 equiv), cyclopropanecarbaldehyde (16.6 mg, 0.24 mmol, 2.00 equiv), piperidine (10 mg, 0.12 mmol, 0.99 equiv), methanol (5 mL). The resulting solution was stirred for 12 h at 25° C. The resulting mixture was concentrated under vacuum and the residue was loaded onto a silica gel column and eluted with dichloromethane/methanol (50:1) to give 43 mg (60%) of (R)-N-[4-(4-amino-1-[1-[2-cyano-2-(cyclopropylmethylidene)acetyl]piperidin-3-yl]-1H-pyrazolo[3,4-d]pyrimidin-3-yl)phenyl]-4-(trifluoromethyl)benzamide as a white solid. MS (ESI, pos. ion) m/z: 601 (M+1), $^1$HNMR (300MHz, $CDCl_3$, ppm), 8.6 (1H, s), 8.348 (1Hs), 8.065~8.038 (2H, d,J=8.1),7.880~7.852 (1H, d,J=8.4), 7.768~7.659 (4H,m), 6.532~6.496 (1H, d,J=10.8), 5.949 (2H,s), 4.976~4.907 (1H,m), 4.638~3.218 (4H,m), 2.436~1.818 (5H,m),1.221~1.198 (2H,m), 0.89~0.772 (2H,m).

Example 10

Preparation of (R)-N-(4-(4-amino-1-(1-(2-cyano-4,4-dimethylpent-2-enoyl)piperidin-3-yl)-1H-pyrazolo[3, 4-d]pyrimidin-3-yl)phenyl)-4-(trifluoromethyl)benzamide

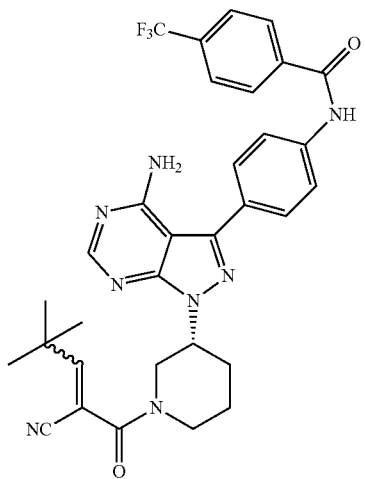 [SMILES: CC(C)(C)C=C(C#N)C(=O)N1CCC[C@@H](n2nc(-c3ccc(NC(=O)c4ccc(C(F)(F)F)cc4)cc3)c3c(N)ncnc32)C1]

Into a 50-mL round-bottom flask, was placed N-(4-[4-amino-1-[1-(2-cyanoacetyl)-piperidin-3-yl]-1H-pyrazolo[3, 4-d]pyrimidin-3-yl]phenyl)-4-(trifluoromethyl)benzamide (130 mg, 0.24 mmol, 1.00 equiv), 2,2-dimethylpropanal (2 mL), piperidine (1 mL), and methanol (30 mL). The resulting solution was stirred for 24 h at 30° C. in an oil bath. The resulting mixture was concentrated under vacuum and residue was loaded onto a silica gel column and eluted with dichloromethane/methanol (50/1 to give 40 mg (27%) of N-[4-(4-amino-1-[1-[2-cyano-2-(2,2-dimethylpropylidene) acetyl]piperidin-3-yl]-1H-pyrazolo[3,4-d]pyrimidin-3-yl) phenyl]-4-(trifluoromethyl)benzamide as a white solid. MS (ESI, pos. ion) m/z: 617 (M+1), $^1$HNMR (300MHz, $CDCl_3$, ppm), 8.364 (1H, s), 8.212 (1H,s), 8.086~8.059(2H,t), 7.929~7.901 (2H, d,J=8.4), 7.827~7.800 (2H, d,J=8.1), 7.742~7.715 (2H, d,J=8.1), 6.963(1H,s), 6.3(2H,s), 5.031~4.934 (1H,m),4.8~3.05 (4H,m), 2.738~2.067 (5H,m), 1.274 (9H,s).

Example 11

Synthesis of (R)-2-(2-((4-amino-3-(4-(3-fluorophenoxy)phenyl)-1H-pyrazolo[3,4-d]pyrimidin-1-yl)methyl)pyrrolidine-1-carbonyl)-3-cyclopropylacrylonitrile

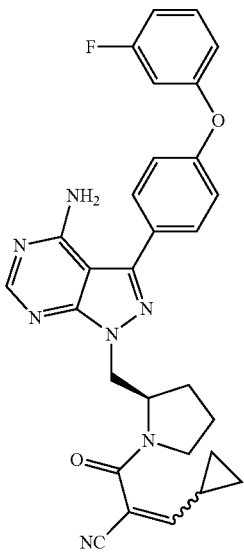 [SMILES: N#CC(=CC1CC1)C(=O)N1CCC[C@@H]1Cn1nc(-c2ccc(Oc3cccc(F)c3)cc2)c2c(N)ncnc21]

Step 1

Into a 100-mL 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv), prepared as described in Example 1 except in the Mitsunobu reaction using (R)-tert-butyl 2-(hydroxymethyl)pyrrolidine-1-carboxylate instead of (S)-tert-butyl 3-hydroxypiperidine-1-carboxylate, 2-[4-(3-fluorophenoxy)phenyl]-4,4,5,5-tetramethyl-1,3,2-dioxaborolane (254 mg, 0.81 mmol, 1.20 equiv), tetrakis(triphenylphosphane)palladium (47 mg, 0.04 mmol, 0.06 equiv), ethylene glycol dimethyl ether (50 mL), sodium carbonate (180 mg, 1.70 mmol, 2.50 equiv), and water (10 mL). The resulting solution was stirred for 12 h at 80° C. in an oil bath. The resulting mixture was concentrated under vacuum and extracted with dichloromethane. The organic layers were combined, dried and concentrated under vacuum. The residue was loaded on a silica gel column and eluted with dichloromethane/methanol (50/1) to give 0.27 g (79%) of tert-butyl (2R)-2-([4-amino-3-[4-(3-fluorophenoxy)phenyl]-1H-pyrazolo[3,4-d]pyrimidin-1-yl]methyl)pyrrolidine-1-carboxylate as a brown solid.

Step 2

Into a 100-mL round-bottom flask, was placed a solution of tert-butyl (2R)-2-([4-amino-3-[4-(3-fluorophenoxy)phenyl]-1H-pyrazolo[3,4-d]pyrimidin-1-yl]methyl)pyrrolidine-1-carboxylate (270 mg, 0.54 mmol, 1.00 equiv) in dichloromethane (50 mL). This was followed by the addition of trifluoroacetic acid (10 mL) dropwise with stirring over 10 min. The resulting solution was stirred for 3 h at 25° C. The resulting mixture was concentrated under vacuum to give 0.216 g (crude) of 3-[4-(3-fluorophenoxy)phenyl]-1-[(2R)-pyrrolidin-2-ylmethyl]-1H-pyrazolo[3,4-d]pyrimidin-4-amine as brown oil.

Step 3

Into a 100-mL round-bottom flask, was placed 3-[4-(3-fluorophenoxy)phenyl]-1-[(2R)-pyrrolidin-2-ylmethyl]-1H-pyrazolo[3,4-d]pyrimidin-4-amine (216 mg, 0.53 mmol, 1.00 equiv), 2-cyanoacetic acid (36.8 mg, 0.43 mmol, 0.80 equiv), HATU (166 mg, 0.44 mmol, 0.80 equiv), triethylamine (109 mg, 1.08 mmol, 2.00 equiv), N,N-dimethylformamide (50 mL). The resulting solution was stirred for 3 h at 25° C. The resulting solution was extracted with ethyl acetate and the organic layers combined and concentrated under vacuum. The residue was loaded on a silica gel column and eluted with dichloromethane methanol (50 1) to give 150 mg (60%) of 3-[(2R)-2-([4-amino-3-[4-(3-fluorophenoxy)phenyl]-1H-pyrazolo[3,4-d]pyrimidin-1-yl]methyl)pyrrolidin-1-yl]-3-oxopropanenitrile as a yellow solid.

Step 4

Into a 10-mL round-bottom flask, was placed 3-[(2R)-2-([4-amino-3-[4-(3-fluorophenoxy)phenyl]-1H-pyrazolo[3,4-d]pyrimidin-1-yl]methyl)pyrrolidin-1-yl]-3-oxopropanenitrile (150 mg, 0.32 mmol, 1.00 equiv), piperidine (27 mg, 0.32 mmol, 1.00 equiv), cyclopropanecarbaldehyde (44.5 mg, 0.63 mmol, 2.00 equiv), methanol (5 mL). The resulting solution was stirred for 12 h at 25° C. and then concentrated under vacuum. The residue was loaded on a silica gel column and eluted with dichloromethane/methanol (50/1) to give 48.5 mg (29%) of the title compound as a off-white solid. LC-MS: (ES, m/z): MS (ESI, pos. ion) m/z: 524 (M+1). H-NMR: (CDCl$_3$, ppm): 1HNMR (300MHz, CD$_3$OD, ppm), 8.253 (1H, s), 7.686~7.749 (2H, t), 7.363~7.440 (1H, t), 7.185~7.232 (2H, t), 6.833~6.941 (3H, m), 6.450~6.600 (1H, d), 4.301~4.555(3H, m), 3.604~3.638 (2H, m), 1.868~2.005 (5H, m), 1.200~1.294 (3H, m), 0.798~0.810 (2H, m).

Example 12

Synthesis of (R)-2-(2-((4-amino-3-(4-(2,6-difluorophenoxy)phenyl)-1H-pyrazolo[3,4-d]pyrimidin-1-yl)methyl)pyrrolidine-1-carbonyl)-3-cyclopropylacrylonitrile

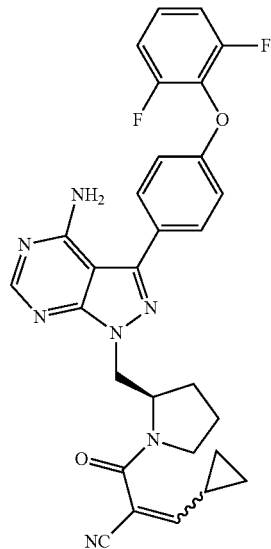 [SMILES: N#CC(=CC1CC1)C(=O)N1CCC[C@@H]1Cn1nc(-c2ccc(Oc3c(F)cccc3F)cc2)c2c(N)ncnc21]

Step 1

Into a 1 L, 2-necked round-bottom flask purged and maintained under an inert atmosphere of nitrogen, was placed 3-iodo-1H-pyrazolo[3,4-d]pyrimidin-4-amine (10 g, 38.31 mmol, 1.00 equiv), tert-butyl (2R)-2-(hydroxymethyl)pyrrolidine-1-carboxylate (15.4 g, 76.52 mmol, 2.00 equiv), PPh$_3$ (20.1 g, 76.63 mmol, 2.00 equiv), and N,N-dimethylformamide (400 mL). DIAD (15.5 g, 76.65 mmol, 2.00 equiv) was added dropwise over 30 min. The resulting solution was stirred for 12 h at 25° C. and then diluted with 1 L of water. The resulting solution was extracted with ethyl acetate and the organic layers combined and washed with brine. The mixture was dried over anhydrous sodium sulfate and concentrated under vacuum and the residue was placed on a silica gel column and eluted with chloroform/methanol (100/1) to give 1.2 g (6%) of tert-butyl (2R)-2-([4-amino-3-iodo-1H-pyrazolo[3,4-d]pyrimidin-1-yl]methyl)pyrrolidine-1-carboxylate as a off-white solid.

Step 2

Into a 500-mL 4-necked round-bottom flask, was placed a solution of sodium hydride (4.05 g, 168.75 mmol, 1.70 equiv) in N,N-dimethylformamide (200 mL). A solution of 1-fluoro-4-nitrobenzene (14 g, 99.22 mmol, 1.00 equiv) in N,N-dimethylformamide (50 mL) was added dropwise with stirring at 0° C. over 20 min. The resulting solution was stirred for 2 hr at room temperature. Cu$_2$Cl$_2$ (9.83 g, 100.31 mmol, 1.01 equiv) was added and a solution of 2,6-difluorophenol (15.5 g, 119.15 mmol, 1.20 equiv) in N,N-dimethylformamide (50 mL) was added dropwise with stirring at 25° C. over 10 min. The resulting solution was stirred for 12 h at 100° C. in an oil bath, diluted with 500 mL of water and extracted with ethyl acetate. The combined organic layers were washed with water and brine, dried over anhydrous sodium sulfate and concentrated under vacuum. The residue was placed on a silica gel column and eluted with ethyl acetate/petroleum ether (1/8) to give 20 g (80%) of 1,3-difluoro-2-(4-nitrophenoxy)benzene as brown oil.

Step 3

Into a 500 mL, 3-necked round-bottom flask purged and maintained under an inert atmosphere of nitrogen, was placed a solution of 1,3-difluoro-2-(4-nitrophenoxy)benzene (20 g, 79.62 mmol, 1.00 equiv) in methanol (200 mL), Raney Nickel (2 g). A solution of hydrazine hydrate (12.67 g) in methanol (50 mL) was added dropwise with stirring in 15 min. The resulting solution was stirred for 12 h at 25° C., then filtrated and the filtrate was concentrated under vacuum. The residue was diluted with f ethyl acetate, washed with water and brine, and dried over anhydrous sodium sulfate and concentrated under vacuum to give 16 g (91%) of 4-(2,6-difluorophenoxy) aniline as black oil.

Step 4

Into a 250-mL 4-necked round-bottom flask, was placed 4-(2,6-difluorophenoxy)-aniline (8.84 g, 39.96 mmol, 1.00 equiv), hydrogen chloride (37%) (10.14 g, 277.81 mmol, 6.95 equiv) and water (20 mL). NaNO$_2$ (3.04 g, 44.06 mmol, 1.10 equiv) in water (10 mL) was added dropwise with stirring at 0° C. over 5 min., and the reaction mixture was stirred for 30 mins at 0° C. The reaction mixture was added into a solution of NaI (18 g, 120.00 mmol, 3.00 equiv) in water (20 mL) at 25° C. in batches over 5 min. The resulting solution was stirred for 2 h at 25° C. and then extracted with of ethyl acetate and the organic layers were combined. The combined organic layers were washed with water and brine, dried over anhydrous sodium sulfate and concentrated under vacuum to give 10.2 g (77%) of 1,3-difluoro-2-(4-iodophenoxy)benzene as brown oil.

Step 5

Into a 100 mL 3-necked round-bottom flask purged and maintained in an inert atmosphere of nitrogen, was placed a solution of 1,3-difluoro-2-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (1.76 g, 17.93 mmol, 3.0 equiv), and Pd(OAc)$_2$ (68 mg, 0.30 mmol, 0.05 equiv). The resulting solution was stirred for 12 h at 85° C. in an oil bath. The reaction mixture was then quenched with water. The resulting solution was extracted with ethyl acetate and the organic layers combined and washed with water and brine. The organics were dried over anhydrous sodium sulfate and concentrated under vacuum. The residue was loaded onto a silica gel column and eluted with ethyl acetate/petroleum ether (1/8) to give 1.5 g (75%) of 2-[4-(2,6-difluorophenoxy)phenyl]-4,4,5,5-tetramethyl-1,3,2-dioxaborolane as a light yellow solid.

Step 6

Into a 100 mL, 3-necked round-bottom flask purged and maintained in an inert atmosphere of nitrogen, was placed a solution of tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv) in 1,4-dioxane/water (60/15 mL), 2-[4-(2,6-difluorophenoxy)phenyl]-4,4,5,5-tetramethyl-1,3,2-dioxaborolane (290 mg, 0.87 mmol, 1.3 equiv), sodium carbonate (180 mg, 1.68 mmol, 2.5 equiv), and tetrakis(triphenylphosphane)palladium (40 mg, 0.03 mmol, 0.05 equiv). The resulting solution was stirred for 12 h at 90° C. in an oil bath and then concentrated under vacuum. The resulting solution was diluted with 50 mL of dichloromethane, washed with water and brine. The organics were dried over anhydrous sodium sulfate and concentrated under vacuum. The residue was loaded onto a silica gel column and eluted with dichloromethane/methanol (20/1) to give 280 mg (79%) of tert-butyl (2R)-2-([4-amino-3-[4-(2,6-difluorophenoxy)phenyl]-1H-pyrazolo[3,4-d]pyrimidin-1-yl]methyl) pyrrolidine-1-carboxylate as a white solid.

Step 7

Into a 50 mL round-bottom flask, was placed a solution of tert-butyl (2R)-2-([4-amino-3-[4-(2,6-difluorophenoxy)phenyl]-1H-pyrazolo[3,4-d]pyrimidin-1-yl]methyl)-pyrrolidine-1-carboxylate (280 mg, 0.54 mmol, 1.00 equiv) in dichloromethane (10 mL). Trifluoroacetic acid (2 mg, 0.02 mmol, 0.03 equiv) was added dropwise with stirring at 25° C. The resulting solution was stirred for 3 h at 25° C. and then concentrated under vacuum. The resulting solution was diluted with 50 mL of dichloromethane, washed with ethyl acetate and H$_2$O, brine and concentrated under vacuum to give 200 mg (88%) of 3-[4-(2,6-difluorophenoxy)phenyl]-1-[(2R)-pyrrolidin-2-ylmethyl]-1H-pyrazolo[3,4-d]pyrimidin-4-amine as a white solid.

Step 8

Into a 100 mL round-bottom flask, was placed a solution of 3-[4-(2,6-difluoro-phenoxy)phenyl]-1-[(2R)-pyrrolidin-2-ylmethyl]-1H-pyrazolo[3,4-d]pyrimidin-4-amine (200 mg, 0.47 mmol, 1.00 equiv) in dichloromethane (10 mL), 2-cyanoacetic acid (121 mg, 1.42 mmol, 3.00 equiv), and 1,1-carbonyldiimidazole (230 mg, 1.42 mmol, 3.00 equiv). The resulting solution was stirred for 12 h at 25° C. and then washed with water and brine. The mixture was dried over anhydrous sodium sulfate and concentrated under vacuum. The residue was loaded onto a silica gel column and eluted with dichloromethane/methanol (50/1) to give 112 mg (48%) of 3-[(2R)-2-([4-amino-3-[4-(2,6-difluorophenoxy)phenyl]-1H-pyrazolo[3,4-d]pyrimidin-1-yl]methyl)pyrrolidin-1-yl]-3-oxopropanenitrile as a white solid.

Step 9

Into a 10 mL sealed tube, was placed a solution of 3-[(2R)-2-([4-amino-3-[4-(2,6-difluorophenoxy)phenyl]-1H-pyrazolo[3,4-d]pyrimidin-1-yl]methyl)pyrrolidin-1-yl]-3-oxopropanenitrile (100 mg, 0.20 mmol, 1.00 equiv) in methanol (3 mL), cyclopropanecarbaldehyde (1 mL), and piperidine (1 mL). The resulting solution was stirred for 12 h at 25° C. and then concentrated under vacuum. The resulting solution was diluted with 10 mL of dichloromethane, washed with saturated aqueous NH$_4$Cl, water and brine. The organics were dried over anhydrous sodium sulfate and concentrated under vacuum and the residue was purified via column chromatography using dichloromethane/methanol (20/1) to give 26 mg (23%) of the title compound as a white solid. LC-MS: (ES, m/z): 542 [M+H]. H-NMR: (CDCl$_3$, ppm): δ8.38 (s, 1H); δ7.66 (d,2H); δ7.26 (d,1H); δ7.11 (d,4H); δ6.77 (d,1H); δ5.51 (s,2H); δ4.81 (m, 1H); δ4.65 (d,2H); δ3.51~δ3.70 (m,2H); δ1.91~δ2.01 (m,4H); δ1.81 (m, 1H); δ0.83~1.25 (m, 4H).

Example 13

Synthesis of (R)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile

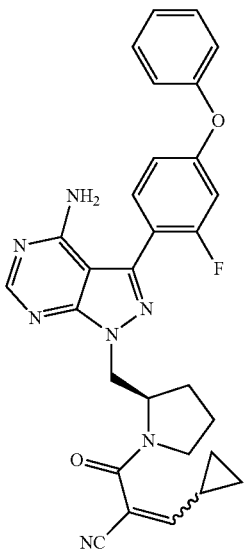 [SMILES: N#CC(=CC1CC1)C(=O)N1CCC[C@@H]1Cn1nc(-c2ccc(Oc3ccccc3)cc2F)c2c(N)ncnc21]

Step 1

Into a 250 mL round-bottom flask, was placed a solution of 4-bromo-3-fluorophenol (5 g, 26.18 mmol, 1.00 equiv) in dichloromethane (100 mL), phenylboronic acid (3.5 g, 28.70 mmol, 1.10 equiv), Cu(AcO)$_2$ (5.7 g), triethylamine (5.3 g), and 4 A molecular sieves (15 g). The resulting solution was stirred overnight at room temperature. The solids were filtered out. The filtrate was dried over anhydrous sodium sulfate and concentrated under vacuum. The residue was loaded onto a silica gel column and eluted with ethyl acetate/petroleum ether (1:100-1:50). This resulted in 2 g (29%) of 1-bromo-2-fluoro-4-phenoxybenzene as colorless oil.

Step 2

Into a 100 mL 3-necked round-bottom flask purged and maintained under an inert atmosphere of nitrogen, was placed a solution of 1-bromo-2-fluoro-4-phenoxybenzene (2 g, 7.49 mmol, 1.00 equiv) in tetrahydrofuran (20 mL). BuLi (1M) (8 mL) was added dropwise with stirring at –70 to –80° C. The resulting solution was stirred for 30 min at –70-80° C. in a liquid nitrogen bath. Tris(propan-2-yl)borate (1.7 g, 9.04 mmol, 1.21 equiv) was added dropwise with stirring at –70 to –80° C. The resulting solution was allowed to react, with stirring, for an additional 2 h while the temperature was maintained at –70 to –80° C. The reaction was then quenched by the addition of 100 mL of water, extracted with ethyl acetate and the organic layers were combined and dried over anhydrous sodium sulfate and concentrated under vacuum. The residue was loaded onto a silica gel column and eluted with ethyl acetate/petroleum ether (1:20) to give 1.6 g (92%) of (2-fluoro-4-phenoxyphenyl)-boronic acid as a white solid.

Step 3

Into a 100 mL, 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (380 mg, 0.86 mmol, 1.00 equiv), (2-fluoro-4-phenoxyphenyl)boronic acid (240 mg, 1.03 mmol, 1.20 equiv), tetrakis-(triphenylphosphane) palladium (60 mg, 0.05 mmol, 0.06 equiv), dioxane (50 mL), sodium carbonate (228 mg, 2.15 mmol, 2.50 equiv) and water (10 mL). The resulting solution was stirred for 12 h at 80° C. in an oil bath. The resulting mixture was concentrated under vacuum and the resulting solution was extracted with dichloromethane and the organic layers combined, dried and concentrated under vacuum. The residue was loaded onto a silica gel column and eluted with dichloromethane/methanol (50/1) to give 0.347 g (80%) of tert-butyl (2R)-2-[[4-amino-3-(2-fluoro-4-phenoxyphenyl)-1H-pyrazolo[3,4-d]pyrimidin-1-yl]methyl]pyrrolidine-1-carboxylate as a brown solid.

Step 4

Into a 100 mL, round-bottom flask, was placed a solution of tert-butyl (2R)-2-[[4-amino-3-(2-fluoro-4-phenoxyphenyl)-1H-pyrazolo[3,4-d]pyrimidin-1-yl]methyl]pyrrolidine-1-carboxylate (347 mg, 0.69 mmol, 1.00 equiv) in dichloromethane (50 mL). Trifluoroacetic acid (10 mL) dropwise with stirring over 10 min and the resulting solution was stirred for 3 h at 25° C. The resulting mixture was concentrated under vacuum to give 0.278 g (crude) of 3-(2-fluoro-4-phenoxyphenyl)-1-[(2R)-pyrrolidin-2-ylmethyl]-1H-pyrazolo[3,4-d]pyrimidin-4-amine as brown oil.

Step 5

Into a 100 mL round-bottom flask, was placed 3-(2-fluoro-4-phenoxyphenyl)-1-[(2R)-pyrrolidin-2-ylmethyl]-1H-pyrazolo[3,4-d]pyrimidin-4-amine (278 mg, 0.69 mmol, 1.00 equiv), 2-cyanoacetic acid (36.8 mg, 0.43 mmol, 0.80 equiv), HATU (210 mg, 0.55 mmol, 0.80 equiv), triethylamine (109 mg, 1.08 mmol, 2.00 equiv), and N,N-dimethylformamide (50 mL). The resulting solution was stirred for 3 h at 25° C., then diluted with 200 mL of water and extracted with ethyl acetate and the organic layers combined, dried and concentrated under vacuum. The residue was loaded onto a silica gel column and eluted with dichloromethane/methanol (50/1) to give 200 mg (62%) of 3-[(2R)-2-[[4-amino-3-(2-fluoro-4-phenoxyphenyl)-1H-pyrazolo[3,4-d]pyrimidin-1-yl]methyl]pyrrolidin-1-yl]-3-oxopropane-nitrile as a yellow solid.

Step 6

Into a 10 mL round-bottom flask, was placed 3-[(2R)-2-[[4-amino-3-(2-fluoro-4-phenoxyphenyl)-1H-pyrazolo[3,4-d]pyrimidin-1-yl]methyl]pyrrolidin-1-yl]-3-oxopropanenitrile (100 mg, 0.21 mmol, 1.00 equiv), piperidine (18 mg, 0.21 mmol, 1.00 equiv), cyclopropanecarbaldehyde (30 mg, 0.43 mmol, 2.00 equiv), and methanol (5 mL). The resulting solution was stirred for 12 h at 25° C. and then concentrated under vacuum. The residue was loaded onto a silica gel column and eluted with dichloromethane/methanol (50/1) to give 38 mg (33%) of the title compound as a off-white solid.

LC-MS; (ES, m/z):MS (ESI, pos. ion) m/z: 524 (M+1). H-NMR (CDCl₃, ppm): 1HNMR (300MHz, CD₃Cl, ppm), 8.263 (1H, s), 7.444~7.918 (3H, t),7.512-7.284 (5H, t), 6.894~6.981 (2H, m), 6.445~6.610 (1H, d), 4.574~4.878(3H, m), 3.604~3.619(2H, m), 1.945~1.988 (5H, m), 1.25~1.306 (3H, m), 0.736~0.834 (2H, m).

Example 14

Synthesis of (R)-2-(2-((4-amino-3-(4-(2,3-difluorophenoxy)phenyl)-1H-pyrazolo[3,4-d]pyrimidin-1-yl)methyl)pyrrolidine-1-carbonyl)-3-cyclopropylacrylonitrile

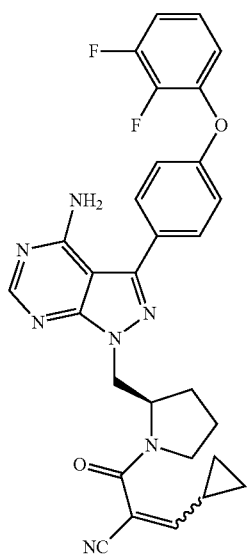 [SMILES: N#CC(=CC1CC1)C(=O)N1CCC[C@@H]1Cn1nc(-c2ccc(Oc3cccc(F)c3F)cc2)c2c(N)ncnc21]

Step 1

Into a 500 mL round-bottom flask, was placed a solution of (2,3-difluorophenyl)-boronic acid (30 g, 189.98 mmol, 1.00 equiv) in dichloromethane (250 mL). H₂O₂ (30 mL) was added dropwise with stirring. The resulting solution was stirred for 2 h at 25° C. The resulting mixture was washed with water and brine, dried over anhydrous magnesium sulfate and concentrated under vacuum to give 23 g (93%) of 2,3-difluorophenol as brown oil.

Step 2

Into a 500 mL, 4-necked round-bottom flask purged and maintained under an inert atmosphere of nitrogen, was placed a solution of sodium hydride (6.8 g, 170.00 mmol, 1.70 equiv, 60%) in N,N-dimethylformamide (200 mL). A solution of 1-fluoro-4-nitrobenzene (14.1 g, 99.93 mmol, 1.00 equiv) in N,N-dimethylformamide (50 mL) was added dropwise with stirring at 0° C. in 15 min. The resulting solution was stirred for 2 h at room temperature. CuCl (10 g, 101.01 mmol, 1.00 equiv) was added and a solution of 2,3-difluorophenol (15.6 g, 119.91 mmol, 1.20 equiv) in N,N-dimethylformamide (50 mL) was added dropwise with stirring. The resulting solution was allowed to react, with stirring, for an additional 12 h while the temperature was maintained at 100° C. in an oil bath. The resulting solution was extracted with ether and the organic layers combined. The organic layers was washed with water and brine, dried over anhydrous sodium sulfate and concentrated under vacuum. The residue was loaded onto a silica gel column and eluted with ethyl acetate/petroleum ether (1:8) to give 21.2 g (84%) of 1,2-difluoro-3-(4-nitrophenoxy)benzene as a brown solid.

Step 3

Into a 500 mL, 3-necked round-bottom flask purged and maintained under an inert atmosphere of nitrogen, was placed a solution of 1,2-difluoro-3-(4-nitrophenoxy)benzene (21.2 g, 84.40 mmol, 1.00 equiv) in methanol (200 mL), and Raney Nickel (2 g). A solution of hydrazine hydrate (12.67 g, 3.00 equiv) in methanol (50 mL) was added dropwise with stirring in 15 min. The resulting solution was stirred for 12 h at 25° C. The solids were filtered out and the filtrate was concentrated under vacuum. The residue was diluted with 200 mL of ethyl acetate and washed with water and brine, dried over anhydrous sodium sulfate and concentrated under vacuum to give 16.3 g (87%) of 4-(2,3-difluorophenoxy)aniline as black oil.

Step 4

Into a 250-mL 4-necked round-bottom flask, was placed 4-(2,3-difluorophenoxy)-aniline (8.84 g, 39.96 mmol, 1.00 equiv), hydrogen chloride (10.14 g, 100.01 mmol, 2.50 equiv), and water (20 mL). A solution of NaNO₂ (3.04 g, 44.06 mmol, 1.10 equiv) in water (10 mL) was added dropwise with stirring in portions at 0° C. The mixture was stirred at 0° C. for half an hour. To this was added urea (1 g, 16.65 mmol). The mixture was stirred at 0° C. for 20 min and poured into the solution of NaI (18 g, 120.00 mmol, 3.00 equiv) in water (20 mL) at room temperature. The resulting solution was stirred at room temperature for 1 h and then extracted with ethyl acetate. The organic layers combined and dried over anhydrous sodium sulfate and concentrated under vacuum to give 10.5 g (79%) of 1,2-difluoro-3-(4-iodophenoxy)benzene as brown oil.

Step 5

Into a 100 mL, 3-necked round-bottom flask purged and maintained under an inert atmosphere of nitrogen, was placed a solution of 1,2-difluoro-3-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (68 mg, 0.69 mmol, 0.05 equiv), and Pd(OAc)₂ (1.76 g, 7.84 mmol, 3.00 equiv). The resulting solution was stirred for 12 h at 85° C. in an oil bath. The reaction was then diluted with water, extracted with ethyl acetate and the organic layers were combined. The organics were washed with water and brine, dried over anhydrous sodium sulfate and concentrated under vacuum. The residue was loaded onto a silica gel column and eluted with ethyl acetate/petroleum ether (1/8) to give 1.5 g (75%) of 2-[4-(2,3-difluorophenoxy)phenyl]-4,4,5,5-tetramethyl-1,3,2-dioxaborolane as a light yellow solid.

Step 6

Into a 100 mL, 3-necked round-bottom flask purged and maintained under an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv), a solution of 2-[4-(2,3-difluorophenoxy)phenyl]-4,4,5,5-tetramethyl-1,3,2-dioxaborolane (290 mg, 0.87 mmol, 1.10 equiv) in dioxane (9 mL), tetrakis(triphenylphosphane)-palladium (40 mg, 0.03 mmol, 0.05 equiv), and a solution of sodium carbonate (179 mg, 1.67 mmol, 2.50 equiv) in water (3 mL). The resulting solution was stirred for 12 h at 100° C. in an oil bath. The resulting mixture was concentrated under vacuum, and the solution was diluted with ethyl acetate. The resulting mixture was washed with water and brine, dried over anhydrous sodium sulfate and concentrated under vacuum. The residue was loaded onto a silica gel column and eluted with dichloromethane/methanol (20/1) to give 250 mg (71%) of tert-butyl (2R)-2-([4-amino-3-[4-(2,3-difluorophenoxy)phenyl]-1H-pyrazolo[3,4-d]pyrimidin-1-yl]methyl)pyrrolidine-1-carboxylate as a white solid.

Step 7

Into a 100 mL, round-bottom flask, was placed a solution of tert-butyl (2R)-2-([4-amino-3-[4-(2,3-difluorophenoxy)phenyl]-1H-pyrazolo[3,4-d]pyrimidin-1-yl]methyl)-pyrrolidine-1-carboxylate (350 mg, 0.67 mmol, 1.00 equiv) in dichloromethane (10 mL). Trifluoroacetic acid (2 mL) dropwise with stirring and the resulting solution was stirred for 3 h at 25° C. The resulting mixture was concentrated under vacuum to give 200 mg (46%) of 3-[4-(2,3-difluorophenoxy)phenyl]-1-[(2R)-pyrrolidin-2-ylmethyl]-1H-pyrazolo[3,4-d]pyrimidin-4-amine bis(trifluoroacetic acid) salt as a brown solid.

Step 8

Into a 100 mL, round-bottom flask, was placed a solution of 3-[4-(2,3-difluorophenoxy)phenyl]-1-[(2R)-pyrrolidin-2-ylmethyl]-1H-pyrazolo[3,4-d]pyrimidin-4-amine bis(trifluoroacetic acid) salt (200 mg, 0.31 mmol, 1.00 equiv) in dichloromethane (10 mL), CDI (324 mg, 2.00 mmol, 6.50 equiv), and 2-cyanoacetic acid (170 mg, 2.00 mmol, 6.50 equiv). The resulting solution was stirred for 12 h at 25° C. and the resulting mixture was washed with water and brine. The organics were dried over anhydrous magnesium sulfate and concentrated under vacuum. The residue was loaded onto a silica gel column and eluted with dichloromethane/methanol (20/1) to give 109 mg (72%) of 3-[(2R)-2-([4-amino-3-[4-(2,3-difluorophenoxy)phenyl]-1H-pyrazolo[3,4-d]pyrimidin-1-yl]methyl)pyrrolidin-1-yl]-3-oxopropanenitrile as a white solid.

Step 9

Into a 50 mL, round-bottom flask, was placed a solution of 3-[(2R)-2-([4-amino-3-[4-(2,3-difluorophenoxy)phenyl]-1H-pyrazolo[3,4-d]pyrimidin-1-yl]methyl)pyrrolidin-1-yl]-3-oxopropanenitrile (109 mg, 0.22 mmol, 1.00 equiv) in methanol (10 mL), cyclopropane-carbaldehyde (1 mL), and piperidine (1 mL). The resulting solution was stirred for 12 h at 25° C. and then concentrated under vacuum. The resulting solution was diluted with ethyl acetate and the resulting mixture was washed with water and brine. The organics were dried over anhydrous sodium sulfate and concentrated under vacuum. The residue was loaded onto a silica gel column and eluted with dichloromethane/methanol (20/1) to give 32 mg (25%) of the title compound as a white solid. LC-MS: (ES, m/z): 542 [M+H]$^+$. $^1$H-NMR: (300 MHz, CDCl$_3$, ppm): δ 8.38 (s, 1H), 7.74 (d, 2H), 7.18 (d, 2H), 7.08 (m, 2H), 6.92 (m, 1H), 6.81 (d, 1H), 5.54 (s, 2H), 4.82 (m, 1H), 4.68 (m, 2H), 3.65 (m, 1H), 3.51 (m, 1H), 2.02 (m, 3H), 1.20 (m, 3H), 0.88 (m, 3H).

Example 15

Synthesis of (R)-2-(2-((4-amino-3-(4-(3,5-difluorophenoxy)phenyl)-1H-pyrazolo[3,4-d]pyrimidin-1-yl)methyl)pyrrolidine-1-carbonyl)-3-cyclopropylacrylonitrile

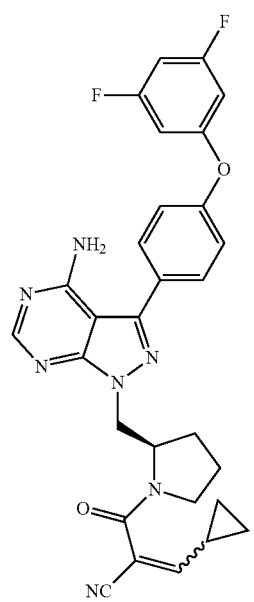 [SMILES: N#CC(=CC1CC1)C(=O)N1CCC[C@@H]1Cn1nc(-c2ccc(Oc3cc(F)cc(F)c3)cc2)c2c(N)ncnc21]

Step 1

Into a 250-mL round-bottom flask, was placed a solution of 4-(tetramethyl-1,3,2-dioxaborolan-2-yl)phenol (5 g, 22.72 mmol, 1.00 equiv) in dichloromethane (100 mL), (3,5-difluorophenyl)boronic acid (4 g, 25.33 mmol, 1.11 equiv), Cu(AcO)2 (5 g), 4 A molecular sieves (15 g), triethylamine (4.6 g). The resulting solution was stirred for overnight at room temperature. The solids were filtered out. The filtrate was dried over anhydrous sodium sulfate and concentrated under vacuum. The residue was applied onto a silica gel column with ethyl acetate/petroleum ether (1:100-1:50). This resulted in 2 g (27%) of 2-[4-(3,5-difluorophenoxy)phenyl]-4,4,5,5-tetramethyl-1,3,2-dioxaborolane as a colorless oil.

Step 2

Into a 100 mL, 3-necked round-bottom flask purged and maintained with an inert atmosphere of nitrogen, was placed tert-butyl (2R)-2-([4-amino-3-iodo-1H-pyrazolo[3,4-d]pyrimidin-1-yl]methyl)pyrrolidine-1-carboxylate (250 mg, 0.56 mmol, 1.00 equiv), 2-[4-(3,5-difluorophenoxy)phenyl]-4,4,5,5-tetramethyl-1,3,2-dioxaborolane (226 mg, 0.68 mmol, 1.20 equiv), tetrakis(triphenylphosphane)palladium (39 mg, 0.03 mmol, 0.06 equiv), dioxane (50 mL), sodium carbonate (149 mg, 1.41 mmol, 2.50 equiv), and water (10 mL). The resulting solution was stirred for 12 h at 80° C. in an oil bath and then concentrated under vacuum. The resulting solution was extracted with dichloromethane and the organic layers combined, dried and concentrated under vacuum. The residue was loaded onto a silica gel column and eluted with dichloromethane/methanol (50/1) to give 0.237 g (81%) of tert-butyl (2R)-2-([4-amino-3-[4-(3,5-difluorophenoxy)phenyl]-1H-pyrazolo[3,4-d]pyrimidin-1-yl]methyl)pyrrolidine-1-carboxylate as a brown solid.

Step 3

Into a 100 mL, round-bottom flask, was placed a solution of tert-butyl (2R)-2-([4-amino-3-[4-(3,5-difluorophenoxy)phenyl]-1H-pyrazolo[3,4-d]pyrimidin-1-yl]methyl)pyrrolidine-1-carboxylate (230 mg, 0.44 mmol, 1.00 equiv) in dichloromethane (50 mL). This was followed by the addition of trifluoroacetic acid (10 mL) dropwise with stirring over 10 min. The resulting solution was stirred for 3 h at 25° C. The resulting mixture was concentrated under vacuum to give 0.185 g (crude) of 3-[4-(3,5-difluorophenoxy)phenyl]-1-[(2R)-pyrrolidin-2-ylmethyl]-1H-pyrazolo[3,4-d]pyrimidin-4-amine as a brown oil.

Step 4

Into a 100 mL, round-bottom flask, was placed 3-[4-(3,5-difluorophenoxy)phenyl]-1-[(2R)-pyrrolidin-2-ylmethyl]-1H-pyrazolo[3,4-d]pyrimidin-4-amine (185 mg, 0.44 mmol, 1.00 equiv), 2-cyanoacetic acid (30.7 mg, 0.36 mmol, 0.80 equiv), HATU (138 mg, 0.36 mmol, 0.80 equiv), triethylamine (91 mg, 0.90 mmol, 2.00 equiv), and N,N-dimethylformamide (50 mL). The resulting solution was stirred for 3 h at 25° C. and then extracted with ethyl acetate and the organic layers combined and concentrated under vacuum. The residue was loaded onto a silica gel column and eluted with dichloromethane/methanol (50/1) to give 101 mg (47%) of 3-[(2R)-2-([4-amino-3-[4-(3,5-difluorophenoxy)phenyl]-1H-pyrazolo[3,4-d]pyrimidin-1-yl]methyl)pyrrolidin-1-yl]-3-oxopropanenitrile as a off-white solid.

Step 5

Into a 10-mL round-bottom flask, was placed cyclopropanecarbaldehyde (28.7 mg, 0.41 mmol, 2.00 equiv), piperidine (17.4 mg, 0.20 mmol, 1.00 equiv), 3-[(2R)-2-([4-amino-3-[4-(3,5-difluorophenoxy)phenyl]-1H-pyrazolo[3,4-d]pyrimidin-1-yl]methyl)pyrrolidin-1-yl]-3-oxopropanenitrile (100 mg, 0.20 mmol, 1.00 equiv), and methanol (5 mL). The resulting solution was stirred for 12 h at 25° C. and then concentrated under vacuum. The residue was loaded onto a silica gel column and eluted with dichloromethane/methanol (50/1) to give 53.12 mg (45%) of the title compound as an off-white solid. LC-MS: (ES, m/z):MS (ESI, pos. ion) m/z: 541 (M+1). H-NMR: (CDCl$_3$, ppm): 1HNMR (300MHz, CD$_3$OD, ppm), 8.28 3(1H, s), 7.777~7.806 (2H,t), 7.269~7.298 (2H,t), 6.703~6.754 (3H,t), 6.455~6.600 (1H,d), 4.400~4.878 (3H, m), 3.338~3.618(2H,m), 1.700~2.188 (4H,m), 1.280~1.305 (4H,m), 0.710~0.912 (2H,m).

Example 16

Synthesis of (R)-2-(3-(4-amino-3-(4-(2-fluorophenoxy)phenyl)-1H-pyrazolo[3,4-d]pyrimidin-1-yl)piperidine-1-carbonyl)-3-cyclopropylacrylonitrile

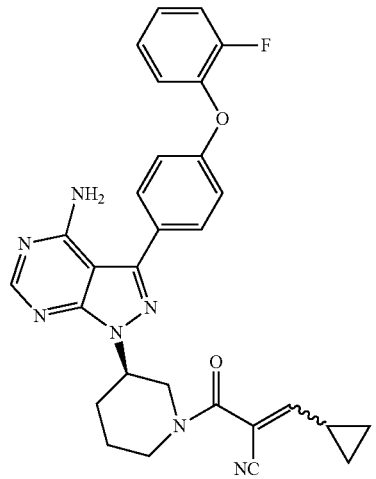 [SMILES: N#CC(=CC1CC1)C(=O)N1CCC[C@@H](n2nc(-c3ccc(Oc4ccccc4F)cc3)c3c(N)ncnc32)C1]

Step 1

Into a 100 mL, 3-necked round-bottom flask purged and maintained with an inert atmosphere of nitrogen, was placed a solution of tert-butyl (3R)-3-[4-amino-3-iodo-1H-pyrazolo[3,4-d]pyrimidin-1-yl]piperidine-1-carboxylate (300 mg, 0.68 mmol, 1.00 equiv) in dioxane/H$_2$O (7/3=V/V) (30 mL), [4-(2-fluorophenoxy)phenyl]boronic acid (500 mg, 2.16 mmol, 6.99 equiv), sodium carbonate (200 mg, 1.89 mmol, 0.26 equiv), and Pd(PPh$_3$)$_4$ (500 mg, 0.43 mmol, 3.19 equiv). The resulting solution was stirred overnight at 100° C. in an oil bath an then concentrated under vacuum. The residue was loaded onto a silica gel column and eluted with dichloromethane/methanol (100:1) to give 0.2 g (59%) of tert-butyl (3R)-3-[4-amino-3-[4-(2-fluorophenoxy)phenyl]-1H-pyrazolo[3,4-d]pyrimidin-1-yl]piperidine-1-carboxylate as a light yellow solid.

Step 2

Into a 100 mL, round-bottom flask purged and maintained under an inert atmosphere of nitrogen, was placed a solution of tert-butyl (3R)-3-[4-amino-3-[4-(2-fluorophenoxy)phenyl]-1H-pyrazolo[3,4-d]pyrimidin-1-yl]piperidine-1-carboxylate (200 mg, 0.40 mmol, 1.00 equiv) in dichloromethane (20 mL), and trifluoroacetic acid (10 g, 87.70 mmol, 221.25 equiv). The resulting solution was stirred overnight at room temperature and then concentrated under vacuum. The pH value of the solution was adjusted to 8-10 with 10% aqueous sodium carbonate. The solution was extracted with dichloromethane and the organic layers were combined and dried over anhydrous sodium sulfate and concentrated under vacuum to give 0.1 g (62%) of 3-[4-(2-fluorophenoxy)phenyl]-1-((3R)-piperidin-3-yl)-1H-pyrazolo[3,4-d]pyrimidin-4-amine as a light yellow solid.

Step 3

Into a 50 mL round-bottom flask, was placed a solution of 3-[4-(2-fluorophenoxy)-phenyl]-1-[(3R)-piperidin-3-yl]-

1H-pyrazolo[3,4-d]pyrimidin-4-amine (100 mg, 0.25 mmol, 1.00 equiv) in dichloromethane (10 mL), 1-[(1H-imidazol-1-yl)carbonyl]-1H-imidazole (60 mg, 0.37 mmol, 1.50 equiv), and 2-cyanoacetic acid (110 mg, 1.29 mmol, 5.23 equiv). The resulting solution was stirred for 60 min at room temperature and then concentrated under vacuum. The residue was loaded onto a silica gel column and eluted with dichloromethane/methanol (100:1) to give 0.06 g (51%) of 3-[(3R)-3-[4-amino-3-[4-(2-fluorophenoxy)phenyl]-1H-pyrazolo[3,4-d]pyrimidin-1-yl]piperidin-1-yl]-3-oxopropanenitrile as a light yellow solid.
Step 4

Into a 10 mL round-bottom flask, was placed a solution of 3-[(3R)-3-[4-amino-3-[4-(2-fluorophenoxy)phenyl]-1H-pyrazolo[3,4-d]pyrimidin-1-yl]piperidin-1-yl]-3-oxopropanenitrile (60 mg, 0.13 mmol, 1.00 equiv) in methanol (10 mL), cyclopropane-carbaldehyde (50 mg, 0.71 mmol, 5.61 equiv), and piperidine (70 mg, 0.82 mmol, 6.46 equiv). The resulting solution was stirred for 30 min at room temperature and then concentrated under vacuum. The residue was loaded onto a silica gel column and eluted with dichloromethane/methanol (100:1) to give 0.015 g (23%) of the title compound as an off-white solid. LC-MS0: (ES, m/z): 524 [M+H]$^+$. H-NMR (CD$_3$OD, ppm) 8.270 (1H, s), 7.711 (2H, d), 7.316~7.242 (4H, m), 7.149 (2H, d), 6.450 (1H,d), 4.872 (1H,s), 4.192 (1H,s), 3.966 (2H,d), 3.556~3.488 (1H,m), 2.392~2.363 (1H,m), 2.253~2.209 (2H,m), 1.951 (1H,s); 1.306-1.181 (3H, m); 0.918~0.793 (2H, m)

Example 17

Synthesis of (R)-2-(3-(4-amino-3-(4-(3-fluorophenoxy)phenyl)-1H-pyrazolo[3,4-d]pyrimidin-1-yl)piperidine-1-carbonyl)-3-cyclopropylacrylonitrile

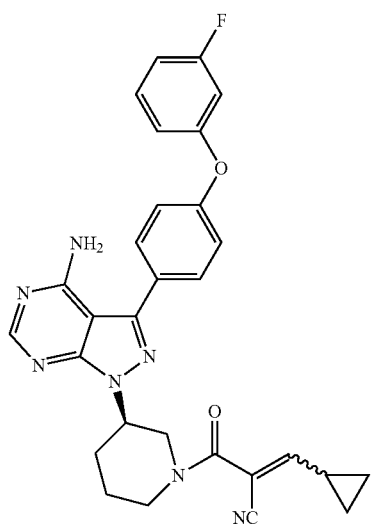 [SMILES: N#CC(=CC1CC1)C(=O)N1CCC[C@@H](n2nc(-c3ccc(Oc4cccc(F)c4)cc3)c3c(N)ncnc32)C1]

Step 1

Into a 250 mL round-bottom flask, was placed a solution of 4-(tetramethyl-1,3,2-dioxaborolan-2-yl)phenol (5 g, 22.72 mmol, 1.00 equiv) in dichloromethane (100 mL), (3-fluorophenyl)boronic acid (3.5 g, 25.01 mmol, 1.10 equiv), Cu(AcO)$_2$ (5 g), 4 A molecular sieves (15 g), and triethylamine (4.6 g). The resulting solution was stirred overnight at room temperature. The solids were filtered out and the filtrate was dried over anhydrous sodium sulfate and concentrated under vacuum. The residue was loaded onto a silica gel column and eluted with ethyl acetate/petroleum ether (1:100-1:50) to give 1.8 g (25%) of 2-[4-(3-fluorophenoxy)phenyl]-4,4,5,5-tetramethyl-1,3,2-dioxaborolane as a colorless oil.
Step 2

Into a 100 mL 3-necked round-bottom flask purged and maintained with an inert atmosphere of nitrogen, was placed tert-butyl (3R)-3-[4-amino-3-iodo-1H-pyrazolo[3,4-d]pyrimidin-1-yl]piperidine-1-carboxylate (300 mg, 0.68 mmol, 1.00 equiv), 2-[4-(3-fluorophenoxy)phenyl]-4,4,5,5-tetramethyl-1,3,2-dioxaborolane (255 mg, 0.81 mmol, 1.20 equiv), sodium carbonate (143 g, 1.35 mol, 1998.01 equiv), ethylene glycol dimethyl ether (50 mL), water (15 mL), and Pd(PPh$_3$)$_4$ (40 mg, 0.03 mmol, 0.05 equiv). The resulting solution was stirred overnight at 80° C. and then concentrated under vacuum. The residue was loaded onto a silica gel column and eluted with dichloromethane/methanol (100/1) to give 260 mg (76%) of tert-butyl (3R)-3-[4-amino-3-[4-(3-fluorophenoxy)phenyl]-1H-pyrazolo[3,4-d]pyrimidin-1-yl]piperidine-1-carboxylate as a yellow solid.
Step 3

Into a 100 mL round-bottom flask, was placed a solution of tert-butyl (3R)-3-[4-amino-3-[4-(3-fluorophenoxy)phenyl]-1H-pyrazolo[3,4-d]pyrimidin-1-yl]piperidine-1-carboxylate (260 mg, 0.52 mmol, 1.00 equiv) in dichloromethane (50 mL). Trifluoroacetic acid (10 mL) was added dropwise with stirring. The resulting solution was stirred for 12 h at room temperature and then concentrated under vacuum. The residue was diluted with 20 mL of water. The pH value of the solution was adjusted to >7 with sodium carbonate. The resulting solution was extracted with dichloromethane and the organic layers combined and dried over anhydrous sodium sulfate and concentrated under vacuum to give 180 mg (86%) of 3-[4-(3-fluorophenoxy)phenyl]-1-[(3R)-piperidin-3-yl]-1H-pyrazolo[3,4-d]pyrimidin-4-amine as a brown solid.
Step 4

Into a 100 mL round-bottom flask, was placed a solution of 3-[4-(3-fluorophenoxy)-phenyl]-1-[(3R)-piperidin-3-yl]-1H-pyrazolo[3,4-d]pyrimidin-4-amine (180 mg, 0.45 mmol, 1.00 equiv) in dichloromethane (50 mL), 2-cyanoacetic acid (56 mg, 0.66 mmol, 1.50 equiv), and 1-[(1H-imidazol-1-yl)carbonyl]-1H-imidazole (108 mg, 0.67 mmol, 1.50 equiv). The resulting solution was stirred for 24 h at room temperature and then diluted with 100 mL dichloromethane. The resulting mixture was washed NH$_4$Cl, dried over anhydrous sodium sulfate and concentrated under vacuum. The residue was loaded onto a silica gel column and eluted with dichloromethane/methanol (100:1) to give 120 mg (57%) of 3-[(3R)-3-[4-amino-3-[4-(3-fluorophenoxy)phenyl]-1H-pyrazolo[3,4-d]pyrimidin-1-yl]piperidin-1-yl]-3-oxopropanenitrile as a white solid.
Step 5

Into a 50 mL round-bottom flask, was placed a solution of 3-[(3R)-3-[4-amino-3-[4-(3-fluorophenoxy)phenyl]-1H-pyrazolo[3,4-d]pyrimidin-1-yl]piperidin-1-yl]-3-oxopropanenitrile (120 mg, 0.25 mmol, 1.00 equiv) in methanol (20 mL), cyclopropanecarbaldehyde (54 mg, 0.77 mmol, 3.00 equiv), piperidine (11 mg, 0.13 mmol, 0.50 equiv), and dichloromethane (5 mL). The resulting solution was stirred for 12 h at room temperature and then concentrated under vacuum. The residue was loaded onto a silica gel column and eluted with dichloromethane/methanol (100:1) to give 36 mg (27%) of the title compounds as a white solid. LC-MS: (ES, m/z): 524 [M+H]$^+$. H-NMR: (300MHz,CDCl$_3$, ppm) 8.396 (1H, s), 7.721~7.674 (2H, m), 7.393~7.316 (1H, m), 7.237~7.191 (2H, m), 6.923~6.786 (3H,m),6.607~6.570

(1H,d,J=11.1), 5.795 (2H, s), 5.018~4.919 (1H, m), 4.8~3.1 (4H,m), 2.465~2.269 (5H,m),1.274 (2H m), 0.887 (2H,m).

Example 18

Synthesis of (R)-2-(3-(4-amino-3-(4-(2,3-difluorophenoxy)phenyl)-1H-pyrazolo[3,4-d]pyrimidin-1-yl)piperidine-1-carbonyl)-3-cyclopropylacrylonitrile

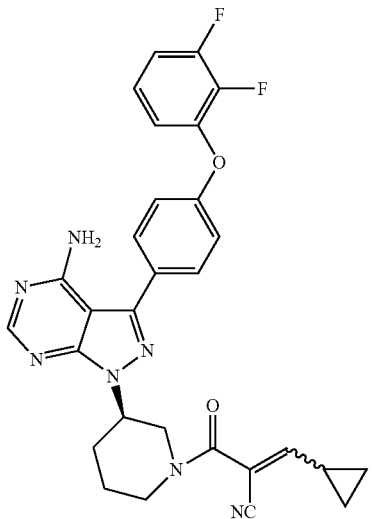 [SMILES: N#CC(=CC1CC1)C(=O)N1CCC[C@@H](n2nc(-c3ccc(Oc4cccc(F)c4F)cc3)c3c(N)ncnc32)C1]

Step 1

Into a 500-mL round-bottom flask, was placed a solution of tert-butyl (3S)-3-hydroxypiperidine-1-carboxylate (10 g, 49.69 mmol, 1.00 equiv) in pyridine (200 mL). 4-Methylbenzene-1-sulfonyl chloride (28.5 g, 149.49 mmol, 3.0 equiv) was added dropwise with stirring at 0° C. in 30 min. The resulting solution was stirred for 5 h at 25° C. and then concentrated under vacuum. The residue was diluted with 200 mL of ethyl acetate. The pH value of the solution was adjusted to 3 with hydrogen chloride (1M) and the resulting mixture was washed with sodium bicarbonate and water. The organics were washed with brine, dried over anhydrous sodium sulfate and concentrated under vacuum to give 15 g (85%) of tert-butyl (3S)-3-[[(4-methylbenzene)sulfonyl]oxy]piperidine-1-carboxylate as a light yellow solid.

Step 2

Into a 1000 mL 3-necked round-bottom flask, was placed a solution of 3-iodo-1H-pyrazolo[3,4-d]pyrimidin-4-amine (6 g, 22.99 mmol, 1.00 equiv) in N,N-dimethylformamide (500 mL), tert-butyl (3S)-3-[[(4-methylbenzene)sulfonyl]oxy]piperidine-1-carboxylate (9.8 g, 27.57 mmol, 1.20 equiv), and cesium carbonate (13.3 g, 40.82 mmol, 1.78 equiv). The resulting solution was stirred for 12 h at 60° C. in an oil bath and then quenched by the addition of 1500 mL of water. The resulting solution was extracted with dichloromethane and the organic layers combined. The organics were washed with brine, dried over anhydrous sodium sulfate and concentrated under vacuum. The residue was loaded onto a silica gel column and elution with ethyl acetate/petroleum ether (60%) gave 2.8 g (27%) of tert-butyl (3R)-3-[4-amino-3-iodo-1H-pyrazolo[3,4-d]pyrimidin-1-yl]piperidine-1-carboxylate (96.5%, e.e.) as a off-white solid.

Step 3

Into a 250 mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H$_2$O (100/30 mL), 2-[4-(2,3-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh$_3$)$_4$ (65 mg, 0.06 mmol, 0.05 equiv). The resulting solution was stirred for 12 h at 90° C. in an oil bath. The resulting mixture was concentrated under vacuum and the residue was diluted with water. The resulting solution was extracted with dichloromethane and the organic layers were combined, washed with brine and filtered. The filtrate was dried over anhydrous sodium sulfate and concentrated under vacuum. The residue was loaded onto a silica gel column and elution with dichloromethane/methanol (10/1) gave 480 mg (82%) of tert-butyl (3R)-3-[4-amino-3-[4-(2,3-difluorophenoxy)phenyl]-1H-pyrazolo[3,4-d]pyrimidin-1-yl]piperidine-1-carboxylate as a white solid.

Step 4

Into a 100 mL round-bottom flask, was placed a solution of tert-butyl (3R)-3-[4-amino-3-[4-(2,3-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL) and CF$_3$COOH (10 mL). The resulting solution was stirred for 3 h at 25° C. and then concentrated under vacuum. The resulting solution was diluted with 50 mL of dichloromethane and washed with aqueous sodium bicarbonate and brine. The organics were dried over anhydrous sodium sulfate and concentrated under vacuum to give 400 mg (crude) of 3-[4-(2,3-difluorophenoxy)phenyl]-1-[(3R)-piperidin-3-yl]-1H-pyrazolo[3,4-d]pyrimidin-4-amine as a white solid.

Step 5

Into a 100 mL round-bottom flask, was placed a solution of 3-[4-(2,3-difluorophenoxy)-phenyl]-1-[(3R)-piperidin-3-yl]-1H-pyrazolo[3,4-d]pyrimidin-4-amine (300 mg, 0.71 mmol, 1.00 equiv) in dichloromethane (30 mL), HATU (400 mg, 1.05 mmol, 1.5 equiv), triethylamine (220 mg, 2.17 mmol, 3.0 equiv), and 2-cyanoacetic acid (90 mg, 1.06 mmol, 1.5 equiv). The resulting solution was stirred for 10 h at 25° C. and then washed with water and brine. The organics were dried over anhydrous sodium sulfate and concentrated. The residue was loaded onto a silica gel column and elution with dichloromethane/methanol (10/1) gave 240 mg (69%) of 3-[(3R)-3-[4-amino-3-[4-(2,3-difluorophenoxy)phenyl]-1H-pyrazolo[3,4-d]pyrimidin-1-yl]piperidin-1-yl]-3-oxopropanenitrile as a white solid.

Step 6

Into a 10 mL sealed tube, was placed a solution of 3-[(3R)-3-[4-amino-3-[4-(2,3-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (5 mL), cyclopropanecarbaldehyde (64 mg, 0.91 mmol, 3.0 equiv), and piperidine (78 mg). The resulting solution was stirred for 12 h at 25° C. and then concentrated under vacuum. The residue was diluted with 10 mL of dichloromethane and the resulting mixture was washed with saturated aqueous ammonium chloride, water and brine and dried over anhydrous sodium sulfate and concentrated. The residue was loaded onto a silica gel column and elution with dichloromethane/methanol (20/1) gave 28.5 mg (17%) of the title compound as a white solid. LC-MS: (ES, m/z): 542 [M+H]$^+$, H-NMR (300MHz, CDCl$_3$, ppm): δ 8.54 (s,1H); δ7.68 (d,2H); δ7.20 (d,2H); δ7.16 (d,2H); δ6.95 (m,1H); δ6.55 (d,1H); δ5.52

(s,2H); δ6.98 (m,1H); δ4.76 (m,1H); δ4.34 (m,1H); δ3.82 (m1H); δ3.23 (m 1H); δ2.01~δ2.42 (m,4H); δ1.88 (m,1H); δ0.85~δ1.21 (m,4H).

Example 19

Synthesis of (R)-2-(3-(4-amino-3-(4-(2,6-difluorophenoxy)phenyl)-1H-pyrazolo[3,4-d]pyrimidin-1-yl)piperidine-1-carbonyl)-3-cyclopropylacrylonitrile

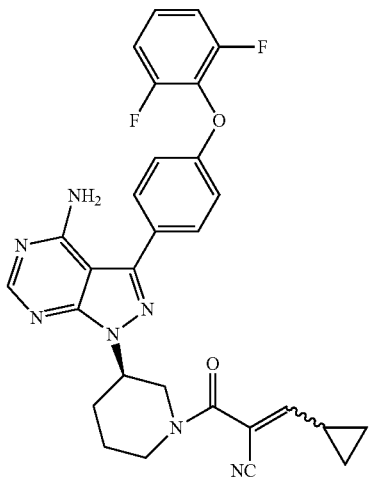 [SMILES: N#CC(=CC1CC1)C(=O)N1CCC[C@@H](n2nc(-c3ccc(Oc4c(F)cccc4F)cc3)c3c(N)ncnc32)C1]

Step 1

Into a 250 mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H2O (100/30 mL), 2-[4-(2,6-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh3)4 (65 mg, 0.06 mmol, 0.05 equiv). The resulting solution was stirred for 15 h at 90° C. in an oil bath and then concentrated under vacuum. The residue was diluted with water and extracted with dichloromethane and the organic layers combined. The organics were washed with brine, dried over anhydrous sodium sulfate and concentrated. The residue was loaded onto a silica gel column and eluted with dichloromethane/methanol (10/1) to give 500 mg (85%) of tert-butyl (3R)-3-[4-amino-3-[4-(2,6-difluorophenoxy)-phenyl]-1H-pyrazolo[3,4-d]pyrimidin-1-yl]piperidine-1-carboxylate as a white solid.

Step 2

Into a 100 mL round-bottom flask, was placed a solution of tert-butyl (3R)-3-[4-amino-3-[4-(2,6-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL). CF3COOH (10 mL) to added dropwise with stirring at 25° C. over 10 min and the resulting solution was stirred for 3 h at 25° C. and then concentrated under vacuum. The resulting solution was diluted with dichloromethane and washed with aqueous sodium bicarbonate and brine. The organics were dried over anhydrous sodium sulfate and concentrated under vacuum to give 410 mg of 3-[4-(2,6-difluorophenoxy)phenyl]-1-[(3R)-piperidin-3-yl]-1H-pyrazolo[3,4-d]pyrimidin-4-amine as a white solid.

Step 3

Into a 100 mL round-bottom flask, was placed a solution of 3-[4-(2,6-difluoro-phenoxy)phenyl]-1-[(3R)-piperidin-3-yl]-1H-pyrazolo[3,4-d]pyrimidin-4-amine (300 mg, 0.71 mmol, 1.00 equiv) in dichloromethane (30 mL), triethylamine (220 mg, 2.17 mmol, 3.0 equiv), HATU (400 mg, 1.05 mmol, 1.5 equiv), and 2-cyanoacetic acid (90 mg, 1.06 mmol, 1.5 equiv). The resulting solution was stirred for 10 h at 25° C., then washed with water and brine. The organics were dried over anhydrous sodium sulfate and concentrated. The residue was loaded onto a silica gel column and eluted with dichloromethane/methanol (10/1) to give. 230 mg (60%) of 3-[(3R)-3-[4-amino-3-[4-(2,6-difluorophenoxy)phenyl]-1H-pyrazolo[3,4-d]pyrimidin-1-yl]piperidin-1-yl]-3-oxopropanenitrile as a white solid.

Step 4

Into a 10 mL sealed tube, was placed a solution of 3-[(3R)-3-[4-amino-3-[4-(2,6-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (5 mL), piperidine (78 mg, 0.92 mmol, 3.0 equiv), and cyclopropanecarbaldehyde (64 mg, 0.91 mmol, 3.0 equiv). The resulting solution was stirred for 12 h at 25° C. and then concentrated under vacuum. The residue was diluted with 10 mL of dichloromethane, and the solution was washed with saturated aqueous ammonium chloride, water and brine. The organics were dried over anhydrous sodium sulfate and concentrated. The residue was loaded onto a silica gel column and eluted with dichloromethane/methanol (20/1) to give 36 mg (21%) of 2-[[(3R)-3-[4-amino-3-[4-(2,6-difluorophenoxy)phenyl]-1H-pyrazolo[3,4-d]pyrimidin-1-yl]piperidin-1-yl]carbonyl]-3-cyclopropylprop-2-enenitrile as a white solid.

LC-MS: (ES, m/z): 542 [M+H]. H-NMR: (CDCl3, ppm): δ8.27 (s,1H); δ7.82 (d,2H); δ7.41 (m,1H); δ7.21 (d,2H); δ7.11 (d,1H); δ6.42 (d,1H); δ4.94 (m,1H); δ4.21 (m,1H); δ3.92 (m,2H); δ3.55 (m,1H); δ2.01~2.29 (m,4H); δ1.94 (m,2H); δ0.83~1.31 (m,4H).

Example 20

Synthesis of (R)-2-(3-(4-amino-3-(4-(3,5-difluorophenoxy)phenyl)-1H-pyrazolo[3,4-d]pyrimidin-1-yl)piperidine-1-carbonyl)-3-cyclopropylacrylonitrile

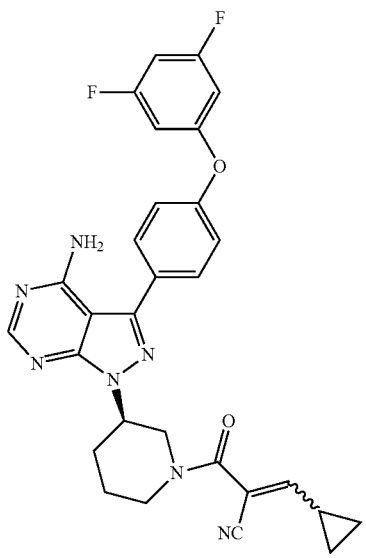 [SMILES: N#CC(=CC1CC1)C(=O)N1CCC[C@@H](n2nc(-c3ccc(Oc4cc(F)cc(F)c4)cc3)c3c(N)ncnc32)C1]

229

Step 1

Into a 100 mL 3-necked round-bottom flask purged and maintained under an inert atmosphere of nitrogen, was placed tert-butyl (3R)-3-[4-amino-3-iodo-1H-pyrazolo[3,4-d]pyrimidin-1-yl]piperidine-1-carboxylate (400 mg, 0.90 mmol, 1.00 equiv), 2-[4-(3,5-difluorophenoxy)phenyl]-4,4,5,5-tetramethyl-1,3,2-dioxaborolane (360 mg, 1.08 mmol, 1.20 equiv), sodium carbonate (190 mg, 1.79 mmol, 1.99 equiv), ethylene glycol dimethyl ether (50 mL), water (15 mL), and Pd(PPh3)4 (52 mg, 0.04 mmol, 0.05 equiv). The resulting solution was stirred for 12 h at 80° C. and then concentrated under vacuum. The residue was loaded onto a silica gel column and eluted with dichloromethane/methanol (100/1) to give 340 mg (72%) of tert-butyl (3R)-3-[4-amino-3-[4-(3,5-difluorophenoxy)phenyl]-1H-pyrazolo[3,4-d]pyrimidin-1-yl]piperidine-1-carboxylate as a yellow solid.

Step 2

Into a 100 mL round-bottom flask, was placed a solution of tert-butyl (3R)-3-[4-amino-3-[4-(3,5-difluorophenoxy)phenyl]-1H-pyrazolo[3,4-d]pyrimidin-1-yl]piperidine-1-carboxylate (340 mg, 0.65 mmol, 1.00 equiv) in dichloromethane (50 mL), followed by the addition of trifluoroacetic acid (10 mL) dropwise with stirring. The resulting solution was stirred for 12 h at room temperature and then concentrated under vacuum. The resulting solution was diluted with 20 mL of water. The pH value of the solution was adjusted to >7 with sodium carbonate and then extracted with dichloromethane and the organic layers combined and dried over anhydrous sodium sulfate and concentrated under vacuum to give 210 mg (76%) of 3-[4-(3,5-difluorophenoxy)phenyl]-1-[(3R)-piperidin-3-yl]-1H-pyrazolo[3,4-d]pyrimidin-4-amine as a brown solid.

Step 3

Into a 100-mL round-bottom flask, was placed a solution of 3-[4-(3,5-difluorophenoxy)phenyl]-1-[(3R)-piperidin-3-yl]-1H-pyrazolo[3,4-d]pyrimidin-4-amine (210 mg, 0.50 mmol, 1.00 equiv) in dichloromethane (50 mL), 2-cyanoacetic acid (63 mg, 0.74 mmol, 1.50 equiv), and 1-[(1H-imidazol-1-yl)carbonyl]-1H-imidazole (120 mg, 0.74 mmol, 1.50 equiv). The resulting solution was stirred for 24 h at room temperature and then diluted with dichloromethane. The resulting mixture was washed with NH4Cl and dried over anhydrous sodium sulfate and concentrated under vacuum. The residue was loaded onto a silica gel column and eluted with dichloromethane/methanol (100:1) to give 150 mg (62%) of 3-[(3R)-3-[4-amino-3-[4-(3,5-difluorophenoxy)phenyl]-1H-pyrazolo[3,4-d]pyrimidin-1-yl]piperidin-1-yl]-3-oxopropanenitrile as a white solid.

Step 4

Into a 50 mL round-bottom flask, was placed a solution of 3-[(3R)-3-[4-amino-3-[4-(3,5-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (20 mL), cyclopropanecarbaldehyde (64 mg, 0.91 mmol, 3.00 equiv), piperidine (13 mg, 0.15 mmol, 0.50 equiv), and dichloromethane (5 mL). The resulting solution was stirred for 12 h at room temperature and then concentrated under vacuum. The residue was loaded onto a silica gel column and eluted with dichloromethane/methanol (100:1) to give 70 mg (42%) of the title compound as a white solid. LC-MS: (ES, m/z): 542 [M+H]+. 1HNMR (300MHz,CDCl3, ppm) 8.405 (1H, s), 7.762~7.715 (2H, m), 7.282~7.223 (2H, m), 6.656~6.575 (4H, m), 6.696 (2H,s),5.022~4.924 (1H,m), 4.8~2.9 (4H,m), 2.424~2.301 (2H,m),2.271~2.259 (3H,d), 1.295~1.228 (2H,t),0.903~0.892 (2H,d).

230

Example 21

Synthesis of (R)-2-(3-(4-amino-3-(4-(2,5-difluorophenoxy)phenyl)-1H-pyrazolo[3,4-d]pyrimidin-1-yl)piperidine-1-carbonyl)-3-cyclopropylacrylonitrile

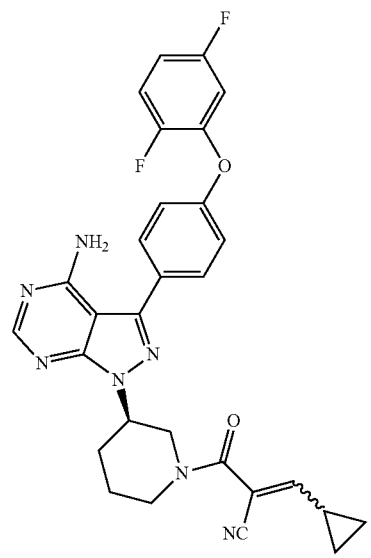 [SMILES: N#CC(=CC1CC1)C(=O)N1CCC[C@@H](n2nc(-c3ccc(Oc4cc(F)ccc4F)cc3)c3c(N)ncnc32)C1]

Step 1

Into a 500 mL 3-necked round-bottom flask, was placed a solution of sodium hydride (3.9 g, 162.50 mmol, 1.7 equiv) in N,N-dimethylformamide (200 mL). This was followed by the addition of a solution of 1-fluoro-4-nitrobenzene (13.6 g, 96.39 mmol, 1.00 equiv) in N,N-dimethylformamide (50 mL) dropwise with stirring at 0° C. over 20 min. The reaction mixture was stirred for 2 hr at 25° C. and then CuCl (9.6 g, 96.97 mmol, 1.0 equiv) was added, followed by addition of a solution of 2,5-difluorophenol (15.5 g, 119.15 mmol, 1.2 equiv) in N,N-dimethylformamide (50 mL) dropwise with stirring at 25° C. over 10 min. The resulting solution was stirred for 12 h at 100° C. in an oil bath and then diluted with water and washed with ether, water and brine. The reaction mixture was dried over anhydrous sodium sulfate and concentrated. The residue was loaded onto a silica gel column and eluted with ethyl acetate/petroleum ether (1/8) to give 19.5 g (81%) of 1,4-difluoro-2-(4-nitrophenoxy)benzene as a brown solid, Step 2

Into a 500 mL 3-necked round-bottom flask purged and maintained under an inert atmosphere of nitrogen, was placed a solution of 1,4-difluoro-2-(4-nitrophenoxy)benzene (19.5 g, 77.63 mmol, 1.00 equiv) in methanol (200 mL), and Raney Nickel (2 g). This was followed by the addition of a solution of hydrazine hydrate (11.66 g) in methanol (50 mL) dropwise with stirring at 25° C. over 15 min. The resulting solution was stirred for 12 h at 25° C. and then filtrated and the filtrate was concentrated under vacuum. The residue was diluted with ethyl acetate, washed with water and brine, dried over anhydrous sodium sulfate and concentrated under vacuum to give 16 g (93%) of 4-(2,5-difluorophenoxy)aniline as black oil.

Step 3

Into a 250 mL 4-necked round-bottom flask, was placed 4-(2,5-difluorophenoxy)-aniline (9 g, 40.69 mmol, 1.00 equiv), hydrogen chloride (37%) (10.2 g, 100 mmol, 2.5 equiv) and water (20 mL). A solution of NaNO$_2$ (3.1 g, 44.93 mmol, 1.10 equiv) in water (10 mL) was added dropwise with stirring at 0° C. over 5 min. After stirring at 0° C. for 30 min, the mixture was added into a solution of NaI (18 g, 120.00 mmol, 3.0 equiv) in water (20 mL) dropwise with stirring at 25° C. The resulting solution was stirred for 12 h at 25° C. and then extracted with ethyl acetate and the organic layers combined. The combined organics were washed with water and brine, dried over anhydrous sodium sulfate and concentrated under vacuum to give 10.5 g (78%) of 1,4-difluoro-2-(4-iodophenoxy)benzene as brown oil.

Step 4

Into a 100 mL 3-necked round-bottom flask purged and maintained under an inert atmosphere of nitrogen, was placed a solution of 1,4-difluoro-2-(4-iodophenoxy)benzene (2 g, 6.02 mmol, 1.00 equiv) in N,N-dimethylformamide (50 mL), 4,4,5,5-tetramethyl-2-(tetramethyl-1,3,2-dioxaborolan-2-yl)-1,3,2-dioxaborolane (1.68 g, 6.62 mmol, 1.10 equiv), potassium acetate (1.76 g, 17.93 mmol, 3.0 equiv), and Pd(OAc)$_2$ (68 mg, 0.30 mmol, 0.05 equiv). The resulting solution was stirred for 12 h at 85° C. in an oil bath and then diluted with water. The resulting solution was extracted with ethyl acetate and the organic layers combined. The combined organics were washed with water and brine and dried over anhydrous sodium sulfate and concentrated. The residue was loaded onto a silica gel column and eluted with ethyl acetate/petroleum ether (1/8) to give 1.5 g (75%) of 2-[4-(2,5-difluorophenoxy)phenyl]-4,4,5,5-tetramethyl-1,3,2-dioxaborolane as a light yellow solid.

Step 5

Into a 250-mL 3-necked round-bottom flask purged and maintained under an inert atmosphere of nitrogen, was placed a solution of tert-butyl (3R)-3-[4-amino-3-iodo-1H-pyrazolo[3,4-d]pyrimidin-1-yl]piperidine-1-carboxylate (500 mg, 1.13 mmol, 1.00 equiv) in 1,4-dioxane/H$_2$O (100/30 mL), 2-[4-(2,5-difluorophenoxy)phenyl]-4,4,5,5-tetramethyl-1,3,2-dioxaborolane (420 mg, 1.26 mmol, 1.1 equiv), sodium carbonate (240 mg, 2.26 mmol, 2.0 equiv), and Pd(PPh$_3$)$_4$ (65 mg, 0.06 mmol, 0.05 equiv). The resulting solution was stirred for 12 h at 90° C. in an oil bath and then concentrated under vacuum. The residue was diluted with water and the resulting solution was extracted with dichloromethane and the organic layers were combined. The combined organics were washed with brine, dried over anhydrous sodium sulfate and concentrated. The residue was loaded onto a silica gel and eluted with dichloromethane/methanol (10/1) to give 510 mg (87%) of tert-butyl (3R)-3-[4-amino-3-[4-(2,5-difluorophenoxy)phenyl]-1H-pyrazolo[3,4-d]pyrimidin-1-yl]piperidine-1-carboxylate as a white solid.

Step 6

Into a 100 mL round-bottom flask, was placed a solution of tert-butyl (3R)-3-[4-amino-3-[4-(2,5-difluorophenoxy)phenyl]-1H-pyrazolo[3,4-d]pyrimidin-1-yl]piperidine-1-carboxylate (450 mg, 0.86 mmol, 1.00 equiv) in dichloromethane (40 mL). This was followed by the addition of CF$_3$COOH (10 mL) dropwise with stirring at 25° C. over 5 min. The resulting solution was stirred for 3 h at 25° C. and then concentrated under vacuum. The residue was diluted with dichloromethane and the resulting mixture was washed with aqueous sodium bicarbonate and brine and dried over anhydrous sodium sulfate and concentrated under vacuum to give 400 mg (99%) of 3-[4-(2,5-difluorophenoxy)phenyl]-1-[(3R)-piperidin-3-yl]-1H-pyrazolo[3,4-d]pyrimidin-4-amine as a white solid.

Step 7

Into a 100 mL round-bottom flask, was placed a solution of 3-[4-(2,5-difluoro-phenoxy)phenyl]-1-[(3R)-piperidin-3-yl]-1H-pyrazolo[3,4-d]pyrimidin-4-amine (300 mg, 0.71 mmol, 1.00 equiv) in dichloromethane (30 mL), HATU (400 mg, 1.05 mmol, 1.5 equiv), triethylamine (220 mg, 2.17 mmol, 3.0 equiv), and 2-cyanoacetic acid (90 mg, 1.06 mmol, 1.5 equiv). The resulting solution was stirred for 10 h at 25° C. and then washed with water and brine and dried over anhydrous sodium sulfate and concentrated. The residue was loaded onto a silica gel column and eluted with dichloromethane/methanol (10/1) to give 200 mg (58%) of 3-[(3R)-3-[4-amino-3-[4-(2,5-difluorophenoxy)phenyl]-1H-pyrazolo[3,4-d]pyrimidin-1-yl]piperidin-1-yl]-3-oxopropanenitrile as a white solid.

Step 8

Into a 10 mL sealed tube, was placed a solution of 3-[(3R)-3-[4-amino-3-[4-(2,5-difluorophenoxy)phenyl]-1H-pyrazolo[3,4-d]pyrimidin-1-yl]piperidin-1-yl]-3-oxopropanenitrile (150 mg, 0.31 mmol, 1.00 equiv) in methanol (5 mL), piperidine (78 mg, 0.92 mmol, 3.0 equiv), and cyclopropanecarbaldehyde (64 mg, 0.91 mmol, 3.0 equiv). The resulting solution was stirred for 12 h at 25° C. and then concentrated under vacuum. The resulting solution was diluted with dichloromethane and washed with saturated aqueous ammonium chloride, water and brine. The organics were dried over anhydrous sodium sulfate and concentrated. The residue was loaded onto a silica gel column and eluted with dichloromethane/methanol (20/1) to give 38 mg (23%) of 2-[[(3R)-3-[4-amino-3-[4-(2,5-difluorophenoxy)phenyl]-1H-pyrazolo[3,4-d]pyrimidin-1-yl]piperidin-1-yl]carbonyl]-3-cyclopropylprop-2-enenitrile as a white solid. LC-MS (ES, m/z): 542 [M+H], H-NMR (CDCl$_3$, ppm): δ8.51 (s,1H); δ7.66 (d,2H); δ7.12 (m,3H); δ6.88 (m,2H); δ6.51 (d,1H); δ5.57 (s,2H); δ4.95 (m,1H); δ4.82 (m,1H); δ4.23 (m,1H); δ3.65 (m,1H); δ3.28 (m,1H); δ2.33 (m,2H); δ2.01 (m,2H); δ1.83 (m 1H); δ1.20 (m,2H); δ0.78 (m,2H).

Example 22

Synthesis of (R)-2-(3-(4-amino-3-(2-fluoro-4-(phenoxy)phenyl)-1H-pyrazolo[3,4-d]pyrimidin-1-yl)piperidine-1-carbonyl)-3-cyclopropylacrylonitrile

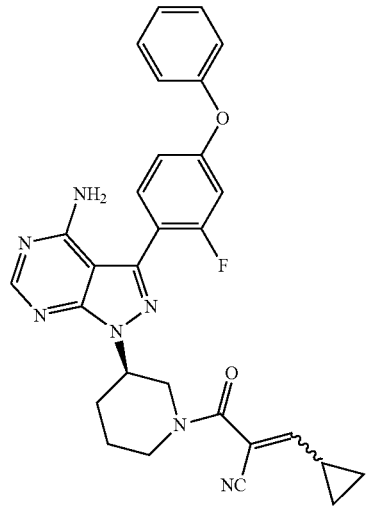 [SMILES: N#CC(=CC1CC1)C(=O)N1CCC[C@@H](n2nc(-c3ccc(Oc4ccccc4)cc3F)c3c(N)ncnc32)C1]

233

Step 1

Into a 100 mL 3-necked round-bottom flask purged and maintained under an inert atmosphere of nitrogen, was placed tert-butyl (3R)-3-[4-amino-3-iodo-1H-pyrazolo[3,4-d]pyrimidin-1-yl]piperidine-1-carboxylate (400 mg, 0.90 mmol, 1.00 equiv), (2-fluoro-4-phenoxyphenyl)boronic acid (250 mg, 1.08 mmol, 1.20 equiv), sodium carbonate (190 mg, 1.79 mmol, 1.99 equiv), ethylene glycol dimethyl ether (50 mL), water (15 mL), and Pd(PPh$_3$)$_4$ (52 mg, 0.04 mmol, 0.05 equiv). The resulting solution was stirred for 12 h at 80° C. and then concentrated under vacuum. The residue was loaded onto a silica gel column and eluted with dichloromethane/methanol (100/1) to give 320 mg (70%) of tert-butyl (3R)-3-[4-amino-3-(2-fluoro-4-phenoxyphenyl)-1H-pyrazolo[3,4-d]pyrimidin-1-yl]piperidine-1-carboxylate as a yellow solid.

Step 2

Into a 100 mL round-bottom flask, was placed a solution of tert-butyl (3R)-3-[4-amino-3-(2-fluoro-4-phenoxyphenyl)-1H-pyrazolo[3,4-d]pyrimidin-1-yl]piperidine-1-carboxylate (320 mg, 0.63 mmol, 1.00 equiv) in dichloromethane (50 mL). This was followed by the addition of trifluoroacetic acid (10 mL) dropwise with stirring. The resulting solution was stirred overnight at room temperature and then concentrated under vacuum. The residue was diluted with water and the pH value of the solution was adjusted to >7 with sodium carbonate. The resulting solution was extracted with dichloromethane and the organic layers combined and dried over anhydrous sodium sulfate and concentrated under vacuum to give 190 mg (74%) of 3-(2-fluoro-4-phenoxyphenyl)-1-[(3R)-piperidin-3-yl]-1H-pyrazolo[3,4-d]pyrimidin-4-amine as a brown solid.

Step 3

Into a 100 mL round-bottom flask, was placed a solution of 3-(2-fluoro-4-phenoxyphenyl)-1-[(3R)-piperidin-3-yl]-1H-pyrazolo[3,4-d]pyrimidin-4-amine (190 mg, 0.47 mmol, 1.00 equiv) in dichloromethane (50 mL), 2-cyanoacetic acid (60 mg, 0.71 mmol, 1.50 equiv), and 1-[(1H-imidazol-1-yl)carbonyl]-1H-imidazole (114 mg, 0.70 mmol, 1.50 equiv). The resulting solution was stirred for 24 h at room temperature and then diluted with dichloromethane. The resulting mixture was washed with NH$_4$Cl and dried over anhydrous sodium sulfate and concentrated under vacuum. The residue was loaded onto a silica gel column and eluted with dichloromethane/methanol (100:1) to give 100 mg (45%) of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile as a white solid.

Step 4

Into a 50 mL round-bottom flask, was placed a solution of 3-[(3R)-3-[4-amino-3-(2-fluoro-4-phenoxyphenyl)-1H-pyrazolo[3,4-d]pyrimidin-1-yl]piperidin-1-yl]-3-oxopropanenitrile (100 mg, 0.21 mmol, 1.00 equiv) in methanol (20 mL), cyclopropanecarbaldehyde (45 mg, 0.64 mmol, 3.00 equiv), piperidine (9 mg, 0.11 mmol, 0.50 equiv), and dichloromethane (5 mL). The resulting solution was stirred for 12 h at room temperature and then concentrated under vacuum. The residue was loaded onto a silica gel column and eluted with dichloromethane/methanol (100:1) to give 24 mg (24%) of the title compound as a white solid, LC-MS (ES, m/z): 524 [M+H]$^+$. H-NMR (CDCl$_3$, ppm): 8.397 (1H,s), 7.628~7.427 (3H, m), 7.283~7.231 (1H, m), 7.203~7.124 (2H, m), 6.979~6.866 (2H,m), 6.722(1H,s), 5.717 (2H,s), 4.973 (1H,s), 4.8~3.1 (4H,m), 2.581~2.045 (5H,m), 1.329~1.228 (2H,m), 0.893 (2H,m).

Proceeding as described above, but substituting cyclopropanecarbaldehyde with acetaldehyde, (R)-2-(3-(4-amino-3-(2-fluoro-4-phenoxyphenyl)-1H-pyrazolo[3,4-d]pyrimidin-1-yl)piperidine-1-carbonyl)-4-methylpent-2-enenitrile was synthesized.

234

Example 23

Synthesis of (R)-2-(2-((4-amino-3-(4-(2-fluorophenoxy)phenyl)-1H-pyrazolo[3,4-d]pyrimidin-1-yl)methyl)pyrrolidine-1-carbonyl)-3-cyclopropylacrylonitrile

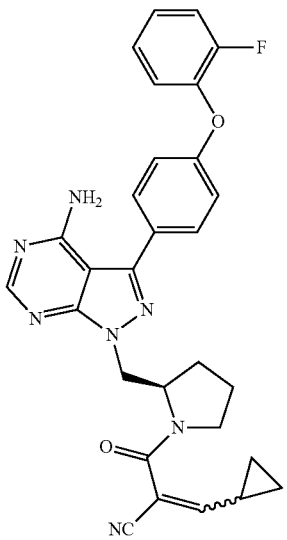 [SMILES: N#CC(=CC1CC1)C(=O)N1CCC[C@@H]1Cn1nc(-c2ccc(Oc3ccccc3F)cc2)c2c(N)ncnc21]

Step 1

Into a 100 mL 3-necked round-bottom flask, was placed a solution of 2-fluorophenol (2.6 g, 23.19 mmol, 1.00 equiv) in N,N-dimethylformamide (30 mL) and CuCl (2.2 g, 2.41 equiv). This was followed by the addition of sodium hydride (1.34 g, 55.83 mmol, 0.86 equiv) in portions and then 1-fluoro-4-nitrobenzene (2.8 g, 19.84 mmol, 0.67 equiv). The resulting solution was stirred for 5 h at 100° C. in an oil bath and the resulting solution was diluted with water/ice. The aqueous mixture was extracted with ethyl acetate and the organic layers combined and dried over anhydrous sodium sulfate, and concentrated under vacuum. The residue was loaded onto a silica gel column and elution with ethyl acetate/petroleum ether (1:100) gave 1.7 g (31%) of 1-(2-fluorophenoxy)-4-nitrobenzene as a light yellow solid.

Step 2

Into a 250 mL 3-necked round-bottom flask, was placed a solution of 1-fluoro-2-(4-nitrophenoxy)benzene (5 g, 21.44 mmol, 1.00 equiv) in methanol/H$_2$O (2/1=V/V) (100 mL), and NH$_4$Cl (1 g, 18.70 mmol, 0.87 equiv). This was followed by the addition of Fe (7 g, 5.83 equiv), in portions at 80° C. in 20 min. The resulting solution was stirred for 1 h at reflux in an oil bath. The reaction mixture was cooled in a water bath. The solids were filtered out and the filtrate was concentrated under vacuum. The resulting solution was extracted with ethyl acetate and the organic layers combined and dried over anhydrous sodium sulfate and concentrated under vacuum to give 3.2 g (73%) of 4-(2-fluorophenoxy)aniline as a light yellow solid.

Step 3

Into a 250 mL 3-necked round-bottom flask, was placed 4-(2-fluorophenoxy)aniline (2 g, 9.84 mmol, 1.00 equiv) and 37% hydrogen chloride (20 mL). NaNO₂ (800 mg, 11.59 mmol, 1.18 equiv) was added in portions at 0° C. The mixture was stirred at 0° C. for 30 min and then urea (1 g, 16.65 mmol, 1.69 equiv) was added. The mixture was stirred at 0° C. for 20 min and poured into the solution of KI (10 g) in water (20 mL) at room temperature. The resulting solution was stirred at room temperature for 1 h and extracted with ethyl acetate and the organic layers combined and dried over anhydrous sodium sulfate and concentrated under vacuum. The residue was loaded onto a silica gel column and eluted with ethyl acetate/petroleum ether (1:100; 1:50) to give 1 g (32%) of 1-fluoro-2-(4-iodophenoxy)-benzene as a light yellow solid.
Step 4

Into a 100 mL 3-necked round-bottom flask purged and maintained under an inert atmosphere of nitrogen, was placed a solution of 1-(2-fluorophenoxy)-4-iodobenzene (3.3 g, 10.51 mmol, 1.00 equiv) in tetrahydrofuran (50 mL). n-BuLi (4.4 mL) was added dropwise with stirring at −78° C. The resulting solution was stirred for 10 mins at −78° C. and then tris(propan-2-yl)borate (2.1 g, 11.17 mmol, 1.06 equiv) was added dropwise with stirring at −78° C. over 10 min. The resulting solution was stirred while the temperature warmed from −78° C. to room temperature. The reaction was then quenched by the addition of saturated aqueous NH₄Cl and concentrated under vacuum. The resulting solution was diluted with 10% aquious potassium hydroxide and then washed with ether. The pH of the aqueous was adjusted to 2-4 with hydrogen chloride (37%). The resulting solution was extracted with ethyl acetate and the organic layers combined and dried over anhydrous sodium sulfate and concentrated under vacuum to give 2.2 g (90%) of [4-(2-fluorophenoxy)phenyl]boronic acid as a white solid
Step 5

Into a 100 mL 3-necked round-bottom flask purged and maintained under an inert atmosphere of nitrogen, was placed a solution of tert-butyl (2R)-2-([4-amino-3-iodo-1H-pyrazolo[3,4-d]pyrimidin-1-yl]methyl)pyrrolidine-1-carboxylate (300 mg, 0.68 mmol, 1.00 equiv) in dioxane/H₂O(7/3=V/V) (30 mL), [4-(2-fluorophenoxy)phenyl]boronic acid (500 mg, 2.16 mmol, 3.19 equiv), sodium carbonate (500 mg, 4.72 mmol, 6.99 equiv), and Pd(PPh₃)₄ (200 mg, 0.17 mmol, 0.26 equiv). The resulting solution was stirred overnight at 100° C. in an oil bath and then concentrated under vacuum. The residue was loaded onto a silica gel column with dichloromethane/methanol (100:1) to give 0.2 g (59%) of tert-butyl (2S)-2-([4-amino-3-[4-(2-fluorophenoxy)phenyl]-1H-pyrazolo[3,4-d]pyrimidin-1-yl]methyl)-pyrrolidine-1-carboxylate as a light yellow solid.
Step 6

Into a 100 mL round-bottom flask purged and maintained under an inert atmosphere of nitrogen, was placed a solution of tert-butyl (2R)-2-[[4-amino-3-[4-(2-fluorophenoxy)phenyl]-1H-pyrazolo[3,4-d]pyrimidin-1-yl]methyl)pyrrolidine-1-carboxylate (200 mg, 0.40 mmol, 1.00 equiv) in dichloromethane (20 mL), and trifluoroacetic acid (10 g, 87.70 mmol, 221.25 equiv). The resulting solution was stirred overnight at room temperature and then concentrated under vacuum. The resulting solution was diluted with 10% aqueous sodium carbonate and the solution was extracted with dichloromethane and the organic layers combined and dried over anhydrous sodium sulfate and concentrated under vacuum to give 0.1 g (62%) of 3-[4-(2-fluorophenoxy)phenyl]-1-((2R)-pyrrolidin-2-ylmethyl)-1H-pyrazolo[3,4-d]pyrimidin-4-amine as a light yellow solid.
Step 7

Into a 50 mL round-bottom flask, was placed a solution of 3-[4-(2-fluorophenoxy)phenyl]-1-((2R)-pyrrolidin-2-ylmethyl)-1H-pyrazolo[3,4-d]pyrimidin-4-amine (100 mg, 0.25 mmol, 1.00 equiv) in dichloromethane (10 mL), 1-[(1H-imidazol-1-yl)carbonyl]-1H-imidazole (80 mg, 0.49 mmol, 1.25 equiv), and 2-cyanoacetic acid (50 mg, 0.59 mmol, 3.80 equiv). The resulting solution was stirred for 1 h at room temperature and then concentrated under vacuum. The residue was loaded onto a silica gel column with dichloromethane/methanol (100:1; 50:1) to give 0.05 g (43%) of 3-[(2R)-2-([4-amino-3-[4-(2-fluorophenoxy)phenyl]-1H-pyrazolo[3,4-d]pyrimidin-1-yl]methyl)pyrrolidin-1-yl]-3-oxopropanenitrile as a light yellow solid.
Step 8

Into a 50 mL round-bottom flask, was placed a solution of 3-[(2R)-2-([4-amino-3-[4-(2-fluorophenoxy)phenyl]-1H-pyrazolo[3,4-d]pyrimidin-1-yl]methyl)pyrrolidin-1-yl]-3-oxopropanenitrile (50 mg, 0.11 mmol, 1.00 equiv) in methanol (10 mL), piperidine (50 mg, 0.59 mmol, 6.73 equiv), and cyclopropanecarbaldehyde (50 mg, 0.71 mmol, 5.54 equiv). The resulting solution was stirred for 1 h at room temperature and then concentrated under vacuum. The residue was loaded onto a silica gel column and eluted with dichloromethane/methanol (100:1, 50:1) to give 0.0179 g (32%) of the title compounds as an off-white solid.

LC-MS (ES, m/z): 524 [M+H]⁺, ¹HNMR(300MHz, CDCl₃, ppm) 8.396 (1H, s), 7.689~7.628 (2H, m), 7.284~7.085 (6H, m), 6.825~6.798 (1H, d); 5.663 (2H, s); 4.868 (1H, d); 4.676 (2H, d); 3.708~3.470 (2H, m); 2.060~1.980 (5H, m); 1.226 (2H, t); 0.873 (2H, s).

Example 24

Synthesis of (S)-4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile bis(2,2,2-trifluoroacetate

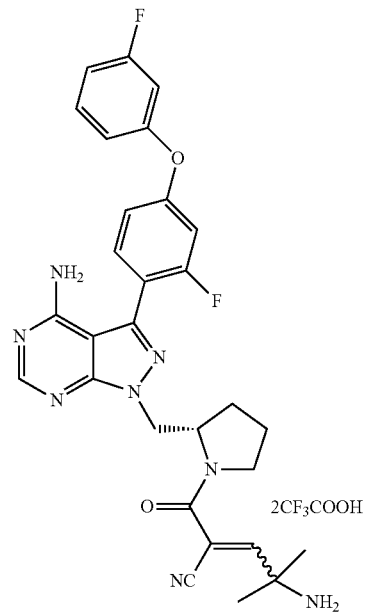 [SMILES: CC(C)(N)C=C(C#N)C(=O)N1CCC[C@H]1Cn1nc(-c2ccc(Oc3cccc(F)c3)cc2F)c2c(N)ncnc21]

Step 1

To a solution of 3-((S)-2-((4-amino-3-(2-fluoro-4-(3-fluorophenoxy)phenyl)-1H-pyrazolo[3,4-d]pyrimidin-1-yl)methyl)pyrrolidin-1-yl)-3-oxopropanenitrile (245 mg, 0.5 mmol, 1 equiv) and tert-butyl 2-methyl-1-oxopropan-2-yl-carbamate (935 mg, 5 mmol, 10 equiv) in dioxane (30 mL) was added 0.5 mL piperidine, 1 drop AcOH and 2 g of 4 A molecular sieves. The resulting mixture was stirred for 6 h at 110° C. The solids was filtered out, the filtrate was diluted with 200 mL of ethyl acetate, washed with brine, dried over $Na_2SO_4$, concentrated and purified with silica gel column (ethyl acetate/MeOH 10/1) to give 60 mg of tert-butyl 5-((S)-2-((4-amino-3-(2-fluoro-4-(3-fluorophenoxy)phenyl)-1H-pyrazolo[3,4-d]pyrimidin-1-yl)methyl)pyrrolidin-1-yl)-4-cyano-2-methyl-5-oxopent-3-en-2-ylcarbamate as white solid.

Step 2

To a solution of tert-butyl 5-((S)-2-((4-amino-3-(2-fluoro-4-(3-fluorophenoxy)phenyl)-1H-pyrazolo[3,4-d]pyrimidin-1-yl)methyl)pyrrolidin-1-yl)-4-cyano-2-methyl-5-oxopent-3-en-2-ylcarbamate (60 mg, 0.091 mmol) in DCM (20 mL) was added $CF_3COOH$ (5 mL). The mixture was stirred for 2 h at room temperature and then concentrated and purified on Prep-HPLC. Conditions: (1#-Pre-HPLC-001(SHIMADZU)): Column, SunFire Prep C18, 19*150 mm 5 um; mobile phase, water with 0.05% TFA and $CH_3CN$ (40% $CH_3CN$ up to 100% in 20 min); Detector, 254 nm to give 12 mg of the title compound as light yellow solid.

LC-MS: m/z 559 (M+H$^+$). H$^1$-NMR (300 MHz, CDCl$_3$, ppm): δ 13.19 (s, 1H), 10.97 (s, 1H), 8.28 (s, 1H), 7.51-7.37 (m, 2H), 7.30 (s, 1H), 7.00-6.84 (m, 5H), 4.87-4.72 (m, 3H), 3.65-3.50 (m, 2H), 2.15-1.76 (m, 4H), 1.56-1.52 (d, 6H).

Example 25

Synthesis of 2-((S)-2-(4-amino-3-(2-fluoro-4-phenoxyphenyl)-1H-pyrazolo[3,4-d]pyrimidin-1-yl) methyl)pyrrolidine-1-carbonyl)-4-methyl-4-(methylamino)pent-2-enenitrile bis(2,2,2-trifluoroacetate

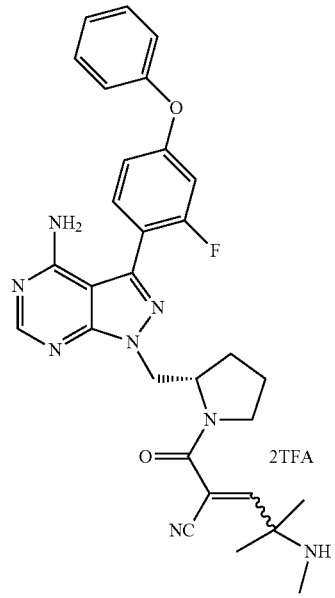 [SMILES: CNC(C)(C)C=C(C#N)C(=O)N1CCC[C@H]1Cn1nc(-c2ccc(Oc3ccccc3)cc2F)c2c(N)ncnc21]

Step 1

To a solution of 3-((S)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (236 mg, 0.5 mmol, 1 equiv) and tert-butyl methyl(2-methyl-1-oxopropan-2-yl)carbamate (2.01 g, 10 mmol, 20 equiv) in dioxane (30 mL) was added 0.5 mL piperidine, 1 drop AcOH and 2 g of 4 A molecular sieves. The resulting mixture was stirred for 6 h at 110° C. The solids was filtered out, the filtrate was diluted with 50 mL of EA, washed with brine, dried over $Na_2SO_4$, concentrated. The residue was purified on silica gel column (EA to EA/MeOH 10/1) to give 60 mg of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(methyl)carbamate as white solid.

Step 2

To a solution of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(methyl)carbamate (60 mg, 0.092 mmol) in DCM (5 mL) was added 1.5 mL of $CF_3COOH$. The mixture was stirred for 2 h at room temperature, concentrated and the residue was purified on Prep-HPLC. Conditions: (1#-Pre-HPLC-001 (SHIMADZU)): Column, SunFire Prep C18, 19*150 mm 5 um; mobile phase, water with 0.05% TFA and $CH_3CN$ (40% $CH_3CN$ up to 100% in 20 min); Detector, 254 nm to give 12 mg of the title compound salt as a white solid.

LC-MS: m/z 555 (M+H$^+$). H$^1$-NMR (400 MHz, CDCl$_3$+ D$_2$O, ppm): 8.32 (s, 1H), 7.51-7.41 (m, 4H), 7.28-7.25 (m, 1H), 7.13 (d, J=8.0 Hz, 2H), 6.96-6.94 (m, 1H), 6.85 (dd, J=11.6 Hz, 2.0 Hz, 1H) 4.88-4.68 (m, 3H), 3.69-3.53 (m, 2H), 3.24 (s, 3H), 2.17-1.80 (m, 4H), 1.48-1.45 (d, 6H).

Example 26

Synthesis of (S)-2-(2-((4-amino-3-(2-fluoro-4-phenoxyphenyl)-1H-pyrazolo[3,4-d]pyrimidin-1-yl) methyl)-4,4-difluoropyrrolidine-1-carbonyl)-3-cyclopropylacrylonitrile trifluoroacetic

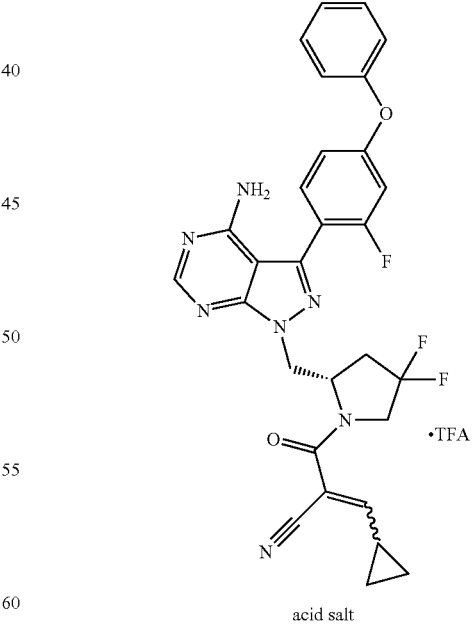

acid salt

Step 1

Into a solution of 1-tert-butyl 2-methyl (2S)-4,4-difluoropyrrolidine-1,2-dicarboxylate (900 mg, 3.39 mmol, 1.00 equiv) in tetrahydrofuran (15 mL) was added LiBH$_4$ (200 mg, 9.1 mmol, 2.7 equiv) in batches at 0° C. The resulting solution was stirred overnight at room temperature, then was diluted with EA and washed with water and brine, dried over anhydrous sodium sulfate and concentrated to give 0.8 g of tert-butyl (2S)-4,4-difluoro-2-(hydroxymethyl)pyrrolidine-1-carboxylate as reddish oil.

Step 2

Under nitrogen, to a solution of 3-iodo-1H-pyrazolo[3,4-d]pyrimidin-4-amine (2.61 g, 10.00 mmol, 1.00 equiv), tert-butyl (2S)-4,4-difluoro-2-(hydroxymethyl)pyrrolidine-1-carboxylate (2.37 g, 9.99 mmol, 1.00 equiv) and TPP (4 g, 15.2 mmol, 1.50 equiv) in THF was DIAD (3.00 g, 15.0 mmol, 1.50 equiv) at 0° C. in 30 min. The resulting solution was stirred overnight at room temperature. The mixture was then concentrated under vacuum and the residue was applied onto a silica gel column with dichloromethane/ethyl acetate (3/1) to give 1 g of tert-butyl (2S)-2-([4-amino-3-iodo-1H-pyrazolo[3,4-d]-pyrimidin-1-yl]methyl)-4,4-difluoropyrrolidine-1-carboxylate as reddish oil.

Step 3

Under nitrogen atmosphere, a suspension of tert-butyl (2S)-2-([4-amino-3-iodo-1H-pyrazolo[3,4-d]pyrimidin-1-yl]methyl)-4,4-difluoropyrrolidine-1-carboxylate (800 mg, 1.67 mmol, 1.00 equiv), (2-fluoro-5-phenoxyphenyl)boronic acid (480 mg, 2.07 mmol, 1.20 equiv), Pd(dppf)Cl₂ (140 mg, 0.17 mmol, 0.10 equiv), sodium carbonate (0.53 g, 5.00 mmol, 3.00 equiv) in 1,4-dioxane/water (40/10 mL) was stirred at 80° C. overnight. The resulting mixture was concentrated under vacuum. The residue was loaded on a silica gel column and eluted with ethyl acetate/petroleum ether (1:2 to 3:1) to give 0.6 g (67%) of tert-butyl (2S)-2-[[4-amino-3-(2-fluoro-4-phenoxyphenyl)-1H-pyrazolo[3,4-d]pyrimidin-1-yl]methyl]-4,4-difluoropyrrolidine-1-carboxylate as a reddish solid.

Step 4

To a solution of tert-butyl (2S)-2-[[4-amino-3-(2-fluoro-4-phenoxyphenyl)-1H-pyrazolo[3,4-d]pyrimidin-1-yl]methyl]-4,4-difluoropyrrolidine-1-carboxylate (600 mg, 1.11 mmol, 1.00 equiv) in dichloromethane (10 mL) was added trifluoroacetic acid (2 mL) dropwise. The resulting solution was stirred at room temperature for 2 h. The mixture was concentrated under vacuum to give 0.85 g (crude) of 1-[[(2S)-4,4-difluoropyrrolidin-2-yl]methyl]-3-(2-fluoro-4-phenoxyphenyl)-1H-pyrazolo[3,4-d]pyrimidin-4-amine trifluoroacetic acid salt as a brown semi-solid.

Step 5

To a solution of 1-[[(2S)-4,4-difluoropyrrolidin-2-yl]methyl]-3-(2-fluoro-4-phenoxyphenyl)-1H-pyrazolo[3,4-d]pyrimidin-4-amine (850 mg, crude), 2-cyanoacetic acid (120 mg, 1.31 mmol, 1.29 equiv) and TEA (650 mg, 6.45 mmol, 5.00 equiv) in dichloromethane (30 mL), was added HATU (500 mg, 1.32 mmol, 1.29 equiv). The resulting solution was stirred at room temperature overnight. The mixture was diluted with DCM, washed with HCl (2N), sat. NaHCO₃, brine, dried over sodium sulfate and concentrated. The residue was submitted to chromatography (SiO₂, DCM:MeOH=30:1) to give 0.4 g (77%) of 3-[(2S)-2-[[4-amino-3-(2-fluoro-4-phenoxyphenyl)-1H-pyrazolo[3,4-d]pyrimidin-1-yl]methyl]-4,4-difluoropyrrolidin-1-yl]-3-oxopropanenitrile as a pale yellow solid.

Step 6

A solution of 3-[(2S)-2-[[4-amino-3-(2-fluoro-4-phenoxyphenyl)-1H-pyrazolo[3,4-d]pyrimidin-1-yl]methyl]-4,4-difluoropyrrolidin-1-yl]-3-oxopropanenitrile (120 mg, 0.24 mmol, 1.00 equiv), cyclopropanecarbaldehyde (80 mg, 1.14 mmol, 5.00 equiv), piperidine (41 mg, 0.48 mmol, 2.00 equiv) in ethanol (10 mL) was stirred at 70° C. for 2 h. The resulting mixture was concentrated under vacuum. The residue was purified on Prep-HPLC. Conditions: (1#-Pre-HPLC-001 (SHIMADZU)): Column, SunFire Prep C18, 19*150 mm 5 um; mobile phase, water with 0.05% TFA and CH₃CN (40% CH₃CN up to 100% in 20 min); Detector, 254 nm, to give 24 mg (18%) of the title compound as a white solid.

LC-MS m/z: 560 (M+1). H-NMR (400MHz, CDCl₃, ppm): 11.94(brs,1H) 8.29 (s,1H), 7.55-7.45(m, 3H), 7.31-7.24(m, 1H), 7.14 (d, J=7.6 Hz, 2H), 7.00 (dd, J=8.8, 2.4 Hz, 1H), 6.90-6.87 (m, 1H), 6.07 (brs, 1H), 4.97-5.05 (m, 1H), 4.70-4.67(m, 1H), 3.94-3.77 (m, 2H), 2.10 (s, 1H), 1.45-1.36 (m, 2H), 1.27-1.14 (m,2H).

Example 27

Synthesis of (R)-2-(3-(4-amino-5-(4-phenoxyphenyl)-7H-pyrrolo[2,3-d]pyrimidin-7-yl)piperidine-1-carbonyl)-3-cyclopropylacrylonitrile

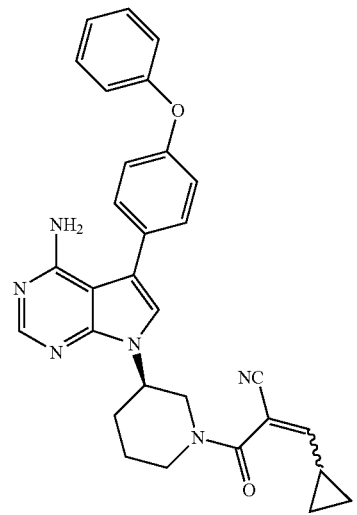 [SMILES: N#CC(=CC1CC1)C(=O)N1CCC[C@@H](n2cc(-c3ccc(Oc4ccccc4)cc3)c3c(N)ncnc32)C1]

Step 1

To the solution of 4-chloro-7H-pyrrolo[2,3-d]pyrimidine (10 g, 65.12 mmol, 1.0 eq) and (S)-tert-butyl 3-hydroxypiperidine-1-carboxylate (13.0 g, 65.12 mmol, 1.0 eq) and PPh₃ (34.20 g, 130.24 mmol, 2.0 eq) in THF (400 mL), DEAD (22.68 g, 130.24 mmol, 2.0 eq) was added at 0° C. The resulted mixture was stirred and warmed to RT for 12 h. The reaction mixture was purified by column (10% EtOAc in petroleum ether) to afford (R)-tert-butyl 3-(4-chloro-7H-pyrrolo[2,3-d]pyrimidin-7-yl)piperidine-1-carboxylate (2.1 g, 10% in yield) as colorless oil.

Step 2

A mixture of (R)-tert-butyl 3-(4-chloro-7H-pyrrolo[2,3-d]pyrimidin-7-yl)piperidine-1-carboxylate (1.7 g, 5.05 mmol) and NIS (1.25 g, 5.55 mmol) in DMF (20 mL) was stirred for 12 h at room temperature. Water was added to the mixture, which was extracted with EA, the combined organic layers were dried and purified by column to give (R)-tert-butyl 3-(4-chloro-5-iodo-7H-pyrrolo[2,3-d]pyrimidin-7-yl)piperidine-1-carboxylate (2.0 g, 86% in yield).

Step 3

A solution of (R)-tert-butyl 3-(4-chloro-5-iodo-7H-pyrrolo[2,3-d]pyrimidin-7-yl)piperidine-1-carboxylate (2.0 g, 4.32 mmol) in IPA saturated with NH$_3$ (20 mL) was stirred at 100° C. for 12 h in a 100 mL of autoclave. The organic layer was concentrated and purified on silica gel chromatography (eluted with PE:EtOAc=1:1) to afford (R)-tert-butyl 3-(4-amino-5-iodo-7H-pyrrolo[2,3-d]pyrimidin-7-yl)piperidine-1-carboxylate (1.5 g, 78% in yield).

Step 4

A mixture of (R)-tert-butyl 3-(4-amino-5-iodo-7H-pyrrolo[2,3-d]pyrimidin-7-yl)piperidine-1-carboxylate (250 mg, 0.56 mmol), 4-phenoxyphenylboronic acid (133 mg, 0.62 mmol), Pd(PPh$_3$)$_4$ (100 mg) and Na$_2$CO$_3$ (150 mg, 1.41 mmol) in dioxane/H$_2$O (40/10 ml) was stirred at 100° C. for 4 h. The reaction mixture was concentrated and purified by Pre-TLC to obtain (R)-tert-butyl 3-(4-amino-5-(4-phenoxyphenyl)-7H-pyrrolo[2,3-d]pyrimidin-7-yl)piperidine-1-carboxylate (150 mg, 55% in yield).

Step 5

To a mixture of (R)-tert-butyl 3-(4-amino-5-(4-phenoxyphenyl)-7H-pyrrolo[2,3-d]pyrimidin-7-yl)piperidine-1-carboxylate (150 mg, 0.31 mmol) in 10 ml DCM was added TFA (10 ml). The reaction mixture was stirred at RT for 2 h. Solvent was removed and sat. NaHCO$_3$ (10 mL) was added. The resulting mixture was extracted with DCM. The organic layer was dried and concentrated to afford (R)-5-(4-phenoxyphenyl)-7-(piperidin-3-yl)-7H-pyrrolo[2,3-d]pyrimidin-4-amine (100 mg, 83% in yield), which was subjected to the next step without any further purification.

Step 6

To a mixture of (R)-5-(4-phenoxyphenyl)-7-(piperidin-3-yl)-7H-pyrrolo[2,3-d]pyrimidin-4-amine (100 mg, 0.26 mmol, 1.0 eq), 2-cyano-3-cyclopropylacrylic acid (45 mg, 0.32 mmol, 1.2 eq) and DIPEA (102 mg, 0.78 mmol, 3 eq) in 10 mL DCM was added HATU (150 mg, 0.40 mmol, 1.5 eq) and the reaction mixture was stirred for 4 h at RT under N$_2$. The reaction mixture was purified by Pre-TLC to give the title compound (60 mg, 54% in yield). LCMS: m/z (505.0) (M+H)$^+$ $^1$HNMR (400 MHz, CDCl$_3$): δ 0.826~0.837 (m, 2H), 1.147~1.183 (m, 6H), 1.744~2.210 (m, 5H), 4.661~4.699 (m, 1H), 5.212~5.226 (m, 2H), 6.499~6.524 (m, 1H), 6.921~7.367 (m, 10H) and 8.223 (S, 1H).

Proceeding as described above but substituting 4-phenoxyphenylboronic acid with 2-(2-fluoro-4-phenoxyphenyl)-4,4,5,5-tetramethyl-1,3,2-dioxaborolane and 2-(4-(3,5-difluorophenoxy)phenyl)-4,4,5,5-tetramethyl-1,3,2-dioxaborolane, (R)-2-(3-(4-amino-5-(2-fluoro-4-phenoxyphenyl)-7H-pyrrolo[2,3-d]pyrimidin-7-yl)piperidine-1-carbonyl)-3-cyclopropylacrylonitrile LCMS m/z 523.1 (M+H)$^+$ and (R)-2-(3-(4-amino-5-(4-(3,5-difluorophenoxy)phenyl)-7H-pyrrolo[2,3-d]pyrimidin-7-yl)piperidine-1-carbonyl)-3-cyclopropylacrylonitrile LCMS m/z 541.1 (M+H)$^+$ were prepared respectively.

Example 28

Synthesis of (S)-2-{2-[4-amino-5-(4-phenoxy-phenyl)-pyrrolo[2,3-d]pyrimidin-7-ylmethyl]-pyrrolidine-1-carbonyl}-3-cyclopropyl-acrylonitrile

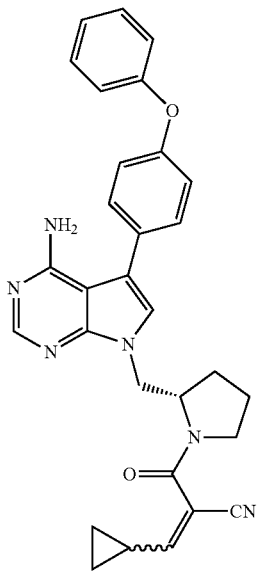 [SMILES: N#CC(=CC1CC1)C(=O)N1CCC[C@H]1Cn1cc(-c2ccc(Oc3ccccc3)cc2)c2c(N)ncnc21]

Step 1

To a solution of 4-chloro-7H-pyrrolo[2,3-d]pyrimidine (8.0 g, 52.32 mmol, 1.0 eq) in DMF (40 mL), NIS (15.7 g, 57.55 mmol, 1.1 eq) was added at 0° C. The reaction mixture was stirred overnight at room temperature. Water (40 mL) was added to the reaction mixture, extracted with EtOAc. The organic layer was dried over Na$_2$SO$_4$ and concentrated under vacuum to give 4-chloro-5-iodo-7H-pyrrolo[2,3-d]pyrimidine (14.6 g, 100% in yield).

Step 2

To a solution of 4-chloro-5-iodo-7H-pyrrolo[2,3-d]pyrimidine (4.0 g, 14.34 mmol, 1.0 eq), (S)-tert-butyl 2-(hydroxymethyl)pyrrolidine-1-carboxylate (4.04 g, 20.08 mmol, 1.4 eq), and PPh$_3$ (7.5 g, 28.68 mmol, 2.0 eq) in dry THF (30 mL), DIAD (5.80 g, 28.68 mmol, 2.0 eq) was added dropwise at 0° C. The mixture was stirred at RT for 5 h. The reaction mixture was concentrated and purified by silica gel chromatography (eluted with PE: EtOAc=1:1) to afford (S)-2-(4-chloro-5-iodo-pyrrolo[2,3-d]pyrimidin-7-ylmethyl)-pyrrolidine-1-carboxylic acid tert-butyl ester (5.1 g, 77% in yield).

Step 3

A solution of (S)-2-(4-chloro-5-iodo-pyrrolo[2,3-d]pyrimidin-7-ylmethyl)-pyrrolidine-1-carboxylic acid tert-butyl ester (3.5 g, 6.93 mmol) in MeOH (saturated with NH$_3$) was stirred 100° C. and overnight in a 100 mL of sealed tube. The organic layer was concentrated under reduced pressure to provide a white solid which was purified by silica gel chromatography eluted with PE: EtOAc=1:1 to afford (S)-2-(4-amino-5-iodo-pyrrolo[2,3-d]pyrimidin-7-ylmethyl)-pyrrolidine-1-carboxylic acid tert-butyl ester (2.7 g, 87.98% in yield).

Step 4

A solution of (S)-2-(4-amino-5-iodo-pyrrolo[2,3-d]pyrimidin-7-ylmethyl)-pyrrolidine-1-carboxylic acid tert-butyl ester (500.00 mg, 1.13 mmol, 1.0 eq), 4-phenoxyphenylboronic acid (240.00 mg, 1.13 mmol, 1.0 eq), Pd(PPh$_3$)$_4$ (100.00 mg), and Na$_2$CO$_3$ (300.00 mg, 2.83 mmol, 2.5 eq) in Dioxane/H$_2$O (40/10 ml) was stirred at 90° C. for 4 h. The reaction mixture was concentrated and purified by Pre-TLC to afford (S)-2-[4-amino-5-(4-phenoxy-phenyl)-pyrrolo[2,3-d]pyrimidin-7-ylmethyl]-pyrrolidine-1-carboxylic acid tert-butyl ester (500 mg, 91% in yield).

Step 5

To a solution of (S)-2-[4-amino-5-(4-phenoxy-phenyl)-pyrrolo[2,3-d]pyrimidin-7-ylmethyl]-pyrrolidine-1-carboxylic acid tert-butyl ester (500 mg, 1.03 mmol) in 10 ml of DCM, TFA (10 ml) was added. The reaction mixture was stirred at RT for 2 h. The mixture was concentrated to give (S)-5-(4-phenoxyphenyl)-7-pyrrolidin-2-ylmethyl-7H-pyrrolo[2,3-d]pyrimidin-4-ylamine (400 mg), which was subjected to the next step without any further purification.

Step 6

To a mixture of (S)-5-(4-phenoxy-phenyl)-7-pyrrolidin-2-ylmethyl-7H-pyrrolo[2,3-d]pyrimidin-4-ylamine (100 mg, 0.26 mmol, 1.0 eq), 2-cyano-3-cyclopropyl-acrylic acid (45 mg, 0.32 mmol, 1.2 eq) and DIEA (102 mg, 0.78 mmol, 3.0 eq) in 10 ml DCM was added HATU (150 mg, 0.40 mmol, 1.5 eq). The reaction mixture was stirred for 4 h at RT under N$_2$. The mixture was purified by Pre-TLC to give the title compound (71 mg). LCMS: m/z 486.2 (M+H)$^+$ Proceeding as described above but substituting 4-phenoxyphenylboronic acid with 3,5-difluoro-phenoxyphenylboronic acid and 2-fluoro-4-phenoxyphenyl-brononic acid, (S)-2-(2-{4-amino-5-[4-(3,5-difluoro-phenoxy)-phenyl]-pyrrolo[2,3-d]pyrimidin-7-ylmethyl}-pyrrolidine-1-carbonyl)-3-cyclopropyl-acrylonitrile LCMS m/z m/z 541.1 (M+H)$^+$ and (S)-2-{2-[4-amino-5-(2-fluoro-4-phenoxy-phenyl)-pyrrolo[2,3-d]pyrimidin-7-ylmethyl}-pyrrolidine-1-carbonyl]-3-cyclopropyl-acrylonitrile LCMS m/z 523.2 (M+H)$^+$ were prepared respectively.

Example 29

Synthesis of (S)-2-(2-((4-amino-6-methyl-5-(4-phenoxyphenyl)-7H-pyrrolo[2,3-d]pyrimidin-7-yl)methyl)pyrrolidine-1-carbonyl)-3-cyclopropylacrylonitrile

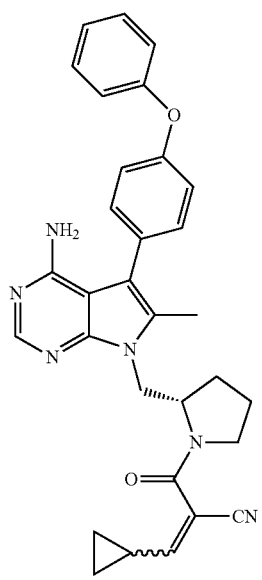 [SMILES: Cc1c(-c2ccc(Oc3ccccc3)cc2)c2c(N)ncnc2n1C[C@@H]1CCCN1C(=O)C(C#N)=CC1CC1]

Step 1

To a solution of 4-chloro-7H-pyrrolo[2,3-d]pyrimidine (10 g, 65.12 mmol, 1.0 eq) in THF (300 mL), NaH (5.30 g, 130.24 mmol, 2 eq) was added at 0° C. After 3 h, benzenesulfonyl chloride (22.53 g, 130.24 mmol, 2 eq) was added. The temperature was warmed to RT and continued for 1 h. The reaction mixture was poured into sat. NH$_4$Cl and extracted with EtOAc. The organic layers were dried, concentrated and purified by column chromatography (eluting with 10% EtOAc in PE) to afford 4-chloro-7-(phenylsulfonyl)-7H-pyrrolo[2,3-d]pyrimidine as brown solid (4.5 g, 24% in yield)

Step 2

To the solution of 4-chloro-7-(phenylsulfonyl)-7H-pyrrolo[2,3-d]pyrimidine (3 g, 12.6 mmol, 1.0 eq) and TMEDA (3.0 mL, 18.9 mmol, 1.5 eq) in THF (120 mL), n-BuLi (7.5 mL, 18.9 mmol, 1.5 eq) was added at −78° C. After 3 min, CH$_3$I (3.7 mL, 59.2 mmol, 4.7 eq) was added. After 3 h, the reaction mixture was warmed to RT over 1 h. The reaction was quenched by addition of sat NH$_4$Cl (10 mL) at −78° C. EtOAc (200 mL) and water (100 mL) was added. The organic layer was separated, dried and concentrated to afford 4-chloro-6-methyl-7-(phenylsulfonyl)-7H-pyrrolo[2,3-d]pyrimidine as a brown solid (6.7 g, 90% in yield).

Step 3

To the solution of 4-chloro-6-methyl-7-(phenylsulfonyl)-7H-pyrrolo[2,3-d]pyrimidine (10 g, 32.5 mmol, 1.0 eq) in THF (400 mL), t-BuOK (18.23 g, 163.0 mmol, 5 eq) was added and stirred at RT for 12 h. Sat. NaHCO$_3$ (50 mL) was added and extracted with EtOAc. The organic layers were separated, dried and concentrated to afford 4-chloro-6-methyl-7H-pyrrolo[2,3-d]pyrimidine as a brown solid (2.7 g, 50% in yield).

Step 4

To the solution of 4-chloro-6-methyl-7H-pyrrolo[2,3-d]pyrimidine (1.0 g, 5.97 mmol, 1.0 eq) and (S)-tert-butyl 2-(hydroxymethyl)pyrrolidine-1-carboxylate (1.32 g, 6.57 mmol, 1.1 eq) and PPh$_3$ (3.03 g, 11.94 mmol, 2.0 eq) in THF (50 mL), DIEA (2.08 g, 11.94 mmol, 2.0 eq) was added at 0° C. The resulted mixture was stirred and warmed to RT for 12 h. Solvent was removed and purified by column chromatography (eluting with 10% EtOAc in PE) to afford (S)-tert-butyl 2-[(4-chloro-6-methyl-7H-pyrrolo[2,3-d]pyrimidin-7-yl]methyl)pyrrolidine-1-carboxylate as a white solid (2.08 g, 100% in yield).

Step 5

To the solution of (S)-tert-butyl 2-((4-chloro-6-methyl-7H-pyrrolo[2,3-d]pyrimidin-7-yl)methyl)pyrrolidine-1-carboxylate (1.0 g, 2.86 mmol, 1.0 eq) in DMF (20 mL), NIS (0.675 g, 3.00 mmol, 1.05 eq) was added at 0° C. The resulted mixture was stirred and warmed to RT for 12 h. Solvent was removed and purified by column chromatography to afford (S)-tert-butyl 2-((4-chloro-5-iodo-6-methyl-7H-pyrrolo[2,3-d]pyrimidin-7-yl)methyl)pyrrolidine-1-carboxylate as white solid (1.0 g, 77% in yield) which was converted to the title compound as described in Example 30 above. LCMS m/z 519.1 (M+H)$^+$.

Proceeding as described above but substituting 4-phenoxyphenylboronic acid with 2-(4-(3,5-difluorophenoxy)phenyl)-4,4,5,5-tetramethyl-1,3,2-dioxaborolane and 2-(2-fluoro-4-phenoxyphenyl)-4,4,5,5-tetramethyl-1,3,2-dioxaborolane, (S)-2-(2-((4-amino-5-(4-(3,5-difluorophenoxy)phenyl)-6-methyl-7H-pyrrolo[2,3-d]pyrimidin-7-yl)methyl)pyrrolidine-1-carbonyl)-3-cyclopropylacrylonitrile LCMS m/z m/z 555.2 (M+H)+ and (S)-2-(4-amino-5-(2-fluoro-4-phenoxyphenyl)-6-methyl-7H-pyrrolo[2,3-d]pyrimidin-7-yl)methyl)pyrrolidine-1-carbonyl)-3-cyclopropylacrylonitrile LCMS m/z 536.6 (M+H)+ were prepared respectively.

Example 30

Synthesis of (S)-2-(2-((4-amino-6-methyl-5-(4-phenoxyphenyl)-7H-pyrrolo[2,3-d]pyrimidin-7-yl)methyl)pyrrolidine-1-carbonyl)-4-(dimethylamino)-4-methylpent-2-enenitrile

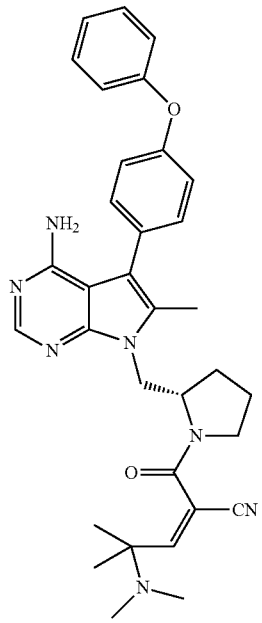 [SMILES: Cc1c(-c2ccc(Oc3ccccc3)cc2)c2c(N)ncnc2n1C[C@@H]1CCCN1C(=O)/C(C#N)=C\C(C)(C)N(C)C]

To a solution of (S)-3-(2-((4-amino-6-methyl-5-(4-phenoxyphenyl)-7H-pyrrolo[2,3-d]pyrimidin-7-yl)methyl)pyrrolidin-1-yl)-3-oxopropanenitrile (0.1 g, 0.21 mmol, 1.0 eq) in EtOH (2 mL) was added 2-(dimethylamino)-2-methylpropanal (0.06 g, 0.53 mmol, 2.5 eq) and piperidine acetate (5 mg). The resulted solution was stirred at 70° C. for 12 h, concentrated and purified by pre-HPLC to afford the title compound as a white solid (5 mg, 4% in yield). LCMS m/z 564.1 (M+H)+.

Example 31

Synthesis of (R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile tris (2,2,2-trifluoroacetate) salt

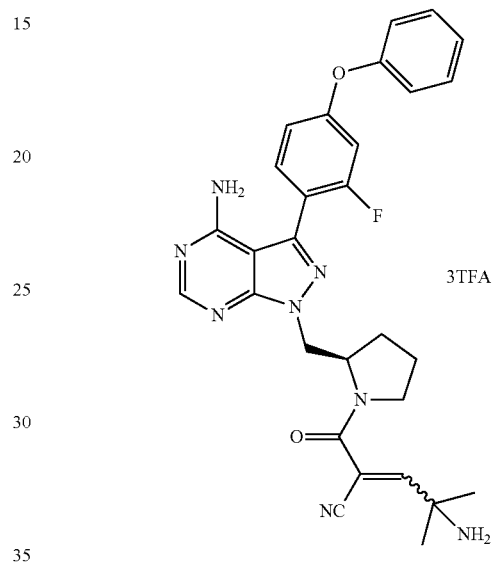

Step 1

A solution of 3-((R)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (141 mg, 0.30 mmol, 1.0 equiv), tert-butyl 2-methyl-1-oxopropan-2-ylcarbamate (1.12 g, 6.00 mmol, 20.0 equiv), piperidine (255 mg, 3.0 mmol, 10.0 equiv) in 1,4-dioxane (15 mL) was refluxed for 2 h. The resulting mixture was concentrated under vacuum. The residue was submitted to flash chromatography eluting with ethyl acetate to give (R)-tert-butyl (5-(2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl)carbamate 90 mg as a pale yellow solid.

Step 2

To a solution of (R,E)-tert-butyl (5-(2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl)carbamate (90 mg, 0.14 mmol, 1 equiv) in 16 mL DCM was added 4 mL trifluoroacetic acid dropwise. The resulting solution was stirred for 3 h at room temperature. The solution was concentrated under reduced pressure. The residue was purified on Prep-HPLC. Conditions: (1#-Pre-HPLC-001(SHIMADZU)): Column, SunFire Prep C18, 19*150 mm 5 um; mobile phase, water with 0.05% TFA and CH3CN (40% $CH_3CN$ up to 100% in 20 min); Detector, 254 nm to give the title compound as a pale light yellow solid.

MS (ESI, pos. ion) m/z: 541 (M+1). H-NMR (400MHz, $CDCl_3$, ppm): 12.23 (brs, 1H), 11.77 (brs, 1H), 10.36 (brs, 1H), 8.32 (s, 1H), 7.95 (brs, 1H), 7.54-7.44 (m, 3H), 7.35-7.28 (m, 2H), 7.19-7.13 (m, 2H), 6.96 (d, J=8.8, 1H), 6.88 (d, J=11.2, 1H), 6.09 (brs, 1H), 4.88-4.74 (m, 3H), 4.76-4.55 (m, 2H), 3.68-3.58 (m, 2H), 2.17-1.74 (m, 4H), 1.56 (d, 6H).

Example 32

Synthesis of (R)-2-(3-(4-amino-3-(4-(2,3-difluorophenoxy)-2-fluorophenyl)-1H-pyrazolo[3,4-d]pyrimidin-1-yl)piperidine-1-carbonyl)-4-methylpent-2-enenitrile

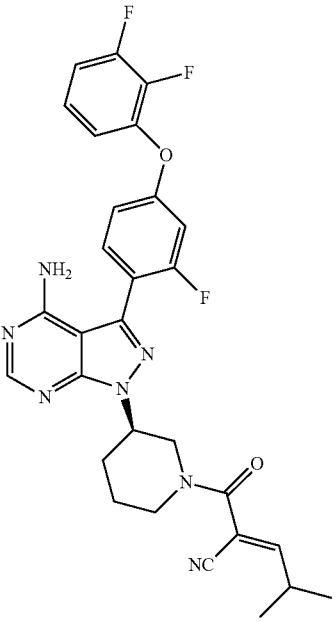 [SMILES: CC(C)/C=C(\C#N)C(=O)N1CCC[C@@H](n2nc(-c3ccc(Oc4cccc(F)c4F)cc3F)c3c(N)ncnc32)C1]

Step 1

To a solution of 1H-pyrazolo[3,4-d]pyrimidin-4-ylamine (3.0 g, 22.20 mmol, 1.0 eq) in DMF (30 mL), NIS (6.7 g, 24.42 mmol, 1.1 eq) was added at room temperature. The reaction mixture was stirred overnight at 60° C. The reaction mixture was cooled to room temperature and 10% aq. NaHCO$_3$ (150 mL) was added to the reaction mixture. The solid was filtered and re-crystallization from DMF solvent to give 3-iodo-1H-pyrazolo[3,4-d]pyrimidin-4-amine (4.0 g, 69% in yield).

Step 2

To a solution of 3-iodo-1H-pyrazolo[3,4-d]pyrimidin-4-ylamine (4.0 g, 15.32 mmol, 1.0 eq), (S)-3-hydroxypiperidine-1-carboxylic acid tert-butyl ester (4.313 g, 21.44 mmol, 1.4 eq), and PPh$_3$ (8.031 g, 30.64 mmol, 2.0 eq) in dry THF (200 mL), DIAD (4.658 g, 22.98 mmol, 1.5 eq) was added at room temperature. The reaction mixture was stirred at 70° C. for 72 h. The reaction mixture was concentrated and purified by silica gel chromatography (eluted with PE: EtOAc=1:1) to afford (R)-tert-butyl 3-(4-amino-3-iodo-1H-pyrazolo[3,4-d]pyrimidin-1-yl)piperidine-1-carboxylate (2.8 g, 41.2% in yield).

Step 3

A solution of (R)-tert-butyl 3-(4-amino-3-iodo-1H-pyrazolo[3,4-d]pyrimidin-1-yl)piperidine-1-carboxylate (2.8 g, 6.16 mmol, 1.0 eq), 2-(4-(2,3-difluorophenoxy)-2-fluorophenyl)-4,4,5,5-tetramethyl-1,3,2-dioxaborolane (1.7 g, 6.16 mmol, 1.0 eq), Pd(PPh$_3$)$_4$ (0.28 g, 0.08 mmol, 0.07 eq) and Na$_2$CO$_3$ (1.7 g, 15.4 mmol, 2.5 eq) in dioxane/H$_2$O (40/10 mL) was stirred at 90° C. overnight. The reaction mixture was concentrated and purified by Pre-TLC to afford (R)-tert-butyl 3-(4-amino-3-(4-(2,3-difluorophenoxy)-2-fluorophenyl)-1H-pyrazolo[3,4-d]pyrimidin-1-yl)piperidine-1-carboxylate (1.7 g, 51.1% yield).

Step 4

To a solution of (R)-tert-butyl 3-(4-amino-3-(4-(2,3-difluorophenoxy)-2-fluorophenyl)-1H-pyrazolo[3,4-d]pyrimidin-1-yl)piperidine-1-carboxylate (1.7 g, 3.15 mmol) in 20 ml of DCM, TFA (20 ml) was added. The reaction mixture was stirred at RT for 4 h. The mixture was washed with sat. NaHCO$_3$ (10 mL) and concentrated to give (R)-3-(4-(2,3-difluorophenoxy)-2-fluorophenyl)-1-(piperidin-3-yl)-1H-pyrazolo[3,4-d]pyrimidin-4-amine (1.1 g, 80% yield).

Step 5

To a mixture of (R)-3-(4-(2,3-difluorophenoxy)-2-fluorophenyl)-1-(piperidin-3-yl)-1H-pyrazolo[3,4-d]pyrimidin-4-amine (100 mg, 0.23 mmol, 1.0 eq), 2-cyano-4-methylpent-2-enoic acid (38 mg, 0.27 mmol, 1.2 eq) and DIEA (88 mg, 0.68 mmol, 3.0 eq) in 10 ml DCM was added HATU (130 mg, 0.34 mmol, 1.5 eq). The reaction mixture was stirred for 4 h at RT under N$_2$. The mixture was purified by Pre-HPLC to give the title compound (25 mg 40% yield). LCMS: m/Z$^+$ (562.2) (M+H)+ 1HNMR (400 MHz, CDCl$_3$): δ 0.784~1.186 (m, 7H), 1.765-2.254 (m, 5H), 2.861-4.937 (m, 4H), 6.218 (m, 0.4H), 6.857~7.600 (m, 6H), 8.255 (s, 1H) and 9.888 (m, 1H).

Example 33

Synthesis of 2-((R)-2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-ethoxy-4-methylpent-2-enenitrile 2,2,2-trifluoroacetate

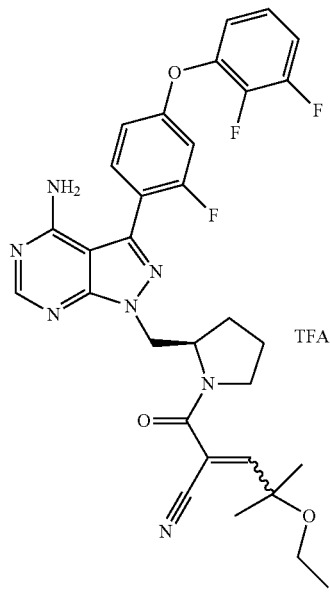 [SMILES: CCOC(C)(C)C=C(C#N)C(=O)N1CCC[C@@H]1Cn1nc(-c2ccc(Oc3cccc(F)c3F)cc2F)c2c(N)ncnc21]

A solution of 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile (202.8 mg, 0.40 mmol, 1.0 equiv), 2-ethoxy-2-methylpropanal (232 mg, 2.00 mmol, 5.0 equiv), piperidine (68 mg, 0.80 mmol, 2.0 equiv) in EtOH (20 mL) was stirred at room temperature overnight.

The volatile phase was removed off under reduced pressure. The residue was purified on Prep-HPLC. Conditions: (1#-Pre-HPLC-001(SHIMADZU)): Column, SunFire Prep C18, 19*150 mm 5 um; mobile phase, water in 0.05% TFA and CH$_3$CN (40% CH$_3$CN up to 100% in 20 min); Detector, 254 nm. This resulted in 30 mg (10.43%) of the title compound as a white solid. MS (ESI, pos. ion) m/z: 606 (M-TFA+1)

H-NMR (400MHz, CDCl$_3$, ppm): 11.51 (brs, 1H), 8.35 (s, 1H), 7.60 (t, J=8.4 Hz, 1H), 7.19-7.13 (m, 3H), 7.03-6.93 (m, 2H), 6.90 (d, J=10.8, 2.0 Hz, 1H), 6.09 (brs, 1H), 4.96-4.93 (m, 1H), 4.72-4.65 (m, 2H), 3.59-3.51 (m, 2H), 3.49-3.43 (q, J=6.8 Hz, 2H), 2.19-1.82 (m, 4H), 1.45 (s, 6H), 1.27-1.24 (t, J=6.8 Hz, 3H).

Example 34

Synthesis of (S)-2-(2-((4-amino-3-(2-fluoro-4-phenoxyphenyl)-1H-pyrazolo[3,4-d]pyrimidin-1-yl)methyl)pyrrolidine-1-carbonyl)-3-cyclopropylacrylonitrile

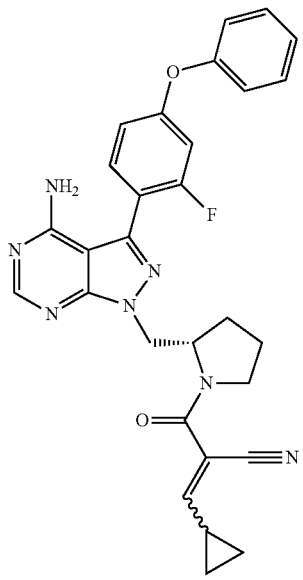 [SMILES: N#CC(=CC1CC1)C(=O)N1CCC[C@H]1Cn1nc(-c2ccc(Oc3ccccc3)cc2F)c2c(N)ncnc21]

To a solution of 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (2173 .mg, 4.61 mmol) in ethanol (36 mL) was added cyclopropanecarbaldehyde (0.53 mL, 6.91 mmol) and piperidine (0.23 mL, 2.3 mmol). The reaction was heated to 90° C. for 75 minutes, then cooled and concentrated. The residue was dissolved in ethyl acetate (200 mL) and washed with water and then brine. The organic layer was dried (MgSO4), filtered and concentrated. The residue was purified by Isolera (100 g column, 1%-7% MeOH/DCM) to provided 1.32 g (55% yield) of the title compound. LCMS m/z 524 (M+H)$^+$.

Example 35

Synthesis of N-(2-(4-amino-3-(4-phenoxyphenyl)-1H-pyrazolo[3,4-d]pyrimidin-1-yl)ethyl)-2-cyano-3-cyclopropylacrylamide

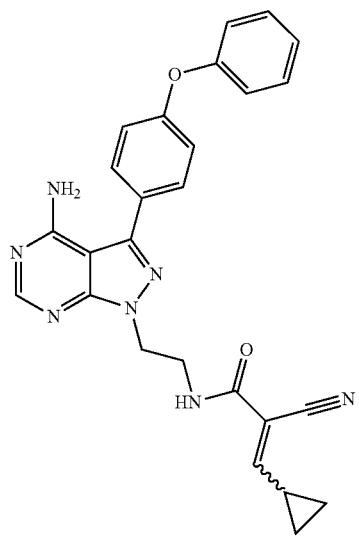 [SMILES: N#CC(=CC1CC1)C(=O)NCCn1nc(-c2ccc(Oc3ccccc3)cc2)c2c(N)ncnc21]

Step 1

To a solution of 3-(4-phenoxyphenyl)-1H-pyrazolo[3,4-d]pyrimidin-4-amine (300 mg, 1.0 mmole), triphenylphosphine (1.04 g, 3.96 mmoles) and tert-butyl (2-hydroxyethyl)carbamate (238 mg, 1.5 mmoles) in THF (25 mL) was added DIAD (0.4 mL, 2 mmoles). The reaction was stirred for 5 hrs at room temperature and then water (30 mL) was added and extracted with ethyl acetate. The organic layers were combined, washed with aq. NaHCO$_3$ and brine, then dried (Na$_2$SO$_4$), filtered and concentrated. The resulting tert-butyl (2-(4-amino-3-(4-phenoxyphenyl)-1H-pyrazolo[3,4-d]pyrimidin-1-yl)ethyl)carbamate was used without further purification.

Step 2

The tert-butyl (2-(4-amino-3-(4-phenoxyphenyl)-1H-pyrazolo[3,4-d]pyrimidin-1-yl)ethyl)carbamate was dissolved in TFA (5 mL). After 30 minutes of stirring at room temperature, the reaction was diluted with water and washed with ethyl acetate. The aqueous layer was basified to pH=11-12 with NaOH and then washed with ethyl acetate. The organic layer was dried (Na$_2$SO$_4$), filtered and concentrated to collect 320 mg of 1-(2-aminoethyl)-3-(4-phenoxyphenyl)-1H-pyrazolo[3,4-d]pyrimidin-4-amine.

Step 3

To a solution of 1-(2-aminoethyl)-3-(4-phenoxyphenyl)-1H-pyrazolo[3,4-d]pyrimidin-4-amine (287 mg, 0.829 mmole), 2-cyanoacetic acid (85 mg, 1.0 mmole) and TEA (0.14 ml, 1.0 mmole) in DMF (10 mL) was added HATU (347 mg, 0.912 mmole). After stirring 3 hr at room temperature, water was added and extracted with ethyl acetate. The organic layer was washed with aq. NaHCO$_3$ and brine, then dried (Na$_2$SO$_4$), filtered and concentrated. The resulting residue was subjected to column chromatography (3% MeOH/DCM) to provide 90 mg (22% yield from step 1) of N-(2-(4-amino-3-(4-phenoxyphenyl)-1H-pyrazolo[3,4-d]pyrimidin-1-yl)ethyl)-2-cyanoacetamide.

Step 4

A solution of N-(2-(4-amino-3-(4-phenoxyphenyl)-1H-pyrazolo[3,4-d]pyrimidin-1-yl)ethyl)-2-cyanoacetamide (90 mg, 0.22 mole), cyclopropylcarboxaldehyde (18 mg, 0.26 mmole) and piperidine (22 mg, 0.26 mmole) in MeOH (5 mL) was stirred for 3 hr at room temperature. Then water was added and extracted with ethyl acetate. The organic layers were combined and washed with aq. NaHCO$_3$ and brine, then dried (Na$_2$SO$_4$), filtered and concentrated. The residue was purified by column chromatography (3% MeOH/DCM) to provide 39 mg (38% yield) of the title compound as a white solid. LCMS m/z 466 (M+H)$^+$.

Example 36

Synthesis of N-(2-(4-amino-3-(4-phenoxyphenyl)-1H-pyrazolo[3,4-d]pyrimidin-1-yl)ethyl)-2-cyano-3-cyclopropyl-N-methylacrylamide

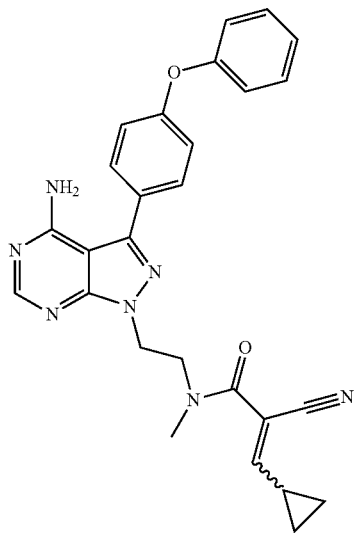 [SMILES: CN(CCn1nc(-c2ccc(Oc3ccccc3)cc2)c2c(N)ncnc21)C(=O)C(C#N)=CC1CC1]

The title compound was prepared as described in Example 35 except tert-butyl (2-hydroxyethyl)(methyl)carbamate was used in step 1. LCMS m/z 480 (M+H)$^+$.

Example 37

Synthesis of (R)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-cyclopropylacrylonitrile

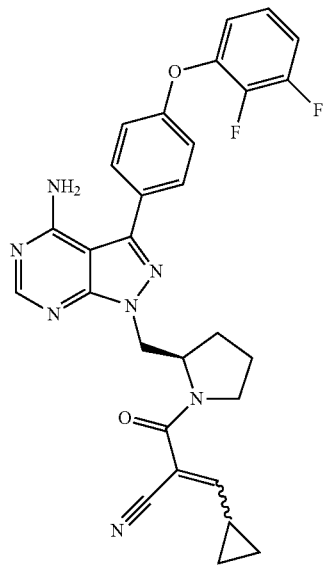 [SMILES: N#CC(=CC1CC1)C(=O)N1CCC[C@@H]1Cn1nc(-c2ccc(Oc3cccc(F)c3F)cc2)c2c(N)ncnc21]

Step 1

A solution of 3-(4-(2,3-difluorophenoxy)-2-fluorophenyl)-1-(R)-pyrrolidin-2-ylmethyl)-1H-pyrazolo[3,4-d]pyrimidin-4-amine (50 mg, 0.12 mmol, 1.00 equiv), 2-cyanoacetic acid (14 mg, 0.18 mmol, 1.50 equiv), HATU (52 mg, 0.18 mmol, 1.5 equiv) and TEA (42 mg, 0.40 mmol, 5.00 equiv) in N,N-dimethylformamide (10 mL) was stirred overnight at 25° C. It was quenched with water (50 mL), which was extracted with EA. The organic layers were combined, washed with brine, dried over sodium sulfate, filtrated and concentrated. The residue was submitted to flash chromatography (SiO$_2$, PE: EtOAc=2:1 to 1:1) to give 48 mg (83%) of 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile as a yellow solid.

Step 2

A solution of 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile (240 mg, 0.47 mmol, 1.00 equiv), cyclopropanecarbaldehyde (98.7 mg, 1.41 mmol, 3.00 equiv) and piperidine (42 mg, 0.47 mmol, 1.00 equiv) in ethanol (15 mL) was stirred for 3 h at 65° C. The resulting mixture was concentrated under vacuum. The residue was purified on Prep-HPLC. Conditions: (1#-Pre-HPLC-001(SHIMADZU)): Column, SunFire Prep C18, 19*150 mm 5 um; mobile phase, water with 0.05% TFA and CH$_3$CN (40% CH$_3$CN up to 100% in 20 min); Detector, 254 nm. This resulted in 100 mg (36%) of the title compound as a white solid. MS (ESI, pos. ion) m/z: 560(M+1) H-NMR (400MHz, CD$_3$OD, ppm): 8.36 (s, 1H), 7.68-7.65 (t, J=7.6 Hz, 1H), 7.30-7.20 (m, 2H), 7.14-7.11 (t, 1H), 7.03-7.00 (d, J=9.2 Hz, 2H), 6.58 (d, J=10.8 Hz, 1H), 4.92-4.87(m, 1H) 3.65-3.60 (m, 1H), 3.50-3.46 (m, 1H), 2.14 (m, 1H), 1.99-1.81 (m, 4H), 1.24-1.23(m, 2H), 0.93-0.77(m, 2H).

Proceeding as described above, but substituting 3-((R)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile with (R)-3-(3-(4-amino-3-(2,3-difluoro-4-phenoxyphenyl)-1H-pyrazolo[3,4-d]pyrimidin-1-yl)piperidin-1-yl)-3-oxopropanenitrile and cyclopropanecarbaldehyde with 2-methyl-2-morpholinopropanal, (R)-2-(3-(4-amino-3-(2,3-difluoro-4-phenoxyphenyl)-1H-pyrazolo[3,4-d]pyrimidin-1-yl)piperidine-1-carbonyl)-4-methyl-4-morpholinopent-2-enenitrile was prepared.

Example 38

Synthesis of (S)-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-3-cyclopropylacrylonitrile

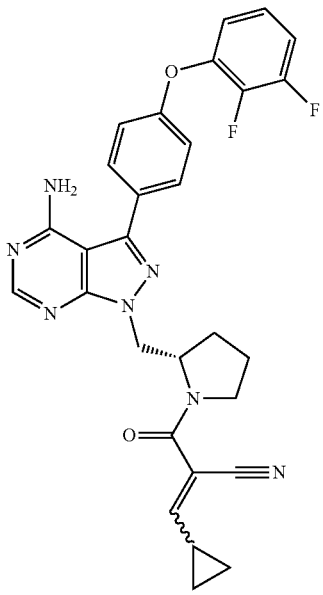 [SMILES: N#CC(=CC1CC1)C(=O)N1CCC[C@H]1Cn1nc(-c2ccc(Oc3cccc(F)c3F)cc2)c2c(N)ncnc21]

Step 1

To a suspension of (S)-tert-butyl 2-((4-amino-3-iodo-1H-pyrazolo[3,4-d]pyrimidin-1-yl)methyl)pyrrolidine-1-carboxylate (2.7 g, 6.00 mmol, 1.00 equiv), 4-(2,3-difluorophenoxy)-2-fluorophenylboronic acid (1.6 g, 6.00 mmol, 1.00 equiv), potassium carbonate (3.3 g, 24.00 mmol, 4.00 equiv) in 1,4-dioxane (40 mL) and water (10 mL) was added Pd(PPh$_3$)$_4$ (488 mg, 0.60 mmol, 0.10 equiv) under nitrogen atmosphere. The resulting solution was stirred overnight at 90° C. The resulting mixture was concentrated under vacuum. The residue was applied onto a silica gel column with ethyl acetate/petroleum ether (1:5 to 2:1). This resulted in 1.97 g (61%) of (2S)-tert-butyl 2-((4-amino-3-(4-(2,3-difluorophenoxy)-2-fluorophenyl)-1H-pyrazolo[3,4-d]pyrimidin-1-yl)methyl)pyrrolidine-1-carboxylate as a reddish solid. MS (ESI, pos. ion) m/z: 541 (M+1)

Step 2

To a solution of (2S)-tert-butyl 2-((4-amino-3-(4-(2,3-difluorophenoxy)-2-fluorophenyl)-1H-pyrazolo[3,4-d]pyrimidin-1-yl)methyl)pyrrolidine-1-carboxylate (1.97 g, 3.65 mmol, 1.00 equiv) in DCM (30 mL) was added trifluoroacetic acid (7.5 mL). The resulting solution was stirred for 4 h at room temperature. This solution was concentrated under reduced pressure. This resulted in 2.4 g (Crude) of 3-(4-(2,3-difluorophenoxy)-2-fluorophenyl)-1-((S)-pyrrolidin-2-ylmethyl)-1H-pyrazolo[3,4-d]pyrimidin-4-amine trifluoroacetic acid salt as a reddish oil. MS (ESI, pos. ion) m/z: 441 (M+1)

Step 3

A solution of 3-(4-(2,3-difluorophenoxy)-2-fluorophenyl)-1-((S)-pyrrolidin-2-ylmethyl)-1H-pyrazolo[3,4-d]pyrimidin-4-amine (2.4 g Crude, 3.65 mmol, 1.00 equiv), 2-cyanoacetic acid (0.47 g, 5.48 mmol, 1.50 equiv), HATU (2.08 g, 5.48 mmol, 1.50 equiv), TEA (2.54 ml, 18.25 mmol, 5.00 equiv) in DCM (40 mL) was stirred overnight at room temperature. The resulting mixture was diluted with water, and extracted with DCM. The DCM layers were combined and washed with brine, dried over Na$_2$SO$_4$ and concentrated. The residue was submitted to flash chromatography (SiO$_2$, PE: EtOAc=2:1 to 1:1) to give 1.28 g (69%) of 3-((S)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile as a yellow solid.

Step 4

A solution of 3-((S)-2-((4-amino-3-(4-(2,3-difluorophenoxy)-2-fluorophenyl)-1H-pyrazolo[3,4-d]pyrimidin-1-yl)methyl)pyrrolidin-1-yl)-3-oxopropanenitrile (304.2 mg, 0.60 mmol, 1.00 equiv), cyclopropanecarbaldehyde (210 mg, 3 mmol, 5 equiv), piperidine (102 mg, 1.20 mmol, 2 equiv) in EtOH (20 mL) was stirred overnight at rt. The resulting mixture was concentrated under vacuum. Then concentrated and purified on Prep-HPLC. Conditions: (1#-Pre-HPLC-001 (SHIMADZU)): Column, SunFire Prep C18, 19*150 mm 5 um; mobile phase, water with 0.05% TFA and CH3CN (40% CH$_3$CN up to 100% in 20 min); Detector, 254 nm. This resulted in 90 mg (22.3%) of the title compound as a white solid. MS (ESI, pos. ion) m/z: 560 (M-TFA+1)H-NMR (400MHz, CDCl$_3$, ppm): 11.94 (brs, 1H), 8.27 (s, 1H), 7.62-7.58 (m, 1H), 7.19-7.13 (m, 2H), 7.04-6.98 (m, 2H), 6.91 (d, J=11.2 Hz, 1H), 6.81 (d, J=11.2 Hz, 1H), 6.01 (brs, 1H), 4.96-4.86 (m, 1H), 4.76-4.62 (m, 2H), 3.71-3.62 (m, 1H), 3.61-3.45 (m, 1H), 2.12-1.82 (m, 5H), 1.30-1.28 (m, 2H), 0.94-0.89 (m, 2H).

Example 39

Synthesis of N-(3-(4-amino-3-(4-phenoxyphenyl)-1H-pyrazolo[3,4-d]pyrimidin-1-yl)-2,2-dimethylpropyl)-2-cyano-3-cyclopropylacrylamide

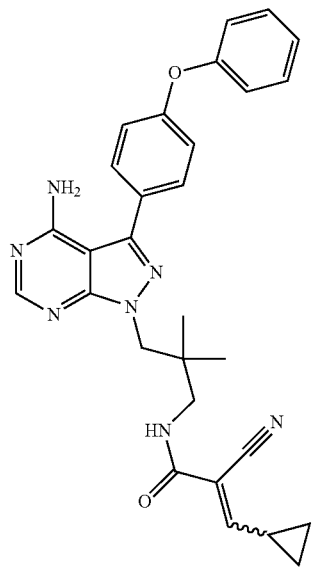 [SMILES: CC(C)(CNC(=O)C(C#N)=CC1CC1)Cn1nc(-c2ccc(Oc3ccccc3)cc2)c2c(N)ncnc21]

Step 1

A solution of 2,2-dimethylpropane-1,3-diol (20.8 g, 199.72 mmol, 1.00 equiv) and HBr (1 mL) was stirred for 1 h at 110° C. in an oil bath, then a solution of HBr (17.82 g, 220 mmol, 1.10 equiv) in AcOH (100 mL) was loaded dropwise, the resulting mixture was stirred for another 11 hr at 110° C. The resulting mixture was concentrated under vacuum. To this residue were added ethylene glycol dimethyl ether (270 mL), water (90 mL) and LiOH (9.6 g, 2.00 equiv). The resulting solution was stirred for 3 h at 25° C., which was extracted with ether. The organic layers were combined, washed with hydrogen chloride (1 N), washed with brine, dried over anhydrous sodium sulfate and concentrated under vacuum to give 15 g (45%) of 3-bromo-2,2-dimethylpropan-1-ol as a colorless oil.

Step 2

To a solution of 2,3-dihydro-1H-isoindole-1,3-dione (3.1 g, 21.07 mmol, 1.00 equiv), 3-bromo-2,2-dimethylpropan-1-ol (3.4 g, 23.2 mmol, 1.10 equiv), triphenylphosphane (10.9 g, 41.56 mmol, 2.00 equiv) in THF (100 mL) was loaded diisopropyl azodicarboxylate (8.3 g, 41.09 mmol, 2.00 equiv) dropwise at 0° C. under nitrogen atmosphere. The resulting solution was stirred for 12 h at 25° C. The resulting mixture was concentrated under vacuum. The residue was applied onto a silica gel column eluting with ethyl acetate/petroleum ether (1/50). This resulted in 3.2 g (51%) of 2-(3-bromo-2,2-dimethylpropyl)-2,3-dihydro-1H-isoindole-1,3-dione as a colorless oil.

Step 3

A suspension of 3-(4-phenoxyphenyl)-1H-pyrazolo[3,4-d]pyrimidin-4-amine (400 mg, 1.3 mmol, 1.00 equiv), 2-(3-bromo-2,2-dimethylpropyl)-2,3-dihydro-1H-isoindole-1,3-dione (570 mg, 1.95 mmol, 1.50 equiv) and cesium carbonate (847 mg, 2.60 mmol, 2.00 equiv) in NMP (50 mL) was stirred at 100° C. for 12 h under nitrogen atmosphere. It was quenched with water (150 mL). The resulting solution was extracted with ethyl acetate (5×30 mL). The organic layers were combined, dried over sodium sulfate and concentrated under vacuum. The residue was applied onto a silica gel column eluting with dichloromethane/methanol (10/1). This resulted in 280 mg (41%) of 2-(2-[[4-amino-3-(4-phenoxyphenyl)-1H-pyrazolo[3,4-d]pyrimidin-1-yl]methyl]-2-methylpropyl)-2,3-dihydro-1H-isoindole-1,3-dione as a yellow oil.

Step 4

A solution of 2-[3-[4-amino-3-(4-phenoxyphenyl)-1H-pyrazolo[3,4-d]pyrimidin-1-yl]-2,2-dimethylpropyl]-2,3-dihydro-1H-isoindole-1,3-dione (200 mg, 0.39 mmol, 1.00 equiv) and hydrazine (130 mg, 3.25 mmol, 8.00 equiv) in ethanol (30 mL) was stirred for 3 h at 70° C. in an oil bath. The resulting mixture was concentrated under vacuum. Water (50 mL) was added to the residue. The resulting solution was extracted with dichloromethane (3×50 mL). The organic layers were combined, dried over sodium sulfate and concentrated under vacuum. The residue was applied onto a silica gel column with dichloromethane/methanol (30/1). This resulted in 0.06 g (40%) of 1-(3-amino-2,2-dimethylpropyl)-3-(4-phenoxyphenyl)-1H-pyrazolo[3,4-d]pyrimidin-4-amine as a yellow oil.

Step 5

A solution of 1-(3-amino-2,2-dimethylpropyl)-3-(4-phenoxyphenyl)-1H-pyrazolo[3,4-d]pyrimidin-4-amine (110 mg, 0.28 mmol, 1.00 equiv), 2-cyanoacetic acid (36 mg, 0.42 mmol, 1.50 equiv), HATU (0.108 g, 1.00 equiv) and triethylamine (57 mg, 0.56 mmol, 2.00 equiv) in N,N-dimethylformamide (10 mL) was stirred for 5 h at 25° C. It was quenched with water (100 mL). The resulting solution was extracted with ethyl acetate (3×50 mL). The organic layers were combined, washed with brine. dried and concentrated under vacuum. The residue was applied onto a silica gel column eluting with dichloromethane/methanol (50/1). This resulted in 100 mg (78%) of N-[3-[4-amino-3-(4-phenoxyphenyl)-1H-pyrazolo[3,4-d]pyrimidin-1-yl]-2,2-dimethylpropyl]-2-cyanoacetamide as a yellow oil.

Step 6

A solution of N-(3-(4-amino-3-(4-phenoxyphenyl)-1H-pyrazolo[3,4-d]pyrimidin-1-yl)-2,2-dimethylpropyl)-2-cyanoacetamide (0.12 g, 0.26 mmol, 1.0 eq.), cyclopropanecarbaldehyde (56 mg, 0.78 mmol, 3.0 eq.) and a drop of piperidine in ethanol (15 mL) was refluxed overnight. The volatile phase was removed under reduced pressure. The residue was applied on silica gel eluting with petroleum: ethyl acetate (1:1). This provided 50 mg (38%) of the title compound as a white solid.MS (ESI, pos. ion) m/z: 508 (M+1) H-NMR (300MHz, DMSO-d6, ppm): 8.59 (t, 1H), 8.29 (s, 1H), 7.69-7.66 (d, J=9.6 Hz, 2H), 7.46-7.41 (t, J=6.6, 7.5 Hz, 2H), 7.21-7.11 (m, 5H), 7.05-7.02 (d, 10.4 Hz, 1H), 4.18 (s, 2H), 3.04-3.02(d, J=6.3Hz, 2H), 1.98-1.93 (m, 1H), 1.21-1.26 (m, 2H), 1.0-0.92 (m, 2H), 0.91 (s, 6H).

Example 40

Synthesis of 2-((S)-2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile

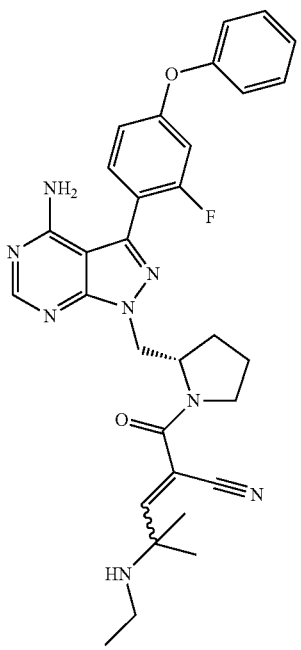 [SMILES: CCNC(C)(C)C=C(C#N)C(=O)N1CCC[C@H]1Cn1nc(-c2ccc(Oc3ccccc3)cc2F)c2c(N)ncnc21]

Step 1

To a solution of 2-amino-2-methylpropanoic acid (10.3 g, 0.1 mol, 1.0 equiv) in 1 N NaOH (100 mL) and THF (30 mL) was added (Boc)₂O (26 g, 0.12 mol, 1.2 equiv) portionwise at room temperature. This mixture was stirred overnight at room temperature. The mixture was concentrated and then extracted with ethyl acetate (100 mL×2). The aqueous phase was adjusted to PH=3~4, then extracted with ethyl acetate (200 mL×2). The organic phases were combined, washed with brine, dried over Na₂SO₄, concentrated to give 9 g (44%) of the desired product 2-(tert-butoxycarbonylamino)-2-methylpropanoic acid as a white solid.

Step 2

To a solution of 2-(tert-butoxycarbonylamino)-2-methylpropanoic acid (8.12 g, 0.04 mol, 1 equiv) in DMF (100 mL) was added NaH (4.8 g, 0.12 mol, 3.0 equiv) portionwise at 0° C. The mixture was stirred for 5 min at this temperature then ethyl iodide (18.7 g, 0.12 mol, 3.0 equiv) was added dropwise at 0° C. The resulting mixture was stirred at room temperature overnight then it was quenched with H₂O, extracted with ethyl acetate. The organic phases were combined, washed with brine, dried and concentrated. The residue was purified on silica gel column (PE/EA=5/1) to give 6 g (57%) of the desired product ethyl 2-(tert-butoxycarbonyl(ethyl)amino)-2-methylpropanoate as a colorless oil.

Step 3

To a suspension of LiAlH₄ (760 mg, 20 mmol, 1.0 equiv) in THF (50 mL) was added ethyl 2-(tert-butoxycarbonyl(ethyl)amino)-2-methylpropanoate (5.18 g, 20 mmol, 1 equiv) at 0° C. under N₂. The mixture was stirred for 4 h at 0° C. It was quenched with ice/water at 0° C., then extracted with ethyl acetate (50 mL×3). The organic layers were combined, washed with brine, dried over Na₂SO₄ and concentrated. The residue was purified by a silica gel column (pet. ether/ethyl acetate=4/1) to give 2 g (45%) of tert-butyl ethyl(1-hydroxy-2-methylpropan-2-yl)carbamate as a colorless oil.

Step 4

To a solution of tert-butyl ethyl(1-hydroxy-2-methylpropan-2-yl)carbamate (2.18 g, 10 mmol, 1.0 equiv) in DCM (150 mL) was added Dess-martin periodinane (4.24 g, 10 mmol, 1.0 equiv) portionwise at 0° C. The resulting mixture was stirred for 4 h at room temperature. Saturated solutions of aqueous sodium hydrogencarbonate and sodium thiosulfate were added. The resulting mixture was stirred for 0.5 h. The organic phase was separated, washed with saturated sodium hydrogencarbonate, brine, dried over sodium sulfate and concentrated to give 1.5 g (71%) of tert-butyl methyl(2-ethyl-1-oxopropan-2-yl)carbamate as a colorless oil.

Step 5

To a solution of 3-((S)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (236 mg, 0.5 mmol, 1 equiv) and tert-butyl ethyl(2-methyl-1-oxopropan-2-yl)carbamate (2.15 g, 10 mmol, 20 equiv) in dioxane (30 mL) was added 0.5 mL piperidine, 1 drop AcOH and 2 g of 4 A molecular sieves. The resulting mixture was stirred for 2 h at 110° C. The solids was filtered out, the filtrate was diluted with 200 mL of ethyl acetate, washed with brine, dried over Na₂SO₄, concentrated and purified by silica gel column (ethyl acetate/MeOH 10/1) to give 60 mg (19%) of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(ethyl)carbamate as a white solid.

Step 6

To a solution of tert-butyl 5-((S)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(ethyl)carbamate (60 mg, 0.089 mmol) in DCM (8 mL) was added 2 mL of CF₃COOH. The mixture was stirred for 2 h at room temperature, then concentrated and purified by Prep-HPLC. Conditions: (1#-Pre-HPLC-001(SHIMADZU)): Column, SunFire Prep C18, 19*150 mm 5 um; mobile phase, water with 0.05% TFA and CH₃CN (40% CH₃CN up to 100% in 20 min); Detector, 254 nm. This resulted in 12 mg (16%) of the title compound as a white solid and bis TFA salt. LC-MS: m/z 569 (M+H⁺). H¹-NMR (400 MHz, CDCl₃+D₂O, ppm): 8.31 (s, 1H), 7.51-7.44 (m, 3H), 7.37 (s, 1H), 7.28-7.25 (m, 1H), 7.13 (d, J=7.6 Hz, 2H), 6.95 (dd, J=8.4, 2.0 Hz, 1H), 6.85

(q, J=11.6 Hz, 2.0 Hz, 1H), 4.89-4.65 (m, 3H), 3.76-3.57 (m, 4H), 2.14-1.83 (m, 4H), 1.50-1.49 (d, 6H), 1.31 (t, q=6.8 Hz, 3H).

Example 41

Synthesis of 2-((R)-2-((4-amino-3-(2-fluoro-4-phenoxyphenyl)-1H-pyrazolo[3,4-d]pyrimidin-1-yl)methyl)pyrrolidine-1-carbonyl)-4-(ethylamino)-4-methylpent-2-enenitrile

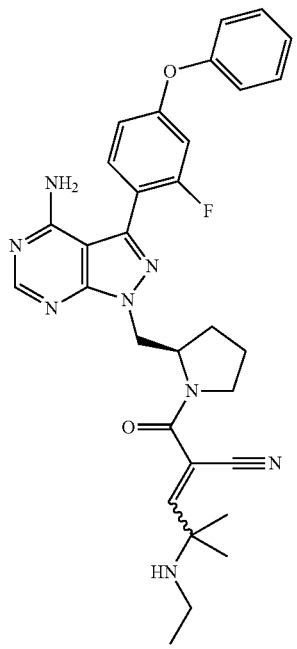 [SMILES: CCNC(C)(C)C=C(C#N)C(=O)N1CCC[C@@H]1Cn1nc(-c2ccc(Oc3ccccc3)cc2F)c2c(N)ncnc21]

Step 1

To a solution of 3-((R)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (236 mg, 0.5 mmol, 1 equiv) and tert-butyl ethyl(2-methyl-1-oxopropan-2-yl)carbamate (2.15 g, 10 mmol, 20 equiv) in dioxane (30 mL) was added 0.5 mL piperidine, 1 drop AcOH and 2 g of 4 A molecular sieves. The resulting mixture was stirred for 2 h at 110° C. The solids was filtered out, the filtrate was diluted with 200 mL of ethyl acetate, washed with brine, dried over $Na_2SO_4$, concentrated and purified on silica gel column (ethyl acetate/MeOH 10/1) to give 60 mg (19%) of tert-butyl 5-((R)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(ethyl)carbamate as a white solid.

Step 2

To a solution of tert-butyl 5-((R)-2-((4-amino-3-(2-fluoro-4-phenoxyphenyl)-1H-pyrazolo[3,4-d]pyrimidin-1-yl)methyl)pyrrolidin-1-yl)-4-cyano-2-methyl-5-oxopent-3-en-2-yl(ethyl)carbamate (60 mg, 0.089 mmol) in DCM (10 mL) was added 2.5 mL of $CF_3COOH$. The mixture was stirred for 2 h at room temperature. The volatile phase was removed under reduced pressure and the residue was purified on Prep-HPLC. Conditions: (1#-Pre-HPLC-001(SHIMADZU)): Column, SunFire Prep C18, 19*150 mm 5 um; mobile phase, water with 0.05% TFA and $CH_3CN$ (40% $CH_3CN$ up to 100% in 20 min); Detector, 254 nm. This resulted 12 mg (16%) of the title compound as a white solid and bis TFA salt. LC-MS: m/z 569 (M+H$^+$). H-NMR (400 MHz, $CD_3OD$, ppm): 8.37 (s, 1H), 7.72 (s, 1H), 7.57 (t, J=8.4 Hz, 1H), 7.48 (t, J=8.0 Hz, 2H), 7.28 (t, J=7.2 Hz, 1H), 7.17 (d, 8.0 Hz, 2H), 6.97 (dd, J=8.4 Hz, 2.0 Hz, 1H), 6.91 (dd, J=11.6 Hz, 2.0 Hz, 1H), 4.95-4.82 (m, 2H), 4.70-4.65 (m, 1H), 3.71-3.65 (m, 3H), 3.59-3.55 (m, 1H), 2.15-2.11 (m, 1H), 2.02-1.93 (m, 2H), 1.81-1.79 (m, 1H), 1.53 (s, 3H), 1.47 (s, 3H), 1.29 (t, J=7.2 Hz, 3H).

Example 42

Synthesis of 2-((S)-2-((4-amino-3-(2-fluoro-4-phenoxyphenyl)-1H-pyrazolo[3,4-d]pyrimidin-1-yl)methyl)pyrrolidine-1-carbonyl)-4-(cyclopropylamino)-4-methylpent-2-enenitrile

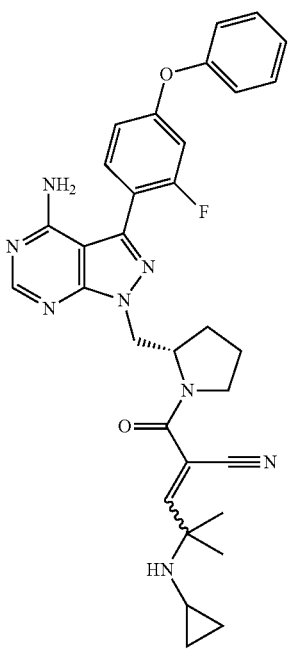 [SMILES: CC(C)(C=C(C#N)C(=O)N1CCC[C@H]1Cn1nc(-c2ccc(Oc3ccccc3)cc2F)c2c(N)ncnc21)NC1CC1]

Step 1

To a 250 mL of sealed tube was added ethyl 2-bromo-2-methylpropanoate (19.4 g, 0.1 mol, 1.0 equiv), cyclopropanamine (11.4 g, 0.2 mol, 2.0 equiv), $K_2CO_3$ (27.6 g, 0.2 mol, 2.0 equiv), KI (1.66 g, 0.01 mol, 0.1 equiv) and 200 mL of MeCN. The mixture was stirred at 100° C. for 12 h then cooled to room temperature and the solids were filtered. The filtrate was concentrated and purified on silica gel column eluting with pet. ether/ethyl acetate=4/1 to give 8.0 g (46%) of ethyl 2-(cyclopropylamino)-2-methylpropanoate.

Step 2

To a solution of $LiAlH_4$ (760 mg, 20 mmol, 1.0 equiv) in THF (50 mL) was added ethyl 2-(cyclopropylamino)-2-methylpropanoate (3.42 g, 20 mmol, 1.0 equiv) in THF (10 mL) at 0° C. under $N_2$. The resulting suspension was stirred at 0° C. for 2 h. The reaction was quenched with $Na_2SO_4 \cdot 10H_2O$ (3.0 g) at 0° C. The solid was filtered off and the filtrate was concentrated under reduced pressure. This resulted in 2-(cyclopropylamino)-2-methylpropan-1-ol 1.3 g (50%) as a white solid.

Step 3

To a solution of oxalyl chloride (11.43 g, 90 mmol, 1.5 equiv) in DCM (300 mL) was added DMSO (11.7 g, 150 mmol, 2.5 equiv) at −78° C. under N₂ atmosphere. The resulting mixture was stirred for 0.5 h then a solution of 2-(cyclopropylamino)-2-methylpropan-1-ol (7.74 g, 60 mmol, 1.0 equiv) in DCM (20 mL) was added dropwise at −78° C. and then stirred for another 1 h. Then TEA (36.4 g, 0.36 mol, 6.0 equiv) was added and stirring was continued for 20 min at room temperature. The reaction was then diluted with DCM (200 mL) and washed with aq. NaHCO₃ and brine, dried over Na₂SO₄, concentrated to give the crude product, which was purified with distillation under reduced pressure. This resulted in 1.0 g (13%) of 2-(cyclopropylamino)-2-methylpropanal was obtained as a colorless oil.

Step 4

A solution of 3-((S)-2-((4-amino-3-(2-fluoro-4-phenoxyphenyl)-1H-pyrazolo[3,4-d]pyrimidin-1-yl)methyl)pyrrolidin-1-yl)-3-oxopropanenitrile (118 mg, 0.25 mmol, 1.0 equiv), 2-(cyclopropylamino)-2-methylpropanal (0.16 g, 1.25 mmol, 5.0 equiv) and one drop of piperidine in MeCN (10 mL) was stirred overnight at 40° C. The solvent was removed and the residue was purified on Prep-HPLC. Conditions: (1#-Pre-HPLC-001(SHIMADZU)): Column, SunFire Prep C18, 19*150 mm 5 um; mobile phase, water with 0.05% TFA and CH₃CN (40% CH₃CN up to 100% in 20 min); Detector, 254 mm. This resulted in 40 mg (27%) of the title compound as a white solid and bis TFA salt. LC-MS: m/z 581 (M+H⁺). H¹-NMR (400 MHz, CDCl₃+D₂O, ppm): 8.33 (s, 1H), 7.54-7.43 (m, 3H), 7.33 (s, 1H), 7.28-7.25 (m, 1H), 7.07 (d, J=8.0 Hz, 2H), 6.94 (dd, J=8.4, 2.0 Hz, 1H), 6.85 (dd, J=11.6, 2.0 Hz, 1H), 4.89-4.64 (m, 3H), 3.65-3.52 (m, 2H), 2.78 (m, 1H), 2.14-1.79 (m, 4H), 1.57-1.55 (d, 6H), 1.20 (m, 2H), 0.98 (m, 2H).

Example 43

Synthesis of 2-((S)-2-((4-amino-3-(2-fluoro-4-phenoxyphenyl)-1H-pyrazolo[3,4-(1]pyrimidin-1-yl)methyl)pyrrolidine-1-carbonyl)-4-(2-methoxyethylamino)-4-methylpent-2-enenitrile

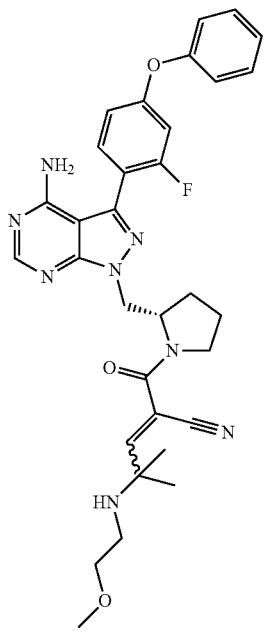 [SMILES: COCCNC(C)(C)C=C(C#N)C(=O)N1CCC[C@H]1Cn1nc(-c2ccc(Oc3ccccc3)cc2F)c2c(N)ncnc21]

To a suspension of 4-amino-2-((S)-2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile (210 mg, 0.39 mmol, 1.0 equiv), KI (130 mg, 0.78 mmol, 2.0 equiv) and potassium carbonate (166 mg, 1.17 mmol, 3.0 equiv) in CH₃CN (15 mL) was added 1-bromo-2-methoxyethane (160 mg, 1.17 mmol, 3.0 equiv). The resulting suspension was stirred at 50° C. overnight. The solvent was removed under reduced pressure and then water (20 mL) was added to the residue. The resulting mixture was extracted with ethyl acetate (30 mL*3). The organic layers were combined, washed with brine, dried over sodium sulfate and concentrated. The residue was purified on Prep-HPLC. Conditions: (1#-Pre-HPLC-001(SHIMADZU)): Column, SunFire Prep C18, 19*150 mm 5 um; mobile phase, WATER WITH 0.5% NH4OH and CH3CN (40% CH3CN up to 100% in 20 min); Detector, 254 nm. This resulted in 8.7 mg (3.7%) of the title compound as an off-white solid. MS (ESI, pos. ion) m/z: 599 (M+1) H-NMR (400MHz, CDCl₃, ppm): 8.38 (s, 1H), 7.54 (t, J=8.4, 7.2Hz, 1H), 7.45 (t, J=7.6, 8.0Hz, 2H), 7.28-7.25 (m, 1H), 7.13 (d, J=8.0Hz, 2H), 6.95 (dd, J=8.4, 2.0Hz, 1H), 6.87 (dd, J=11.2, 2.4Hz, 1H), 6.77 (s, 1H), 5.42 (brs, 2H), 4.93-4.90 (m, 1H), 4.83-4.82 (m, 1H), 4.70-4.65 (m, 1H), 3.67-3.65 (m, 5H), 3.36 (s, 3H), 3.36-3.31 (m, 1H), 2.20-2.89 (m, 3H), 1.88-1.71 (m, 1H), 1.61-1.51 (m, 4H), 1.35 (s, 3H), 1.33 (s, 3H).

Example 44

Synthesis of 2-{2-[4-amino-5-(2-fluoro-4-phenoxyphenyl)-pyrrolo[2,3-d]pyrimidin-7-ylmethyl]-pyrrolidine-1-carbonyl}-3-cyclopropyl-acrylonitrile

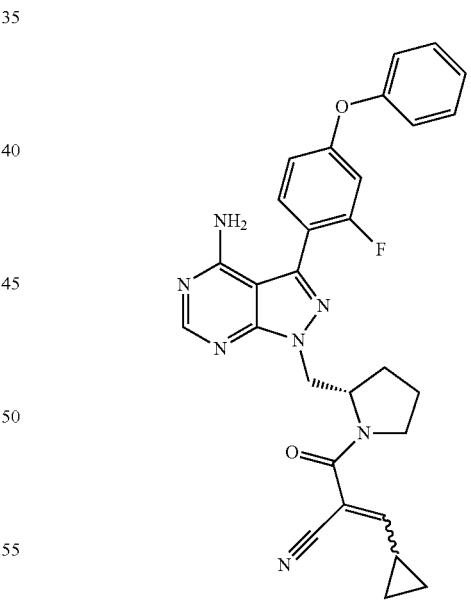

Step 1

The mixture of 2-(4-amino-5-iodo-pyrrolo[2,3-d]pyrimidin-7-ylmethyl)-pyrrolidine-1-carboxylic acid tert-butyl ester (500.00 mg, 1.13 mmol, 1.0 eq), 3-fluoro-4-phenoxyphenyl-boronic acid (240.00 mg, 1.13 mmol, 1.0 eq), Pd(PPh₃)₄ (100.00 mg) and Na₂CO₃ (300.00 mg, 2.83 mmol, 2.5 eq) in dioxane/H₂O (40/10 ml) was stirred at 90° C. for 4 h. The reaction mixture was concentrated and purified by Pre-TLC to afford 400 mg (70%) of 2-[4-amino-5-(2-fluoro- 4-phenoxy-phenyl)-pyrrolo[2,3-d]pyrimidin-7-ylmethyl]-pyrrolidine-1-carboxylic acid tert-butyl ester.

Step 2

To a solution of 2-[4-amino-5-(2-fluoro-4-phenoxy-phenyl)-pyrrolo[2,3-d]pyrimidin-7-ylmethyl]-pyrrolidine-1-carboxylic acid tert-butyl ester (400 mg, 0.79 mmol) in 10 ml of DCM, was added TFA (10 ml). The reaction mixture was stirred at RT for 2 h. The mixture was then concentrated to give 5-(2-fluoro-4-phenoxy-phenyl)-7-pyrrolidin-2-ylmethyl-7H-pyrrolo[2,3-d]pyrimidin-4-ylamine (320 mg), which was used in the next step without any further purification.

Step 3

To a mixture of 5-(2-fluoro-4-phenoxy-phenyl)-7-pyrrolidin-2-ylmethyl-7H-pyrrolo[2,3-d]pyrimidin-4-ylamine (100 mg, 0.25 mmol, 1.0 eq), 2-cyano-3-cyclopropyl-acrylic acid (42 mg, 0.3 mmol, 1.2 eq) and DIEA (97 mg, 0.75 mmol, 3.0 eq) in 10 ml of DCM was added HATU (145 mg, 0.38 mmol, 1.5 eq). The mixture was stirred for 4 h at RT under $N_2$. LCMS showed the reaction was completed. The reaction mixture was concentrated and purified by Pre-TLC to provide 71 mg (54%) of the title compound. LCMS: m/z 523.2 $(M+H)^+$. $^1$HNMR (400 MHz, DMSO-$d_6$): δ 0.866~0.920 (m, 2H), 1.177~1.194 (m, 2H), 1.569 (m, 1H), 1.721 (m, 2H), 1.883 (m, 2H), 3.200 (m, 2H), 3.511 (m, 1H), 4.360~4.475 (m, 2H), 6.125(m, 2H), 6.642-6.664 (m, 1H), 6.898-6.920 (m, 1H), 6.977-7.010 (m, 1H), 7.150~7.232 (m, 4H), 7.371-7.471 (m, 3H) and 8.131 (m, 1H).

Example 45

Synthesis of (R)-2-(2-((4-amino-3-(2-fluoro-4-phenoxyphenyl)-1H-pyrazolo[3,4-d]pyrimidin-1-yl)methyl)pyrrolidine-1-carbonyl)-3-(1-aminocyclopropyl)acrylonitrile

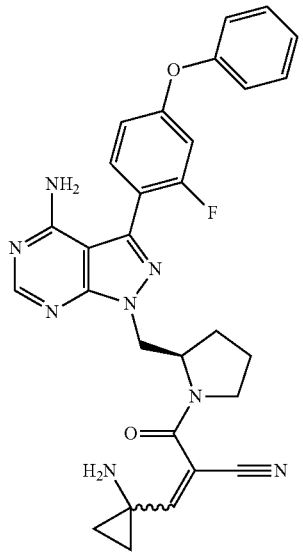 [SMILES: N#CC(=CC1(N)CC1)C(=O)N1CCC[C@@H]1Cn1nc(-c2ccc(Oc3ccccc3)cc2F)c2c(N)ncnc21]

Step 1

To a solution of tert-butyl (1-(hydroxymethyl)cyclopropyl)carbamate (Bioorg. Med. Chem. Lett., 2008, 18(6), 2188) (135 mg, 0.72 mmoles) in DCM (8 mL) was added Dess-Martin periodinane (277 mg, 0.65 mmole). After stirring 1 hr, the reaction was filtered through celite and concentrated to a yellow oil which was further purified by Isolera (7%-70% ethyl acetate/hexanes) to provide 84 mg (87%) of tert-butyl (1-formylcyclopropyl)-carbamate as a white solid.

Step 2

To a solution of 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (100 mg, 0.2100 mmol) dissolved in methanol (4 mL) and DCM (4 mL) was added piperidine (0.1 mL, 0.8500 mmol) and tert-butyl N-(1-formylcyclopropyl)carbamate (58.9 mg, 0.3200 mmol). The reaction was heated to reflux for 6 hrs and then cooled and concentrated. The residue was and dissolved in ethyl acetate (50 mL) and washed with water (50 mL) and then brine. The organic layer was dried ($MgSO_4$), filtered and concentrated. The residue was purified by Isolera (1%-8% MeOH/DCM) to provide 39 mg (13% yield) of tert-butyl N-[1-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]cyclopropyl]carbamate.

Step 3

To a solution of tert-butyl N-[1-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]cyclopropyl]carbamate (27 mg, 0.04 mmol) in DCM (3 mL) was added TFA (1 mL). The solution was stirred for 5 hrs. and then concentrated. The residue was purified by prep-TLC (5% MeOH/DCM) to provide 2.68 mg (12%) of the title compound. MS (pos. ion) m/z: 539 (M+1).

Example 46

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-morpholino-pent-2-enenitrile

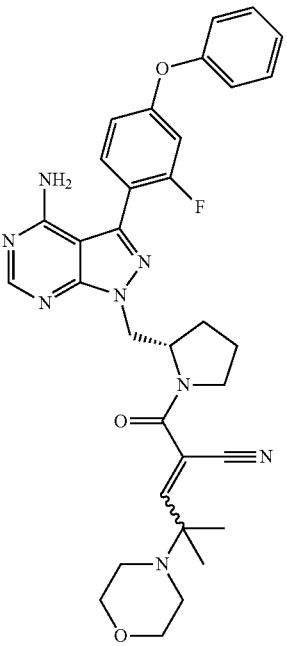 [SMILES: CC(C)(C=C(C#N)C(=O)N1CCC[C@H]1Cn1nc(-c2ccc(Oc3ccccc3)cc2F)c2c(N)ncnc21)N1CCOCC1]

To a sealed tube was added 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (900 mg, 1.91 mmol), ethanol (12 mL), piperidine (0.23 mL, 2.29 mmol) and 2-methyl-2-morpholino-propanal (0.49 mL, 2.86 mmol). The tube was sealed and heated to 105° C. for 24 hrs. The mixture was then cooled, concentrated and then dissolved in ethyl acetate (100 mL) and washed with 5% citric acid (100 ml) and then brine. The organic layer was dried (MgSO₄), filtered and concentrated. The crude material was purified by Isolera (column size 100 g. Solvent system 4%-8% MeOH/EtOAc) to obtain 245 mg (21% yield) of the title compound. MS (pos. ion) m/z: 611 (M+1).

Proceeding as described above by substituting 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile with (R)-3-(3-(4-amino-3-(2-fluoro-4-phenoxyphenyl)-1H-pyrazolo[3,4-d]pyrimidin-1-yl)piperidin-1-yl)-3-oxopropanenitrile, (R)-2-(3-(4-amino-3-(2-fluoro-4-phenoxyphenyl)-1H-pyrazolo[3,4-d]pyrimidin-1-yl)piperidine-1-carbonyl)-4-methyl-4-morpholinopent-2-enenitrile was prepared.

Example 47

Synthesis of 2-[(2S)-2-[[4-amino-3-(2-fluoro-4-phenoxy-phenyl)pyrazolo[3,4-d]pyrimidin-1-yl]methyl]pyrrolidine-1-carbonyl]-4-methyl-4-morpholino-pent-2-enenitrile

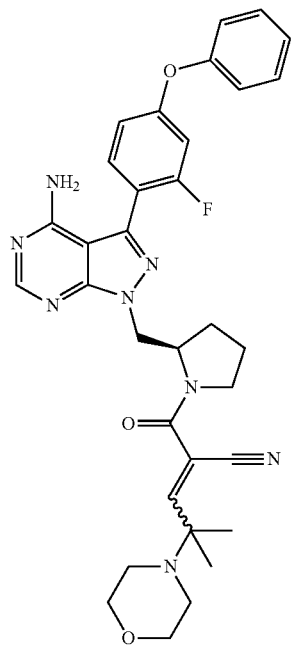 [SMILES: CC(C)(C=C(C#N)C(=O)N1CCC[C@@H]1Cn1nc(-c2ccc(Oc3ccccc3)cc2F)c2c(N)ncnc21)N1CCOCC1]

To a sealed tube was added 3-[(2R)-2-[[4-amino-3-(2-fluoro-4-phenoxy-phenyl)-pyrazolo[3,4-d]pyrimidin-1-yl]methyl]pyrrolidin-1-yl]-3-oxo-propanenitrile (762.6 mg, 1.62 mmol), 2-methyl-2-morpholino-propanal (508.54 mg, 3.23 mmol), piperidine (0.08 mL, 0.81 mmol) and ethanol (6 mL). The tube was sealed and heated at 100° C. After 22 hrs, the reaction was cooled and evaporated. The residue was purified by Isolera (column size 100 g, 3%-7% MeOH/EtOAc) to obtain 550 mg (56% yield) of the title compound. MS (pos. ion) m/z: 611 (M+1).

Example 48

Synthesis of 2-[(2R)-2-[[4-amino-3-(2-fluoro-4-phenoxy-phenyl)pyrazolo[3,4-d]pyrimidin-1-yl]methyl]pyrrolidine-1-carbonyl]-4-methyl-4-(1-piperidyl)pent-2-enenitrile

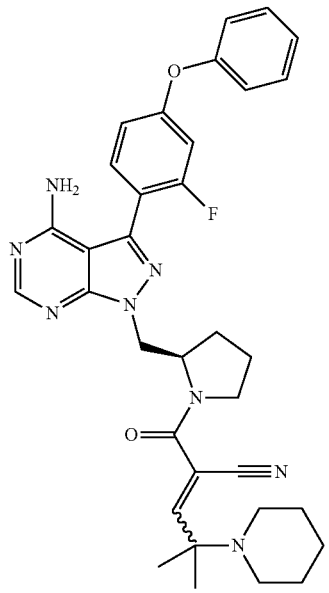 [SMILES: CC(C)(C=C(C#N)C(=O)N1CCC[C@@H]1Cn1nc(-c2ccc(Oc3ccccc3)cc2F)c2c(N)ncnc21)N1CCCCC1]

A solution of 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (150 .mg, 0.32 mmol), piperidine (0.03 mL, 0.32 mmol) and 2-methyl-2-(1-piperidyl)propanal (74.08 mg, 0.48 mmol) in ethanol (8 mL) was heated in a sealed tube at 90° C. for 16 hrs. The solution was cooled and concentrated. The residue was dissolved in ethyl acetate and washed with 5% citric acid and brine and then dried (MgSO₄), filtered and concentrated. The crude material was purified by Isolera (10 grams column at 0% to 6% MeOH/ethyl acetate) to obtain 15 mg (8%) of the title compound. MS (pos. ion) m/z: 609 (M+1).

Example 49

Synthesis of 2-[(2S)-2-[[4-amino-3-(2-fluoro-4-phenoxy-phenyl)pyrazolo[3,4-(1]pyrimidin-1-yl]methyl]pyrrolidine-1-carbonyl]-4-methyl-4-(1-piperidyl)pent-2-enenitrile

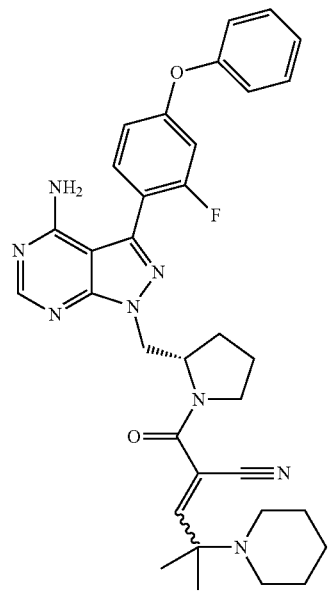 [SMILES: CC(C)(C=C(C#N)C(=O)N1CCC[C@H]1Cn1nc(-c2ccc(Oc3ccccc3)cc2F)c2c(N)ncnc21)N1CCCCC1]

To a microwave vial was added 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (139.3 mg, 0.30 mmol), piperidine (0.04 mL, 0.35 mmol), 2-methyl-2-(1-piperidyl)propanal (68.8 mg, 0.4400 mmol) and toluene (3 mL). The vial was heated under microwave conditions at 160° C. for 3 hrs. The reaction was cooled and concentrated, then dissolved in ethyl acetate (30 mL) and washed with 2M HCl. The aqueous layer was basified to pH ~7.5 with sat. NaHCO3 and washed with ethyl acetate. The organic layer was dried (MgSO4), filtered and concentrated and the crude material was purified by Isolera (1%-10% MeOH/ethyl acetate) to obtain 32 mg (18%) of the title compound. MS (pos. ion) m/z: 609 (M+1).

Example 50

Synthesis of N-[(1R)-2-[4-amino-3-(2-fluoro-4-phenoxy-phenyl)pyrazolo[3,4-d]pyrimidin-1-yl]-1-methyl-ethyl]-2-cyano-4-ethoxy-4-methyl-pent-2-enamide

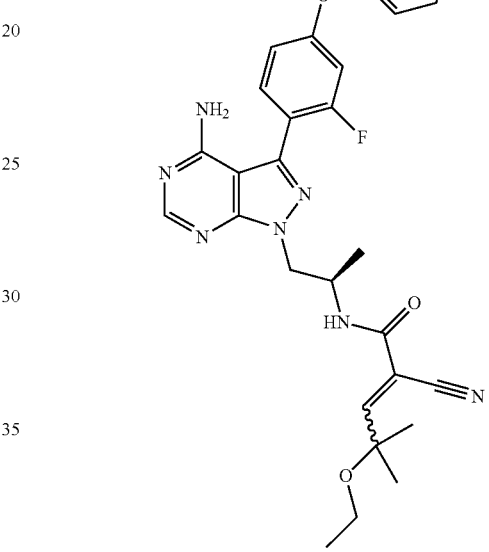

Step 1

To a solution of tert-butyl N-[(1R)-2-hydroxy-1-methyl-ethyl]carbamate (1.9 g, 10.8 mmol), 3-iodo-1H-pyrazolo[3,4-d]pyrimidin-4-amine (2.0 g, 7.7 mmol), and PPh3 (6.1 g, 23.2 mmol) in THF (80 mL) cooled with an ice bath was added DIAD (3.0 mL, 15.5 mmol; in 28 mL of THF) dropwise over a 1 hour period. The reaction was then stirred for 24 h at room temperature. The mixture was diluted into ethyl acetate (50 mL) and washed with water and brine. The organic layer was dried (MgSO4), filtered and concentrated. The resulting material was suspended in 20% ethyl acetate in dioxane (1000 mL) and sonicate for 1 hr. The solid was collected by filtration to obtain 2.1 g (66%) of tert-butyl N-[(1R)-2-(4-amino-3-iodo-pyrazolo[3,4-(1]pyrimidin-1-yl)-1-methyl-ethyl]carbamate as a white solid.

Step 2

To a microwave tube was added tert-butyl N-[(1R)-2-(4-amino-3-iodo-pyrazolo[3,4-d]pyrimidin-1-yl)-1-methyl-ethyl]carbamate (1.7 g, 4.1 mmol), (2-fluoro-4-phenoxy-phenyl)boronic acid (1.4 g, 6.1 mmol), K2CO3 (1.27 g, 9.2 mmol), and tetrakis(triphenylphosphine)palladium(0) (213 mg, 0.18 mmol) and 1,4-dioxane (12 mL) and water (3 mL).

The mixture was capped and heated under microwave conditions for 140° C. for 10 minutes. The reaction was cooled and diluted with ethyl acetate (50 mL) and washed with water (50 mL) and brine. The organic layer was dried (MgSO$_4$), filtered and evaporated to obtain 2.56 g of crude tert-butyl N-[(1R)-2-[4-amino-3-(2-fluoro-4-phenoxy-phenyl)pyrazolo[3,4-d]pyrimidin-1-yl]-1-methyl-ethyl]carbamate. This was used in the next step without further purification.

Step 3

To a solution of tert-butyl N-[(1R)-2-[4-amino-3-(2-fluoro-4-phenoxy-phenyl)pyrazolo[3,4-d]pyrimidin-1-yl]-1-methyl-ethyl]carbamate (2.56 g, 5.35 mmol) in DCM (20 mL) was added 4N HCl in dioxane (15 ml). After stirring 18 h at room temperature, the reaction was diluted with DCM (100 mL) and extracted with water (200 mL). The aqueous layer was washed again with DCM (50 mL). The aqueous layer was placed in a 2 L beaker along with ethyl acetate (50 mL) and stirred while adding NaOH (beads) to adjust the pH to ~11. More ethyl acetate (100 mL) was added and then the layers were separated and the aqueous layer was washed with ethyl acetate. The combined organic layers were washed with brine and then dried (MgSO$_4$), filtered and concentrated to obtain 1.8 g (90%) of 1-[(2R)-2-aminopropyl]-3-(2-fluoro-4-phenoxy-phenyl)pyrazolo[3,4-d]pyrimidin-4-amine as a solid.

Step 4

To a solution of 1-[(2R)-2-aminopropyl]-3-(2-fluoro-4-phenoxy-phenyl)pyrazolo[3,4-d]pyrimidin-4-amine (1826.mg, 4.83 mmol), 2-cyanoacetic acid (821 mg, 9.7 mmol) and TEA (2.0 mL, 14.5 mmol) in DMF (25 mL) was added HATU (2.75 g, 7.24 mmol). The reaction mixture was stirred at room temperature for 20 hr. The mixture was then evaporated to an oil and dissolved in ethyl acetate (100 mL) and washed with 5% citric acid (50 mL) and brine. The organic layer was dried (MgSO$_4$), filtered and evaporated. The crude material was purified by Isolera (10 g col, 2%-6% MeOH/DCM) to obtain 2.1 g (98%) of N-[(1R)-2-[4-amino-3-(2-fluoro-4-phenoxy-phenyl)pyrazolo[3,4-d]pyrimidin-1-yl]-1-methyl-ethyl]-2-cyano-acetamide.

Step 5

To a sealed tube was added N-[(1R)-2-[4-amino-3-(2-fluoro-4-phenoxy-phenyl)pyrazolo[3,4-d]pyrimidin-1-yl]-1-methyl-ethyl]-2-cyano-acetamide (105 mg, 0.24 mmol), piperidine (0.01 mL, 0.12 mmol), 2-ethoxy-2-methyl-propanal (0.07 mL, 0.47 mmol) and ethanol (4 mL). The tube was capped, and heated to 85° C. for 60 hrs. The reaction was cooled and evaporated. The resulting crude oil was dissolved in DCM (30 mL) and washed with water (30 mL) and brine, then dried (MgSO$_4$), filtered and concentrated. The resulting material was purified by Isolera (10 g column, 3%-7% MeOH/DCM) to obtain 10 mg (8%) of the title compound. MS (pos. ion) m/z: 544 (M+1).

Example 51

Synthesis of 4-amino-N-[(1R)-2-[4-amino-3-(2-fluoro-4-phenoxy-phenyl)pyrazolo[3,4-d]pyrimidin-1-yl]-1-methyl-ethyl]-2-cyano-4-methyl-pent-2-enamide HCl

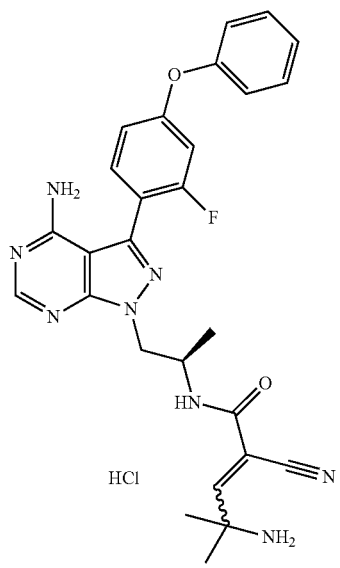 [SMILES: C[C@H](Cn1nc(-c2ccc(Oc3ccccc3)cc2F)c2c(N)ncnc21)NC(=O)C(C#N)=CC(C)(C)N ; Cl]

Step 1

To a sealed tube was added N-[(1R)-2-[4-amino-3-(2-fluoro-4-phenoxy-phenyl)pyrazolo[3,4-d]pyrimidin-1-yl]-1-methyl-ethyl]-2-cyano-acetamide (160 mg, 0.36 mmol), tert-butyl N-(1,1-dimethyl-2-oxo-ethyl)carbamate (0.13 mL, 0.54 mmol) piperidine (0.02 mL, 0.18 mmol) and ethanol (4 mL). The tube was capped and heated to 110° C. for 2 hrs. The reaction was cooled and concentrated then dissolved in ethyl acetate (30 mL) and washed with water (30 mL) and brine. The organic layer was dried (MgSO$_4$), filtered and concentrated. The crude material was purified by isolera (25 g column, 2%-7% MeOH/DCM) to obtain 77 mg, (35%) of tert-butyl N-[4-[[(1R)-2-[4-amino-3-(2-fluoro-4-phenoxy-phenyl)pyrazolo[3,4-d]pyrimidin-1-yl]-1-methyl-ethyl]amino]-3-cyano-1,1-dimethyl-4-oxo-but-2-enyl]carbamate as a solid. MS (pos. ion) m/z: 615 (M+1).

Step 2

To a solution of tert-butyl N-[4-[[(1R)-2-[4-amino-3-(2-fluoro-4-phenoxy-phenyl)pyrazolo[3,4-d]pyrimidin-1-yl]-1-methyl-ethyl]amino]-3-cyano-1,1-dimethyl-4-oxo-but-2-enyl]carbamate (71 mg, 0.12 mmol) in methanol (1 mL) was added 4N HCl in Dioxane (2 mL). The solution was stirred for 4 days and then it was added dropwise to stirring ethyl ether (70 mL). The suspension was stirred for 30 minutes and then filtered and rinse with ethyl ether (10 mL) to obtain 57 mg (95%) of the title compound as an HCl salt.

Example 52

Synthesis of 2-[(2R)-2-[[4-amino-3-(2-fluoro-4-phenoxy-phenyl)pyrazolo[3,4-d]pyrimidin-1-yl]methyl]pyrrolidine-1-carbonyl]-3-[(2S)-pyrrolidin-2-yl]prop-2-enenitrile HCl

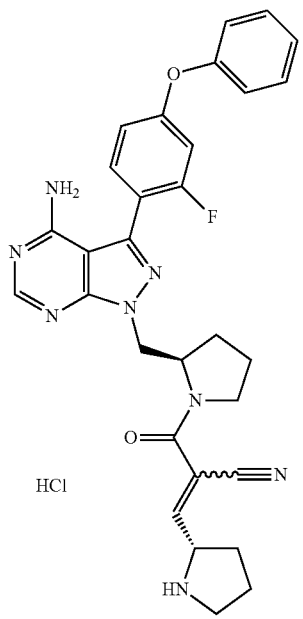 [SMILES: N#CC(=C[C@@H]1CCCN1)C(=O)N1CCC[C@@H]1Cn1nc(-c2ccc(Oc3ccccc3)cc2F)c2c(N)ncnc21 ; Cl]

Step 1

To a sealed tube was added 3-[(2R)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (507 mg, 1.07 mmol), tert-butyl (2S)-2-formylpyrrolidine-1-carboxylate (0.2 mL, 1.1 mmol), piperidine (0.05 mL, 0.54 mmol) and ethanol (3 mL). The tube was capped and heated to 100° C. for 16 hrs. The reaction was not complete so an additional amount of tert-butyl (2S)-2-formylpyrrolidine-1-carboxylate (732 mg, 3 eq) was added and heating was continued for 4 hrs at 110° C. The reaction was cooled and concentrated then dissolved in DCM (50 mL) and washed with water (50 mL) and brine. The organic layer was dried (MgSO$_4$), filtered and concentrated. The resulting material was purified by Isolera (250 g column; 2%-3% MeOH/DCM) to provide 403 mg (57%) of tert-butyl (2S)-2-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]pyrrolidine-1-carboxylate as a solid.

Step 2

To a solution of tert-butyl (2S)-2-[3-[(2R)-2-[[4-amino-3-(2-fluoro-4-phenoxy-phenyl)pyrazolo[3,4-d]pyrimidin-1-yl]methyl]pyrrolidin-1-yl]-2-cyano-3-oxo-prop-1-enyl]pyrrolidine-1-carboxylate (84 mg, 0.13 mmol) in 1,4-dioxane (2 mL) and added 4N HCl in dioxane (0.16 mL). The solution was stirred for 16 hr at room temperature then concentrated. The residue was dissolved in methanol (~1 mL) and added dropwise to ethyl ether (20 mL) while stirring. The resulting solid was collected by filtration to provide 42 mg (59%) of the title compound as an HCl salt. MS (pos. ion) m/z: 553 (M+1).

Example 53

Synthesis of N-((S)-1-(4-amino-3-(2-fluoro-4-phenoxyphenyl)-1H-pyrazolo[3,4-d]pyrimidin-1-yl)propan-2-yl)-2-cyano-4-methylpent-2-enamide

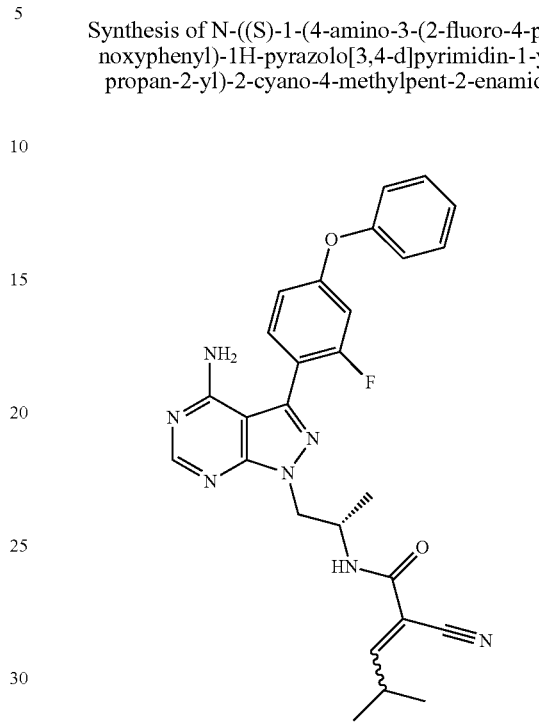

Step 1

Into a 500-mL 3-necked round-bottom flask purged and maintained with an inert atmosphere of nitrogen, to a mixture of 3-iodo-1H-pyrazolo[3,4-d]pyrimidin-4-amine (7.83 g, 30.00 mmol, 1.00 equiv), TPP (11.8 g, 44.99 mmol, 1.50 equiv), tetrahydrofuran (200 mL), tert-butyl N-[(2S)-1-hydroxypropan-2-yl]carbamate (6.3 g, 35.95 mmol, 1.00 equiv) was added DIAD (9.1 g, 45.00 mmol, 1.50 equiv) was added dropwise at 0° C. Most of the solvent was removed under reduced pressure and the solid was collected by filtration, which was washed with pet. ether. This resulted in 5.6 g (45%) of tert-butyl-N-[(2S)-1-[4-amino-3-iodo-1H-pyrazolo [3,4-d]pyrimidin-1-yl]propan-2-yl]carbamate as a yellow powder solid.

Step 2

A mixture of tert-butyl N-[(2S)-1-[4-amino-3-iodo-1H-pyrazolo[3,4-d]pyrimidin-1-yl]propan-2-yl]carbamate (3.5 g, 8.37 mmol, 1.00 equiv), Pd(dppf)Cl$_2$ (310 mg, 0.42 mmol, 0.05 equiv), potassium carbonate (3.5 g, 25.32 mmol, 3.00 equiv), (2-fluoro-4-phenoxyphenyl)boronic acid (2.05 g, 8.84 mmol, 1.10 equiv) in dioxane/H2O (4/1) (50 mL) was stirred for 4 h at 100° C. The resulting mixture was concentrated under vacuum. The residue was applied onto a silica gel column with ethyl acetate/petroleum ether (1/1). This resulted in 3.7 g (92%) of tert-butyl N-[(2S)-1-[4-amino-3-(2-fluoro-4-phenoxyphenyl)-1H-pyrazolo[3,4-d]pyrimidin-1-yl]propan-2-yl]carbamate as a yellow solid.

Step 3

A mixture of tert-butyl N-[(2S)-1-[4-amino-3-(2-fluoro-4-phenoxyphenyl)-1H-pyrazolo[3,4-d]pyrimidin-1-yl]propan-2-yl]carbamate (3.7 g, 7.73 mmol, 1.00 equiv) and trifluoroacetic acid (10 mL) in dichloromethane (40 mL) was stirred at room temperature overnight. The resulting mixture was concentrated under vacuum. This resulted in 4.5 g (crude) of 1-[(2S)-2-aminopropyl]-3-(2-fluoro-4-phenoxyphenyl)-1H- pyrazolo[3,4-d]pyrimidin-4-amine; trifluoroacetic acid as a brown solid.

Step 4

To a mixture of N-[(2R)-1-[4-amino-3-(2-fluoro-4-phenoxyphenyl)-1H-pyrazolo[3,4-d]pyrimidin-1-yl]propan-2-yl]-2,2,2-trifluoroacetamide (4.5 g, 9.49 mmol, 1.00 equiv), triethylamine (4.6 g, 45.4 mmol, 6.00 equiv), 2-cyanoacetic acid (980 mg, 11.52 mmol, 1.50 equiv) in DMF (40 mL) was added HATU (4.4 g, 11.57 mmol, 1.50 equiv). The resulting solution was stirred overnight at room temperature and then diluted with 50 mL of water. The solid was filtrated off and washed with pet. ether. This resulted in 2.5 g (59%, two step) of N-[(2S)-1-[4-amino-3-(2-fluoro-4-phenoxyphenyl)-1H-pyrazolo[3,4-d]pyrimidin-1-yl]propan-2-yl]-2-cyanoacetamide as a yellow solid.

Step 5

A suspension of N-[(2S)-1-[4-amino-3-(2-fluoro-4-phenoxyphenyl)-1H-pyrazolo[3,4-d]pyrimidin-1-yl]propan-2-yl]-2-cyanoacetamide (250 mg, 0.56 mmol, 1.00 equiv), 2-methylpropanal (81 mg, 1.12 mmol, 2.00 equiv) and piperidine (47 mg, 0.55 mmol, 1.00 equiv) in methanol (15 mL) was stirred at room temperature overnight. The resulting mixture was concentrated under vacuum. The residue was applied onto a silica gel column with ethyl acetate/petroleum ether (1/1). The purified product was re-purified on Prep-HPLC eluting with TFA (0.05%)/H$_2$O and CH$_3$CN. The organic phase was removed off under reduced pressure. The aqueous phase was adjusted to 10 with potassium carbonate, which was extracted with DCM. The organic layers were combined, washed with brine, dried over sodium sulfated, filtrated and concentrated. This resulted in 46.4 mg (17%) of the title compound as a white solid. LC-MS m/z: 500 (M+1). H-NMR (400MHz, CDCl$_3$, ppm): 8.49 (s, 1H), 8.12 (d, J=7.2Hz, 1H), 7.60 (t, J=8.8 Hz, 1H), 7.44 (m, 3H), 7.25-7.21 (m, 1H), 7.13 (d, J=8.4Hz, 2H), 6.94 (dd, J=8.4, 2.4Hz, 1H), 6.88 (dd, J=11.2, 2.4Hz, 1H), 5.51 (brs, 2H), 4.74-4.55 (m, 3H), 3.00-2.95 (m, 1H), 1.21 (d, J=6.8, 3H), 1.15 (d, J=6.8Hz, 6H).

Example 54

2-[(2S)-2-[[4-amino-3-(2-fluoro-4-phenoxy-phenyl)pyrazolo[3,4-d]pyrimidin-1-yl]methyl]-pyrrolidine-1-carbonyl]-3-(3-methyloxetan-3-yl)prop-2-enenitrile

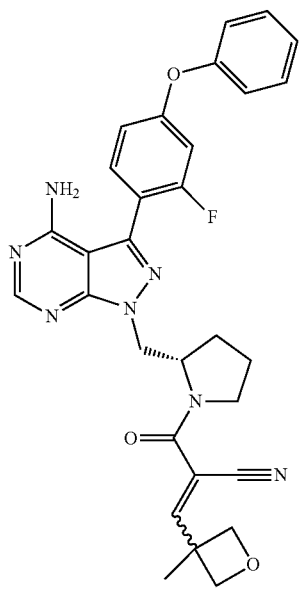 [SMILES: CC1(C=C(C#N)C(=O)N2CCC[C@H]2Cn2nc(-c3ccc(Oc4ccccc4)cc3F)c3c(N)ncnc32)COC1]

To a slurry of 3-[(2S)-2-[[4-amino-3-(2-fluoro-4-phenoxy-phenyl)pyrazolo[3,4-d]pyrimidin-1-yl]methyl]pyrrolidin-1-yl]-3-oxo-propanenitrile (74 .mg, 0.16 mmol) in ethanol (3 mL) was added 3-methyloxetane-3-carbaldehyde (78.54 mg, 0.78 mmol) and then piperidine (0.02 mL, 0.16 mmol) and the mixture heated to 80° C. with stirring. After 3 h, the mixture was cooled and partitioned between ethyl acetate and water. The organic phase was washed with brine, dried over sodium sulfate, and the filtered. Solvents were removed to afford an oil which was purified by column chromatography (gradient from neat methylene chloride to 95-5 methylene chloride:MeOH). The pure fractions were concentrated, then taken up in acetonitrile/water, frozen and lyophilized to afford 2-[(2S)-2-[[4-amino-3-(2-fluoro-4-phenoxy-phenyl)pyrazolo[3,4-d]pyrimidin-1-yl]methyl]pyrrolidine-1-carbonyl]-3-(3-methyloxetan-3-yl)prop-2-enenitrile as a colorless solid weighing 14 mg.

Biological Examples

Tyrosine Kinase TR-FRET Assay

Inhibition of tyrosine kinase enzymatic activity by compounds is measured using time-resolved fluorescence resonance energy transfer (TR-FRET) (Invitrogen pamphlet: Optimization of a LanthaScreen Kinase assay for BTK). Here, a signal is observed only when a Europium-coupled phophotyrosine antibody binds the phosphorylated peptide. Compounds are first prepared in 100% DMSO and serially diluted 10 times via 3-fold dilution. 2.5 µl of inhibitor at 4-fold the final assay concentration is next transferred to the 384-well assay plate (Corning Catalog #3676). A solution of 2-fold the final concentration of appropriate kinase enzyme and Alexafluor 647-coupled peptide substrate (Invitrogen Catalog #5693) is next prepared in advance in a kinase buffer of 50 mM Hepes pH 7.5, 10 mM MgCl2, and 1 mM EGTA. For this solution, the final concentration of the appropriate kinase and peptide is typically 1 nM and 100 nM, respectively. 5 µL of this 2-fold mix of kinase and peptide is added as the second step of the procedure to the 384-well assay plate. To initiate the enzymatic reaction, 2.5 µl of a 4-fold excess ATP solution in kinase buffer is added to the 384-well assay plate. Final ATP concentration is typically set to the Km for ATP. The reaction is allowed to proceed for 60 minutes. During the kinase reaction, a stop solution consisting of EDTA and a Europium-containing phosphotyrosine antibody (Invtrogen Catalog #5692) is prepared in TR-FRET dilution buffer (Invitrogen Catalog #3574). The stop solution contains an EDTA concentration of 20 mM and an antibody concentration of 4 nM. After the 60 minute reaction, 10 µl of the stop solution is added to all wells. Each well is mixed and incubated for 30 minutes at room temperature. Plates are read on a Perkin Elmer Envision TR-FRET plate reader under LanthaScreen settings. Excitation wavelength is 337 nm and Emission wavelengths are 620 nm and 665 nm Data are acquired as the ratio of emission at 665 nm/emission at 620 nm and plotted as a function of compound concentration to ascertain compound potency. Here, a signal is observed only when a Europium-coupled phophotyrosine antibody binds the phosphorylated peptide.

Example 2

BTK Radiometric Enzyme Assay

BTK activity is measured by product formation based on the incorporation of $^{33}PO_4$ from [33P]ATP into a biotin-tagged substrate peptide (see Dinh M., et. al., Activation mechanism and steady state kinetics of Bruton's tyrosine kinase. *J. Biol. Chem.* 282:8768-76. 2007). The peptide Is isolated from unreacted [$^{33}$P]ATP using streptavidin-coated beads. Each well of a 96-well V bottom plate (Greiner, Monroe, N.C.), contains assay buffer (8 mM imidazole, pH 7.2, 8 mM glycerol 2-phosphate, 200 uM EGTA, 20 mM MgCl2, 1 mM $MnCl_2$, 0.1 mg/ml bovine serum albumin, and 2 mM dithiothreitol) which was combined to 40 ul with a mixture of substrates dissolved in assay buffer such that the final concentrations were 1 uCi of [$^{33}$P]ATP, 100 uM ATP, and peptide substrate (biotin-Aca-AAAEEIYGEI-NH2). Initiation of the reaction is by addition of BTK to a final concentration of 10 nM. The reaction is incubated at 30° C. for 15 min. The reaction is stopped by transferring 25 ul of sample to a 96-well 1.2 -um hydrophilic polyvinylidene difluoride filter plate (Millipore, Billerica, Mass.) containing 10% streptavidin-Sepharose beads (GE Healthcare) dissolved in phosphate-buffered saline plus 50 mM EDTA. Filter plates are washed with 2 M NaCl, then with 2 M NaCl with 1% phosphoric acid, and then with $H_2O$. Plates were allowed to dry and microscint-20 (PerkinElmer Life Sciences, Boston, Mass.) was added. The [$^{33}$P]phosphoproduct is detected by a top-count scintillation counter. The enzyme activity is calculated for each data point. The corrected number of counts in each well is determined by subtracting the background counts from the measured counts. This value is then divided by the total number of counts that were originally present in the solution (determined by spotting and counting an equivalent volume of unwashed sample on a filter plate) and multiplied by the concentration of ATP in solution to give the concentration of phosphorylated product formed. Selectivity for BTK will be determined using commercially available kinase cross-screening services (DiscoveRx, San Diego, Calif.).

Example 3

BTK TR-FRET Assay

Inhibition of BTK enzymatic activity by compounds is measured using time-resolved fluorescence resonance energy transfer (TR-FRET) (Invitrogen pamphlet: Optimization of a LanthaScreen Kinase assay for BTK). Here, a signal is observed only when a Europium-coupled phophotyrosine antibody binds the phosphorylated peptide. Compounds are first prepared in 100% DMSO and serially diluted 10 times via 3-fold dilution. 2.5 ul of inhibitor at 4-fold the final assay concentration is next transferred to the 384-well assay plate (Corning Catalog #3676). A solution of 2-fold the final concentration of BTK enzyme (Invitrogen Catalog #PV3363) and Alexafluor 647-coupled peptide substrate (Invitrogen Catalog #5693) is next prepared in advance in a kinase buffer of 50 mM Hepes pH 7.5, 10 mM MgCl2, and 1 mM EGTA. For this solution, the final concentration of BTK and peptide is typically 1 nM and 100 nM, respectively. 5 uL of this 2-fold mix of BTK and peptide is added as the second step of the procedure to the 384-well assay plate. To initiate the enzymatic reaction, 2.5 ul of a 4-fold excess ATP solution in kinase buffer is added to the 384-well assay plate. Final ATP concentration is typically set to the Km for ATP of 100 uM. The reaction is allowed to proceed for 60 minutes. During the kinase reaction, a stop solution consisting of EDTA and a Europium-containing phosphotyrosine antibody (Invtrogen Catalog #5692) is prepared in TR-FRET dilution buffer (Invitrogen Catalog #3574). The stop solution contains an EDTA concentration of 20 mM and an antibody concentration of 4 nM. After the 60 minute reaction, 10 ul of the stop solution is added to all wells. Each well is mixed and incubated for 30 minutes at room temperature. Plates are read on a Perkin Elmer Envision TR-FRET plate reader under LanthaScreen settings. Excitation wavelength is 337 nm and Emission wavelengths are 620 nm and 665 mm Data are acquired as the ratio of emission at 665 nm/emission at 620 nm and plotted as a function of compound concentration to ascertain compound potency. Here, a signal is observed only when a Europium-coupled phophotyrosine antibody binds the phosphorylated peptide.

Example 4

Cellular BTK Activity Measured by Reporter Assay in Ramos Cells

The beta lactamase-based select-screen reporter assay is used to measure BTK cell-based activity (Invitrogen Selectscreen Screening Protocol and Assay Conditions document. Revised 8 Feb. 2010). 32 µL of NFAT-bla RA1 (Invitrogen) cells diluted in Assay Media to appropriate cell density are added to the Poly-D-Lysine assay plate containing 4 µL of a 10× serial dilution of a BTK control compound or test compounds. Pre-incubation at 37° C./5% CO2 in a humidified incubator with compounds and control inhibitor titration is for 30 minutes. 4 µL of 10× control activator Goat anti-Human IgM at the pre-determined EC80 concentration is added to wells containing the control inhibitor or compounds. The plate is incubated for 5 hours at 37° C./5% $CO_2$ in a humidified incubator. 8 µL of 1 µM Substrate Loading Solution is added to each well and the plate is incubated for 2 hours at room temperature. The plate is read on a fluorescence plate reader and the data is analyzed. A response ratio is calculated from the emissions of cleaved and uncleaved substrate. The response ratio of wells with compound dilutions is compared with wells that contain only DMSO to calculate the percent inhibition at each compound concentration. A dose response curve is constructed and an $IC_{50}$ is calculated.

Example 5

Btk Enzymatic Activity Assay

A Caliper-based kinase assay (Caliper Life Sciences, Hopkinton, Mass.) was used to measure inhibition of Btk kinase activity of a compound of Formula (IA), (I') or (I). Serial dilutions of test compounds were incubated with human recombinant Btk (2 nM), ATP (40 µM) and a phosphoacceptor peptide substrate FAM-GEEPLYWSFPAKKK-NH$_2$ (1 µM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the $IC_{50}$. The $IC_{50}$ for a representative no. of compounds of the disclosure are provided below.

| Cpd # | IC$_{50}$ (um) | Cpd # | IC$_{50}$ (um) |
|---|---|---|---|
| Cpd Table 1 | | | |
| 1 | 0.0031 | 7 | .0013 |
| 2 | .0037 | 8 | .13 |
| 3 | .175 | 9 | .98 |
| 4 | .061 | 10 | .0054 |
| 5 | .001 | 11 | .014 |
| 6 | .365 | 15A | 0.0017 |
| 17A | .0021 | 24A | .0062 |
| 18A | .0023 | 25A | .0096 |
| 22A | .0018 | 27A | .004 |
| 28 | .017 | 30A | .0017 |
| 31A | .002 | 36A | .0043 |
| 32A | .0017 | 37A | .0042 |
| 34 | .0048 | 39A | .0071 |
| 35A | .0044 | 22B | .0026 |
| 25B | 0.14 | 44A | 0.005 |
| 27B | 0.0006 | 44B | 0.003 |
| 39B | 0.0038 | 54A | 0.002 |
| 41A | 0.0032 | 56A | 0.0033 |
| 43A | 0.0018 | 57B | 0.01 |
| 63B | 0.033 | 69A | 0.005 |
| 65B | 0.056 | 70A | 0.011 |
| 67 | 0.027 | 72A | 0.0016 |
| 42A | .0028 | 72B | 0.028 |
| 73B | 0.011 | 79B | 0.003 |
| 77B | 0.007 | 59B | 0.026 |
| 71A | 0.007 | 80B | 0.004 |
| 74B | 0.008 | 81A | 0.0044 |
| 75B | 0.10 | 81B | 0.0059 |
| 76B | 0.007 | 82A | 0.0022 |
| 78B | 0.0075 | 82B | 0.113 |
| 87B | 0.012 | 83A | 0.0014 |
| 84A | 0.0036 | 83B | 0.016 |
| 84B | 0.0004 | 85A | 0.0004 |
| 85B | 0.0172 | 89A | 3.1 |
| 87B | 0.012 | 89B | 6.6 |
| 88B | 0.029 | 90A | 0.052 |
| 95A | 0.0265 | 95B | 0.0032 |
| 102A | 0.002 | 102B | 0.006 |
| 104A | 0.001 | 104B | 0.020 |
| 105A | 0.0013 | 105B | 0.0255 |
| 106A | 0.006 | 124A | 0.002 |
| 106B | 0.0015 | 126A | 0.003 |
| 133A | 0.007 | 139A | 0.0007 |
| 156A | 0.0073 | 171B | 0.007 |
| 173B | 0.034 | 175A | 0.003 |
| 175B | 0.001 | 182B | 0.002 |
| 183B | 0.003 | 184B | 0.005 |
| 185B | 0.011 | 186 | 0.0037 |
| 188 | 0.0007 | 195 | 0.006 |
| 180A | 0.037 | 180B | 0.004 |
| 162A | 0.0009 | 197B | 0.0325 |
| 29 A | 0.0027 | 125 A | 0.002 |
| Cpd Table 2 | | | |
| 1 | .062 | 3 | .013 |
| 2 | >1 | 5 | .18 |
| 6 | >1 | 8 | >1 |
| 9 | .62 | 10 | >1 |

Example 6

Blockade of CD69 Expression in Whole Blood Samples

Activation of the B cell receptor leads to increased BTK activity, calcium mobilization and B cell activation (see Honigberg L. A., et. al., Proc Natl Acad Sci USA. 107:13075-80. 2010). BTK inhibitors have been shown to block B cell activation as measured by CD69 expression (see Karp, R., et. al., Inhibition of BTK with AVL-292 Translates to Protective Activity in Animal Models of Rheumatoid Arthritis Inflammation Research Association Meeting, September, 2010). We used expression of CD69 following B cell activation as a measure of BTK activity in whole blood. Aliquots of whole blood are pre-incubated with serial dilutions of test compound for 30 minutes followed by activation with anti-IgM (goat Fab'2, 50 ug/ml). Samples are incubated overnight at 37 C and then stained with PE labeled anti-CD20 and APC labeled anti-CD69 (BD Pharmingen) for 30 minutes according to the manufacturer's directions. Whole blood is then lysed and cells gated on CD20 expression are quantified for CD 69 expression by FACS. The percent inhibition is calculated based on a DMSO control for no inhibition and plotted as a function of test compound concentration from which an IC$_{50}$ value is calculated.

Example 7

Inhibition of Mouse Collagen-Induced Arthritis

Inhibition of murine collagen-induced arthritis (mCIA) is a standard animal disease model for rheumatoid arthritis. Previous studies have demonstrated that inhibition of BTK is efficacious in blocking mCIA (see Honigberg L. A., et. al., Proc Natl Acad Sci USA. 107:13075-80. 2010). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by Elisa at the end of the study (Bolder BioPath, Boulder, Colo.).

Example 8

Recovery of Kinase Activity Upon Dialysis

Standard experimental methods to establish reversibility are known in the art. Protein dialysis is one such method. A solution containing a protein kinase that is inhibited by a compound of Formula I may be subjected to extensive dialysis to establish if the kinase inhibitor is reversible. Partial or complete recovery of protein kinase activity over time during dialysis is indicative of reversibility.

Method:
A compound of Formula I described herein (1 uM) is added to a solution of protein kinase (50 nM, pre-activated if necessary) in a buffer containing 20 mM Hepes [pH 8.0], 10 mM MgCl2, 2.5 mM tris(2-carboxyethyl)phosphine (TCEP), 0.25 mg/mL BSA, and 100 uM ATP. After 60 min at rt, the reactions is transferred to a dialysis cassette (0.1-0.5 mL Slide-A-Lyzer, MWCO 10 kDa, Pierce) and dialyzed against 2 L of buffer (20 mM Hepes [pH 8.0], 10 mM MgCl2, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for protein kinase activity in triplicate. Kinase activity for each sample is normalized to the DMSO control for that time point and expressed as the mean±SD.

Results: Kinase activity recovers from inhibition by reversible kinase inhibitors upon dialysis. Upon extensive dialysis at 4° C. or at room temperature, kinase activity partially or completely recovers in a time-dependent manner from inhibition by an excess (20 equiv, 1.0 uM) of reversible kinase inhibitor.

Example 9

Mass Spectral Analysis

A protein kinase that is inhibited by compound of Formula I may be subjected to mass spectral analysis to assess the formation of permanent, irreversible covalent adducts. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase
Method:

A protein kinase (5 uM) is incubated with a compound of Formula I (25 uM, 5 equiv) for 1 h at room temperature in buffer (20 mM Hepes [pH 8.0], 100 mM NaCl, 10 mM MgCl2). A control sample is also prepared which does not have a compound of Formula I. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results: High-resolution intact mass spectrometry analysis of a kinase that is inhibited by a compound of Formula I will reveal a spectrum similar to the kinase in the absence of inhibitor (e.g. control sample). There will be no formation of a new peak in the mass spectrum corresponding to the molecular mass of the kinase plus the molecular mass of the compound of Formula I. On the basis of this experiment no permanent, irreversible protein adduct will be apparent to one skilled in the art.

Mass Spectral Analysis of Kinase Tryptic Digest
Method:

A protein (10-100 pmols) is incubated with a compound of Formula I (100-1000 pmols, 10 equiv) for 3 hrs prior to tryptic digestion. Iodoacetamide may be used as the alkylating agent after compound incubation. A control sample is also prepared which does not the compound of Formula I. For tryptic digests a 1 ul aliquot (3.3 pmols) is diluted with 10 ul of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50).

Results: High-resolution mass spectrometry analysis of the tryptic fragments of a kinase that is inhibited by a compound of Formula I will reveal a spectrum similar to the kinase in the absence of inhibitor (e.g. control sample). There will be no evidence of any modified peptides that are not present in the control sample. On the basis of this experiment, no permanent, irreversible protein adducts will be apparent to one skilled in the art. Cellular assays are also optionally used to assess the inhibiting properties of a compound of Formula I provided herein or embodiments thereof. Cellular assays include cells from any appropriate source, including plant and animal cells (such as mammalian cells). The cellular assays are also optionally conducted in human cells. Cellular assays of BTK inhibition are well known in the art, and include methods in which an inhibitor is delivered into the cell (e.g. by electroporation, passive diffusion, microinjection and the like) and an activity endpoint is measured, such as the amount of phosphorylation of a cellular substrate, the amount of expression of a cellular protein, or some other change in the cellular phenotype known to be affected by the catalytic activity of BTK. For example, phosphorylation of a particular cellular substrate is optionally assessed using a detection antibody specific or the phosphorylated cellular substrate followed by western blotting techniques and visualization using any appropriate means (e.g. fluorescent detection of a fluorescently labeled antibody).

Measuring the reduction in the BTK catalytic activity in the presence of an inhibitor disclosed herein relative to the activity in the absence of the inhibitor is optionally performed using a variety of methods known in the art, such as the assays described in the Examples section below. Other methods for assaying BTK activity are known in the art.

Example 10

Determination of Drug-Kinase Residence Time . . . Drug Off-Rate Assay

The following is a protocol to distinguish whether a compound displays a slow or non-existent dissociation rate from BTK, such as typically would occur if a covalent bond is formed between the compound and the target. The read-out for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM MgCl2, 0.01% Triton X-100, and 1 mM EGTA.

The first step of the procedure was incubation of 500 nM BTK (Invitrogen Cat. #PV3587) with 1.5 uM of a compound of Formula (IA) for 30 minutes in a volume of 10 uL. The mixture was then diluted 5-fold by addition of 40 uL of buffer. A 10 uL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For BTK, the competition solution contained 1.5 uM Tracer 178 (Invitrogen Cat. #PV5593), which is a proprietary high affinity ligand for BTK coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in BTK.

After addition of 10 uL of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to BTK was detected using TR-FRET between the Europium moiety of the Anti-histidine antibody and the AlexaFluor 647 group of Tracer 178. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of BTK from the reaction.

Reversibility of Binding

The following approach was developed to differentiate compounds that form irreversible bonds with their targets, such as acrylamide compounds, from compound that bind reversibly. Reactions were prepared with the protein target at a higher concentration than the compounds of interest. Both irreversible and reversible compounds bound the target and became depleted from solution. The reactions were then treated with perturbations including both denaturation with 5 M guanidine hydrochloride and digestion with trypsin, disrupting proper folding of the target. It was found that the perturbation returned reversible compounds to solution due to dissociation from the target while irreversible compounds remained bound to the target. The concentration of compound in solution was assessed both preceding and following perturbation using high performance liquid chromatography (HPLC) coupled to tandem mass spectrometry. Using this technique, it was demonstrated that an acrylamide-containing compound 1 (shown in table below) was depleted from solution in both the native and perturbed state, while reversible compounds 1 and 27 were depleted in the folded state but returned to solution following perturbation of the target (See table below).

| Cpd | Compound in solution in the native state? | Compound in solution in the denatured or digested state? |
|---|---|---|
| Irreversible inhibitor | no | no |
| 1 | no | yes |
| 27 | no | yes |

Formulation Examples

The following are representative pharmaceutical formulations containing a compound of Formula (IA).

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound I) in 2% HPMC, 1% Tween 80 in DI water, pH 2.2 with MSA, q.s. to at least 20 mg/mL The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A method of treating inflammatory bowel disease, arthritis, lupus, rheumatoid arthritis, psoriatic arthritis, juvenile arthritis, Sjogren's syndrome, multiple sclerosis, ankylosing spondylitisis, idiopathic thrombocytopenic purpura, scleroderma, Wegener's granulomatosis, psoriasis, asthma, colitis, conjunctivitis, dermatitis, uveitis, eczema, diffuse large B cell lymphoma, follicular lymphoma, chronic lymphocytic lymphoma, chronic lymphocytic leukemia, B-cell prolymphocytic leukemia, lymphoplamascytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, non-Hodgkin lymphoma, intravascular large B cell lymphoma, primary effusion lymphoma, burkitt's lymphoma/leukemia, or lymphomatoid granulomatosis, which method comprises administering to the patient in need thereof, a pharmaceutical composition comprising a (R) isomer, (S) isomer, or a mixture of (R) and (S) isomers of a compound or a pharmaceutically acceptable salt thereof, and a pharmaceutically acceptable excipient, wherein the compound is 4-amino-2-(2-((4-amino-3-(2-fluoro-4-(3-fluorophenoxy)phenyl)-1H-pyrazolo[3,4-d]pyrimidin-1-yl)methyl)pyrrolidine-1-carbonyl)-4-methylpent-2-enenitrile having the structure:

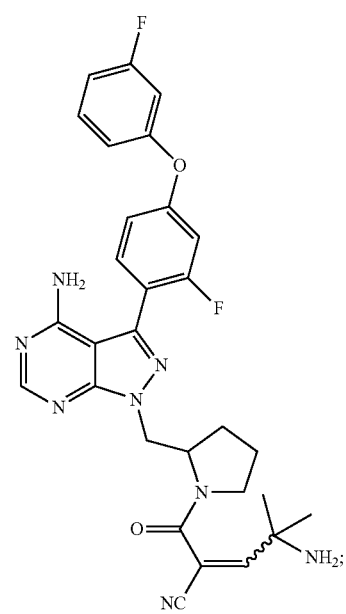 [SMILES: CC(C)(N)C=C(C#N)C(=O)N1CCCC1Cn1nc(-c2ccc(Oc3cccc(F)c3)cc2F)c2c(N)ncnc21]

4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile having the structure:

2-(2-((4-amino-3-(2-fluoro-4-phenoxyphenyl)-1H-pyrazolo[3,4-d]pyrimidin-1-yl)methyl)pyrrolidine-1-carbonyl)-4-methyl-4-morpholinopent-2-enenitrile having the structure:

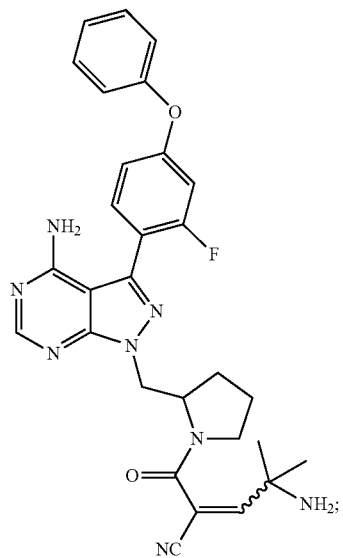 [SMILES: CC(C)(N)C=C(C#N)C(=O)N1CCCC1Cn1nc(-c2ccc(Oc3ccccc3)cc2F)c2c(N)ncnc21]

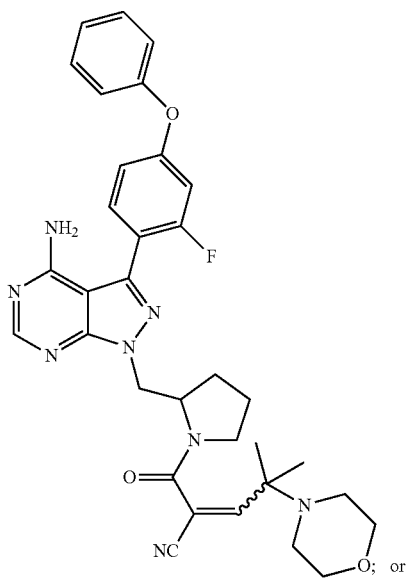 [SMILES: CC(C)(C=C(C#N)C(=O)N1CCCC1Cn1nc(-c2ccc(Oc3ccccc3)cc2F)c2c(N)ncnc21)N1CCOCC1]

or 4-amino-2-(2-((4-amino-3-(4-(2,3-difluorophenoxy)-2-fluorophenyl)-1H-pyrazolo[3,4-d]pyrimidin-1-yl)methyl)pyrrolidine-1-carbonyl)-4-methylpent-2-enenitrile having the structure:

285

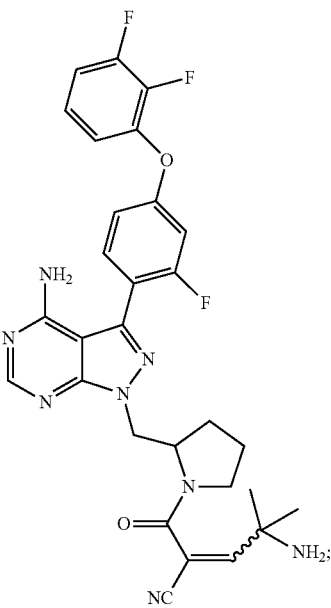 [SMILES: CC(C)(N)C=C(C#N)C(=O)N1CCCC1Cn1nc(-c2ccc(Oc3cccc(F)c3F)cc2F)c2c(N)ncnc21]

or an (E) or (Z) isomer, or a mixture of (E) and (Z) isomers of any of the foregoing.

2. The method of claim 1 wherein the (R) isomer, (S) isomer, or a mixture of (R) and (S) isomers of a compound or a pharmaceutically acceptable salt thereof is (R)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile having the structure:

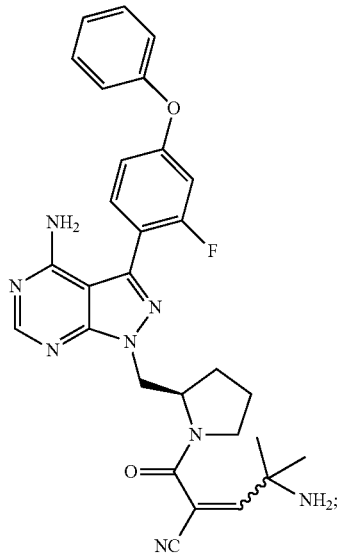 [SMILES: CC(C)(N)C=C(C#N)C(=O)N1CCC[C@@H]1Cn1nc(-c2ccc(Oc3ccccc3)cc2F)c2c(N)ncnc21]

or an (E) or (Z) isomer, or a mixture of (E) and (Z) isomers thereof; or a pharmaceutically acceptable salt of any of the foregoing.

3. The method of claim 1 wherein the (R) isomer, (S) isomer, or a mixture of (R) and (S) isomers of a compound or a pharmaceutically acceptable salt thereof; or an (E) or (Z) isomer, or a mixture of (E) and (Z) isomers of any of the foregoing, is (R,E)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile having the structure:

286

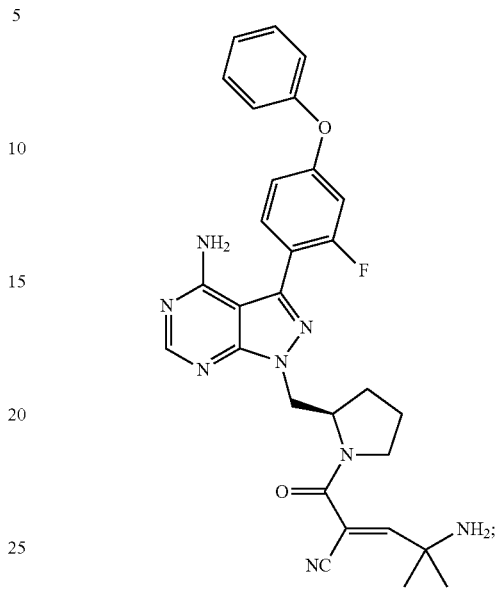

or a pharmaceutically acceptable salt thereof.

4. The method of claim 1 wherein the (R) isomer, (S) isomer, or a mixture of (R) and (S) isomers of a compound or a pharmaceutically acceptable salt thereof; or an (E) or (Z) isomer, or a mixture of (E) and (Z) isomers of any of the foregoing, is (R,Z)-4-amino-2-(2-((4-amino-3-(2-fluoro-4-phenoxyphenyl)-1H-pyrazolo[3,4-d]pyrimidin-1-yl)methyl)pyrrolidine-1-carbonyl)-4-methylpent-2-enenitrile having the structure:

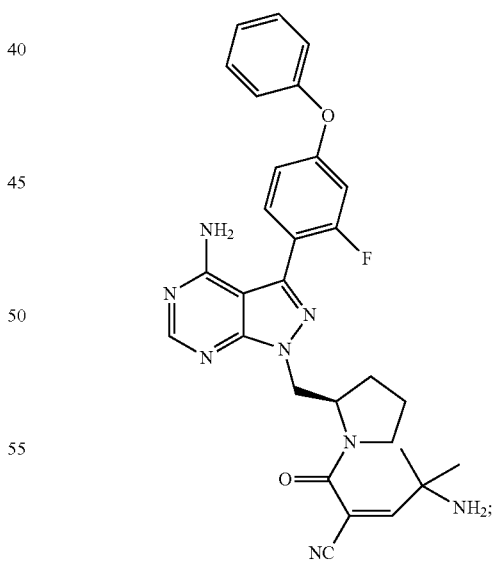

or a pharmaceutically acceptable salt thereof.

5. The method of claim 1 wherein the (R) isomer, (S) isomer, or a mixture of (R) and (S) isomers of a compound or a pharmaceutically acceptable salt thereof is (S)-2-(2-((4-amino-3-(2-fluoro-4-phenoxyphenyl)-1H-pyrazolo[3,4-d]pyrimidin-1-yl)methyl)-pyrrolidine-1-carbonyl)-4-methyl-4-morpholinopent-2-enenitrile having the structure:

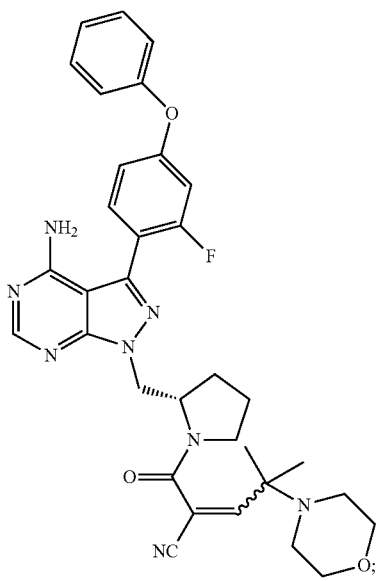 [SMILES: CC(C)(C=C(C#N)C(=O)N1CCC[C@H]1Cn1nc(-c2ccc(Oc3ccccc3)cc2F)c2c(N)ncnc21)N1CCOCC1]

or an (E) or (Z) isomer, or a mixture of (E) and (Z) isomers thereof; or a pharmaceutically acceptable salt of any of the foregoing.

6. The method of claim 1 wherein the (R) isomer, (S) isomer, or a mixture of (R) and (S) isomers of a compound or a pharmaceutically acceptable salt thereof; or an (E) or (Z) isomer, or a mixture of (E) and (Z) isomers of any of the foregoing, is (S,E)-2-(2-((4-amino-3-(2-fluoro-4-phenoxyphenyl)-1H-pyrazolo[3,4-d]pyrimidin-1-yl)methyl)-pyrrolidine-1-carbonyl)-4-methyl-4-morpholinopent-2-enenitrile having the structure:

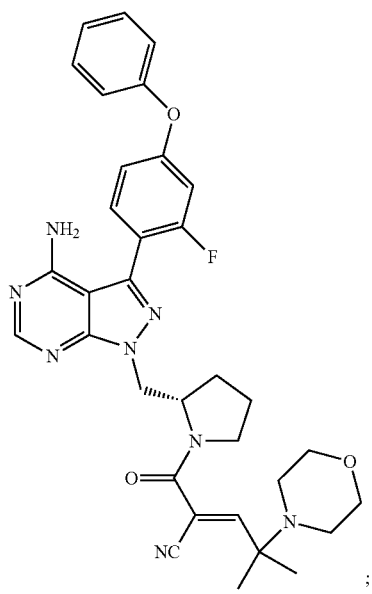 [SMILES: CC(C)(/C=C(\C#N)C(=O)N1CCC[C@H]1Cn1nc(-c2ccc(Oc3ccccc3)cc2F)c2c(N)ncnc21)N1CCOCC1]

or a pharmaceutically acceptable salt thereof.

7. The method of claim 1 wherein the (R) isomer, (S) isomer, or a mixture of (R) and (S) isomers of a compound or a pharmaceutically acceptable salt thereof; or an (E) or (Z) isomer, or a mixture of (E) and (Z) isomers of any of the foregoing, is (S,Z)-2-(2-((4-amino-3-(2-fluoro-4-phenoxyphenyl)-1H-pyrazolo[3,4-d]pyrimidin-1-yl)methyl)-pyrrolidine-1-carbonyl)-4-methyl-4-morpholinopent-2-enenitrile having the structure;

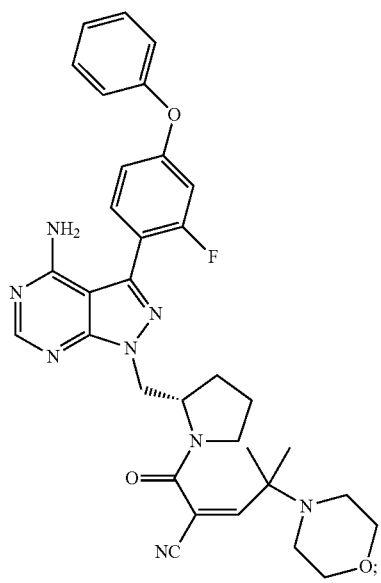 [SMILES: CC(C)(/C=C(/C#N)C(=O)N1CCC[C@H]1Cn1nc(-c2ccc(Oc3ccccc3)cc2F)c2c(N)ncnc21)N1CCOCC1]

or a pharmaceutically acceptable salt thereof.

8. The method of claim 1 wherein the pharmaceutical composition comprising
  a (R) isomer, (S) isomer, or a mixture of (R) and (S) isomers of a compound or a pharmaceutically acceptable salt thereof; or an (E) or (Z) isomer, or a mixture of (E) and (Z) isomers of any of the compounds, and
  a pharmaceutically acceptable excipient,
is administered optionally in combination with one or more anticancer or anti-inflammatory agents.

* * * * *